United States Patent
Shiomi et al.

(10) Patent No.: US 12,157,747 B2
(45) Date of Patent: Dec. 3, 2024

(54) ORGANIC ELECTROLUMINESCENT ELEMENT, COMPOUND, MATERIAL FOR ORGANIC ELECTROLUMINESCENT ELEMENT, AND ELECTRONIC DEVICE

(71) Applicant: IDEMITSU KOSAN CO., LTD., Tokyo (JP)

(72) Inventors: Takushi Shiomi, Sodegaura (JP); Hiromi Nakano, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 757 days.

(21) Appl. No.: 17/413,248

(22) PCT Filed: Dec. 11, 2019

(86) PCT No.: PCT/JP2019/048468
§ 371 (c)(1),
(2) Date: Jun. 11, 2021

(87) PCT Pub. No.: WO2020/122118
PCT Pub. Date: Jun. 18, 2020

(65) Prior Publication Data
US 2022/0081450 A1 Mar. 17, 2022

(30) Foreign Application Priority Data
Dec. 14, 2018 (JP) .................. 2018-234819

(51) Int. Cl.
*C07D 519/00* (2006.01)
*H10K 85/60* (2023.01)
(Continued)

(52) U.S. Cl.
CPC ....... *C07D 519/00* (2013.01); *H10K 85/6572* (2023.02); *H10K 85/6574* (2023.02); *H10K 50/11* (2023.02); *H10K 2101/10* (2023.02)

(58) Field of Classification Search
None
See application file for complete search history.

(56) References Cited

U.S. PATENT DOCUMENTS

| | | |
|---|---|---|
| 2009/0017330 A1 | 1/2009 | Iwakuma et al. |
| 2009/0017331 A1 | 1/2009 | Iwakuma et al. |

(Continued)

FOREIGN PATENT DOCUMENTS

| | | | | |
|---|---|---|---|---|
| CN | 103688384 A | * | 3/2014 | ........... C07C 255/58 |
| CN | 104136440 A | | 11/2014 | |

(Continued)

OTHER PUBLICATIONS

Machine translation of CN-103688384-A, translation generated Feb. 2024, 19 pages. (Year: 2024).*

(Continued)

*Primary Examiner* — Robert S Loewe
(74) *Attorney, Agent, or Firm* — Oblon, McClelland, Maier & Neustadt, L.L.P.

(57) ABSTRACT

An organic EL device includes an anode, a cathode, and an emitting layer interposed between the anode and the cathode, in which the emitting layer includes a delayed fluorescent compound M2 and a compound M3 represented by a formula (100), and a singlet energy $S_1(M2)$ of the compound M2 and a singlet energy $S_1(M3)$ of the compound M3 satisfy a numerical formula (Numerical Formula 1). In the formula (100), $X_1$ is an oxygen atom or a sulfur atom, $C_1$ is a carbon atom, $R_{11}$ to $R_{18}$, $R_2$, $R_{31}$, $R_{32}$, $R_{34}$, $R_{35}$, $R_4$ and $R_{45}$ to $R_{48}$ are each independently a hydrogen atom, substituent or the like, n is 1, 2, or 3. When $L_1$ is a single bond, n is 1, k is 1, 2, or 3, m is 2, 3, or 4, k+m=5, and $L_1$ is a single bond or linking group.

(Continued)

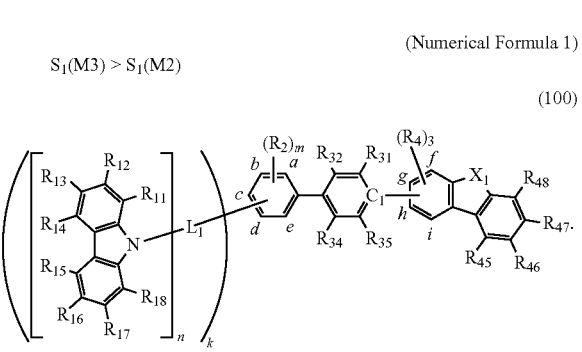

(Numerical Formula 1)

$S_1(M3) > S_1(M2)$ (100)

51 Claims, 5 Drawing Sheets

Figure 1:
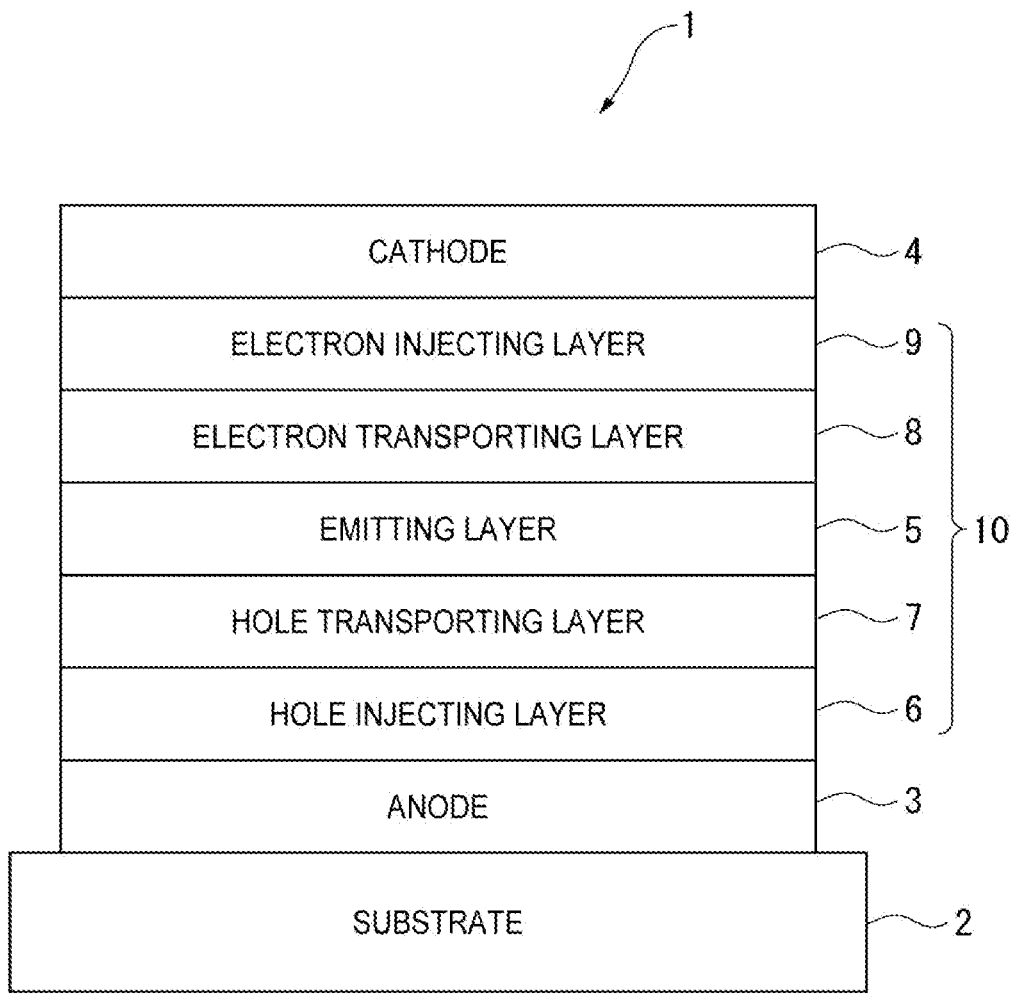

(51) Int. Cl.
*H10K 50/11* (2023.01)
*H10K 101/10* (2023.01)

(56) References Cited

U.S. PATENT DOCUMENTS

| | | |
|---|---|---|
| 2012/0097937 A1 | 4/2012 | Iwakuma et al. |
| 2016/0190478 A1 | 6/2016 | Nakanotani et al. |
| 2016/0276604 A1 | 9/2016 | Kwong et al. |
| 2017/0062718 A1 | 3/2017 | Numata et al. |
| 2017/0141340 A1 | 5/2017 | Tanaka et al. |
| 2017/0237004 A1 | 8/2017 | Molaire |
| 2017/0369439 A1 | 12/2017 | Jung et al. |
| 2018/0248127 A1 | 8/2018 | Lee et al. |
| 2018/0261775 A1 | 9/2018 | Molaire |
| 2019/0044071 A1 | 2/2019 | Parham et al. |
| 2020/0343452 A1 | 10/2020 | Lee et al. |
| 2021/0074927 A1 | 3/2021 | Nakanotani et al. |

FOREIGN PATENT DOCUMENTS

| | | | |
|---|---|---|---|
| CN | 105198868 | A | 12/2015 |
| CN | 105263937 | A | 1/2016 |
| CN | 105684180 | A | 6/2016 |
| CN | 108140733 | A | 6/2018 |
| CN | 108912099 | A | 11/2018 |
| CN | 109232382 | A | 1/2019 |
| EP | 3 035 401 | A1 | 6/2016 |
| JP | 2018-503622 | A | 2/2018 |
| KR | 10-2015-0077219 | A | 7/2015 |
| KR | 10-2016-0027940 | A | 3/2016 |
| KR | 2016-0149879 | A | 12/2016 |
| KR | 10-2017-0136256 | A | 12/2017 |
| KR | 2018-0015209 | A | 2/2018 |
| KR | 10-2018-0112962 | A | 10/2018 |
| KR | 10-2019-0078117 | A | 7/2019 |
| WO | WO 2009/008099 | A1 | 1/2009 |
| WO | WO 2013/109045 | A1 | 7/2013 |
| WO | WO 2016/102040 | A1 | 6/2016 |
| WO | WO 2017/053426 | A1 | 3/2017 |
| WO | WO-2018113538 | A1 * | 6/2018 ........... C07D 495/04 |
| WO | WO 2019-191665 | A1 | 10/2019 |

OTHER PUBLICATIONS

Machine translation of WO-2018113538-A1, translation generated Feb. 2024, 18 pages. (Year: 2024).*
Combined Chinese Office Action and Search Report issued Nov. 14, 2023, in corresponding Chinese Patent Application No. 201980081332.8 (with English Translation of Category of Cited Documents), 12 pages.
International Search Report issued on Feb. 25, 2020 in PCT/JP2019/048468 filed on Dec. 11, 2019, 3 pages.
Nakanotani, H. et al., "High-efficiency organic light-emitting diodes with fluorescent emitters," Nature Communications, vol. 5, 4016, 2014, pp. 1-7.
Adachi, C., "Yuki Hando-tai no Debaisu Bussei (Device Physics of Organic Semiconductors)," Kodansha, 2012, pp. 261-268, 19 total pages (with English translation).
Uoyama, H. et al., "Highly efficient organic light-emitting diodes from delayed fluorescence," Nature, vol. 492, pp. 234-238, 2012, 7 total pages.
Office Action issued Sep. 5, 2023, in corresponding Japanese Patent Application No. 2020-559283, 2 pages.
Extended European Search Report issued Aug. 5, 2022 in European Patent Application No. 19897214.3, 14 pages.
Extended European Search Report issued Oct. 18, 2022 in European Patent Application No. 19897214.3, 15 pages.
Office Action received Aug. 9, 2024, in corresponding Chinese patent application No. 201980081332.8, (with machine translation).
Office Action received on Oct. 7, 2024, in corresponding Korean patent application No. 10-2021-7022021(with machine translation).

* cited by examiner

ORGANIC ELECTROLUMINESCENT ELEMENT, COMPOUND, MATERIAL FOR ORGANIC ELECTROLUMINESCENT ELEMENT, AND ELECTRONIC DEVICE

TECHNICAL FIELD

The present invention relates to an organic electroluminescence device, a compound, an organic-electroluminescence-device material, and an electronic device.

BACKGROUND ART

When a voltage is applied to an organic electroluminescence device (hereinafter, occasionally referred to as "organic EL device"), holes are injected from an anode and electrons are injected from a cathode into an emitting layer. The injected electrons and holes are recombined in the emitting layer to form excitons. Specifically, according to the electron spin statistics theory, singlet excitons and triplet excitons are generated at a ratio of 25%:75%.

A fluorescent organic EL device using light emission from singlet excitons has been applied to a full-color display such as a mobile phone and a television set, but an internal quantum efficiency is said to be at a limit of 25%. Accordingly, studies has been made to improve a performance of the organic EL device.

Moreover, it is expected to further efficiently emit the organic EL device using triplet excitons in addition to singlet excitons. In view of the above, a highly efficient fluorescent organic EL device using thermally activated delayed fluorescence (hereinafter, sometimes simply referred to as "delayed fluorescence") has been proposed and studied.

For instance, a TADF (Thermally Activated Delayed Fluorescence) mechanism has been studied. The TADF mechanism uses such a phenomenon that inverse intersystem crossing from triplet excitons to singlet excitons thermally occurs when a material having a small energy difference ($\Delta ST$) between singlet energy level and triplet energy level is used. Thermally activated delayed fluorescence is explained in "Yuki Hando-tai no Debaisu Bussei (Device Physics of Organic Semiconductors)" (edited by ADACHI, Chihaya, published by Kodansha, issued on Apr. 1, 2012, on pages 261-268).

Non-Patent Literature 1 discloses an emitting layer including: a TADF compound as an assist dopant; mCP (1,3-Bis(N-carbazolyl)benzene), mCBP (3,3-di(9H-carbazol-9-yl)biphenyl, or CBP (4,4'-bis(9-carbazolyl)-1,1'-biphenyl) as a host material; and a fluorescent material.

Patent Literature 1 discloses an organic EL device including an emitting layer including an assist dopant, a host material and a fluorescent dopant. As the assist dopant, a compound in which a triazine ring and a fused carbazole ring are bonded through a phenylene group is disclosed.

Patent Literature 2 discloses a compound in which an aryl group is bonded to a dibenzothiophene ring or a dibenzofuran ring as an organic-EL-device material used along with a phosphorescent metal complex.

CITATION LIST

Patent Literature(s)

Patent Literature 1: US Patent Application Publication No. 2017/0062718

Patent Literature 2: International Publication No. WO2009/008099

Non-Patent Literature(s)

Non-Patent Literature 1

Hajime Nakanotani et al, "High-efficiency organic light-emitting diodes with fluorescent emitters", Nature Communications, 5, 4016, 2014

SUMMARY OF THE INVENTION

Problems to be Solved by the Invention

An organic EL device using a TADF mechanism is desired to have higher performance such as longer lifetime.

In order to achieve the higher performance of the organic EL device, it is important to select a molecular structure of a material used along with the TADF compound.

An object of the invention is to provide a high-performance organic EL device, for instance, an organic EL device configured to emit light with along lifetime, and an electronic device including the organic EL device.

An object of the invention is also to provide: a compound capable of achieving a high-performance organic EL device, for instance, an organic EL device configured to emit light with a tong lifetime, and an electronic device including the organic EL device; and an organic-EL-device material containing the compound.

Means for Solving the Problems

According to an aspect of the invention, provided is an organic electroluminescence device including, an anode;
  a cathode; and
  an emitting layer provided between the anode and the cathode, in which the emitting layer includes a delayed fluorescent compound M2 and a compound M3 represented by a formula (100) below, and
  a singlet energy $S_1(M2)$ of the compound M2 and a singlet energy $S_1(M3)$ of the compound M3 satisfy a relationship of a numerical formula (Numerical Formula 1).

$S_1(M3) > S_1(M2)$

[Formula 1]

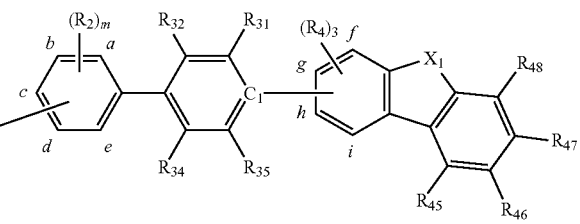

(Numerical Formula 1)

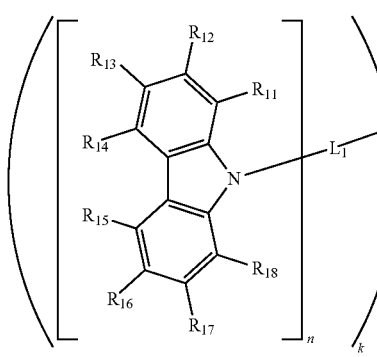

(100)

In the formula (100), $X_1$ is an oxygen atom or a sulfur atom, $C_1$ is a carbon atom, n is 1, 2 or 3, k is 1, 2 or 3, m is 2, 3, or 4, k+m=5, $R_{11}$ to $R_{18}$ are each independently a hydrogen atom or a substituent, or at least one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ are mutually bonded to form a ring, when at least one of n or k is 2 or more, a plurality of $R_{11}$ are mutually the same or different, a plurality of $R_{12}$ are mutually the same or different, a plurality of $R_{13}$ are mutually the same or different, a plurality of $R_{14}$ are mutually the same or different, a plurality of $R_{15}$ are mutually the same or different, a plurality of $R_{16}$ are mutually the same or different, a plurality of $R_{17}$ are mutually the same or different, and a plurality of $R_{18}$ are mutually the same or different, $L_1$ is a single bond or a linking group, when $L_1$ is a single bond, n is 1, when k is 2 or more, a plurality of $L_1$ are mutually the same or different, $L_1$ as a linking group is a group derived from a substituted or unsubstituted aryl group having 6 to 30 ring carbon atoms, a group derived from a substituted or unsubstituted heterocyclic group having 5 to 30 ring atoms, or a group in which two group selected from the group consisting of a group derived from a substituted or unsubstituted aryl group having 6 to 30 ring carbon atoms and a group derived from a substituted or unsubstituted heterocyclic group having 5 to 30 ring atoms are bonded, when k is 1 and m is 4, four $R_2$ are respectively bonded to carbon atoms at any ones of positions of a, b, c, d and e shown in the formula (100), and one $L_1$ is bonded to a carbon atom at the position of a, b, c, d or e which is not bonded to $R_2$, when k is 2 and m is 3, three $R_2$ are respectively bonded to carbon atoms at any ones of positions of a, b, c, d and e shown in the formula (100), and two $L_1$ are respectively bonded to carbon atoms at any ones of positions of a, b, c, d and e which are not bonded to $R_2$, when k is 3 and m is 2, two $R_2$ are respectively bonded to carbon atoms at any ones of positions of a, b, c, d and e shown in the formula (100), and three $L_1$ are respectively bonded to carbon atoms at any ones of positions of a, b, c, d and e which are not bonded to $R_2$, $R_2$, $R_{31}$, $R_{32}$, $R_{34}$ and $R_{35}$ are each independently a hydrogen atom or a substituent, a plurality of $R_2$ are mutually the same or different when m is 2 or more, $R_4$ and $R_{45}$ to $R_{48}$ are each independently a hydrogen atom or a substituent, or at least one pair of a pair of $R_{45}$ and $R_{46}$, a pair of $R_{46}$ and $R_{47}$, or a pair of $R_{47}$ and $R_{48}$ is mutually bonded to form a ring, or at least one pair of pairs including at least two of a plurality of $R_4$ is mutually bonded to form a ring, three $R_4$ are mutually the same or different, three $R_4$ are respectively bonded to carbon atoms at any ones of positions of f, g, h and i shown in the formula (100), and $C_1$ is bonded to a carbon atom at the position of f, g, h or i which is not bonded to $R_4$, $R_{11}$ to $R_{18}$, $R_2$, $R_{31}$, $R_{32}$, $R_{34}$, $R_{35}$, $R_4$ and $R_{45}$ to $R_{48}$ as the substituent are each independently, a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms.

According to another aspect of the invention, an electronic device including the organic electroluminescence device according to the above aspect of the invention is provided.

According to still another aspect of the invention, a compound represented by a formula (201), a formula (202), or a formula (203) is provided.

[Formula 2]

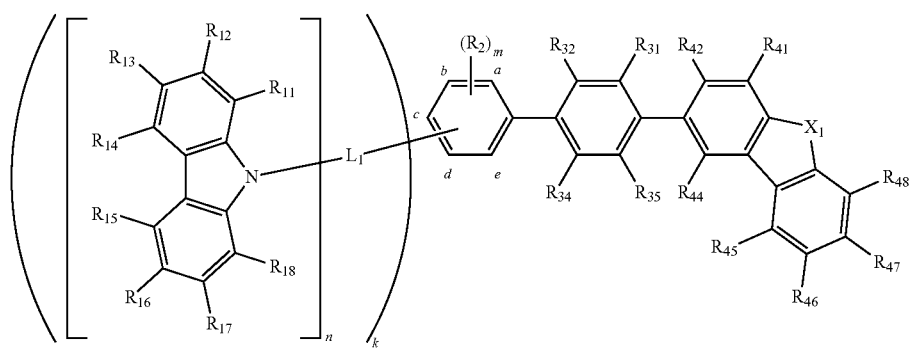

(201)

[Formula 3]

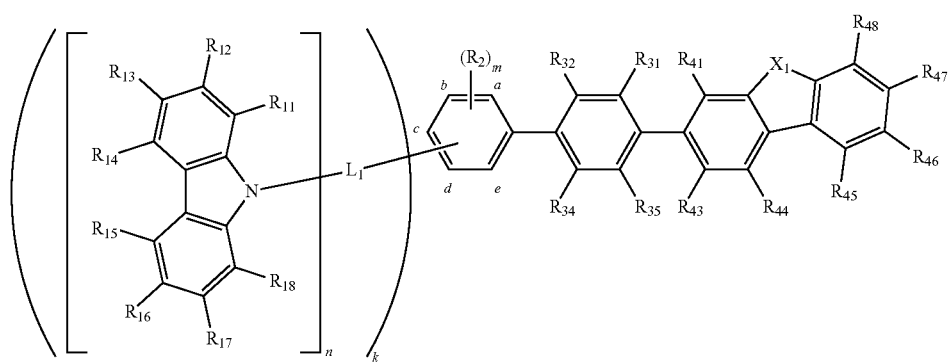

(202)

[Formula 4]

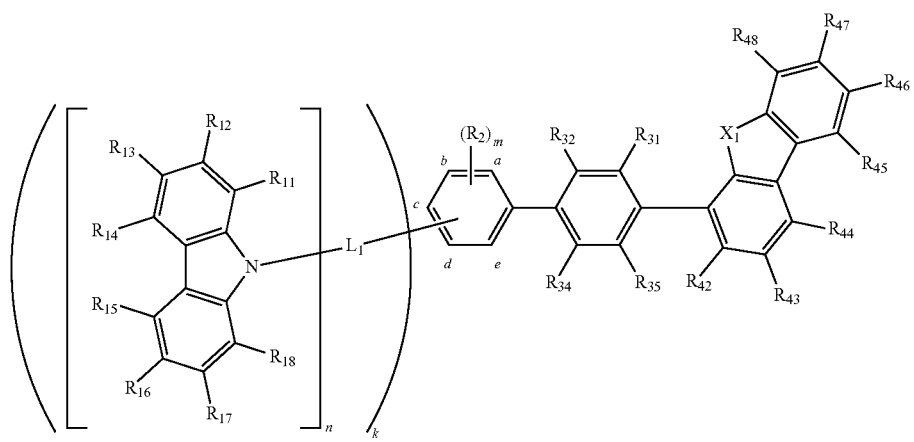

(203)

In the formulae (201) to (203), $X_1$ is an oxygen atom or a sulfur atom, n is 1, 2 or 3, k is 1, 2 or 3, m is 2, 3, or 4, k+m=5, $R_{11}$ to $R_{16}$ are each independently a hydrogen atom or a substituent, or a pair of $R_{11}$ and $R_{12}$, a pair of $R_{11}$ and $R_{13}$, a pair of $R_{13}$ and $R_{14}$, a pair of $R_{15}$ and $R_{16}$, a pair of $R_{16}$ and $R_{17}$, and a pair of $R_{17}$ and $R_{16}$ are not mutually bonded, when at least one of n or k is 2 or more, a plurality of $R_{11}$ are mutually the same or different, a plurality of $R_{12}$ are mutually the same or different, a plurality of $R_{13}$ are mutually the same or different, a plurality of $R_{14}$ are mutually the same or different, a plurality of $R_{18}$ are mutually the same or different, a plurality of $R_{10}$ are mutually the same or different, a plurality of $R_{17}$ are mutually the same or different, and a plurality of $R_{18}$ are mutually the same or different, $L_1$ is a single bond or a linking group, when $L_1$ is a single bond, n is 1, when k is 2 or more, a plurality of $L_1$ are mutually the same or different, $L_1$ as a linking group is a group derived from a substituted or unsubstituted aryl group having 6 to 30 ring carbon atoms, a group derived from a substituted or unsubstituted heterocyclic group having 5 to 30 ring atoms, or a group in which two group selected from the group consisting of a group derived from a substituted or unsubstituted aryl group having 6 to 30 ring carbon atoms and a group derived from a substituted or unsubstituted heterocyclic group having 5 to 30 ring atoms are bonded, when k is 1 and m is 4, four $R_2$ are respectively bonded to carbon atoms at any ones of positions of a, b, c, d and e shown in the formula (201), (202) or (203), and one $L_1$ is bonded to a carbon atom at the position of a, b, c, d or e which is not bonded to $R_2$, when k is 2 and m is 3, three $R_2$ are respectively bonded to carbon atoms at any ones of positions of a, b, c, d and e shown in the formula (201), (202) or (203), and two $L_1$ are respectively bonded to carbon atoms at any ones of positions of a, b, c, d and e which are not bonded to $R_2$, when k is 3 and m is 2, two $R_2$ are respectively bonded to carbon atoms at any ones of positions of a, b, c, d and e shown in the formula (201), (202) or (203), and three $L_1$ are respectively bonded to carbon atoms at any ones of positions of a, b, c, d and e which are not bonded to $R_2$, $R_2$, $R_{31}$, $R_{32}$, $R_{34}$ and $R_{35}$ are each independently a hydrogen atom or a substituent, a plurality of $R_2$ are mutually the same or different when m is 2 or more, $R_{41}$ to $R_{48}$ are each independently a hydrogen atom or a substituent, or at least one pair of a pair of $R_{41}$ and $R_{42}$, a pair of $R_{42}$ and $R_{43}$, a pair of $R_{43}$ and $R_{44}$, a pair of $R_{45}$ and $R_{46}$, a pair of $R_{46}$ and $R_{47}$, or a pair of $R_{47}$ and $R_{48}$ are mutually bonded to form a ring, $R_{11}$ to $R_{18}$, $R_2$, $R_{31}$, $R_{32}$, $R_{34}$, $R_{35}$, and $R_{41}$ to $R_{48}$ as the substituent are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms, and at least one of $R_{11}$ to $R_{16}$ is an unsubstituted aryl group having 6 to 30 ring carbon atoms.

According to a further aspect of the invention, a compound represented by a formula (300) is provided.

[Formula 5]

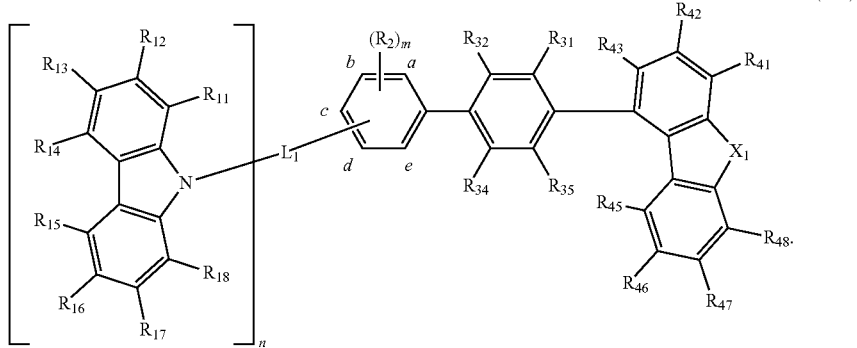

(300)

In the formula (300), $X_1$ is an oxygen atom or a sulfur atom, n is 1, 2 or 3, k is 1, 2 or 3, m is 2, 3, or 4, k+m=5, $R_{11}$ to $R_{18}$ are each independently a hydrogen atom or a substituent, or at least one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ are mutually bonded to form a ring, when at least one of n or k is 2 or more, a plurality of $R_{11}$ are mutually the same or different, a plurality of $R_{12}$ are mutually the same or different, a plurality of $R_{13}$ are mutually the same or different, a plurality of $R_{14}$ are mutually the same or different, a plurality of $R_{15}$ are mutually the same or different, a plurality of $R_{16}$ are mutually the same or different, a plurality of $R_{17}$ are mutually the same or different, and a plurality of $R_{18}$ are mutually the same or different, $L_1$ is a single bond or a linking group, when $L_1$ is a single bond, n is 1, when k is 2 or more, a plurality of $L_1$ are mutually the same or different, $L_1$ as a linking group is a group derived from a substituted or unsubstituted aryl group having 6 to 30 ring carbon atoms, a group derived from a substituted or unsubstituted heterocyclic group having 5 to 30 ring atoms, or a group in which two group selected from the group consisting of a group derived from a substituted or unsubstituted aryl group having 6 to 30 ring carbon atoms and a group derived from a substituted or unsubstituted heterocyclic group having 5 to 30 ring atoms are bonded, when k is 1 and m is 4, four $R_2$ are respectively bonded to carbon atoms at any ones of positions of a, b, c, d and e shown in the formula (300), and one $L_1$ is bonded to a carbon atom at the position of a, b, c, d or e which is not bonded to $R_2$, when k is 2 and m is 3, three $R_2$ are respectively bonded to carbon atoms at any ones of positions of a, b, c, d and e shown in the formula (300), and two $L_1$ are respectively bonded to carbon atoms at any ones of positions of a, b, c, d and e which are not bonded to $R_2$, when k is 3 and m is 2, two $R_2$ are respectively bonded to carbon atoms at any ones of positions of a, b, c, d and e shown in the formula (300), and three $L_1$ are respectively bonded to carbon atoms at any ones of positions of a, b, c, d and e which are not bonded to $R_2$, $R_2$, $R_{31}$, $R_{32}$, $R_{34}$ and $R_{35}$ are each independently a hydrogen atom or a substituent, a plurality of $R_2$ are mutually the same or different when m is 2 or more, $R_{41}$, $R_{42}$, $R_{43}$ and $R_{45}$ to $R_{48}$ are each independently a hydrogen atom or a substituent, or at least one pair of a pair of $R_{41}$ and $R_{42}$, a pair of $R_{42}$ and $R_{43}$, a pair of $R_{45}$ and $R_{46}$, a pair of $R_{46}$ and $R_{47}$, or a pair of $R_{47}$ and $R_{48}$ are mutually bonded to form a ring, $R_{11}$ to $R_{18}$, $R_2$, $R_{31}$, $R_{32}$, $R_{34}$, $R_{35}$, $R_{41}$ to $R_{43}$, and $R_{45}$ to $R_{48}$ as the substituent are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms; and According to a further aspect of the invention, a compound represented by one of formulae (501) to (514) is provided.

[Formula 6]

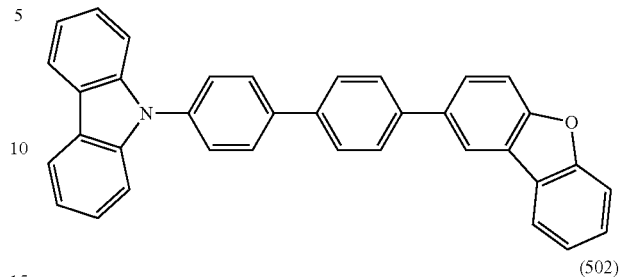

(501)

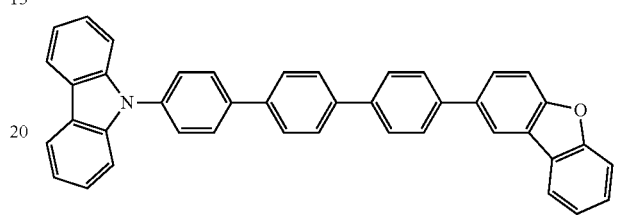

(502)

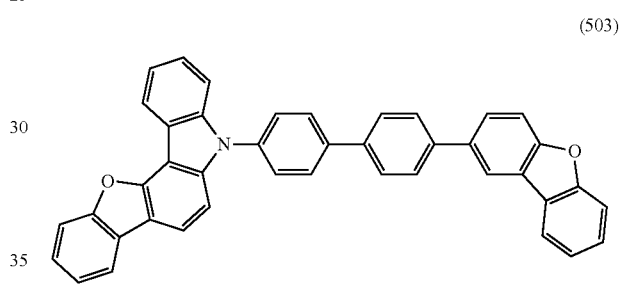

(503)

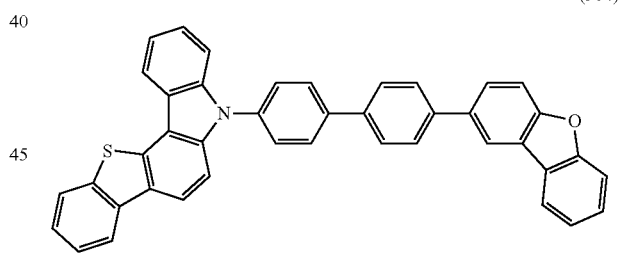

(504)

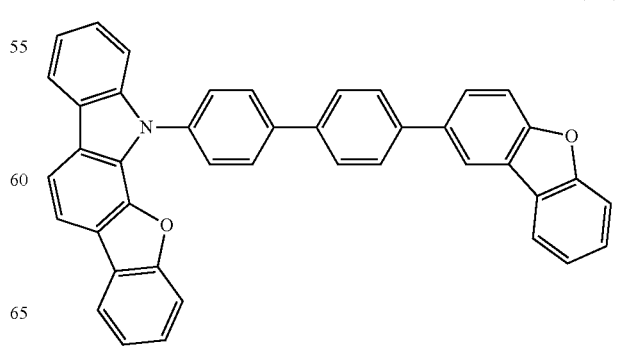

(505)

(506)
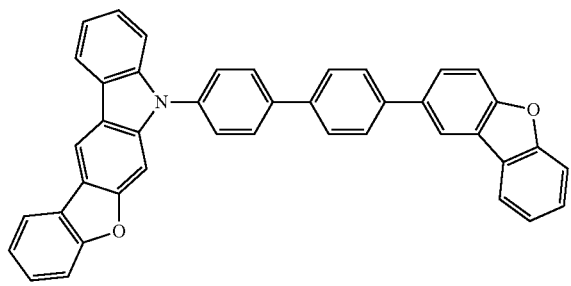

[Formula 7]

(507)
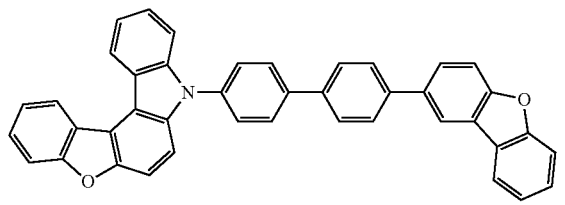

(508)
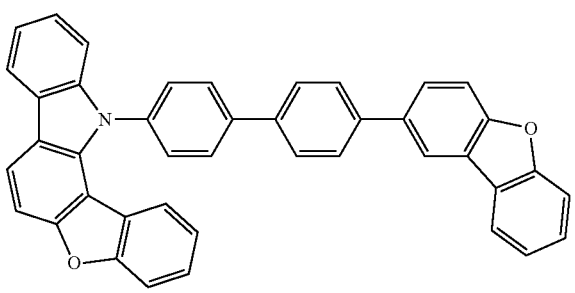

(509)
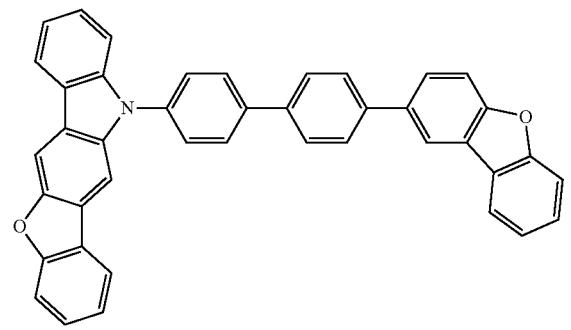

(510)
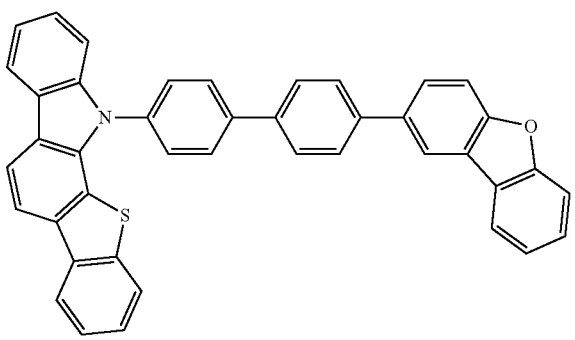

(511)
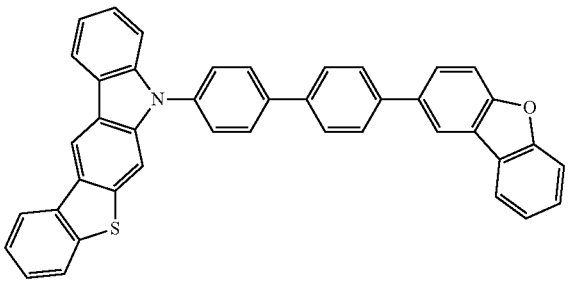

(512)
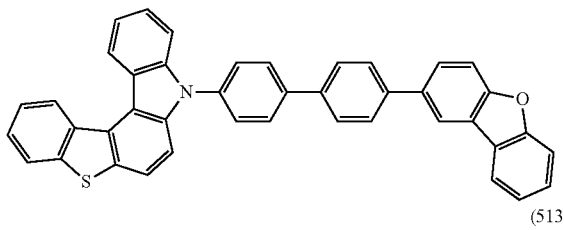

(513)
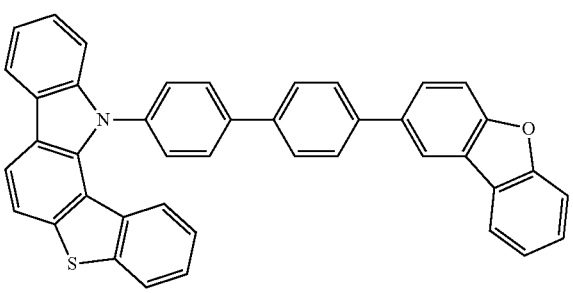

(514)
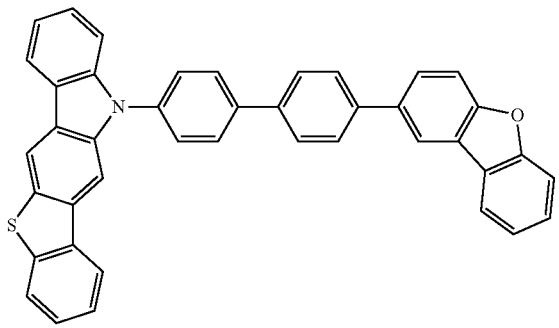

According to a still further aspect of the invention, an organic-electroluminescence-device material containing the compound according to the aforementioned aspect of the invention is provided.

According to the aforementioned aspects of the invention, a high-performance organic EL device, for instance, an organic EL device configured to emit light with having a long lifetime, and an electronic device including the organic EL device can be provided.

According to the aforementioned aspects of the invention, a compound capable of achieving a high-performance organic EL device, for instance, an organic EL device configured to emit light with a long lifetime, and an electronic device including the organic EL device; and an organic-EL-device material containing the compound can be provided.

BRIEF DESCRIPTION OF DRAWING(S)

FIG. 1 schematically shows an example of an organic electroluminescence device according to a first exemplary embodiment of the invention.

Figure 2:
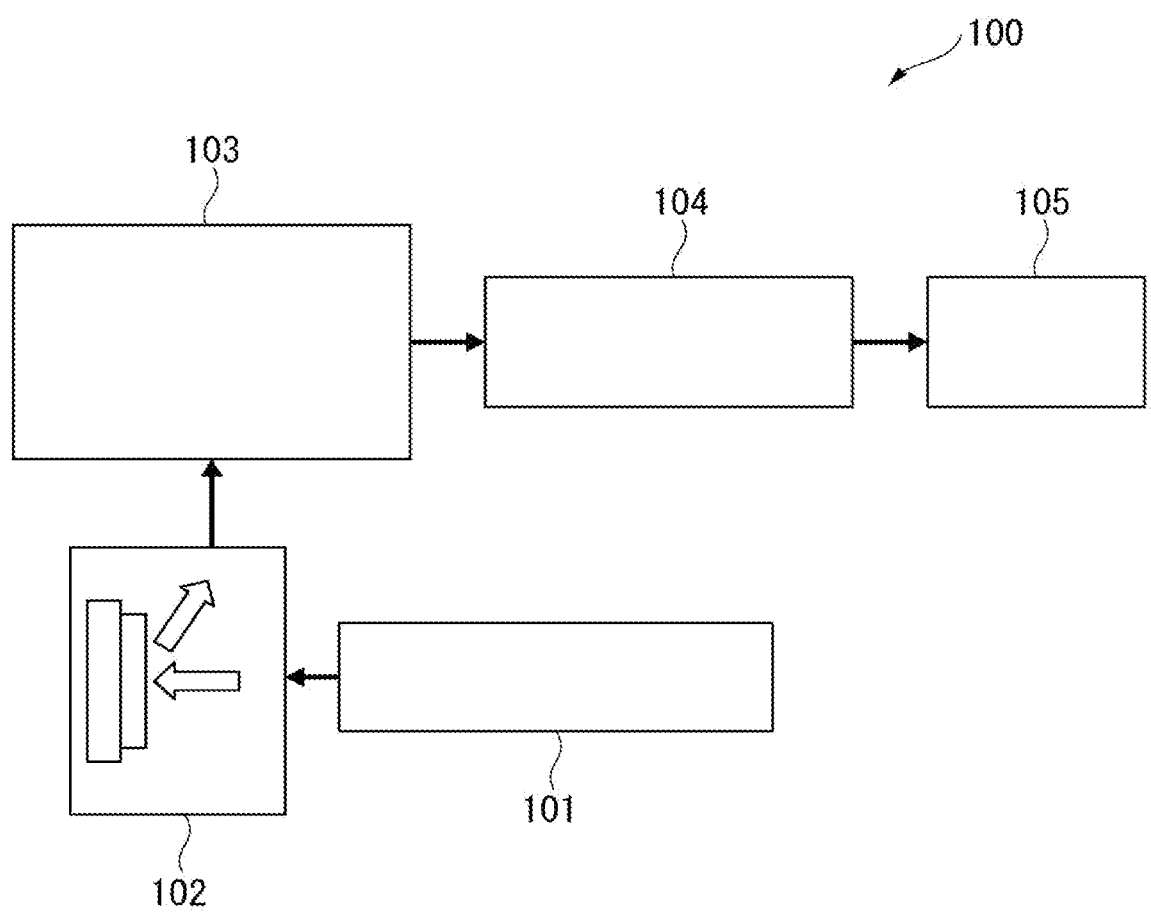

FIG. 2 schematically shows a device of measuring transient PL.

Figure 3:
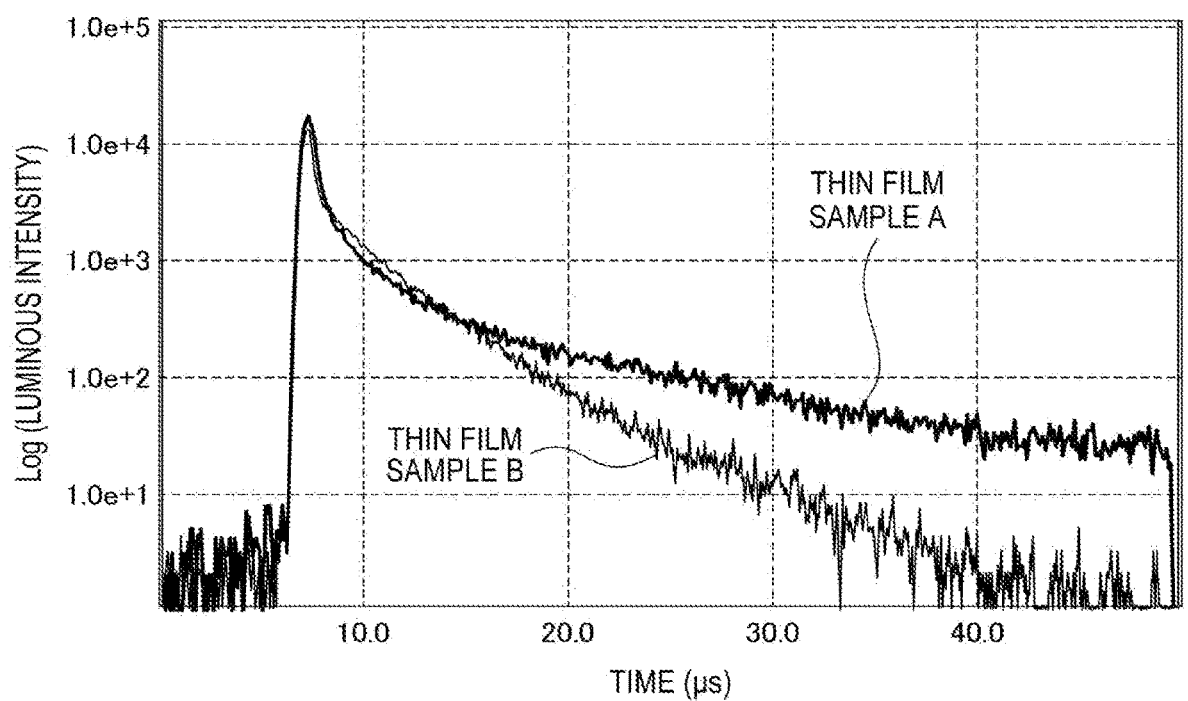

FIG. 3 shows an example of a decay curve of the transient PL.

Figure 4:
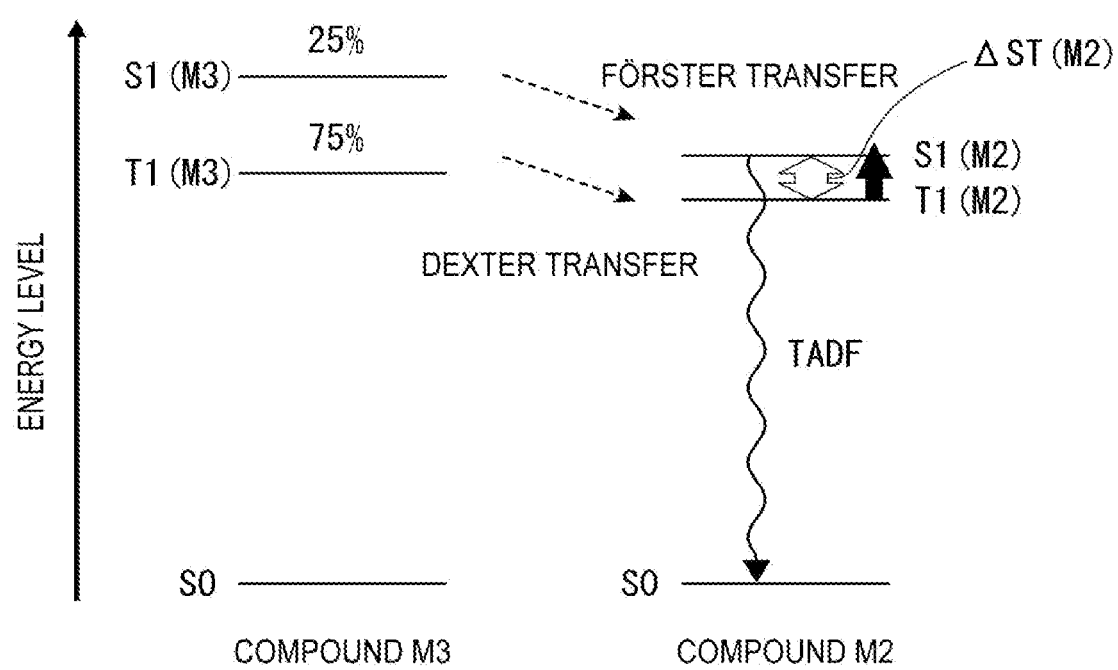

FIG. 4 schematically shows a relationship in energy level and energy transfer between a compound M3 and a compound M2 in an emitting layer of an exemplary organic electroluminescence device according to the first exemplary embodiment of the invention.

Figure 5:
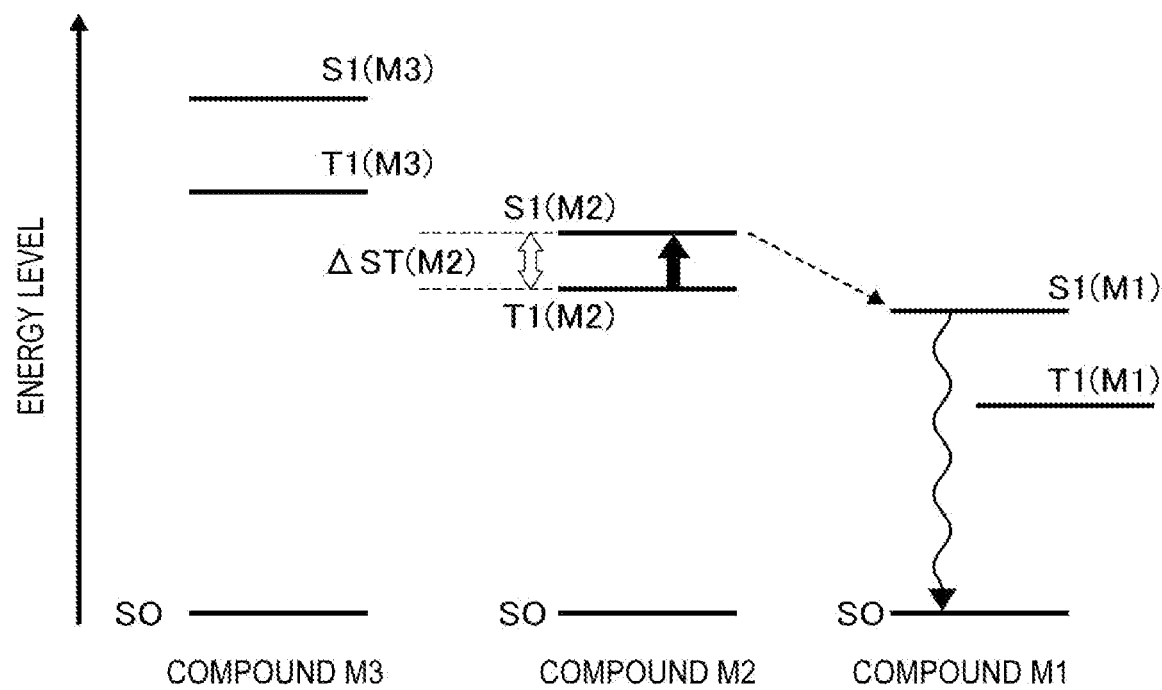

FIG. 5 schematically shows a relationship in energy level and energy transfer between a compound M3, a compound M2, and a compound M1 in an emitting layer of an exemplary organic electroluminescence device according to a second exemplary embodiment of the invention.

DESCRIPTION OF EMBODIMENT(S)

First Exemplary Embodiment

An arrangement of an organic EL device according to a first exemplary embodiment of the invention will be described below.

The organic EL device includes an anode, a cathode, and at least one organic layer between the anode and the cathode. This organic layer includes at least one layer formed of an organic compound. Alternatively, the organic layer includes a plurality of layers formed of an organic compound(s). The organic layer may further include an inorganic compound. In the organic EL device of the exemplary embodiment, at least one of the organic layer(s) is the emitting layer. Accordingly, the organic layer may consist of a single emitting layer or, alternatively, may further include at least one layer usable in organic EL devices. Examples of the layer usable in the organic EL device, which are not particularly limited, include at least one layer selected from the group consisting of a hole injecting layer, hole transporting layer, electron injecting layer, electron transporting layer, and blocking layer.

The organic EL device of the exemplary embodiment includes an emitting layer between the anode and the cathode.

FIG. 1 schematically shows an example of an organic EL device according to the first exemplary embodiment.

An organic EL device 1 includes a light-transmissive substrate 2, an anode 3, a cathode 4, and an organic layer 10 provided between the anode 3 and the cathode 4. The organic layer 10 includes a hole injecting layer 6, a hole transporting layer 7, an emitting layer 5, an electron transporting layer 8, and an electron injecting layer 9, which are sequentially laminated on the anode 3.

The emitting layer 5 may contain a metal complex.

It is preferable that the emitting layer 5 does not contain a phosphorescent material (dopant material).

It is preferable that the emitting layer 5 does not contain a heavy-metal complex and a phosphorescent rare-earth metal complex. Examples of the heavy-metal complex herein include iridium complex, osmium complex, and platinum complex.

It is also preferable that the emitting layer 5 does not contain a metal complex.

In the organic EL device 1 of the exemplary embodiment, the emitting layer 5 includes a delayed fluorescent compound M2 and a compound M3 represented by the formula (100).

In this arrangement, the compound M2 is preferably a dopant material (also referred to as a guest material, emitter or luminescent material), and the compound M3 is preferably a host material (also referred to as a matrix material).

The compound M3 may be a delayed fluorescent compound or a compound exhibiting no delayed fluorescence.

The inventors have found that a high-performance organic EL device is achievable by using the compound M3 represented by the formula (100) in addition to the delayed fluorescent compound M2.

The compound M3 has a structure such that an electron transporting moiety in a form of a dibenzofuran ring or a dibenzothiophene ring is substituted by a carbon atom at a position 4 or a carbon atom at a position 4' of a [1,1'-biphenyl]-diyl group. Accordingly, a conjugation length of the compound M3 of the exemplary embodiment extends longer as the entire electron transporting moiety than that of a compound having a structure such that a dibenzofuran ring or a dibenzothiophene ring is substituted, for instance, by a carbon atom at a position 3 or a carbon atom at a position 3' of a [1,1'-biphenyl]-diyl group.

In the exemplary embodiment, it is considered that by containing the compound M3 in which a conjugation length of the electron transporting moiety extends long in the emitting layer, electrons can be transported into an inside of the emitting layer to expand a recombination region of the electrons and holes. As a result, it is considered that burden on the emitting layer can be reduced. In general, in a delayed fluorescent compound, a moiety having a large absolute value of LUMO (lowest unoccupied molecular orbital) is often introduced into a molecule in order to reduce $\Delta ST$. However, if the emitting layer contains a delayed fluorescent compound into which the moiety is introduced, electron transportability of the emitting layer may be hindered.

In the exemplary embodiment, it is considered that since the compound M3 in which a conjugation length of the electron transporting moiety extends long as well as the delayed fluorescent compound M2 are contained in the emitting layer, electron transportability of the emitting layer is prevented from being hindered, resulting in improving a reduction degree of the burden on the emitting layer.

Moreover, it is considered that in the compound M3 in which the conjugation length of the electron transporting moiety extends long, burden in electron transportation of the compound per se is also reducible.

Further, the compound M3 has a structure such that an appropriate amount of holes can be injected into the emitting layer, since a carbazole ring, which is a hole injecting moiety, is bonded to a partial structure represented by the formula (X) through a single bond or a linking group.

Accordingly, according to the exemplary embodiment, a high-performance organic EL device is achievable.

"High performance" in the exemplary embodiment means at least one of light emission with a long life, an improvement in a luminous efficiency, a decrease in a drive voltage, or an improvement in a luminance.

An arrangement of an organic EL device according to the first exemplary embodiment will be described below. Codes will be omitted in the description below.

Emitting Layer
Compound M3

The emitting layer of the exemplary embodiment includes the compound M3 represented by the formula (100) below.

The compound M3 of the exemplary embodiment may be a thermally activated delayed fluorescent compound or a compound exhibiting no thermally activated delayed fluorescence. However, the compound M3 is preferably a compound exhibiting no thermally activated delayed fluorescence.

[Formula 8]

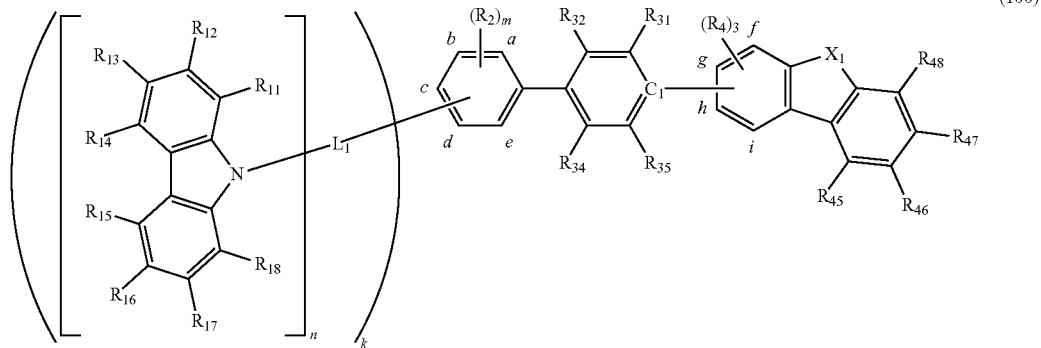

(100)

In the formula (100): $X_1$ is an oxygen atom or a sulfur atom, $C_1$ is a carbon atom, n is 1, 2, or 3, k is 1, 2, or 3, m is 2, 3, or 4, k+m=5, $R_{11}$ to $R_{18}$ are each independently a hydrogen atom or a substituent, or at least one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ are mutually bonded to form a ring, when at least one of n or k is 2 or more, a plurality of $R_{11}$ are mutually the same or different, a plurality of $R_{12}$ are mutually the same or different, a plurality of $R_{13}$ are mutually the same or different, a plurality of $R_{14}$ are mutually the same or different, a plurality of $R_{15}$ are mutually the same or different, a plurality of $R_{16}$ are mutually the same or different, a plurality of $R_{17}$ are mutually the same or different, and a plurality of $R_{18}$ are mutually the same or different, $L_1$ is a single bond or a linking group, when $L_1$ is a single bond, n is 1, when k is 2 or more, a plurality of $L_1$ are mutually the same or different, $L_1$ as a linking group is a group derived from a substituted or unsubstituted aryl group having 6 to 30 ring carbon atoms, a group derived from a substituted or unsubstituted heterocyclic group having 5 to 30 ring atoms, or a group in which two group selected from the group consisting of a group derived from a substituted or unsubstituted aryl group having 6 to 30 ring carbon atoms and a group derived from a substituted or unsubstituted heterocyclic group having 5 to 30 ring atoms are bonded, when k is 1 and m is 4, four $R_2$ are respectively bonded to carbon atoms at any ones of positions of a, b, c, d and e shown in the formula (100), and one $L_1$ is bonded to a carbon atom at the position of a, b, c, d or e which is not bonded to $R_2$, when k is 2 and m is 3, three $R_2$ are respectively bonded to carbon atoms at any ones of positions of a, b, c, d and e shown in the formula (100), and two $L_1$ are respectively bonded to carbon atoms at any ones of positions of a, b, c, d and e which are not bonded to $R_2$, when k is 3 and m is 2, two $R_2$ are respectively bonded to carbon atoms at any ones of positions of a, b, c, d and e shown in the formula (100), and three $L_1$ are respectively bonded to carbon atoms at any ones of positions of a, b, c, d and e which are not bonded to $R_2$, $R_2$, $R_{31}$, $R_{32}$, $R_{34}$ and $R_{35}$ are each independently a hydrogen atom or a substituent, a plurality of $R_2$ are mutually the same or different when m is 2 or more, $R_4$ and $R_{45}$ to $R_{48}$ are each independently a hydrogen atom or a substituent, or at least one pair of a pair of $R_{45}$ and $R_{46}$, a pair of $R_{46}$ and $R_{47}$, or a pair of $R_{47}$ and $R_{48}$ is mutually bonded to form a ring, or at least one pair of pairs including at least two of a plurality of $R_4$ is mutually bonded to form a ring, three $R_4$ are mutually the same or different, three $R_4$ are respectively bonded to carbon atoms at any ones of positions of f, g, h and i shown in the formula (100), and $C_1$ is bonded to a carbon atom at any position of f, g, h or i which is not bonded to $R_4$, $R_{11}$ to $R_{18}$, $R_2$, $R_{31}$, $R_{32}$, $R_{34}$, $R_{35}$, $R_4$ and $R_{45}$ to $R_{48}$ as the substituent are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms.

In the formula (100), detailed bonding patterns of $R_2$ and $L_1$ to carbon atoms at positions of a, b, c, d, and e shown in the formula (100) are as follows.

When n is 1, $L_1$ is a divalent linking group, k is 1 and m is 4, four $R_2$ are respectively bonded to carbon atoms at any ones of positions of a, b, c, d end e shown in the formula (100), and one $L_1$ is bonded to a carbon atom at the position of a, b, c, d or e which is not bonded to $R_2$. However, a plurality of $R_2$ are not bonded to a carbon atom at the same position.

When n is 1, $L_1$ is a divalent linking group, k is 2 and m is 3, three $R_2$ are respectively bonded to carbon atoms at any ones of positions of a, b, c, d and e shown in the formula (100), and two $L_1$ are respectively bonded to carbon atoms at any ones of positions of a, b, c, d and e which are not bonded to $R_2$. However, a plurality of $R_2$ are not bonded to a carbon atom at the same position.

When n is 1, $L_1$ is a divalent linking group, k is 3 and m is 2, two $R_2$ are respectively bonded to carbon atoms at any ones of positions of a, b, c, d and a shown in the formula (100), and three $L_1$ are respectively bonded to carbon atoms at any ones of positions of a, b, c, d and e which are not bonded to $R_2$. However, a plurality of $R_2$ are not bonded to a carbon atom at the same position.

A formula (B1) represents an exemplary bonding pattern that in a case where n is 1, $L_1$ is a divalent (inking group, k is 1 and m is 4, four $R_2$ are respectively bonded to carbon atoms at positions of a, b, d and a shown in the formula (100), and one $L_1$ is bonded to a carbon atom at the position of c shown in the formula (100).

[Formula 9]

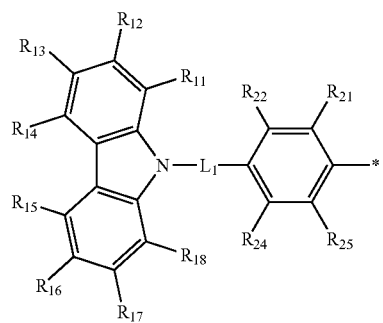

(B1)

In the formula (B1), $R_{11}$ to $R_{18}$ respectively represent the same as $R_{11}$ to $R_{18}$ in the formula (100), and $R_{21}$, $R_{22}$, $R_{24}$, and $R_{25}$ each independently represent the same as $R_2$ in the formula (100). In the formula (B1), * represents a bonding position to a carbon atom between a carbon atom of a benzene ring bonded to $R_{32}$ and a carbon atom of the benzene ring bonded to $R_{34}$ in the formula (100).

When n is 2, $L_1$ is a trivalent linking group, k is 1 and m is 4, four $R_2$ are respectively bonded to carbon atoms at any ones of positions of a, b, c, d and e shown in the formula (100), and one $L_1$ is bonded to a carbon atom at the position of a, b, c, d or e which is not bonded to $R_2$. However, a plurality of $R_2$ are not bonded to a carbon atom at the same position.

When n is 2, $L_1$ is a trivalent linking group, k is 2 and m is 3, three $R_2$ are respectively bonded to carbon atoms at any ones of positions of a, b, c, d and e shown in the formula (100), and two $L_1$ are respectively bonded to carbon atoms at any ones of positions of a, b, c, d and e which are not bonded to $R_2$. However, a plurality of $R_2$ are not bonded to a carbon atom at the same position.

When n is 2, $L_1$ is a trivalent linking group, k is 3 and m is 2, two $R_2$ are respectively bonded to carbon atoms at any ones of positions of a, b, c, d and e shown in the formula (100), and three $L_1$ are respectively bonded to carbon atoms at any ones of positions of a, b, c, d and e which are not bonded to $R_2$. However, a plurality of $R_2$ are not bonded to a carbon atom at the same position.

A formula (B2) represents an exemplary bonding pattern that in a case where n is 2, $L_1$ is a trivalent linking group, k is 1 and m is 4, four $R_2$ are respectively bonded to carbon atoms at positions of a, b, d and e shown in the formula (100), and one $L_1$ is bonded to a carbon atom at the position of c shown in the formula (100).

[Formula 10]

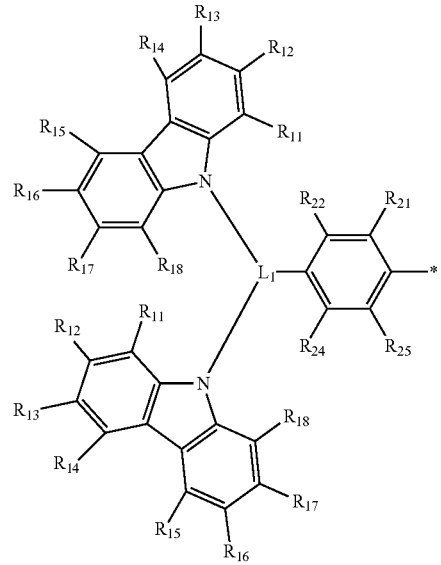

(B2)

In the formula (B2), $R_{11}$ to $R_{18}$ respectively represent the same as $R_{11}$ to $R_{18}$ in the formula (100); and $R_{21}$, $R_{22}$, $R_{24}$, and $R_{25}$ each independently represent the same as $R_2$ in the formula (100), in the formula. (B2), * represents a bonding position to a carbon atom between a carbon atom of a benzene ring bonded to $R_{32}$ and a carbon atom of the benzene ring bonded to $R_{34}$ in the formula (100).

In the formula (B2), two $R_{11}$ are mutually the same or different, two $R_{12}$ are mutually the same or different, two $R_{13}$ are mutually the same or different, two $R_{14}$ are mutually the same or different, two $R_{18}$ are mutually the same or different, two $R_{16}$ are mutually the same dr different, two $R_{17}$ are mutually the same or different, and two $R_{16}$ are mutually the same or different.

When n is 3, $L_1$ is a tetravalent linking group, k is 1 and m is 4, four $R_2$ are respectively bonded to carbon atoms at any ones of positions of a, b, c, d and e shown in me formula (100), and one $L_1$ is bonded to a carbon atom at the position of a, b, c, d or e which is not bonded to $R_2$. However, a plurality of $R_2$ are not bonded to a carbon atom at the same position.

When n is 3. $L_1$ is a tetravalent (inking group, k is 2 and m is 3, three $R_2$ are respectively bonded to carbon atoms at any ones of positions of a, b, c, d and e shown in the formula (100), and two $L_1$ are respectively bonded to carbon atoms at any ones of positions of a, b, c, d and e which are not bonded to $R_2$. However, a plurality of $R_2$ are not bonded to a carbon atom at the same position.

When n is 3, $L_1$ is a tetravalent linking group, k is 3 and m is 2, two $R_2$ are respectively bonded to carbon atoms at any ones of positions of a, b, c, d and e shown in the formula (100), and three $L_1$ are respectively bonded to carbon atoms at any ones of positions of a, b, c, d and e which are not bonded to $R_2$. However, a plurality of $R_2$ are not bonded to a carbon atom at the same position.

In the formula (100), detailed bonding patterns of $R_2$ and a nitrogen atom at a position 9 of a carbazole ring shown in the formula (100) to carbon atoms at positions of a, b, c, d, and e shown in the formula (100) are as follows.

When n is 1, $L_1$ is a single bond, k is 1 and m is 4, four $R_2$ are respectively bonded to carbon atoms at any ones of positions of a, b, c, d and e shown in the formula (100), and a nitrogen atom at a position 9 of a carbazole ring is bonded to a carbon atom at the position of a, b, c, d or e which is not bonded to $R_2$. However, a plurality of $R_2$ are not bonded to a carbon atom at the same position.

When n is 1, $L_1$ is a single bond, k is 2 and m is 3, three $R_2$ are respectively bonded to carbon atoms at any ones of positions of a, b, c, d and e shown in the formula (100), and nitrogen atoms at positions 9 of two carbazole rings shown in the formula (100) are respectively bonded to carbon atoms at any ones of positions of a, b, c, d and e which are not bonded to $R_2$. However, a plurality of $R_2$ are not bonded to a carbon atom at the same position.

When n is 1, $L_1$ is a single bond, k is 3 and m is 2, two $R_2$ are respectively bonded to carbon atoms at any ones of positions of a, b, c, d and e shown in the formula (100), and nitrogen atoms at positions 9 of three carbazole rings in the formula (100) are respectively bonded to carbon atoms at any ones of positions of a, b, c, d and e which are not bonded to $R_2$. However, a plurality of $R_2$ are not bonded to a carbon atom at the same position.

A formula (B3) represents an exemplary bonding pattern that in a case where n is 1, $L_1$ is a single bond, k is 1 and m is 4, four $R_2$ are respectively bonded to carbon atoms at positions of a, b, d and e shown in the formula (100), and a nitrogen atom at a position 9 of one carbazole ring shown in the formula (100) is bonded to a carbon atom at the position of c shown in the formula (100).

[Formula 11]

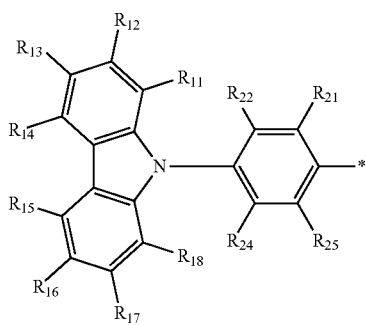

(B3)

In the formula (B3), $R_1$ to $R_{16}$, $R_{21}$, $R_{22}$, $R_{24}$, and $R_{25}$ respectively represent the same as $R_{11}$ to $R_{18}$, $R_{21}$, $R_{22}$, $R_{24}$, and $R_{25}$ in the formula (B1), in the formula (B3). * represents a bonding position to a carbon atom between a carbon atom of a benzene ring bonded to $R_{32}$ and a carbon atom of the benzene ring bonded to $R_{34}$ in the formula (100).

A formula (B4) represents an exemplary bonding pattern that in a case where n is 1. $L_1$ is a single bond, k is 2 and m is 3, three $R_2$ are respectively bonded to carbon atoms at positions of a, c and e shown in the formula (100), and nitrogen atoms at a position 9 of two carbazole rings shown in the formula (100) are respectively bonded to carbon atoms at the positions of b and d shown in the formula (100)

[Formula 12]

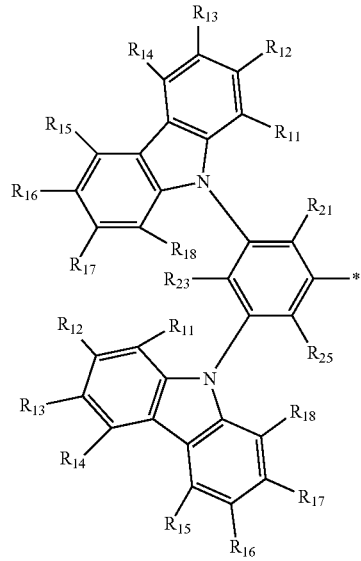

(B4)

In the formula (B4), $R_{11}$ to $R_{18}$ respectively represent the same as $R_{11}$ to $R_{18}$ in the formula (B2), and $R_{21}$, $R_{23}$, and $R_{25}$ each independently represent the same as $R_{21}$, $R_{22}$, $R_{24}$, and $R_{25}$ in the formula (B2). In the formula (B4), * represents a bonding position to a carbon atom between a carbon atom of a benzene ring bonded to $R_{32}$ and a carbon atom of the benzene ring bonded to $R_{34}$ in the formula (100).

Preferable arrangements of the compound M3 according to the first exemplary embodiment will be described below.

In the following description, when the compound M3 of the exemplary embodiment is represented by formulae, in each of the formulae, positions corresponding to a, b, c, d, e, f, g, h, and i shown in the formula (100) are respectively defined as a, b, c, d, e, f, g, h, and i. In each of the formulae, the description of a, b, c, d, e, f, g, h, and i is sometimes omitted.

In the compound M3 of the exemplary embodiment, it is preferable that at least one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ is bonded to each other to form a ring.

In the compound M3 of the exemplary embodiment, it is preferable that at least one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ is bonded to each other to form a ring and that a pair of $R_{45}$ and $R_{46}$, a pair of $R_{46}$ and $R_{47}$, a pair of $R_{47}$ and $R_{48}$ and a pair of two or more of a plurality of $R_4$ are not mutually bonded.

In the compound M3 of the exemplary embodiment, it is preferable that one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, and a pair of $R_{17}$ and $R_{18}$ is bonded to each other to form a ring.

In the compound M3 of the exemplary embodiment, it is preferable that one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, and a pair of $R_{17}$ and $R_{18}$ is bonded to each other to form a ring and that a pair of $R_{45}$ and $R_{46}$, a pair of $R_{46}$ and $R_{47}$, a pair of $R_{47}$ and $R_{48}$ and a pair of two or more of a plurality of $R_4$ are not mutually bonded.

In the compound M3 of the exemplary embodiment, when at least one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ is bonded to each other to form a ring, the ring preferably has a cyclic structure represented by a formula (400) below.

[Formula 13]

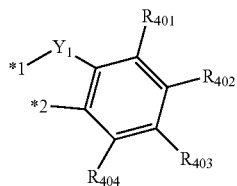

(400)

In the formula (400), $Y_1$ is an oxygen atom or a sulfur atom, $R_{401}$ to $R_{404}$ each independently represent the same as $R_{11}$ to $R_{18}$ in the formula (100), however, at least one pair of a pair of $R_{401}$ and $R_{402}$, a pair of $R_{402}$ and $R_{403}$, or a pair of $R_{403}$ and $R_{404}$ is bonded to each other to form a ring or not bonded.

When at least two pairs of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ in the formula (100) are mutually bonded to form the cyclic structure represented by the formula (400), a plurality of $Y_1$ are mutually the same or different, a plurality of $R_{401}$ are mutually the same or different, a plurality of $R_{402}$ are mutually the same or different, a plurality of $R_{403}$ are mutually the same or different, and a plurality of $R_{404}$ are mutually the same or different.

When at least one of n or k is 2 or more in the formula (100), a plurality of $Y_1$ are mutually the same or different, a plurality of $R_{401}$ are mutually the same or different, a plurality of $R_{402}$ are mutually the same or different, a plurality of $R_{403}$ are mutually the same or different, and a plurality of $R_{404}$ are mutually the same or different.

*1 and *2 in the cyclic structure represented by the formula (400) represent carbon atoms of at least one pair of a pair of two carbon atoms bonded to $R_{11}$ and $R_{12}$, a pair of two carbon atoms bonded to $R_{12}$ and $R_{13}$, a pair of two carbon atoms bonded to $R_{13}$ and $R_{14}$, a pair of two carbon atoms bonded to $R_{15}$ and $R_{16}$, a pair of two carbon atoms bonded to $R_{16}$ and $R_{17}$, or a pair of two carbon atoms bonded to $R_{17}$ and $R_{18}$ in the formula (100).

In the formula (400), it is preferable that a pair of $R_{401}$ and $R_{402}$, a pair of $R_{402}$ and $R_{403}$, and a pair of $R_{403}$ and $R_{404}$ are not mutually bonded.

In the formula (400), $Y_1$ is preferably an oxygen atom.
In the formula (400), $Y_1$ is also preferably a sulfur atom.
In the compound M3 of the exemplary embodiment, for instance, when at least one pair of a pair of $R_{11}$ and $R_{12}$, a pair of $R_{12}$ and $R_{13}$, or a pair of $R_{13}$ and $R_{14}$ is bonded to each other to form the cyclic structure represented by the formula (400), a cyclic structure having $R_{11}$ to $R_{18}$ in the formula (100) is represented by one of formulae (400-1) to (400-6).

[Formula 14]

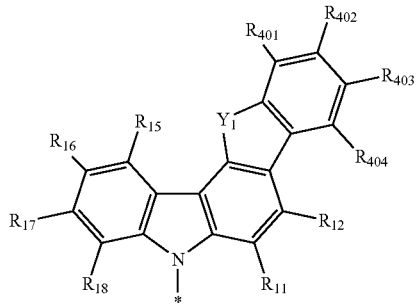

(400-1)

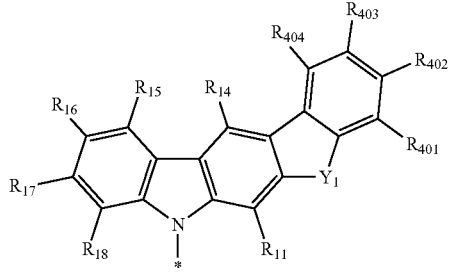

(400-2)

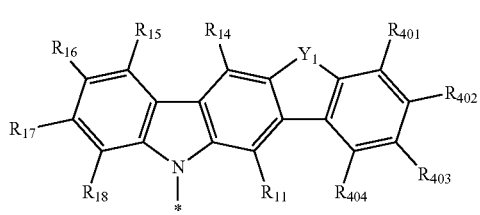

(400-3)

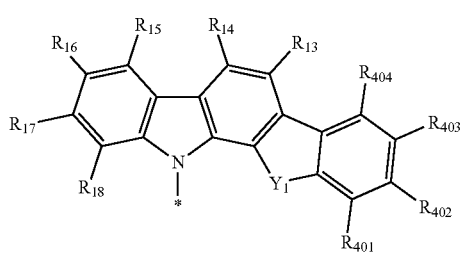

(400-4)

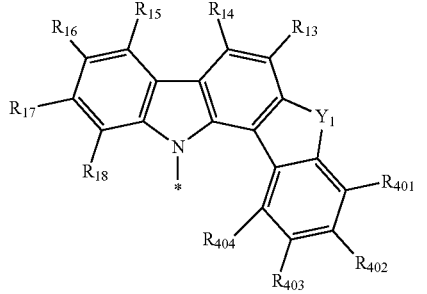

(400-5)

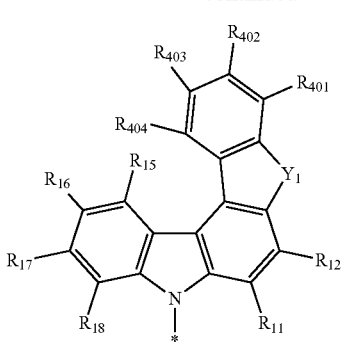

(400-6)

In the formulae (400-1) to (400-6), $Y_1$ and $R_{401}$ to $R_{404}$ respectively represent the same as $Y_1$ and $R_{401}$ to $R_{404}$ in the formula (400), and $R_{11}$ to $R_{18}$ each independently represent the same as $R_{11}$ to $R_{18}$ in the formula (100).

When $L_1$ is a linking group in the formula (100), * represents a bonding position to $L_1$.

When $L_1$ is a single bond, n is 1, k is 1, and m is 4 in the formula (100), * is bonded to a carbon atom at the position of a, b, c, d or e which is not bonded to four $R_2$.

When $L_1$ is a single bond, n is 1, k is 2, and m is 3 in the formula (100), * is bonded to a carbon atom at any one of the positions of a, b, c, d and e which are not bonded to three $R_2$.

When $L_1$ is a single bond, n is 1, k is 3, and m is 2 in the formula (100), * is bonded to a carbon atom at any one of the positions of a, b, c, d and e which are not bonded to two $R_2$.

In the formulae (400-1) to (400-6), it is preferable that a pair of $R_{11}$ and $R_{12}$, a pair of $R_{13}$ and $R_{14}$, a pair of $R_{15}$ and $R_{16}$, a pair of $R_{16}$ and $R_{17}$, a pair of $R_{17}$ and $R_{18}$, a pair of $R_{401}$ and $R_{402}$, a pair of $R_{402}$ and $R_{403}$, and a pair of $R_{403}$ and $R_{404}$ are not mutually bonded.

In the formulae (400-1) to (400-6), $Y_1$ is preferably an oxygen atom.

In the formulae (400-1) to (400-6), $Y_1$ is preferably a sulfur atom.

In the formula (100), for instance, when one pair of a pair of $R_{11}$ and $R_{12}$, a pair of $R_{12}$ and $R_{13}$, and a pair of $R_{13}$ and $R_{14}$ is bonded to each other to form the cyclic structure represented by the formula (400), the compound M3 of the exemplary embodiment is represented by one of formulae (401) to (406).

[Formula 15]

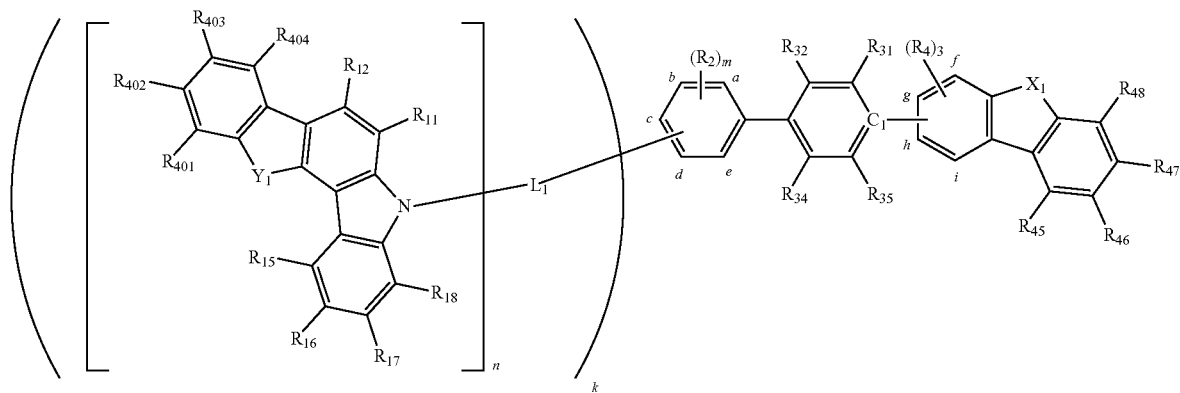

(401)

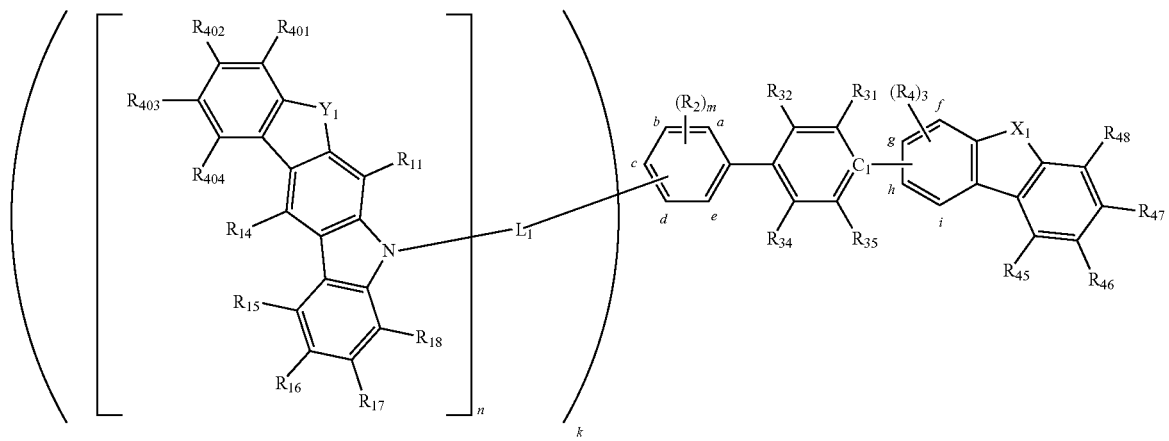

(402)

-continued
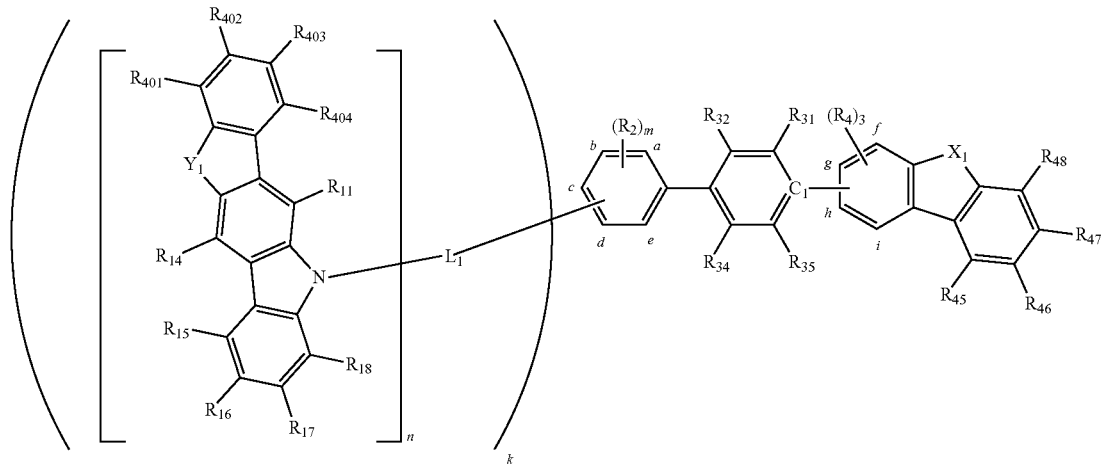
(403)
[Formula 16]
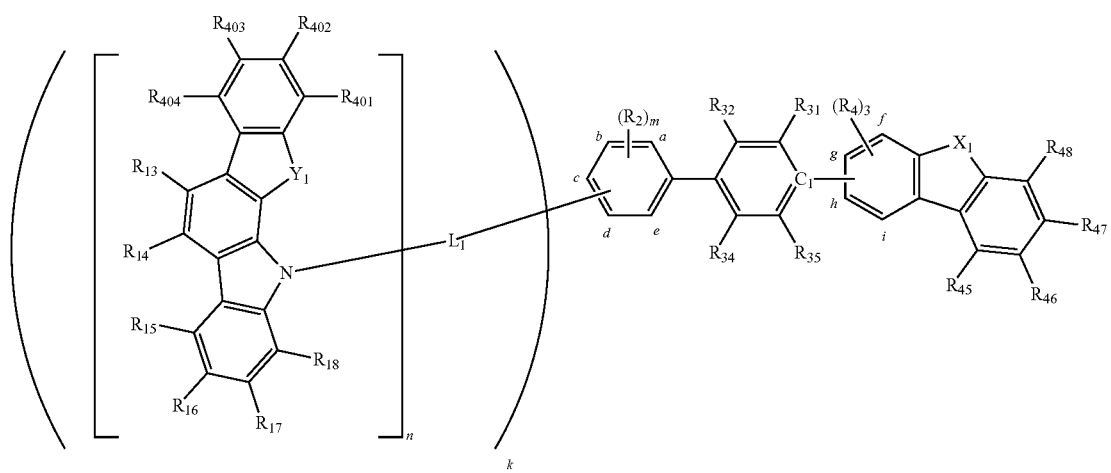
(404)
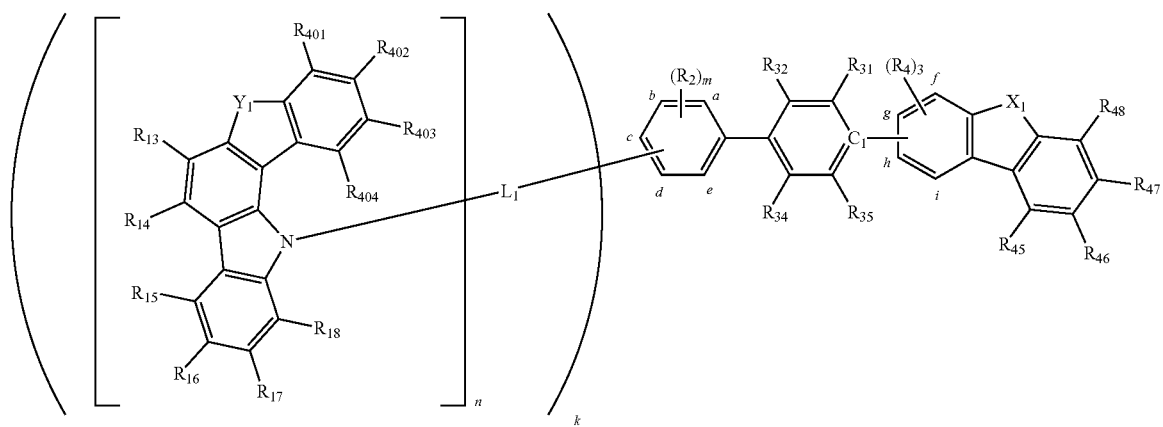
(405)

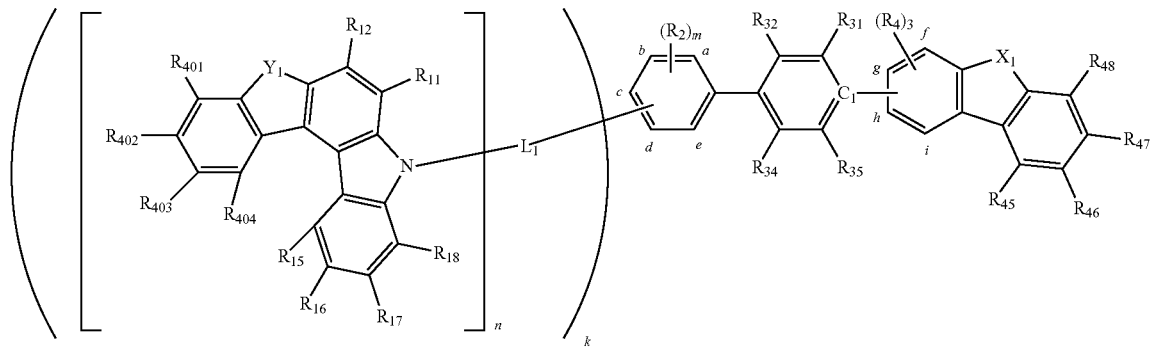

(406)

In the formulae (401) to (406), $X_1$, $R_4$, $R_{45}$ to $R_{48}$, $C_1$, $R_{31}$ to $R_{32}$, $R_{34}$ to $R_{35}$, $R_2$, $L_1$, $R_{11}$ to $R_{18}$, m, n, and k respectively represent the same as $X_1$, $R_4$, $R_{45}$ to $R_{48}$, $C_1$, $R_{31}$ to $R_{32}$, $R_{34}$ to $R_{35}$, $R_2$, $L_1$, $R_{11}$ to $R_{18}$, m, n, and k in the formula (100), $Y_1$ is an oxygen atom or a sulfur atom, $R_{401}$ to $R_{404}$ each independently represent the same as $R_{11}$ to $R_{18}$ in the formula (100), however, at least one pair of a pair of $R_{401}$ and $R_{402}$, a pair of $R_{402}$ and $R_{403}$, or a pair of $R_{403}$ and $R_{404}$ is bonded to each other to form a ring or not bonded.

In the formulae (401) to (406), it is preferable that a pair of $R_{11}$ and $R_{12}$, a pair of $R_{13}$ and $R_{14}$, a pair of $R_{401}$ and $R_{402}$, a pair of $R_{402}$ and $R_{403}$, and a pair of $R_{403}$ and $R_{404}$ are not mutually bonded.

The compound M3 of the exemplary embodiment is preferably represented by one of formulae (401A) to (406A) below.

[Formula 17]

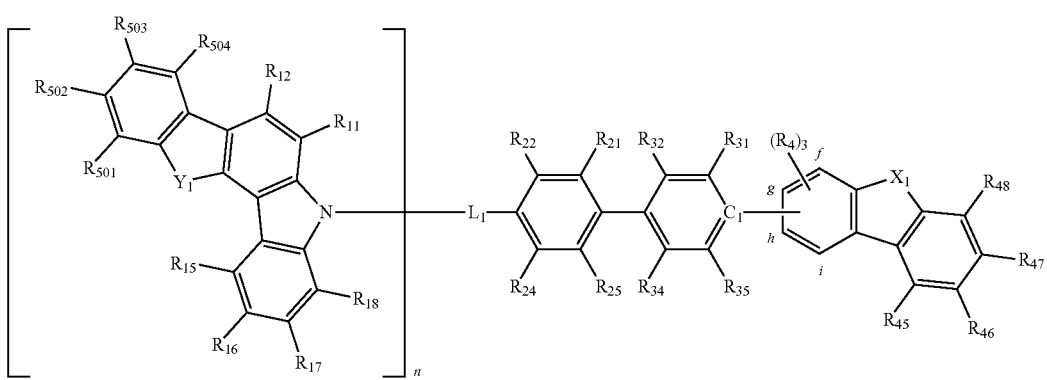

(401A)

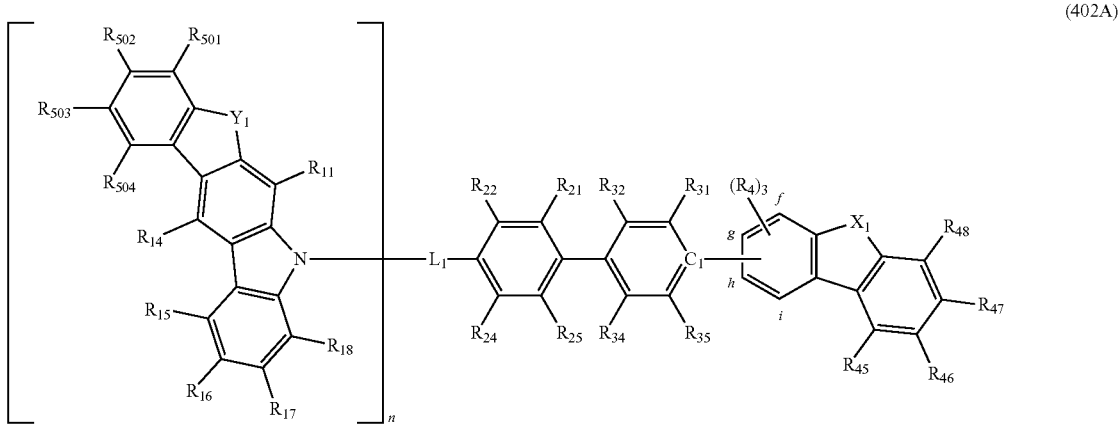

(402A)

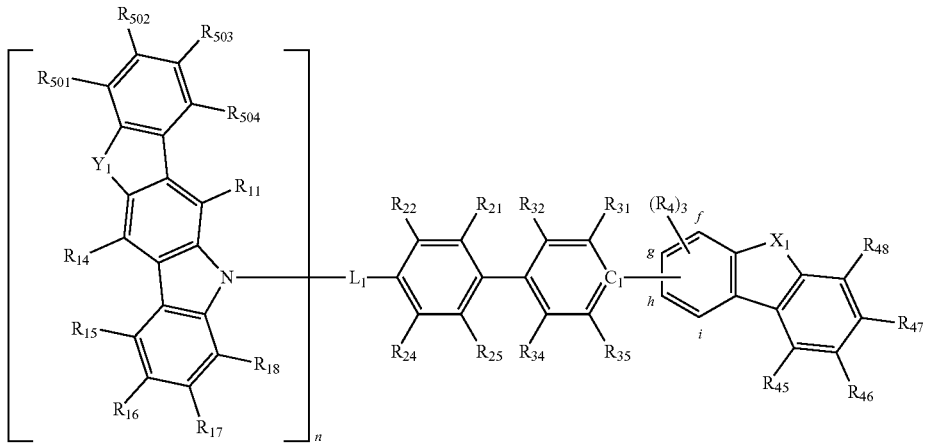
(403A)
[Formula 18]
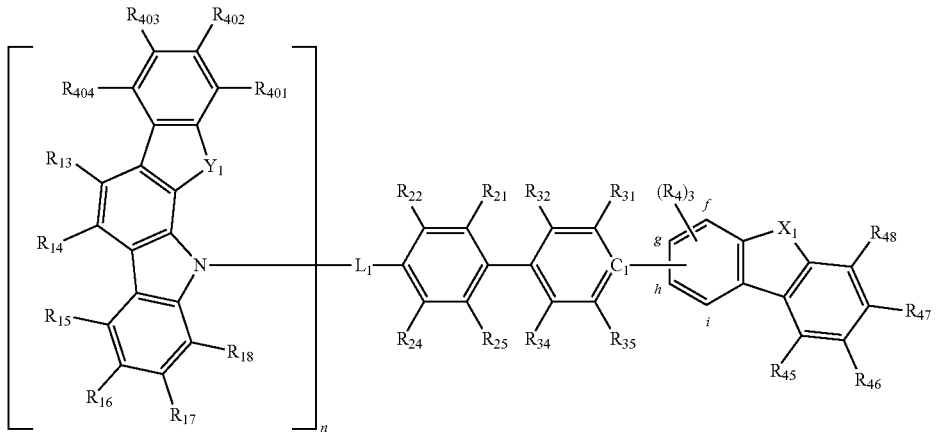
(404A)
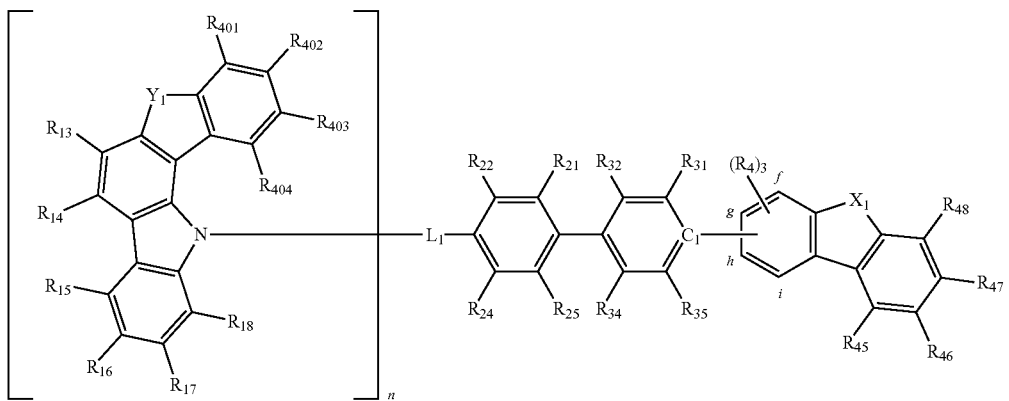
(405A)

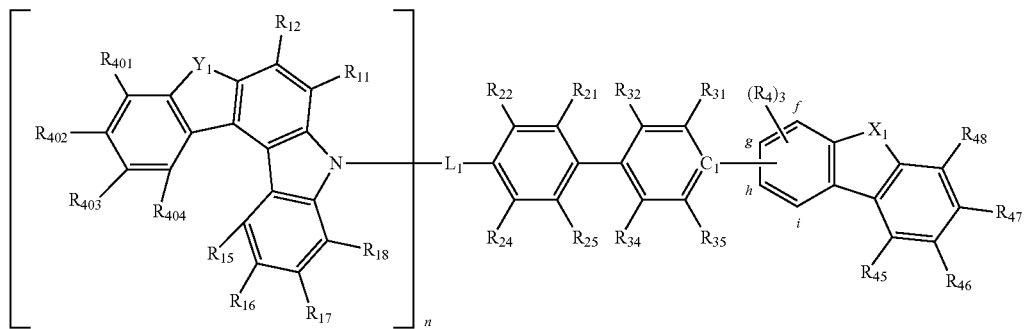
(406A)

In the formulae (401A) to (406A), $X_1$, $R_4$, $R_{45}$ to $R_{48}$, $C_1$, $R_{31}$ to $R_{32}$, $R_{34}$ to $R_{35}$, $L_1$, $R_{11}$ to $R_{18}$, and n respectively represent the same as $X_1$, $R_4$, $R_{45}$ to $R_{48}$, $C_1$, $R_{31}$ to $R_{32}$, $R_{34}$ to $R_{35}$, $L_1$, $R_{11}$ to $R_{18}$, and n in the formula (100), $R_{21}$ to $R_{22}$ and $R_{24}$ to $R_{25}$ each independently represent the same as $R_2$ in the formula (100), $Y_1$ is an oxygen atom or a sulfur atom, $R_{401}$ to $R_{404}$ each independently represent the same as $R_{11}$ to $R_{18}$ in the formula (100), however, at least one pair of a pair of $R_{401}$ and $R_{402}$, a pair of $R_{402}$ and $R_{403}$, or a pair of $R_{403}$ and $R_{404}$ is bonded to each other to form a ring or not bonded.

In the formulae (401A) to (406A), it is preferable that a pair of $R_{11}$ and $R_{12}$, a pair of $R_{13}$ and $R_{14}$, a pair of $R_{401}$ and $R_{402}$, a pair of $R_{402}$ and $R_{403}$, and a pair of $R_{403}$ and $R_{404}$ are not mutually bonded.

The compound M3 of the exemplary embodiment is preferably represented by one of formulae (401B) to (406B) below.

[Formula 19]

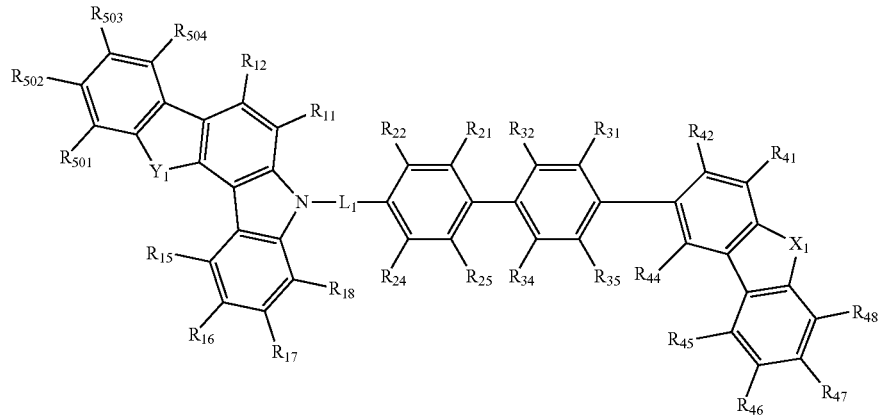
(401B)

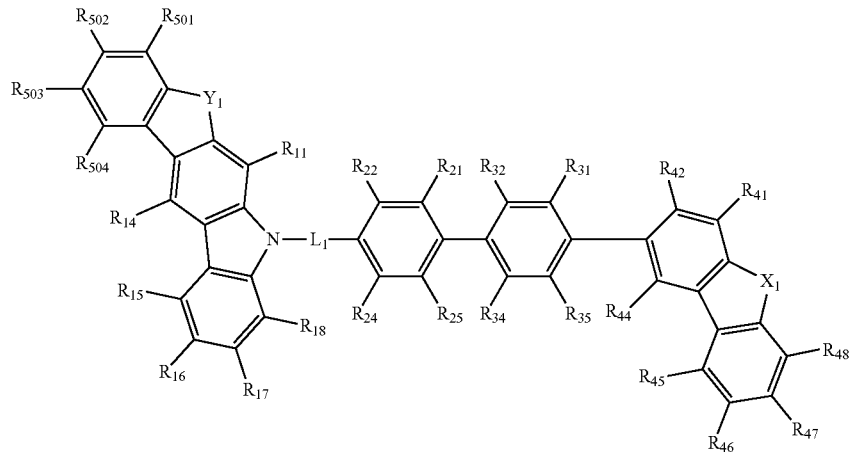
(402B)

-continued
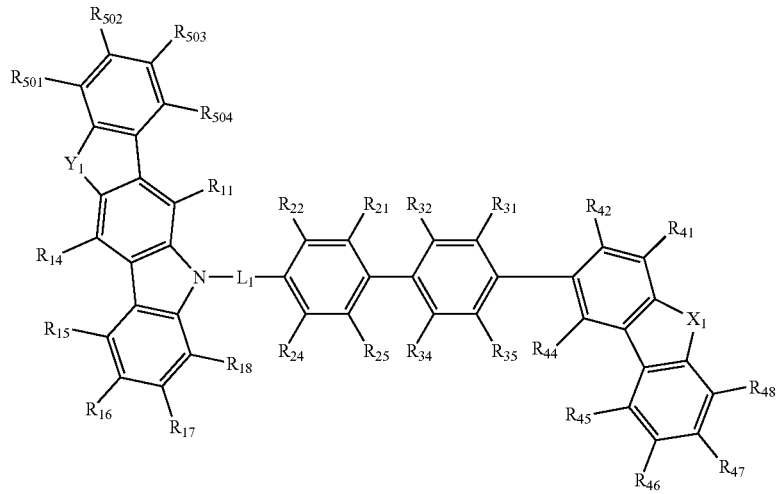
(403B)
[Formula 20]
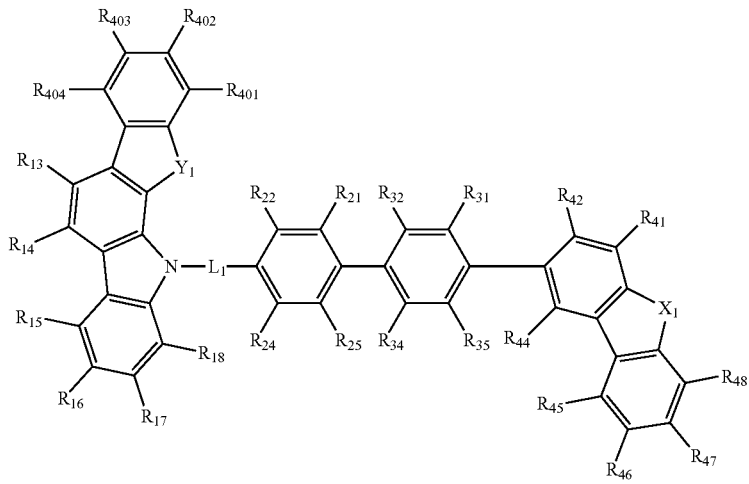
(404B)
(405B)

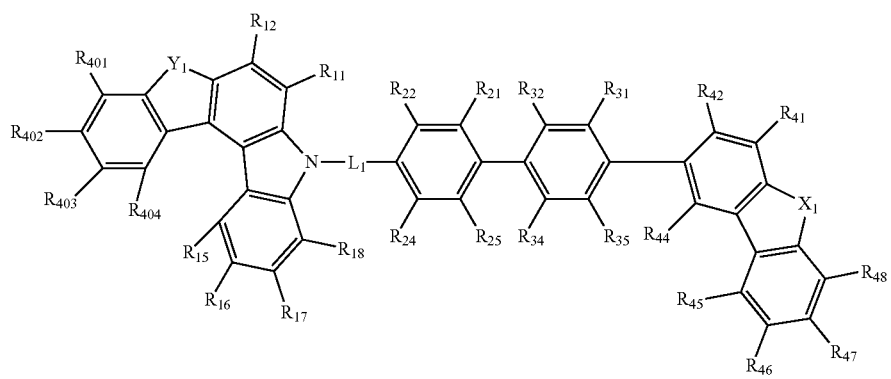

(406B)

In the formulae (401B) to (406B), $X_1$, $R_{45}$ to $R_{48}$, $R_{31}$ to $R_{32}$, $R_{34}$ to $R_{35}$, $L_1$, and $R_{11}$ to $R_{18}$ respectively represent the same as $X_1$, $R_{45}$ to $R_{48}$, $R_{31}$ to $R_{32}$, $R_{34}$ to $R_{35}$, $L_1$, and $R_{11}$ to $R_{18}$ in the formula (100), $R_{41}$, $R_{42}$ and $R_{44}$ each independently represent the same as $R_4$ in the formula (100), $R_{21}$ to $R_{22}$ and $R_{24}$ to $R_{25}$ each independently represent the same as $R_2$ in the formula (100), $Y_1$ is an oxygen atom or a sulfur atom, $R_{401}$ to $R_{404}$ each independently represent the same as $R_{11}$ to $R_{18}$ in the formula (100), however, at least one pair of a pair of $R_{401}$ and $R_{402}$, a pair of $R_{402}$ and $R_{403}$, or a pair of $R_{403}$ and $R_{404}$ is bonded to each other to form a ring or not bonded.

In the formulae (401B) to (406B), it is preferable that a pair of $R_{11}$ and $R_{12}$, a pair of $R_{13}$ and $R_{14}$, a pair of $R_{401}$ and $R_{402}$, a pair of $R_{402}$ and $R_{403}$, and a pair of $R_{403}$ and $R_{404}$ are not mutually bonded.

In the compound M3 of the exemplary embodiment, it is also preferable that a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, and a pair of $R_{17}$ and $R_{18}$, a pair of $R_{45}$ and $R_{46}$, a pair of $R_{46}$ and $R_{47}$, a pair of $R_{47}$ and $R_{48}$ and a pair of two or more or a plurality of $R_4$ are not bonded.

$R_2$, $R_{31}$, $R_{32}$, $R_{34}$, and $R_{35}$ in the compound M3 of the exemplary embodiment are preferably hydrogen atoms.

When the compound M3 of the exemplary embodiment is a compound represented by one of the formulae (401) to (406), (401A) to (406A) and (401B) to (406B), $R_2$, $R_{21}$ to $R_{22}$, $R_{24}$ to $R_{25}$, $R_{31}$ to $R_{32}$ and $R_{34}$ to $R_{35}$ are preferably hydrogen atoms.

In the compound M3 of the exemplary embodiment, it is preferable that $R_2$, $R_{31}$, $R_{32}$, $R_{34}$ and $R_{35}$ are hydrogen atoms, and $L_1$ is a single bond, a group derived from an unsubstituted aryl group having 6 to 30 ring carbon atoms, or a group derived from an unsubstituted heterocyclic group having 5 to 30 ring atoms.

When the compound M3 of the exemplary embodiment is a compound represented by one of the formulae (401) to (406), (401A) to (406A) and (401B) to (406B), it is preferable that $R_2$, $R_{21}$ to $R_{22}$, $R_{24}$ to $R_{25}$, $R_{31}$ to $R_{32}$ and $R_{34}$ to $R_{35}$ are hydrogen atoms, and $L_1$ is a single bond, a group derived from an unsubstituted aryl group having 6 to 30 ring carbon atoms, or a group derived from an unsubstituted heterocyclic group having 5 to 30 ring atoms.

Specifically, the compound M3 with this arrangement is represented by a formula (100X) below.

[Formula 21]

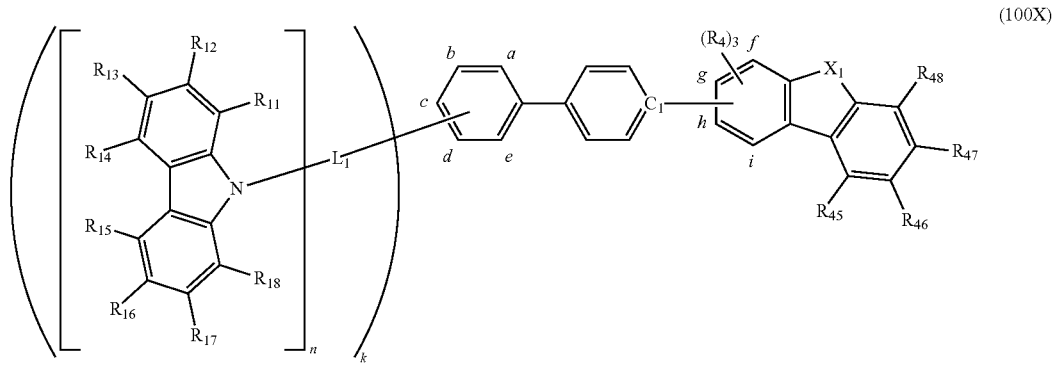

(100X)

In the formula (100X), $X_1$, $R_4$, $R_{45}$ to $R_{48}$, $C_1$, $R_{11}$ to $R_{19}$, n, and k represent the same as $X_1$, $R_4$, $R_{45}$ to $R_{46}$, $C_1$, $R_{11}$ to $R_{18}$, n, and k in the formula (100), and $L_1$ is a single bond, a group derived from an unsubstituted aryl group having 6 to 30 ring carbon atoms, or a group derived from an unsubstituted heterocyclic group having 5 to 30 ring atoms, however, when $L_1$ is a single bond, n is 1, when k is 2 or more, a plurality of $L_1$ are mutually the same or different.

In the formula (100X), it is also preferable that a cyclic structure having $R_{11}$ to $R_{18}$ is represented by one of the formulae (400-1) to (400-6).

In the compound M3 of the exemplary embodiment, n is preferably 1 or 2, more preferably 1.

In the compound M3 of the exemplary embodiment, k is preferably 1 or 2.

In the compound M3 of the exemplary embodiment, it is also more preferable that n is 1 or 2 and k is 1 or 2.

In the compound M3 of the exemplary embodiment, it is also more preferable that n is 1 and k is 1 or 2. In the compound M3 of the exemplary embodiment, it is also more preferable that n is 2 and k is 1 or 2.

Specifically, the compound M3 of the exemplary embodiment when n is 2 is represented by a formula (100Y) below. The compound M3 of the exemplary embodiment when n is 1 is represented by a formula (100Z) below.

In the formula (100Z), it is also preferable that a cyclic structure having $R_{11}$ to $R_{18}$ is represented by one of the formulae (400-1) to (400-6).

In the compound M3 of the exemplary embodiment, it is preferable that $R_{11}$ to $R_{18}$, $R_4$ and $R_{45}$ to $R_{48}$ are each independently a hydrogen atom, a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms.

In the compound M3 of the exemplary embodiment, it is more preferable that $R_{11}$ to $R_{18}$, $R_4$ and $R_{45}$ to $R_{48}$ are each independently a hydrogen atom, a substituted or unsubsti-

[Formula 22]

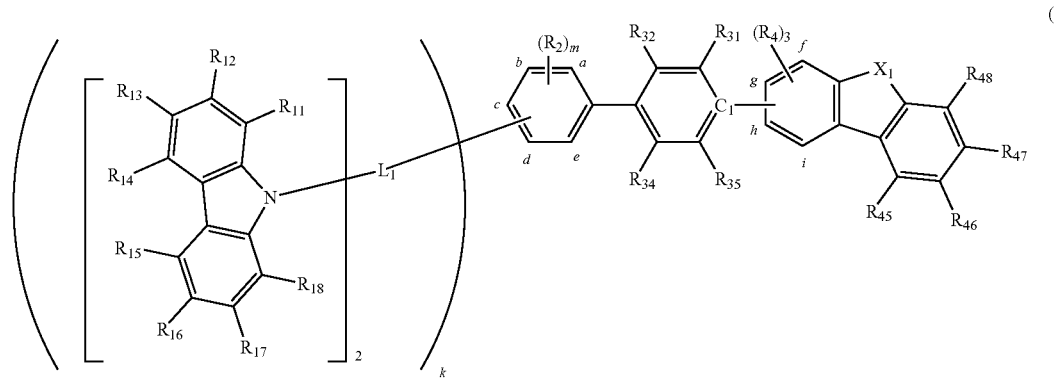

(100Y)

In the formula (100Y), $X_1$, $R_4$, $R_{45}$ to $R_{48}$, $C_1$, $R_2$, $R_{31}$, $R_{32}$, $R_{34}$, $R_{35}$, $L_1$, $R_{11}$ to $R_{16}$, m, and k represent the same as $X_1$, $R_4$, $R_{45}$ to $R_{48}$, $C_1$, $R_2$, $R_{31}$, $R_{32}$, $R_{34}$, $R_{35}$, $L_1$, $R_{11}$ to $R_{18}$, m, and k in the formula (100).

In the formula (100Y), k is preferably 1 or 2.

In the formula (100Y), it is also preferable that a cyclic structure having $R_{11}$ to $R_{18}$ is represented by one of the formulae (400-1) to (400-6).

tuted aryl group having 6 to 30 ring carbon atoms, or a substituted or unsubstituted heterocyclic group having 5 to 30 ring atoms.

In the compound M3 of the exemplary embodiment, it is further preferable that $R_{11}$ to $R_{18}$, $R_4$ and $R_{45}$ to $R_{48}$ are each independently a hydrogen atom or a substituted or unsubstituted aryl group having 6 to 30 ring carbon atoms.

[Formula 23]

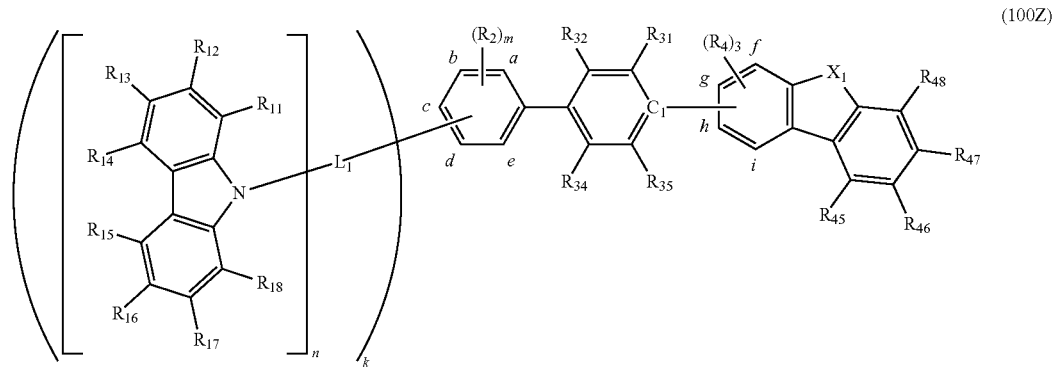

(100Z)

In the formula (100 Z), $X_1$, $R_4$, $R_{45}$ to $R_{48}$, $C_1$, $R_2$, $R_{31}$, $R_{32}$, $R_{34}$, $R_{35}$, $L_1$, $R_{11}$ to $R_{18}$, m, and k represent the same as $X_1$, $R_4$, $R_{46}$ to $R_{48}$, $C_1$, $R_2$, $R_{31}$, $R_{32}$, $R_{34}$, $R_{35}$, $L_1$. $R_{11}$ to $R_{18}$, m, and k in the formula (100).

In the formula (100Z), k is preferably 1 or 2.

In the compound M3 of the exemplary embodiment, it is more further preferable that $R_{11}$ to $R_{18}$, $R_4$ and $R_{45}$ to $R_{48}$ are each independently a hydrogen atom or a substituted or unsubstituted phenyl group.

In the compound M3 of the exemplary embodiment, it is preferable that $R_{11}$ to $R_{18}$ are each independently a hydrogen atom or a substituted or unsubstituted phenyl group, and $R_4$ and $R_{45}$ to $R_{48}$ each independently a hydrogen atom.

When the compound M3 of the exemplary embodiment is a compound represented by one of the formulae (401) to (406), (401A) to (406A) and (401B) to (406B), it is preferable that $R_{11}$ to $R_{18}$, $R_{401}$ to $R_{404}$, $R_4$, $R_{41}$, $R_{42}$ and $R_{44}$ to $R_{48}$ are each independently a hydrogen atom, a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms, more preferably, a substituted or unsubstituted aryl group having 6 to 30 ring carbon atoms, or a substituted or unsubstituted heterocyclic group having 5 to 30 ring atoms, further preferably, a substituted In the compound M3 of the exemplary embodiment, it is preferable that $L_1$ is a single bond or a group derived from an unsubstituted aryl group having 6 to 30 ring carbon atoms.

In the compound M3 of the exemplary embodiment, it is preferable that $L_1$ is a single bond or a group derived from an unsubstituted benzene ring.

In the compound M3 of the exemplary embodiment, $L_1$ is preferably a single bond.

The compound M3 of the exemplary embodiment is also preferably a compound represented by a formula (100A) or (10 GB) below.

The compound M1 of the exemplary embodiment is also more preferably a compound represented by the formula (100A).

[Formula 24]

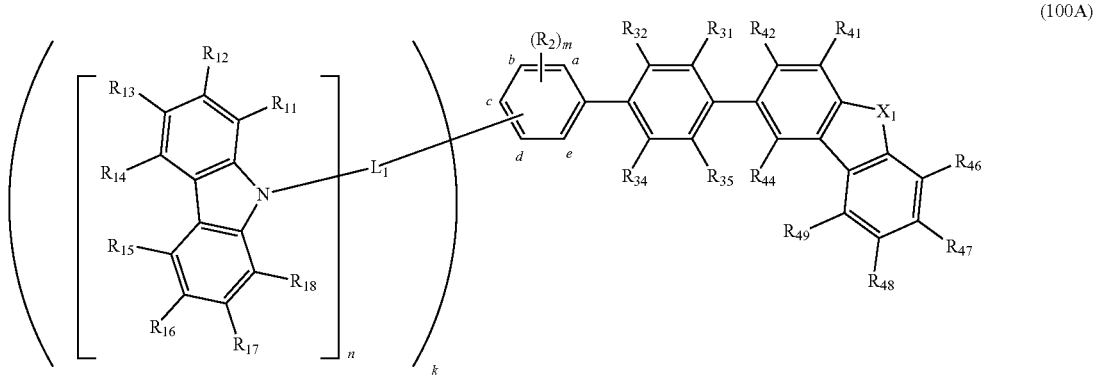

(100A)

[Formula 25]

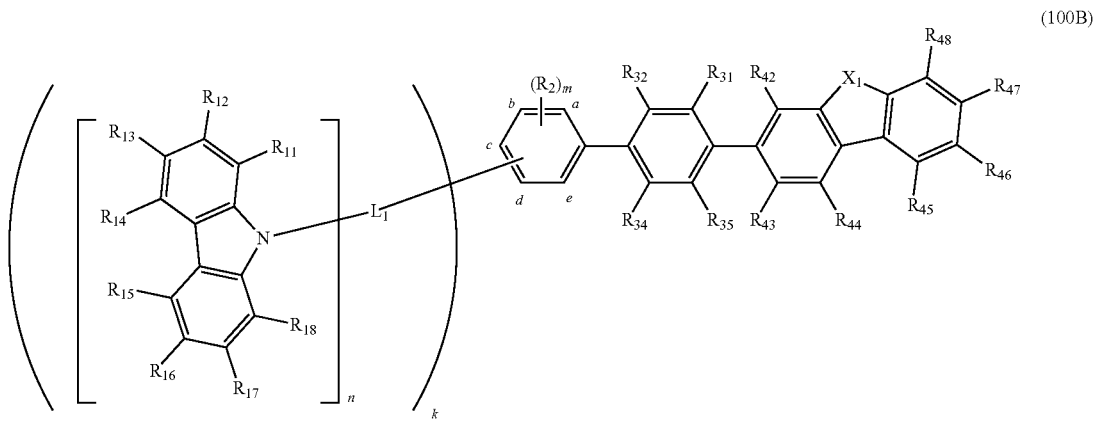

(100B)

or unsubstituted aryl group having 6 to 30 ring carbon atoms, more further preferably, a hydrogen atom or a substituted or unsubstituted phenyl group.

When the compound M3 of the exemplary embodiment is a compound represented by one of the formulae (401) to (406). (401A) to (406A) and (401B) to (406B), it is preferable that $R_{11}$ to $R_{16}$ and $R_{401}$ to $R_{404}$ are each independently a hydrogen atom or a substituted or unsubstituted phenyl group, and $R_4$, $R_{41}$, $R_{42}$ and $R_{44}$ to $R_{48}$ are each independently a hydrogen atom.

In the formulae (100A) and (1008), $X_1$, $R_{11}$ to $R_{18}$, n, k, m, $L_1$, $R_2$, $R_{31}$, $R_{32}$, $R_{34}$, $R_{35}$, and $R_{45}$ to $R_{48}$ respectively represent the same as $X_1$, $R_{11}$ to $R_{18}$, n, k, m, $L_1$, $R_2$, $R_{31}$, $R_{32}$, $R_{34}$, $R_{35}$, and $R_{45}$ to $R_{48}$ in the formula (100), and $R_{41}$ to $R_{44}$ each independently represent the same as $R_4$ in the formula (100).

In the formula (100A), it is also preferable that a cyclic structure having $R_{11}$ to $R_{18}$ is represented by one of the formulae (400-1) to (400-8).

In the formula (100B), it is also preferable that a cyclic structure having $R_{11}$ to $R_{18}$ is represented by one of the formulae (400-1) to (400-6).

In the compound M3 of the exemplary embodiment, when $L_1$ is a linking group, $L_1$ is preferably banded to a carbon atom at a position of b, c or d shown in the formula (100).

In the compound M3 of the exemplary embodiment, when $L_1$ is a divalent linking group, n is 1 and k is 1. $L_1$ is preferably bonded to a carbon atom at the position of c shown in the formula (100).

In the compound M3 of the exemplary embodiment, when $L_1$ is a trivalent linking group, n is 2 and k is 1. $L_1$ is preferably bonded to a carbon atom at the position of c shown in the formula (100).

In the compound M3 of the exemplary embodiment, when $L_1$ is a single bond, n is 1 and k is 1, and a nitrogen atom at a position 9 of a carbazole ring shown in the formula (100) is preferably bonded to a carbon atom at the position of c shown in the formula (100).

In the compound M3 of the exemplary embodiment, when $L_1$ is a single bond, n is 2 and k is 2, K is preferable that nitrogen atoms at positions 9 of two carbazole rings shown in the formula (100) are respectively bonded to carbon atoms at the positions of b and d shown in the formula (100).

In the compound M3 of the exemplary embodiment, when $L_1$ is a single bond, n is 3 and k is 3, it is preferable that nitrogen atoms at positions 9 of three carbazole rings shown in the formula (100) are respectively bonded to carbon atoms at the positions of b, e and d shown in the formula (100).

The compound M3 of the exemplary embodiment is also preferably a compound represented by the formula (100C).

[Formula 26]

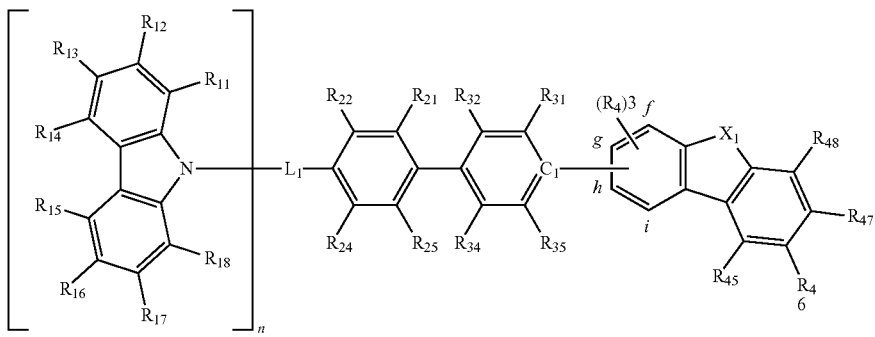

(100C)

In the formula (100C), $X_1$, $C_1$, $R_{11}$ to $R_{18}$, n, $L_1$, $R_{31}$, $R_{32}$, $R_{34}$, $R_{35}$, $R_4$, and $R_{45}$ to $R_{48}$ respectively represent the same as $X_1$, $C_1$, $R_{11}$ to $R_{18}$, n, $L_1$, $R_{31}$, $R_{32}$, $R_{34}$, $R_{35}$, $R_4$, and $R_{45}$ to $R_{48}$ in the formula (100), and $R_{21}$, $R_{22}$, $R_{24}$, and $R_{25}$ each independently represent the same as $R_2$ in the formula (100).

In the formula (100C), it is also preferable that a cyclic structure having $R_{11}$ to $R_{18}$ is represented by one of the formulae (400-1) to (400-8).

The compound M3 of the exemplary embodiment is also more preferably a compound represented by the formula (100D)

[Formula 27]

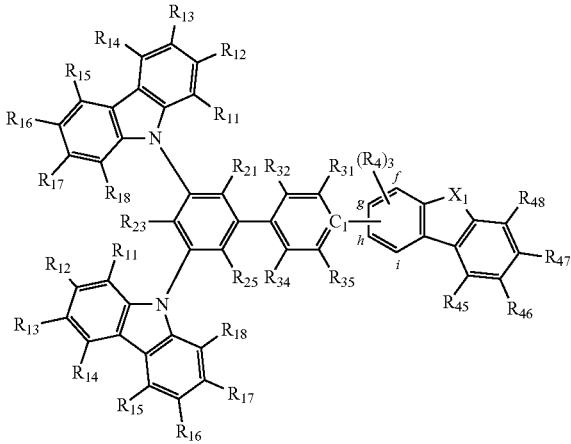

(100D)

In the formula (100D), $X_1$, $C_1$, $R_{11}$ to $R_{18}$, $R_{31}$, $R_{32}$, $R_{34}$, $R_{35}$, $R_4$, and $R_{45}$ to $R_{48}$ respectively represent the same as $X_1$, $C_1$, $R_{11}$ to $R_{18}$, $R_{31}$, $R_{32}$, $R_{34}$, $R_{35}$, $R_4$, and $R_{45}$ to $R_{48}$ in the formula (100), and $R_{21}$, $R_{23}$, and $R_{25}$ each independently represent the same as $R_2$ in the formula (100).

In the formula (100D), two $R_{11}$ are the same or different, two $R_{12}$ are mutually the same or different, two $R_{13}$ are the same or different, two $R_{14}$ are the same or different, two $R_{15}$ are the same or different, two $R_{16}$ are the same or different, two $R_{17}$ are the same or different, and two $R_{18}$ are the same or different.

In the formula (100D), it is also preferable that two cyclic structure having $R_{11}$ to $R_{18}$ are each independently represented by one of the formulae (400-1) to (400-6).

The compound M3 of the exemplary embodiment is also more preferably a compound represented by the formula (100E).

[Formula 28]

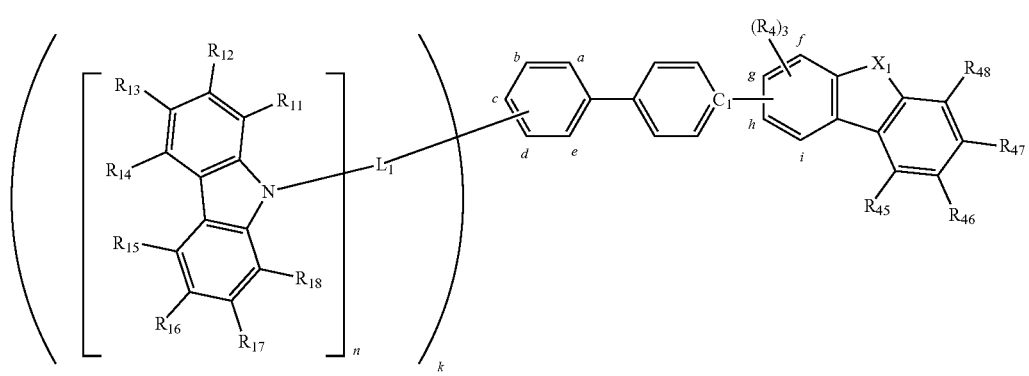

(100E)

In the formula (100E), $X_1$ and $C_1$ respectively represent the same as $X_1$ and $C_1$ in the formula (100), n is 1 or 2, K is 1 or 2, $R_{11}$ to $R_{18}$, $R_4$ and $R_{45}$ to $R_{48}$ are each independently a hydrogen atom or a substituted or unsubstituted aryl group having 6 to 30 ring carbon atoms, when at least one of n or k is 2, a plurality of $R_{11}$ are mutually the same or different a plurality of $R_{12}$ are mutually the same or different, a plurality of $R_{13}$ are mutually the same or different, a plurality of $R_{14}$ are mutually the same or different, a plurality of $R_{15}$ are mutually the same or different, a plurality of $R_{16}$ are mutually the same or different, a plurality of $R_{17}$ are mutually the same or different, and a plurality of $R_{18}$ are mutually the same or different.

However, a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, and a pair of $R_{17}$ and $R_{18}$, a pair of $R_{45}$ and $R_{46}$, a pair of $R_{46}$ and $R_{47}$, a pair of $R_{47}$ and $R_{48}$ and a pair of two or more or a plurality of $R_4$ are not bonded.

$L_1$ is a single bond or a group derived from an unsubstituted aryl group having 6 to 30 ring carbon atoms, however, when $L_1$ is a single bond, n is 1, and when k is 2, a plurality of $L_1$ are mutually the same or different.

When $L_1$ is a linking group and k is 1, one $L_1$ is bonded to a carbon atom at the position of a, b, c, d or e.

When $L_1$ is a linking group and k is 2, two $L_1$ are respectively bonded to carbon atoms at any ones of positions of a, b, c, d and e, however, a plurality of $L_1$ are not bonded to a carbon atom at the same position.

When $L_1$ is a single bond and k is 1, a nitrogen atom at a position 9 of one carbazole ring shown in the formula (100E) is bonded to a carbon atom at the position of a, b, c, d are shown in the formula (100E).

When $L_1$ is a single bond and k is 2, nitrogen atoms at positions 9 of two carbazole rings shown in the formula (100E) are respectively ponded to carbon atoms at any ones of the positions of a, b, c, d and e shown in the formula (100E), however, nitrogen atoms at positions 9 of a plurality of carbazole rings are not bonded to a carbon atom at the same position.

The compound M3 of the exemplary embodiment is also more preferably a compound represented by a formula (100F) below.

[Formula 29]

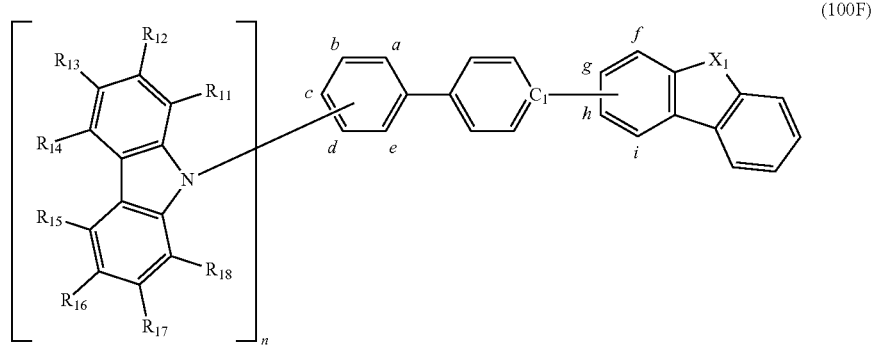

(100F)

In the formula (100F), $X_1$ and $C_1$ respectively represent the same as $X_1$ and $C_1$ in the formula (100), n is 1 or 2.

When n is 1, a nitrogen atom at a position 9 of one carbazole ring shown in the formula (100F) is bonded to a carbon atom at the position of a, b, c, d or e shown in the formula (100F).

When n is 2, nitrogen atoms at the positions 9 of two carbazole rings are respectively bonded to carbon atoms at any ones of the positions a, b, c, d and e, however, nitrogen atoms at the positions 9 of a plurality of carbazole rings are not bonded to a carbon atom at the same position, $R_{11}$ to $R_{18}$ are each independently a hydrogen atom or a substituted or unsubstituted phenyl group, when n is 2, a plurality of $R_{11}$ are mutually the same or different, a plurality of $R_{12}$ are mutually the same or different, a plurality of $R_{13}$ are mutually the same or different, a plurality of $R_{14}$ are mutually the same or different, a plurality of $R_{15}$ are mutually the same or different, a plurality of $R_{16}$ are mutually the same or different a plurality of $R_{17}$ are mutually the same or different, and a plurality of $R_{18}$ are mutually the same or different.

However, a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, and a pair of $R_{17}$ and $R_{18}$ are not bonded.

In the compound M3 of the exemplary embodiment, $X_1$ is preferably an oxygen atom.

In the compound M3 of the exemplary embodiment, it is also preferable that $C_1$ in the formula (100) is bonded to a carbon atom at a position of h shown in the formula (100) and that at least one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ is an unsubstituted aryl group having 6 to 30 ring carbon atoms.

The compound M3 with this arrangement is represented by a formula (201A) below.

[Formula 30]

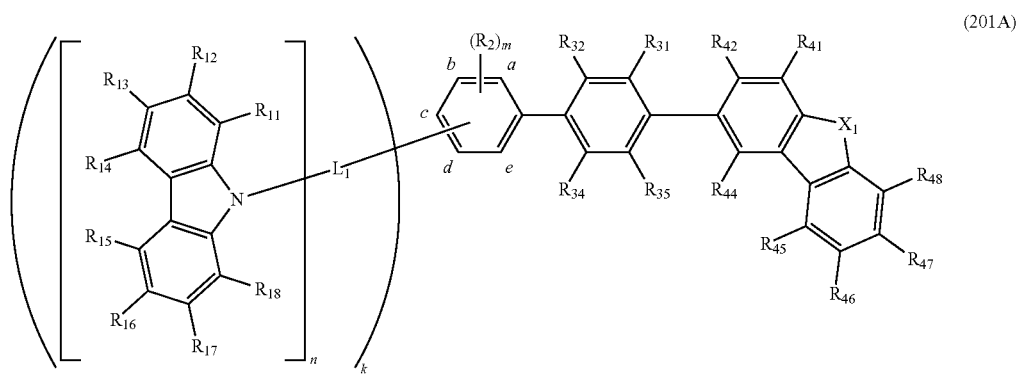

(201A)

In the formula (201A), $X_1$, $R_{11}$ to $R_{18}$, n, k, m, $L_1$, $R_2$, $R_{31}$, $R_{32}$, $R_{34}$, $R_{35}$, and $R_{45}$ to $R_{48}$ respectively represent the same as $X_1$, $R_{11}$ to $R_{18}$, n, k, m, $L_1$, $R_2$, $R_{31}$, $R_{32}$, $R_{34}$, $R_{35}$, and $R_{45}$ to $R_{48}$ in the formula (100), and $R_{41}$, $R_{42}$ and $R_{44}$ each independently represent the same as $R_4$ in the formula (100). However, in the formula (201A), a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, and a pair of $R_{17}$ and $R_{18}$ are not bonded to each other and at least one of $R_{11}$ to $R_{18}$ is an unsubstituted aryl group having 6 to 30 ring carbon atoms.

The compound represented fay the formula (201A) represents the same as a compound represented by a formula (201) according to a fourth exemplary embodiment described later.

Specifically, in the formula (201A), $X_1$, $R_{11}$ to $R_{16}$, n, k, m, $L_1$, $R_2$, $R_{31}$, $R_{32}$, $R_{34}$, $R_{35}$, $R_{41}$, $R_{42}$, $R_{44}$ and $R_{45}$ to $R_{48}$ respectively represent the same as $X_1$, $R_{11}$ to $R_{18}$, n, k, m, $L_1$, $R_2$, $R_{31}$, $R_{32}$, $R_{34}$, $R_{35}$, $R_{41}$, $R_{42}$, $R_{44}$ and $R_{45}$ to $R_{48}$ in the formula (201).

The compound according to the fourth exemplary embodiment is a compound capable of achieving a high-performance organic EL device, for instance, an organic EL device configured to emit light with a tong lifetime. Accordingly, the compound according to the fourth exemplary embodiment is usable as the compound M3 in the first exemplary embodiment.

In the compound MS of the exemplary embodiment, it is also preferable that $C_1$ in the formula (100) is bonded to a carbon atom at a position of g shown in the formula (100) and that at least one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ is an unsubstituted aryl group having 6 to 30 ring carbon atoms.

The compound M3 with this arrangement is represented by a formula (202A) below.

[Formula 31]

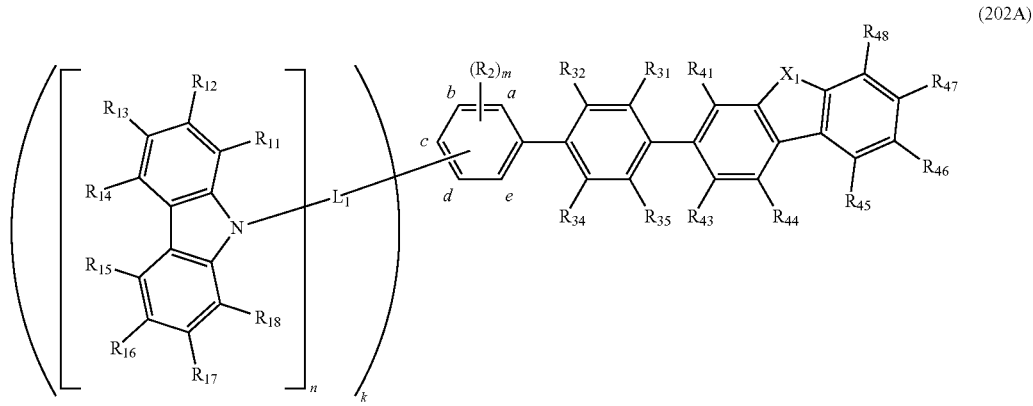

(202A)

In the formula (202A), $X_1$, $R_{11}$ to $R_{18}$, a k, m, $L_1$, $R_2$, $R_{31}$, $R_{32}$, $R_{34}$, $R_{35}$, and $R_{45}$ to $R_{48}$ respectively represent the same as $X_1$, $R_{11}$ to $R_{18}$, n, k, m, $L_1$, $R_2$, $R_{31}$, $R_{32}$, $R_{34}$, $R_{35}$, and $R_{45}$ to $R_{48}$ in the formula (100), and $R_{41}$, $R_{43}$ and $R_{44}$ each independently represent the same as $R_4$ in the formula (100). However, in the formula (202A), a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, and a pair of $R_{17}$ and $R_{18}$ are not bonded to each other and at least one of $R_{11}$ to $R_{18}$ is an unsubstituted aryl group having 6 to 30 ring carbon atoms.

The compound represented by the formula (202A) represents the same as a compound represented by a formula (202) according to a fourth exemplary embodiment described later.

Specifically, in the formula (202A), $X_1$, $R_{11}$ to $R_{18}$, n, k, m, $L_1$, $R_2$, $R_{31}$, $R_{32}$, $R_{34}$, $R_{35}$, $R_{41}$, $R_{43}$, $R_{44}$ and $R_{45}$ to $R_{48}$ respectively represent the same as $X_1$, $R_{11}$ to $R_{18}$, n, k, m, $L_1$, $R_2$, $R_{31}$, $R_{32}$, $R_{34}$, $R_{35}$, $R_{41}$, $R_{43}$, $R_{44}$ and $R_{45}$ to $R_{48}$ in the formula (201).

The compound according to the fourth exemplary embodiment is a compound capable of achieving a high-performance organic EL device, for instance, an organic EL device configured to emit light with a long lifetime. Accordingly, the compound according to the fourth exemplary embodiment is usable as the compound M3 in the first exemplary embodiment.

In the compound M3 of the exemplary embodiment, it is also preferable that $C_1$ in the formula (100) is bonded to a carbon atom at a position of f shown in the formula (100) and that at least one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ is an unsubstituted aryl group having 6 to 30 ring carbon atoms.

The compound M3 with this arrangement is represented by a formula (203A) below.

[Formula 32]

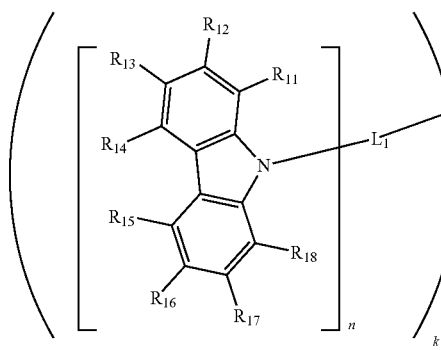

(203A)

In the formula (203A), $X_1$, $R_{11}$ to $R_{18}$, n, k, m, $L_1$, $R_2$, $R_{31}$, $R_{32}$, $R_{34}$, $R_{35}$, and $R_{45}$ to $R_{48}$ respectively represent the same as $X_1$, $R_{11}$ to $R_{18}$, n, k, m, $L_1$, $R_2$, $R_{31}$, $R_{32}$, $R_{34}$, $R_{35}$, and $R_{45}$ to $R_{48}$ in the formula (100), and $R_{42}$ to $R_{44}$ each independently represent the same as $R_4$ in the formula (100). However, in the formula (203A), a pair of $R_{11}$ and $R_{12}$, a pair of $R_{12}$ and $R_{13}$, a pair of $R_{13}$ and RH a pair of $R_{15}$ and $R_{16}$, a pair of $R_{16}$ and $R_{17}$, and a pair of $R_{17}$ and $R_{16}$ are not bonded to each other and at least one of $R_{11}$ to $R_{16}$ is an unsubstituted aryl group having 6 to 30 ring carbon atoms.

The compound represented by the formula (203A) represents the same as a compound represented by a formula (203) according to a fourth exemplary embodiment described later.

Specifically, in the formula (203A), $X_1$, $R_{11}$ to $R_{15}$, n, k, m, $L_1$, $R_2$, $R_{31}$, $R_{32}$, $R_{34}$, $R_{35}$, $R_{42}$ to $R_{44}$ and $R_{45}$ to $R_{46}$ respectively represent the same as $X_1$, $R_{11}$ to $R_{18}$, n, k, m, $L_1$, $R_2$, $R_{31}$, $R_{32}$, $R_{34}$, $R_{35}$, $R_{42}$ to $R_{44}$ and $R_{45}$ to $R_{48}$ in the formula (201).

The compound according to the fourth exemplary embodiment is a compound capable of achieving a high-performance organic EL device, for instance an organic EL device configured to emit light with a long lifetime. Accordingly, the compound according to the fourth exemplary embodiment is usable as the compound M3 in the first exemplary embodiment.

In the compound M3 of the exemplary embodiment, it is also preferable that $C_1$ in the formula (100) is bonded to a carbon atom at the position of t shown in the formula (100).

The compound M3 with this arrangement is represented by a formula (300A) below.

[Formula 33]

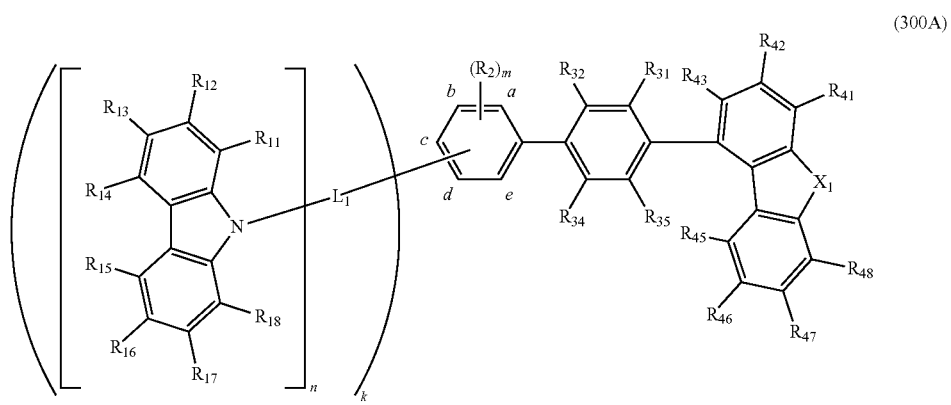

(300A)

In the formula (300A), $X_1$, $R_{11}$ to $R_{18}$, a k, m, $L_1$, $R_2$, $R_{31}$, $R_{32}$, $R_{34}$, $R_{35}$, and $R_{45}$ to $R_{48}$ respectively represent the same as $X_1$, $R_{11}$ to $R_{18}$, n, k, m, $L_1$, $R_2$, $R_{31}$, $R_{32}$, $R_{34}$, $R_{35}$, and $R_{45}$ to $R_{48}$ in the formula (100), and $R_{41}$ to $R_{43}$ each independently represent the same as $R_4$ in the formula (100).

The compound represented by the formula (300A) represents the same as a compound represented by a formula (300) according to a fifth exemplary embodiment described later.

Specifically, in the formula (300A), $X_1$, $R_{11}$ to $R_{18}$, n, k, m, $L_1$, $R_2$, $R_{31}$, $R_{32}$, $R_{34}$, $R_{35}$, $R_{41}$ to $R_{43}$ and $R_{45}$ to $R_{48}$ respectively represent the same as $X_1$, $R_{11}$ to $R_{18}$, n, k, m, $L_1$, $R_2$, $R_{31}$, $R_{32}$, $R_{34}$, $R_{35}$, $R_{41}$ to $R_{43}$ and $R_{45}$ to $R_{48}$ in the formula (300).

In the formula (300A), it is also preferable that a cyclic structure having $R_{11}$ to $R_{18}$ is represented by one of the formulae (400-1) to (400-6).

The compound according to the fifth exemplary embodiment is a compound capable of achieving a high-performance organic EL device, for instance, an organic EL device configured to emit light with a long lifetime. Accordingly, the compound according to the fifth exemplary embodiment is usable as the compound M3 in the first exemplary embodiment.

Manufacturing Method of Compound M3

The compound M3 of the exemplary embodiment can be manufactured, for instance, by a method described later in Examples. The compound M3 of the exemplary embodiment can be manufactured, for instance, by application of known substitution reactions and/or materials depending on a target compound according to reactions described later in Examples.

Specific examples of the compound M3 of the exemplary embodiment include compounds below. It should however be noted that the invention is not limited to the specific examples of the compound.

[Formula 34]
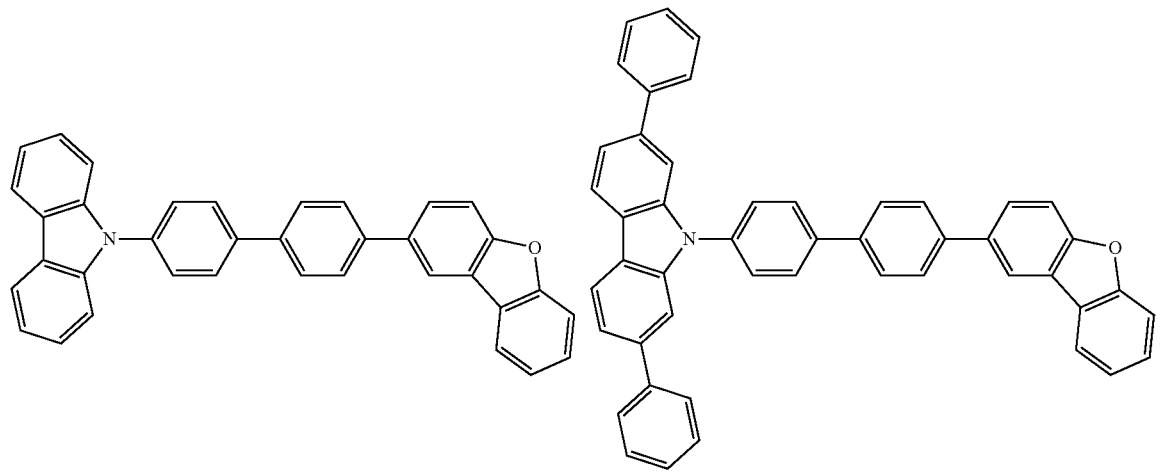
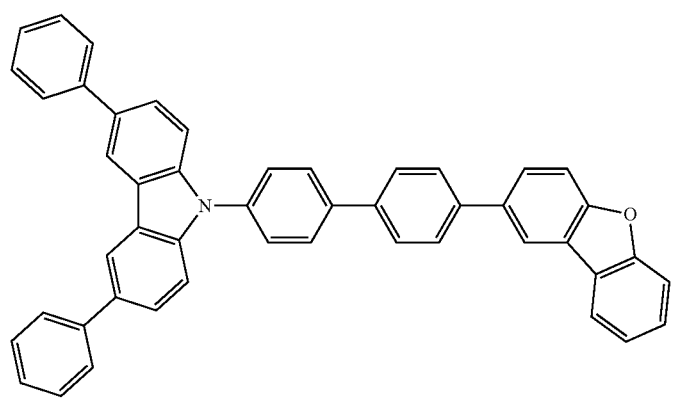
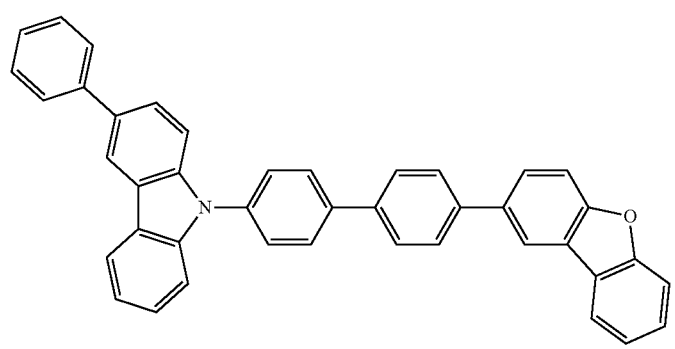
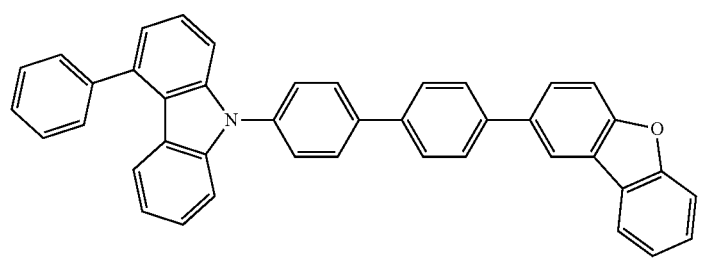

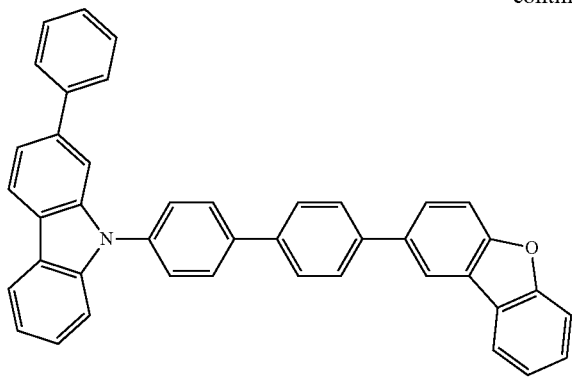
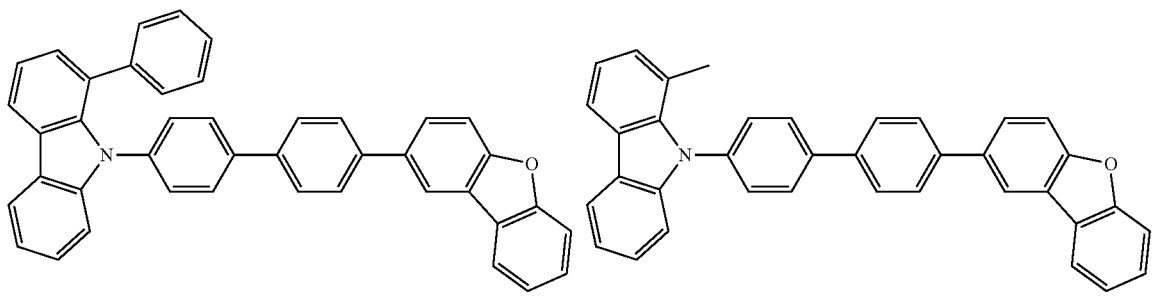
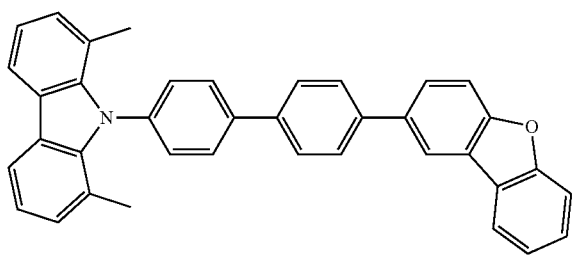
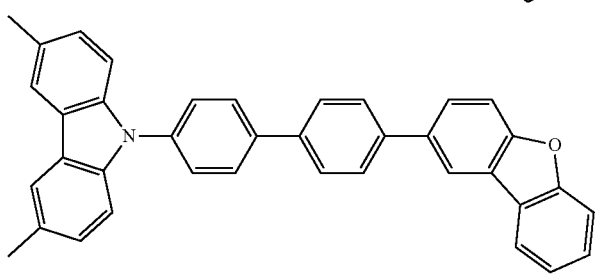
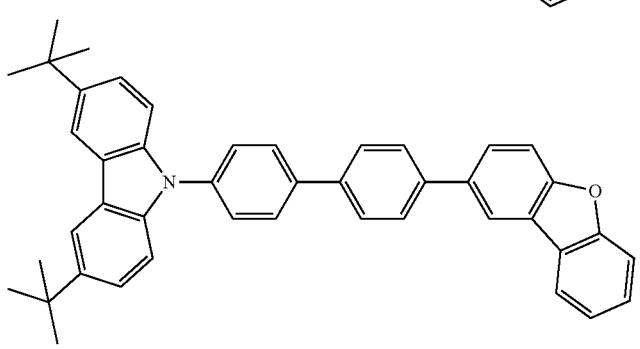

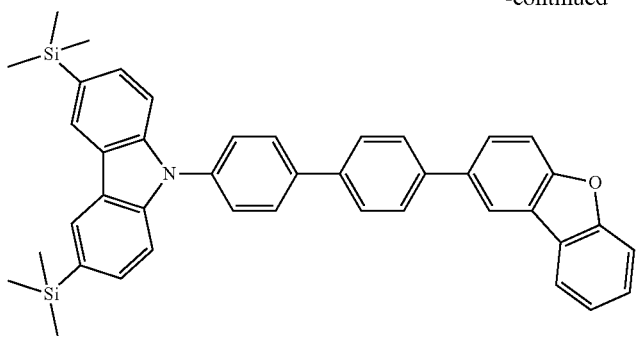
[Formula 35]
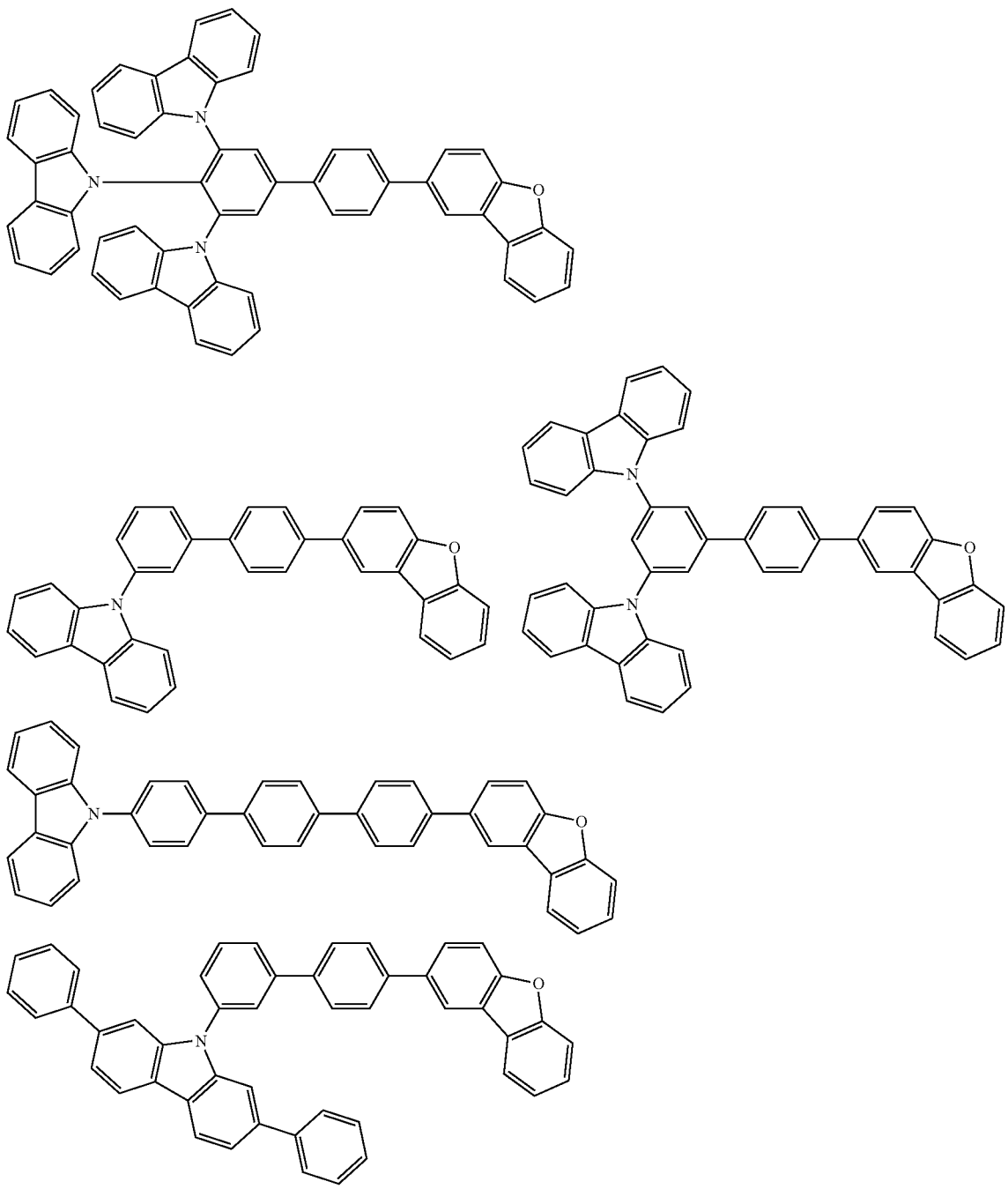

-continued
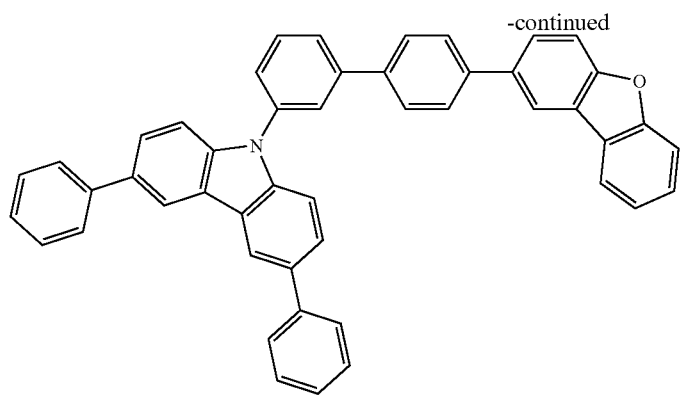
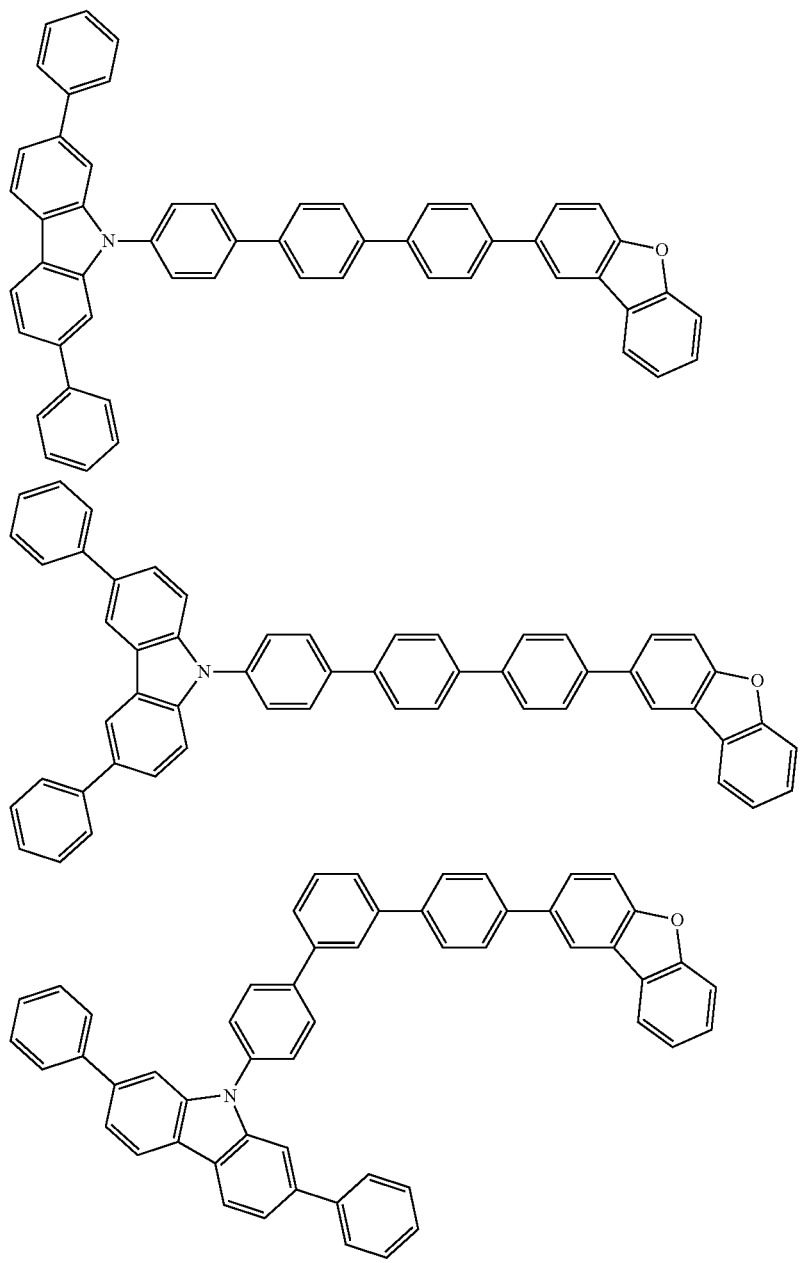

-continued
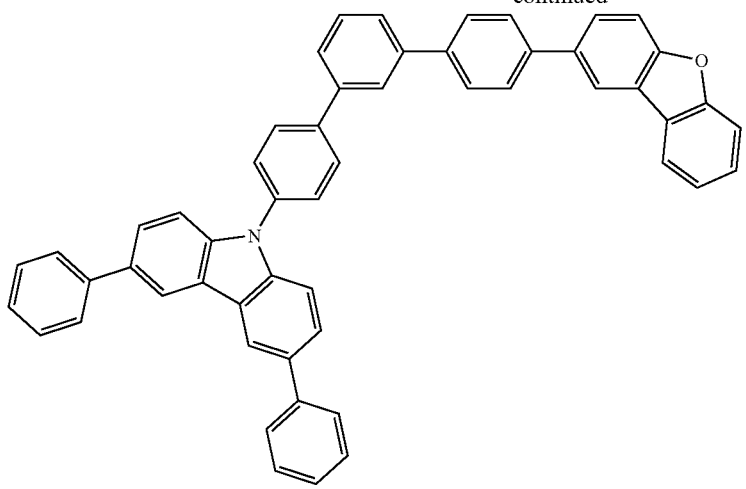
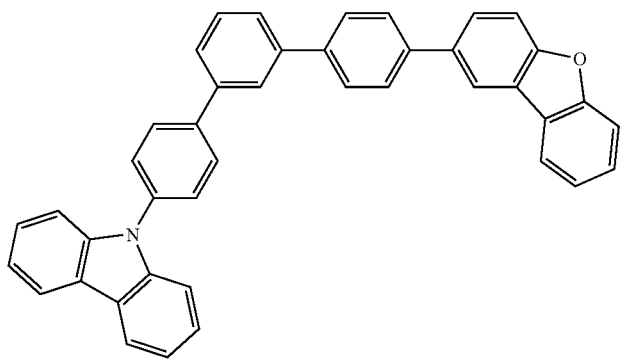
[Formula 36]
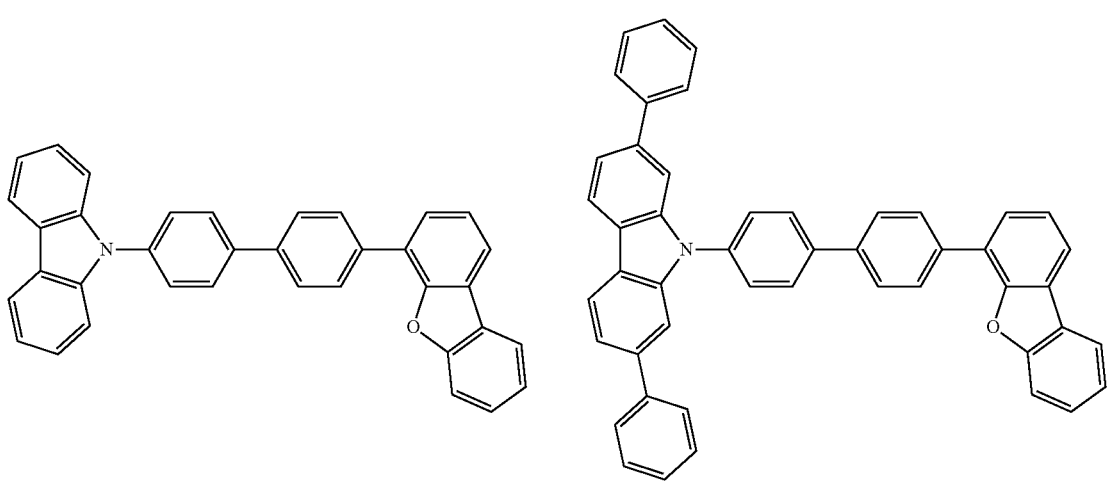

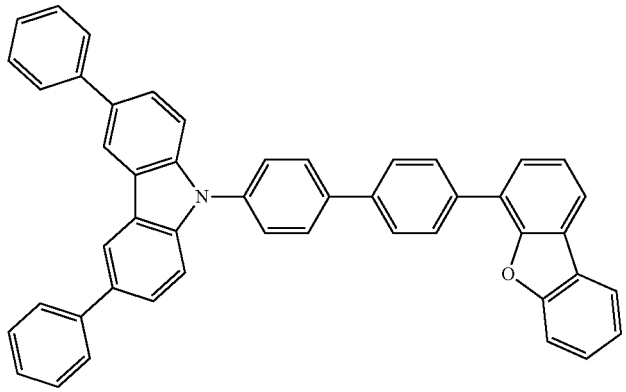
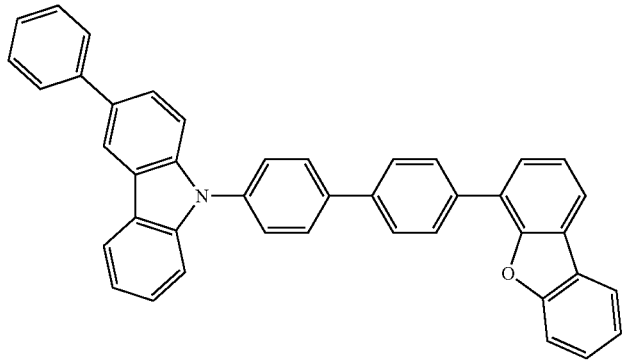
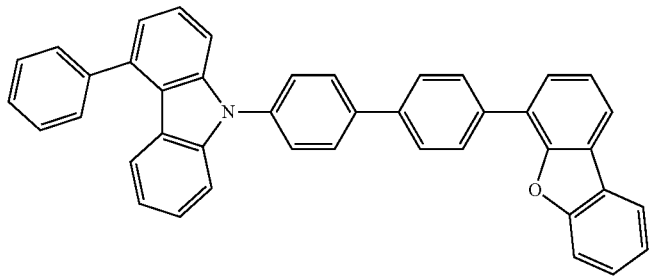
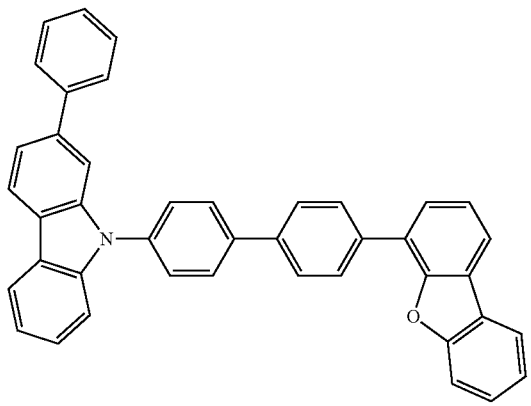
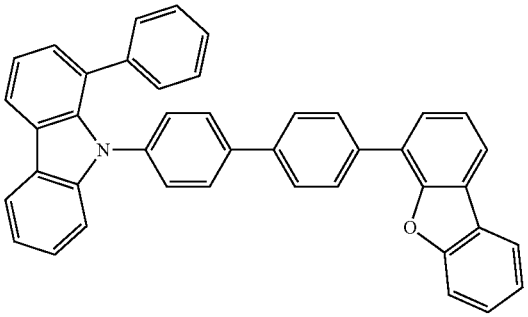
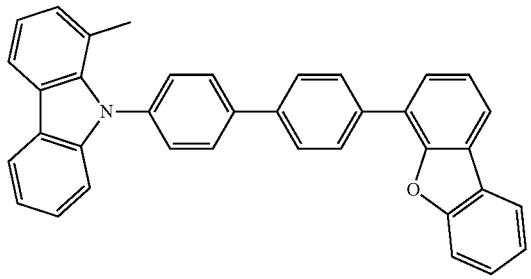
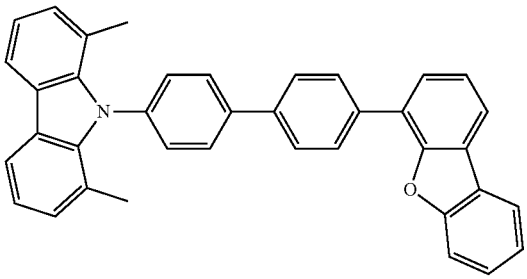

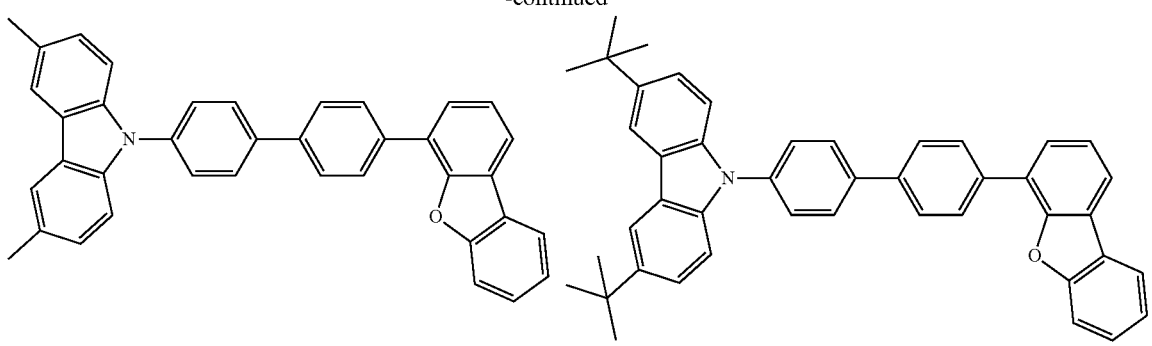
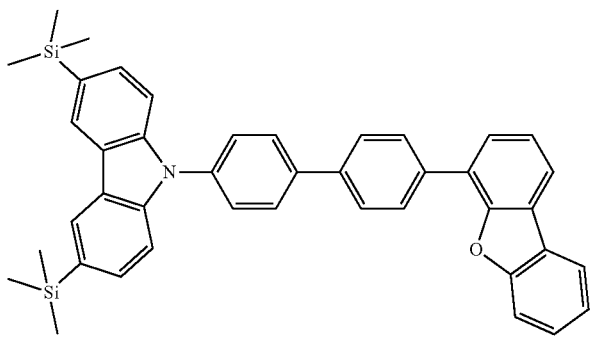
[Formula 37]
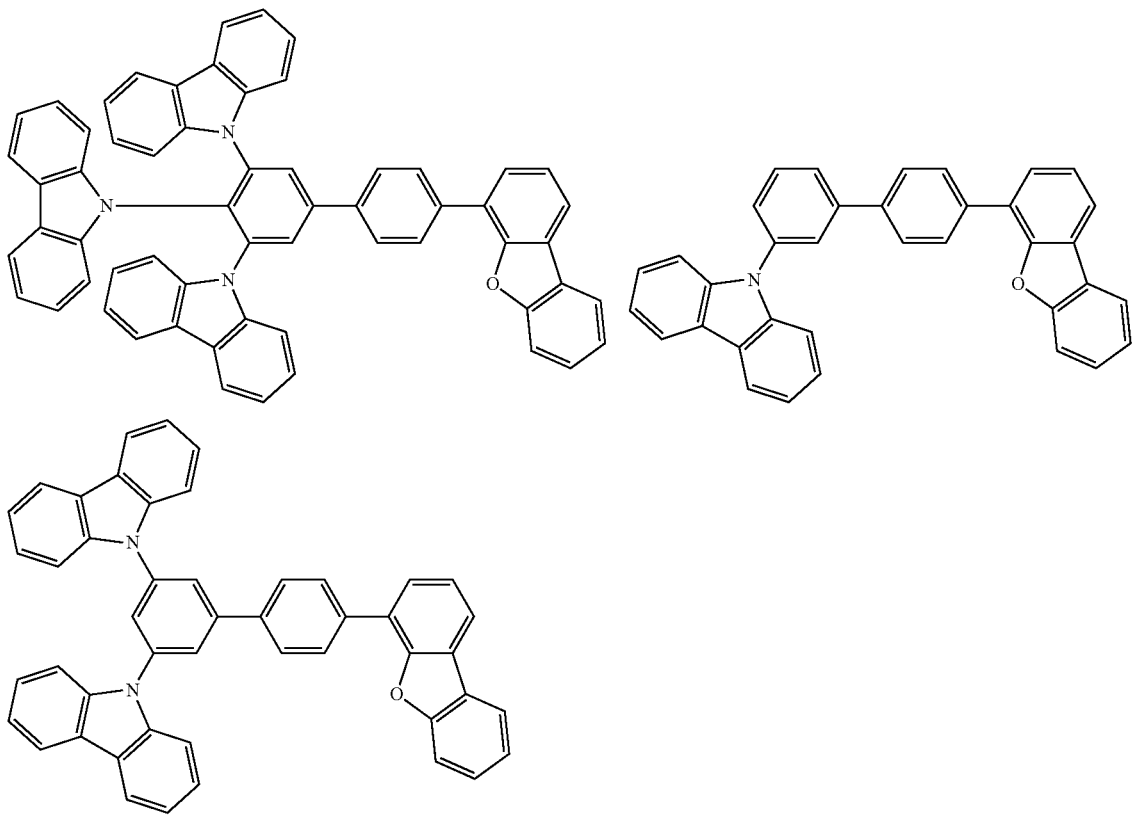

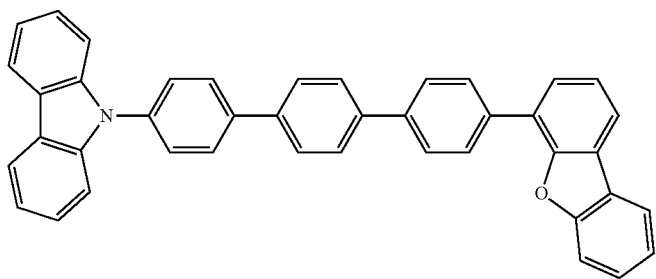
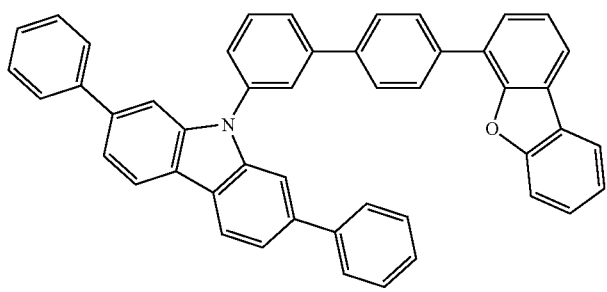
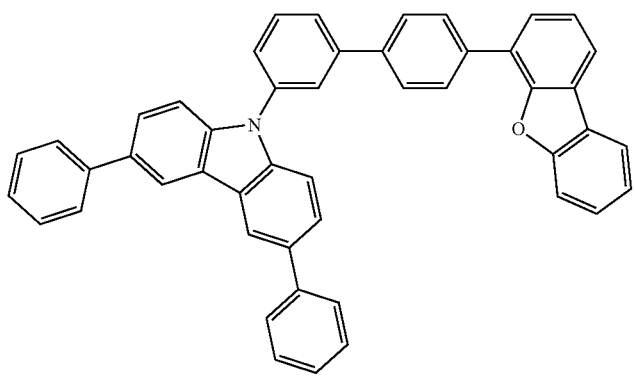
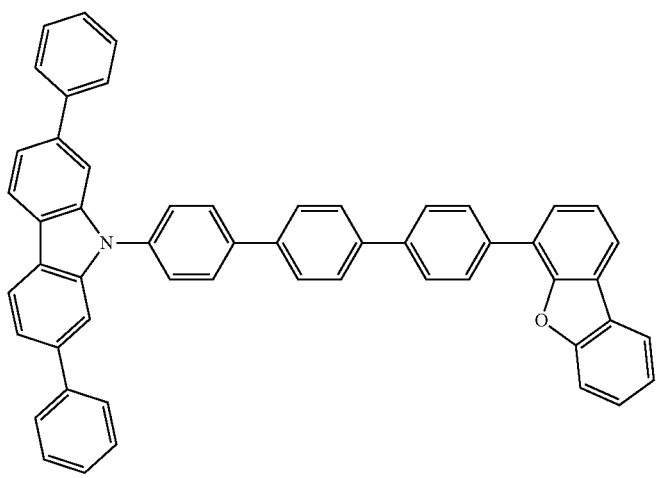

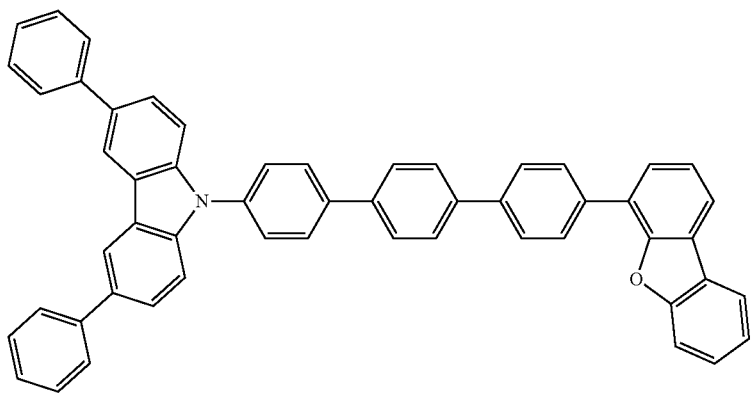
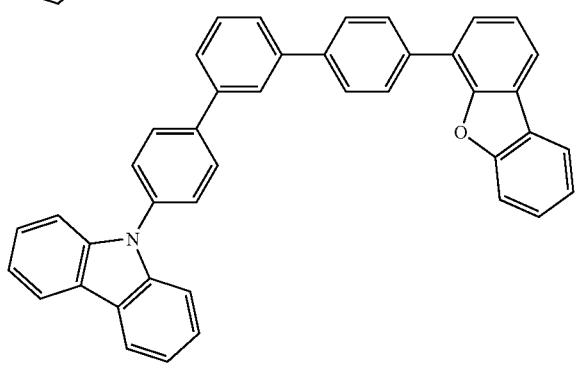
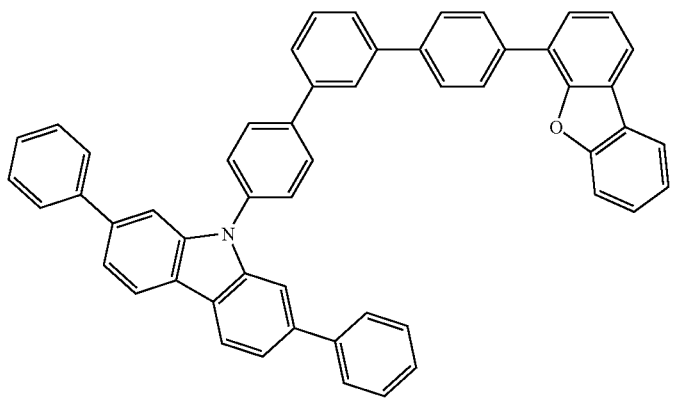
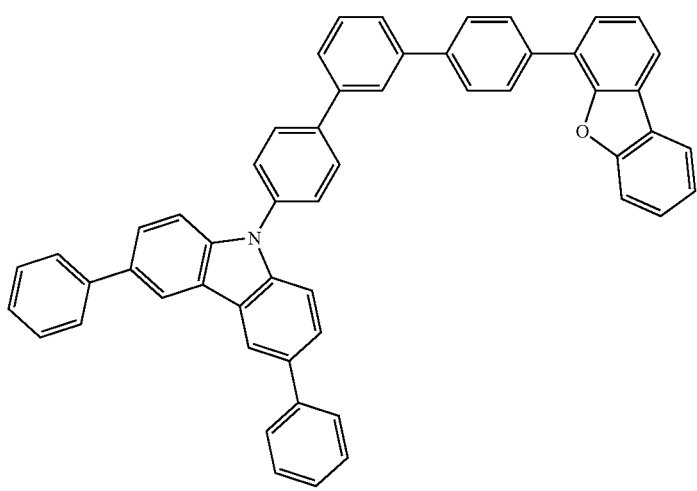

[Formula 38]
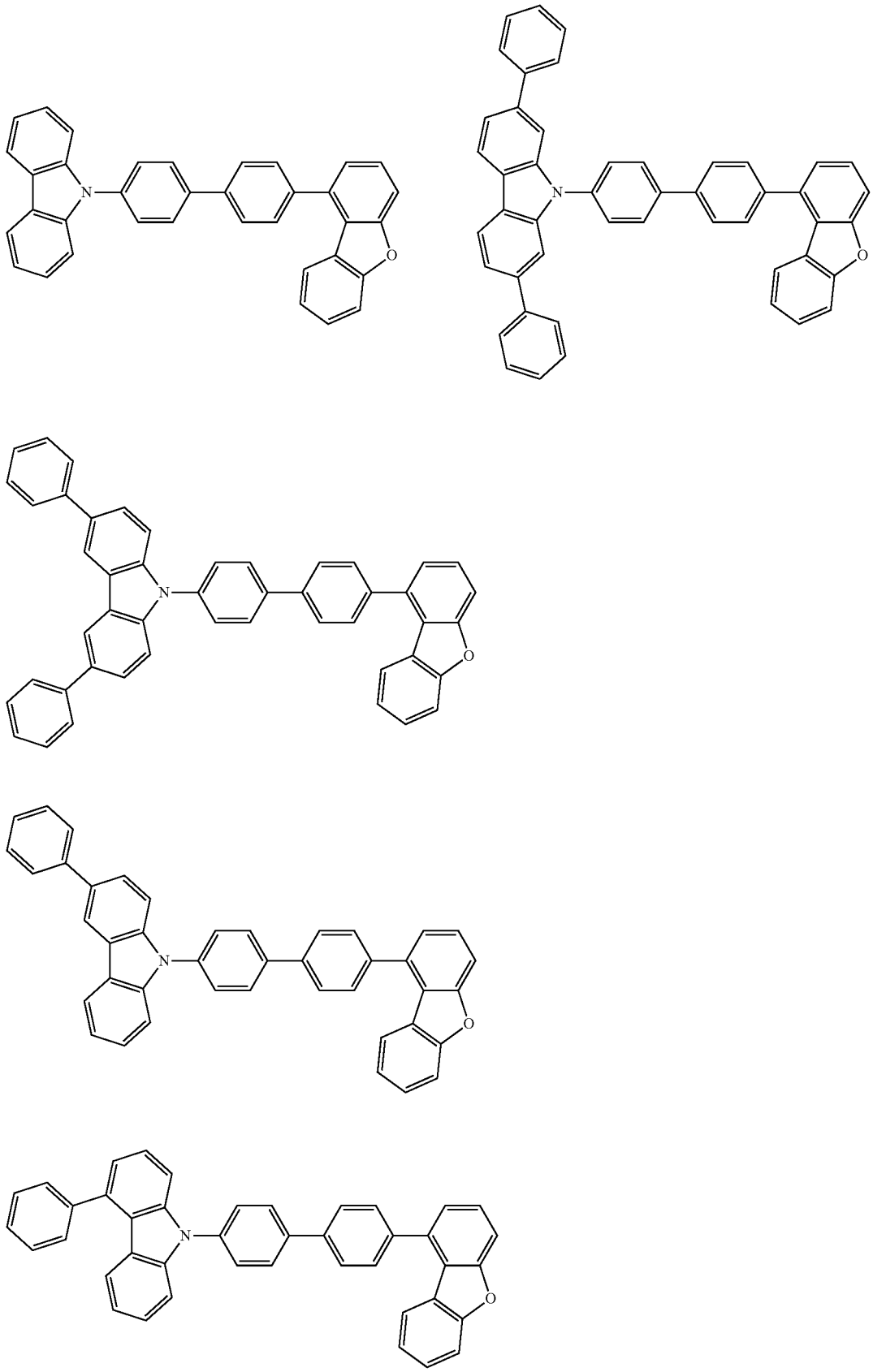

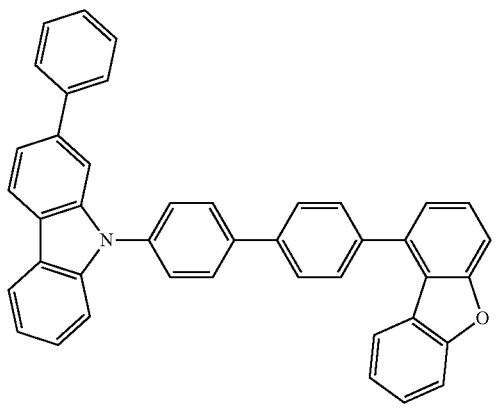
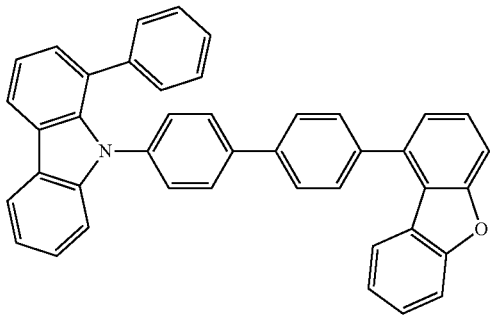
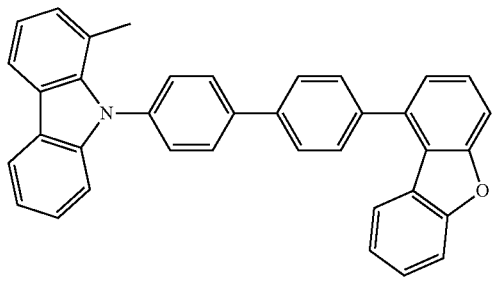
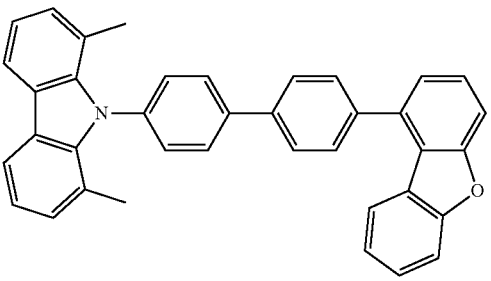
[Formula 39]
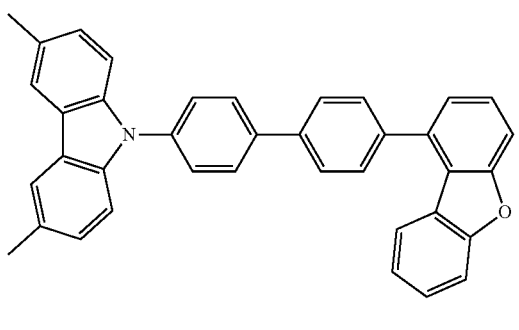
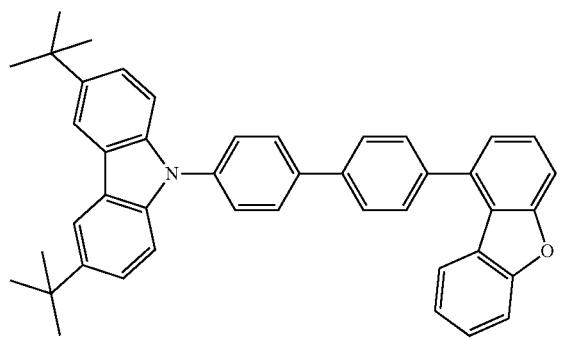
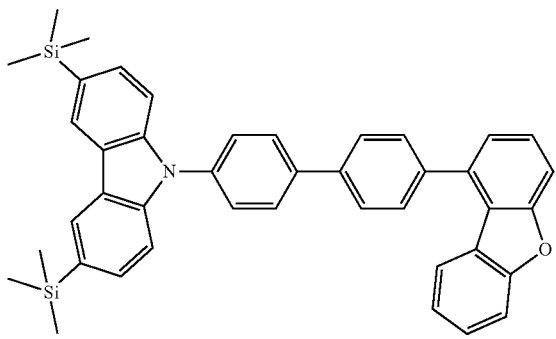

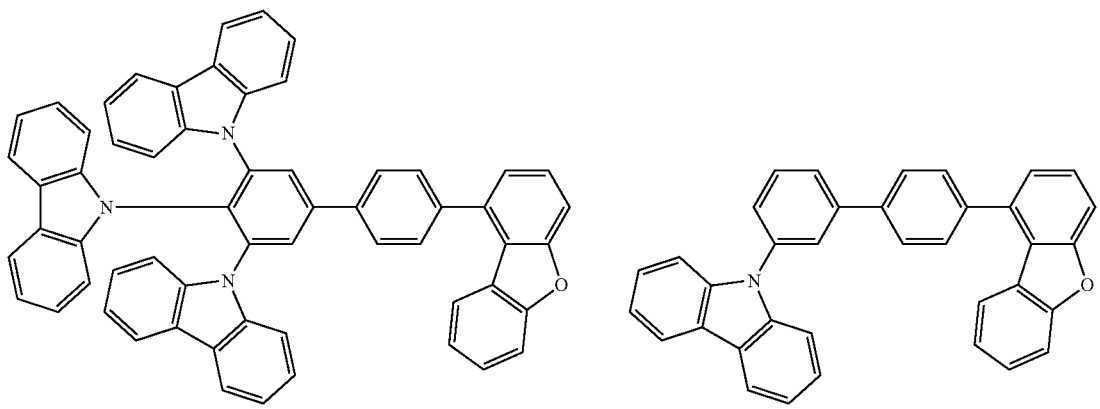
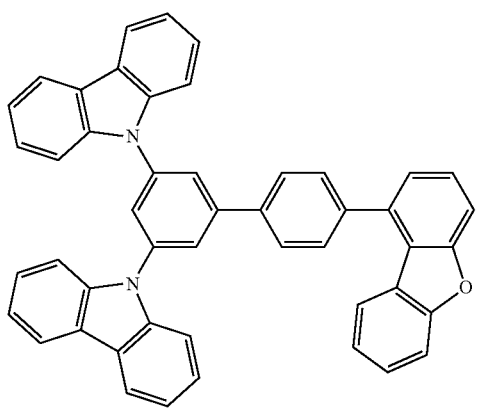
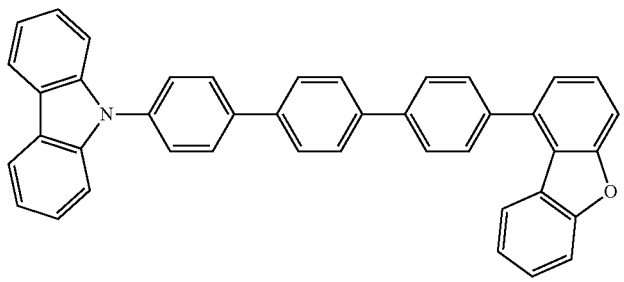
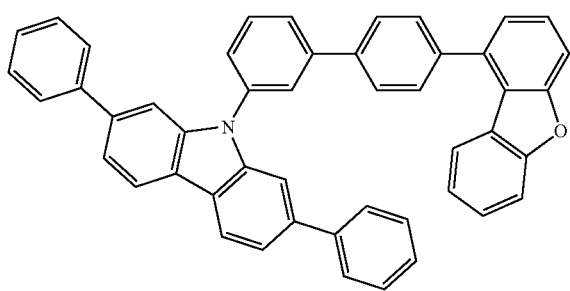

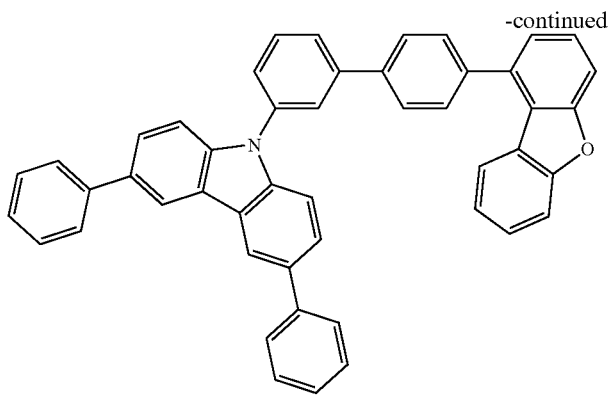
[Formula 40]
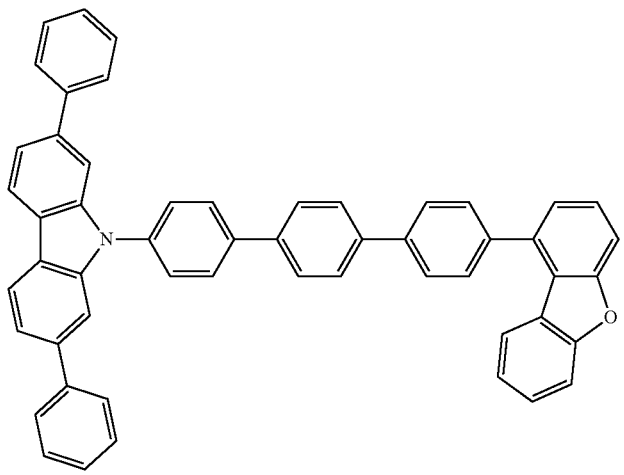
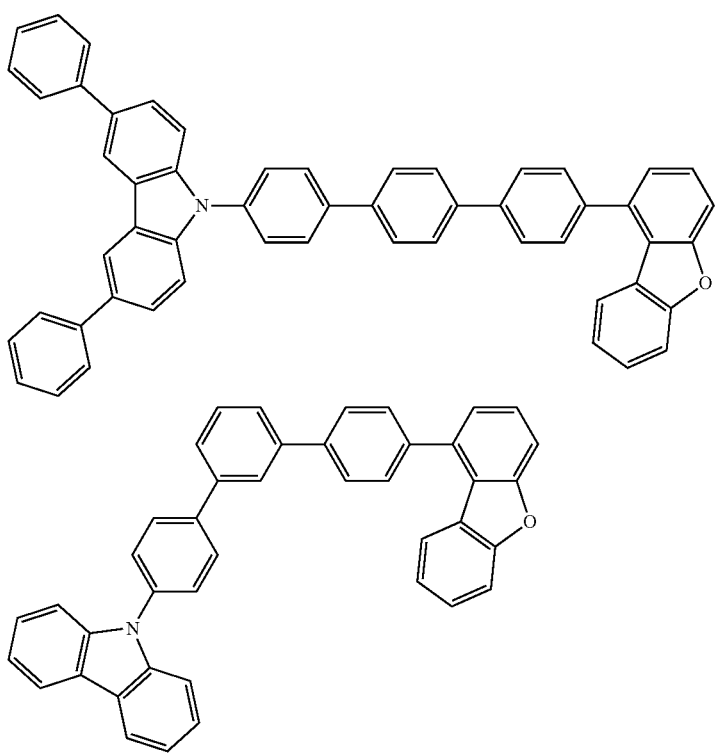

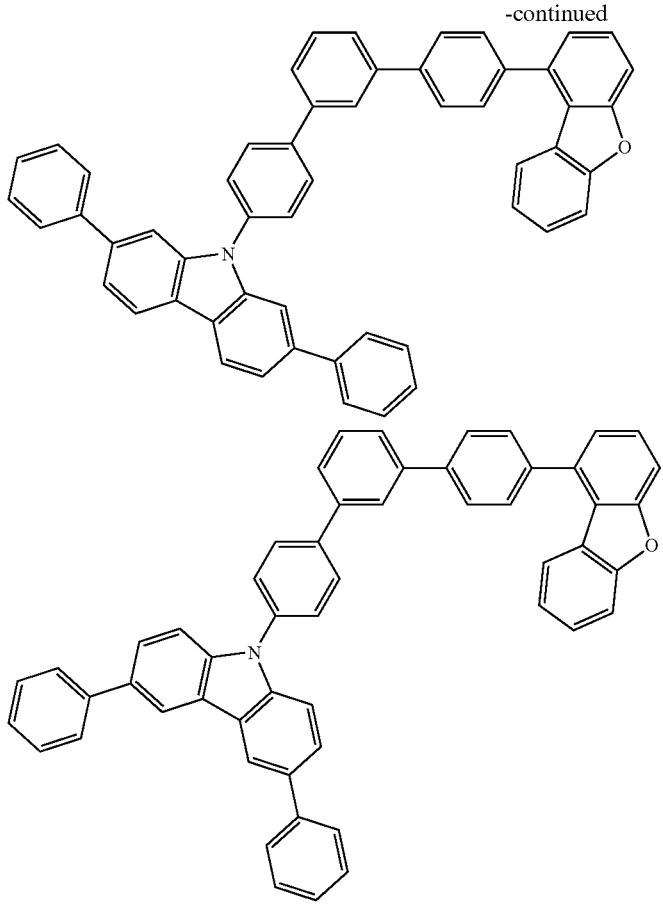
[Formula 41]
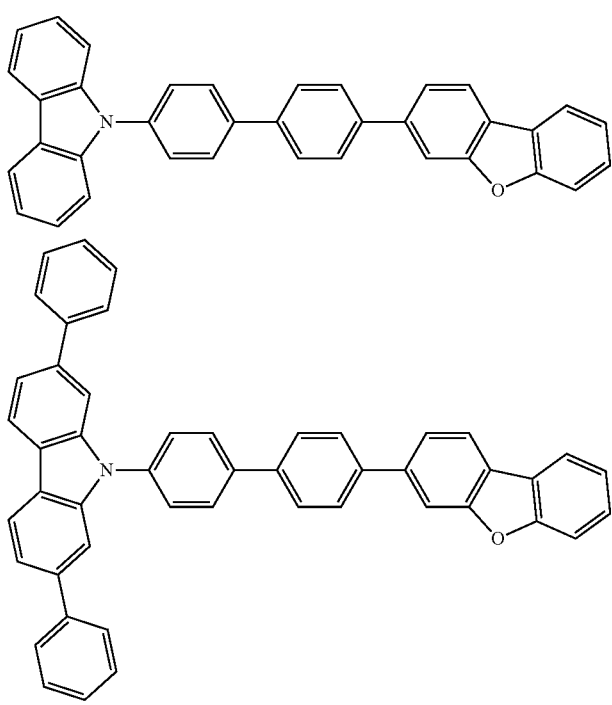

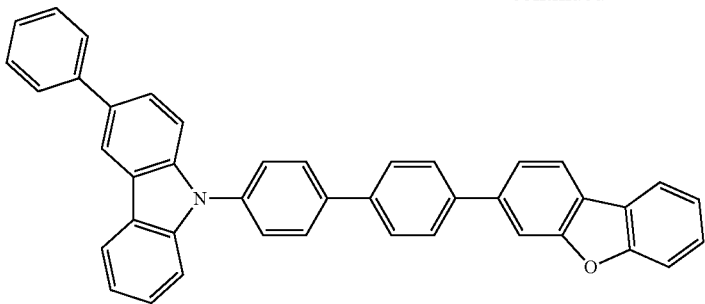
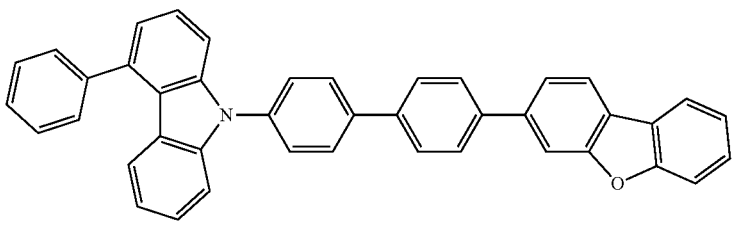
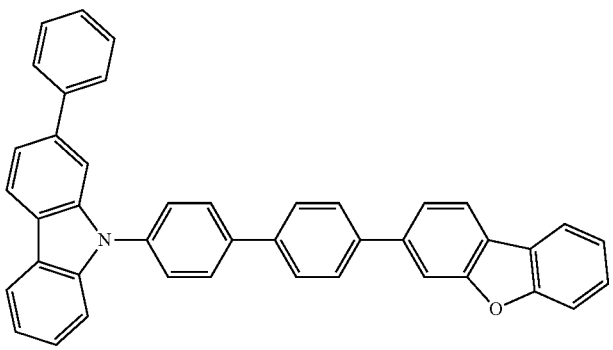

-continued
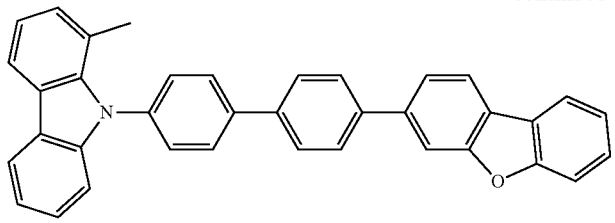
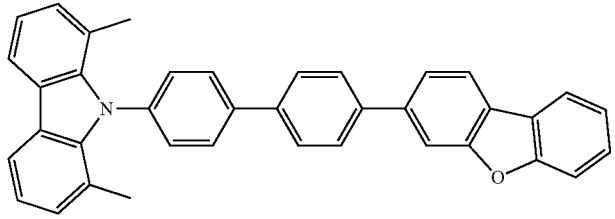
[Formula 42]
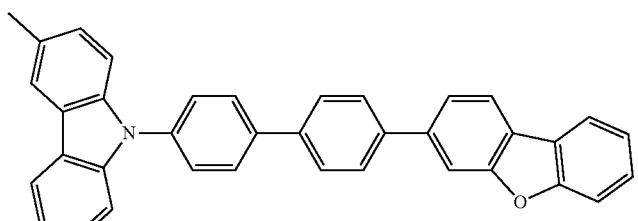
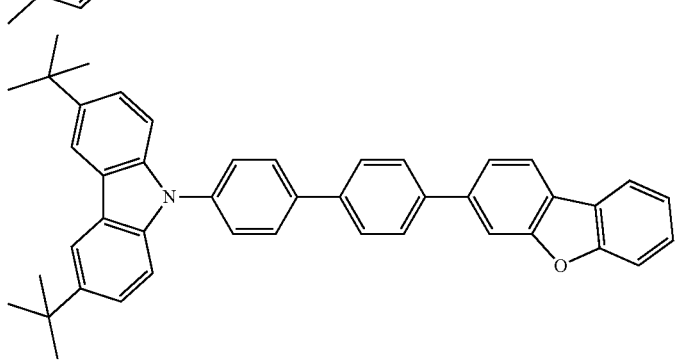
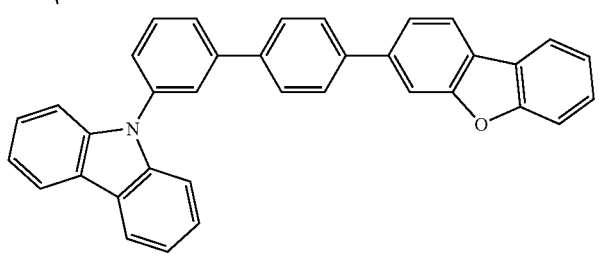
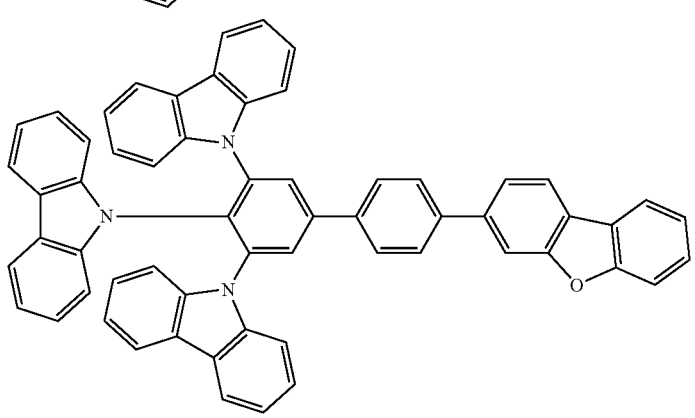

-continued
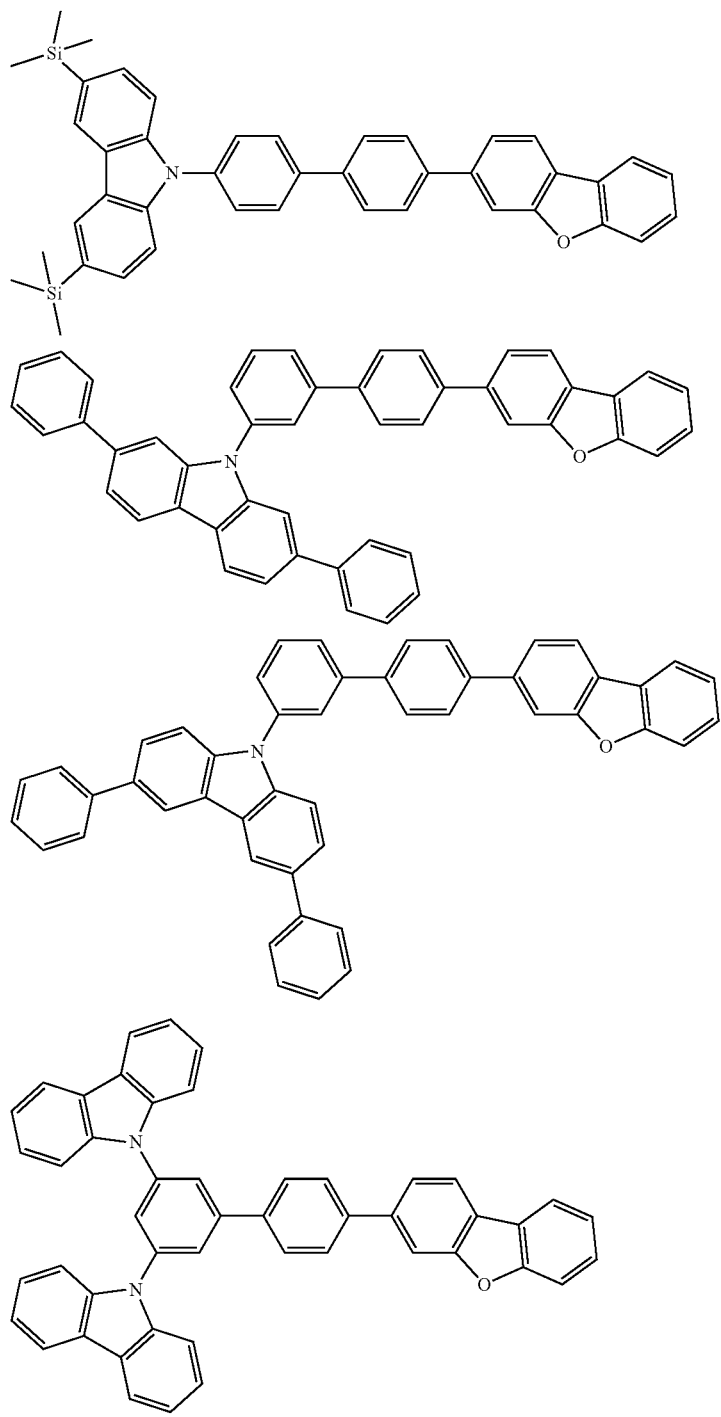
[Formula 43]
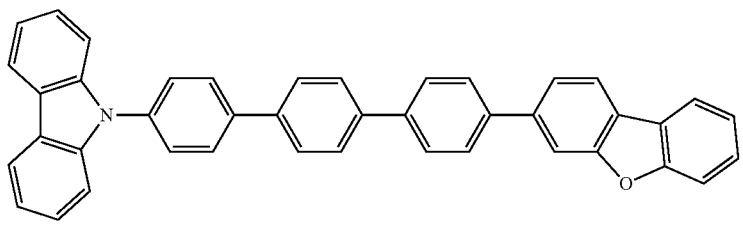

-continued
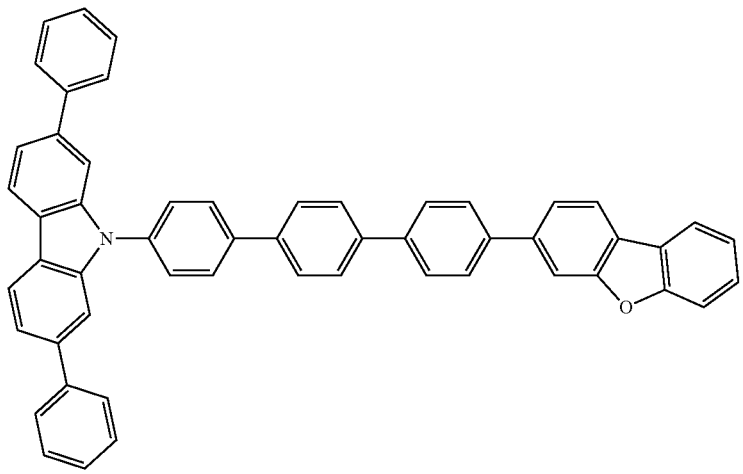
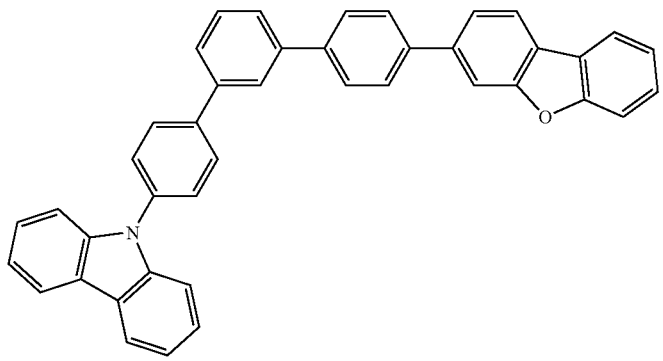
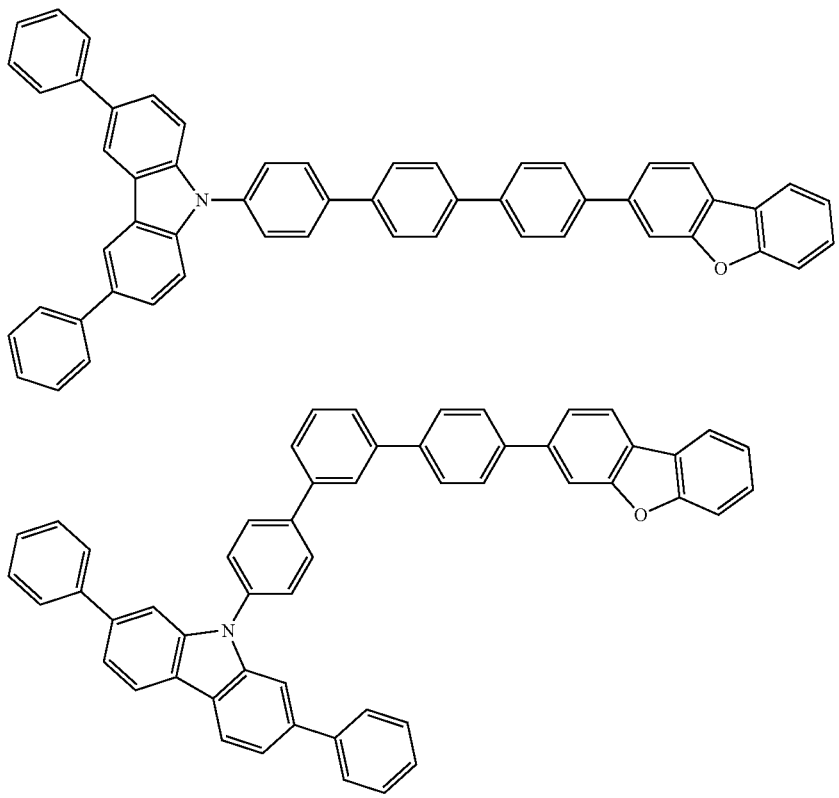

-continued
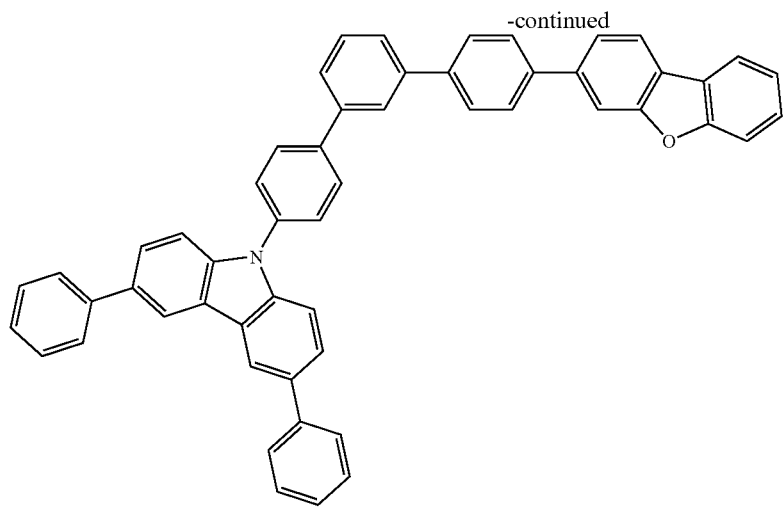
[Formula 44]
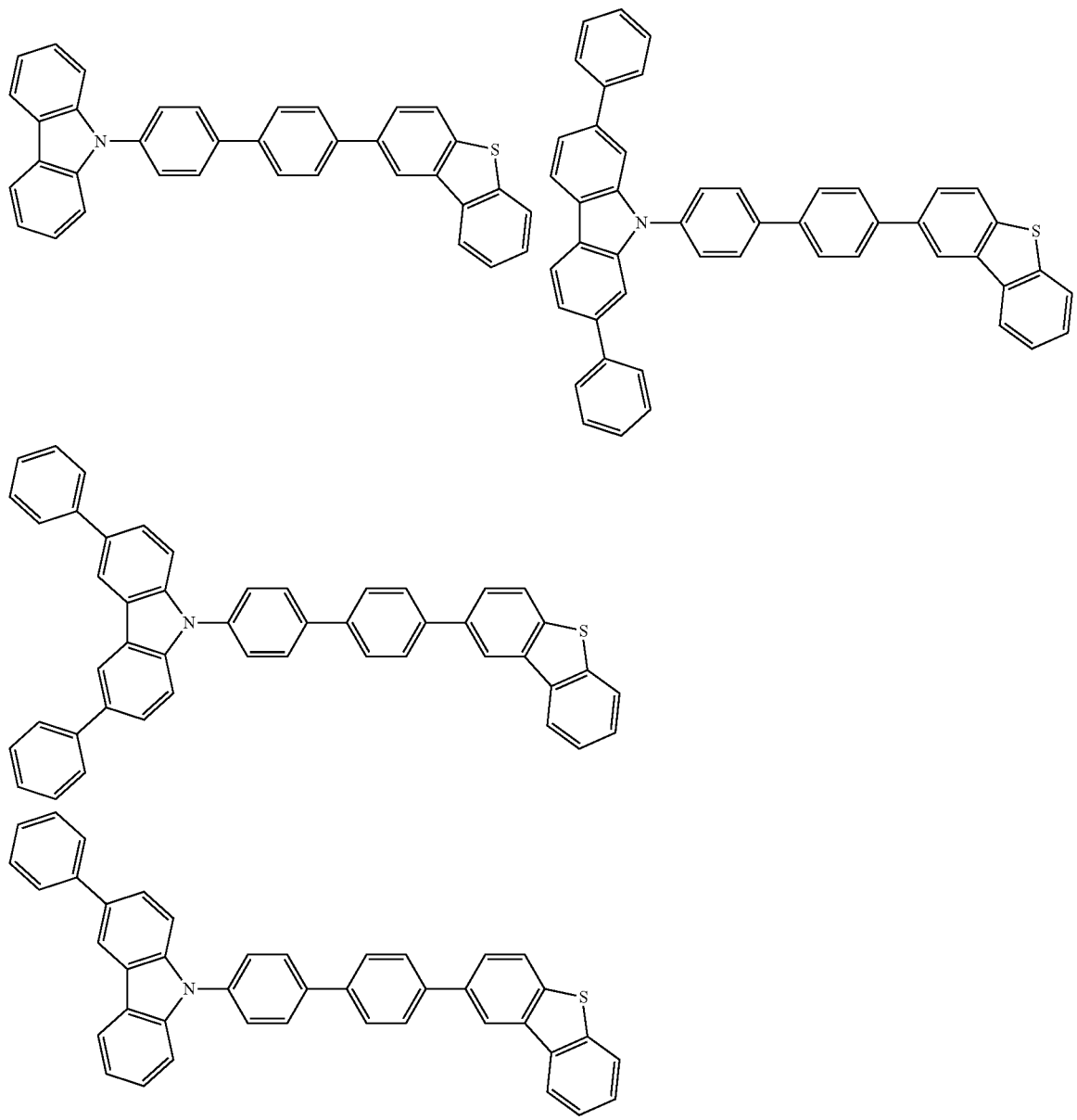

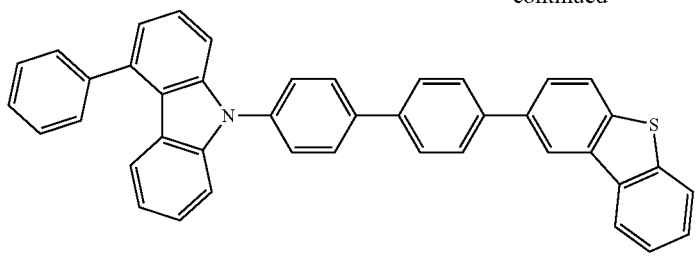
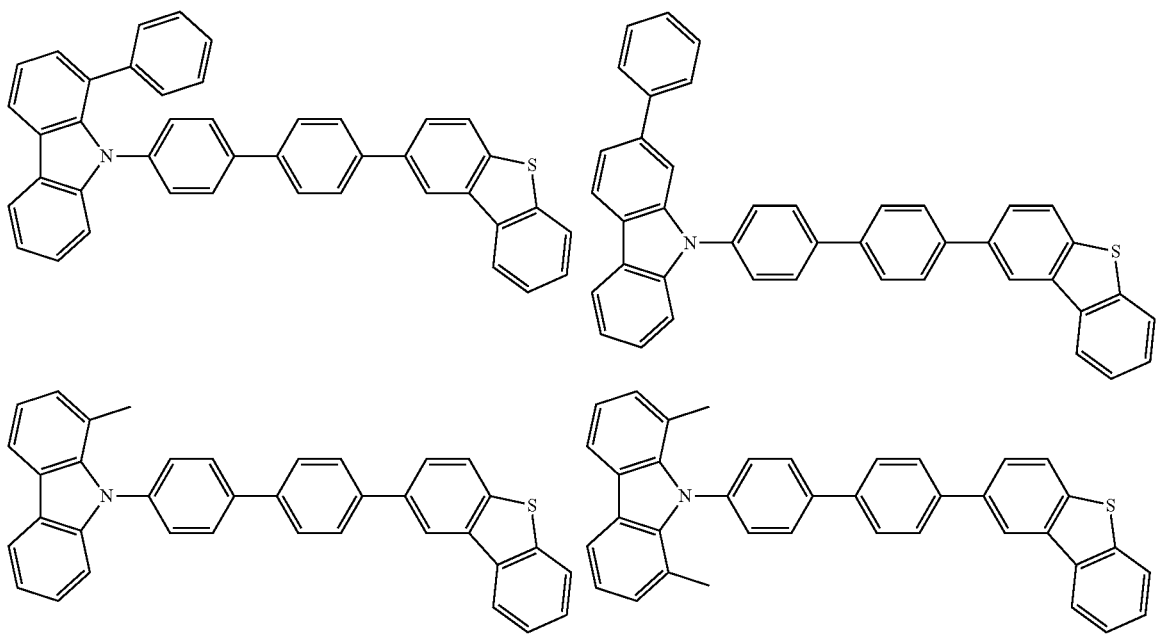
[Formula 45]
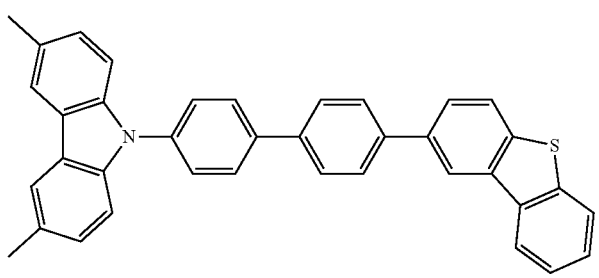
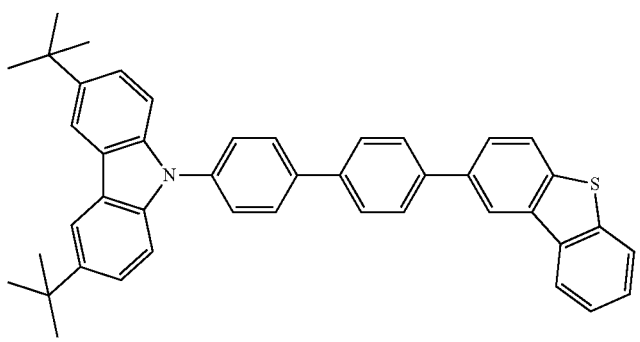

-continued
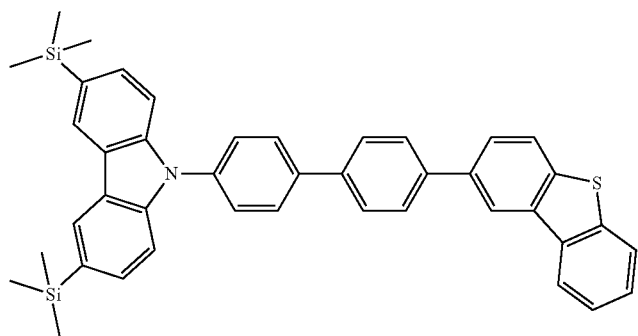
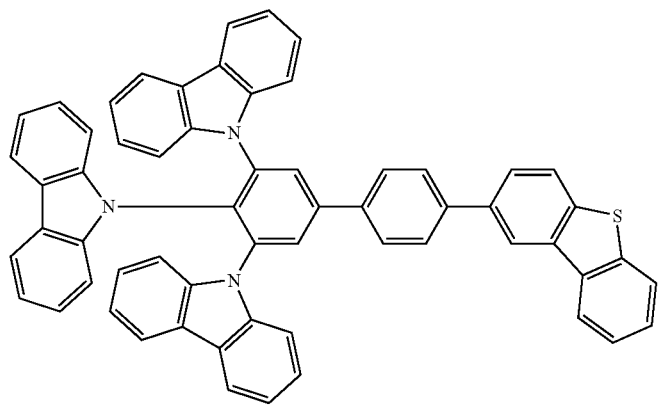
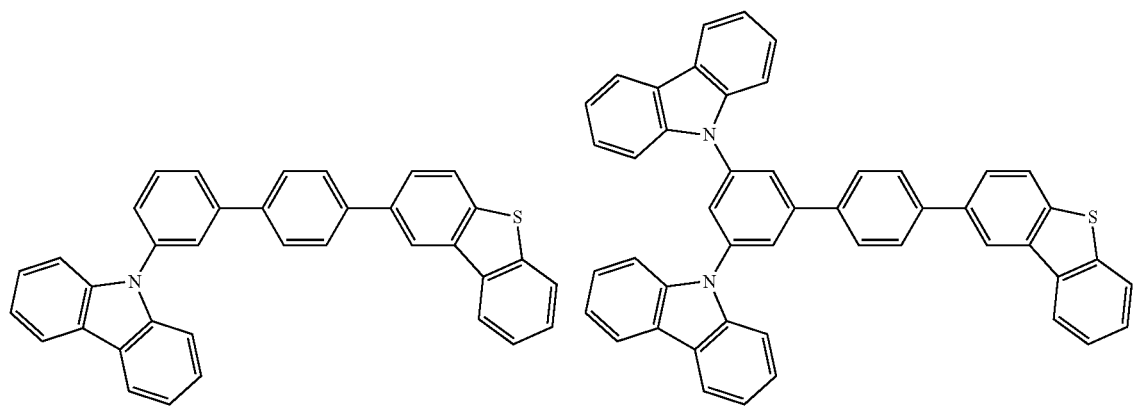
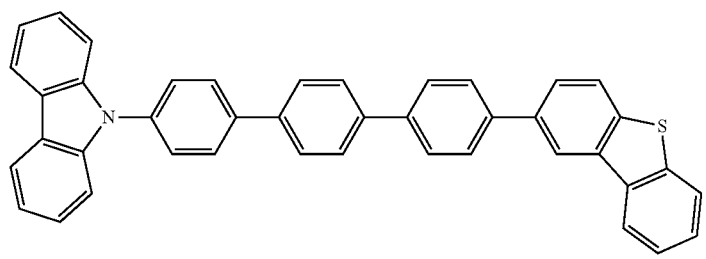
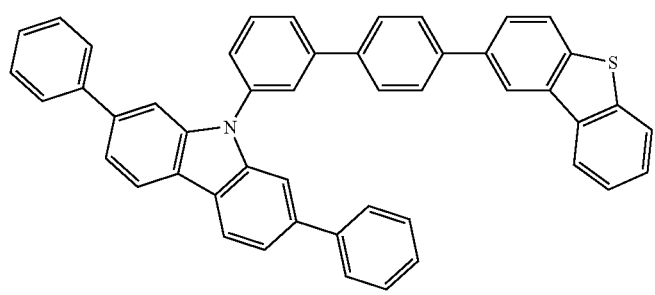

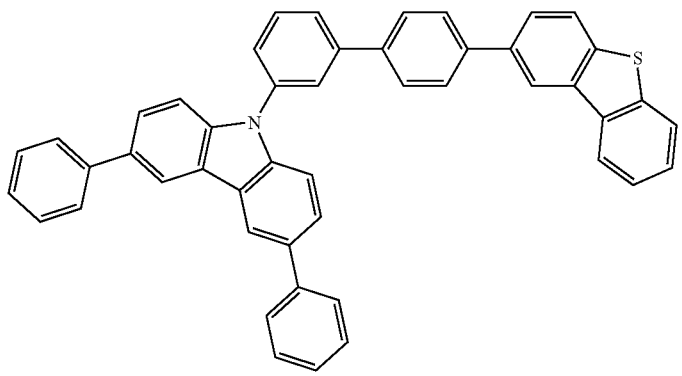 [SMILES: c1ccc(-c2ccc3c(c2)c2cc(-c4ccccc4)ccc2n3-c2cccc(-c3ccc(-c4ccc5sc6ccccc6c5c4)cc3)c2)cc1]
[Formula 46]
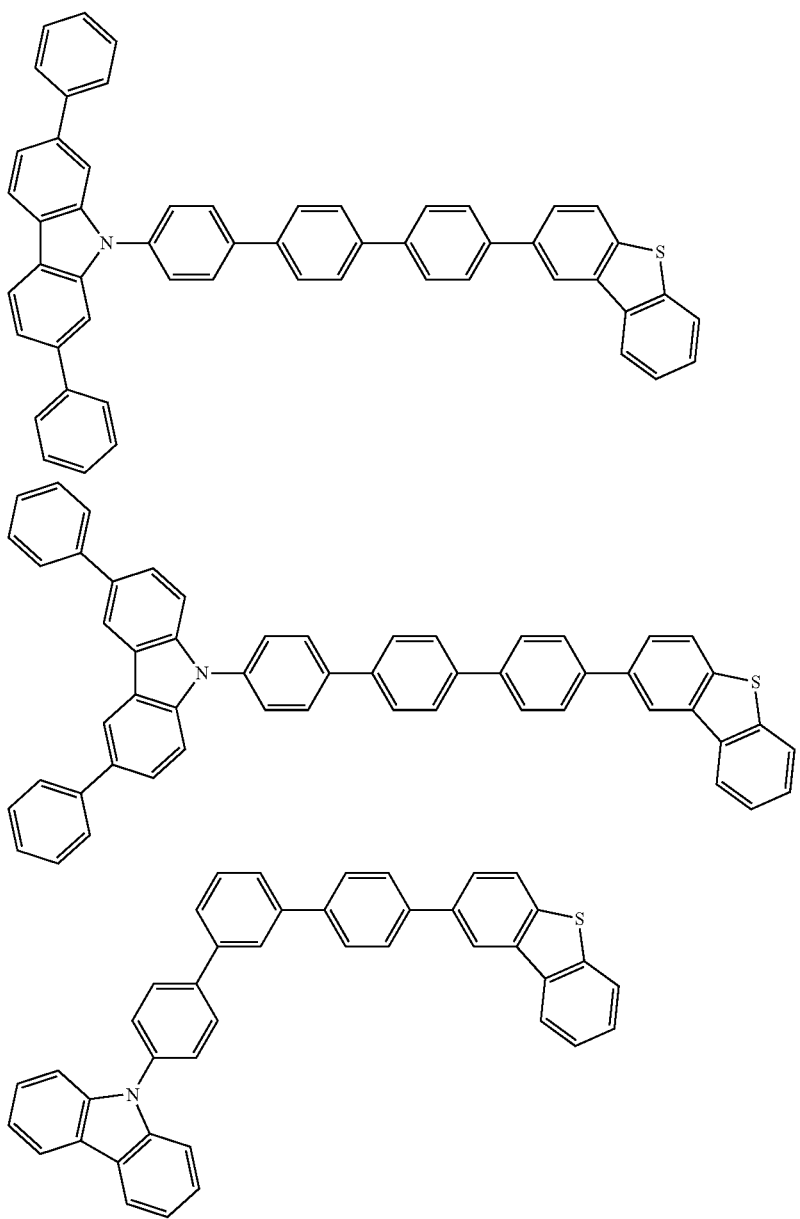

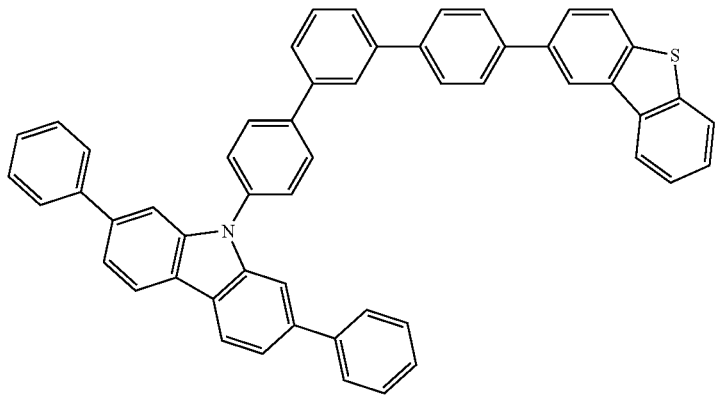
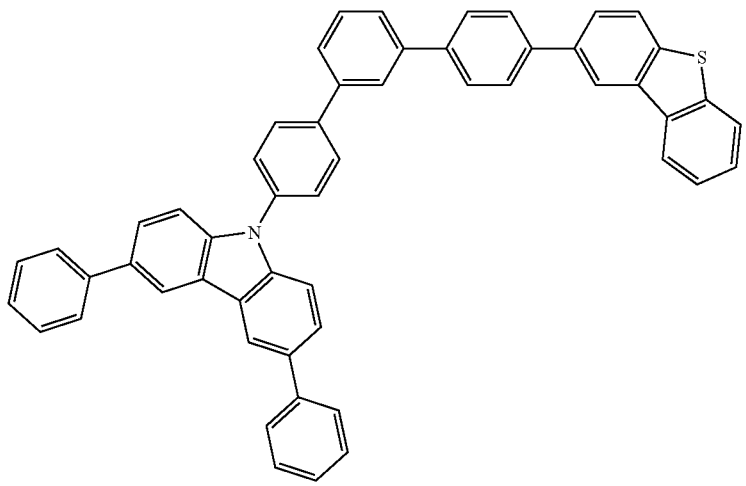
[Formula 47]
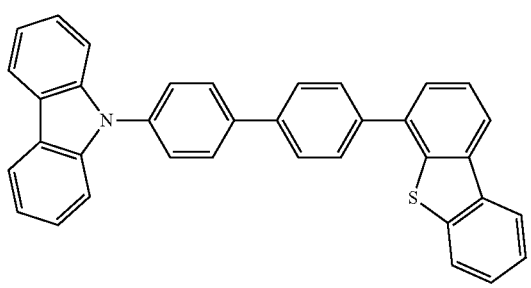
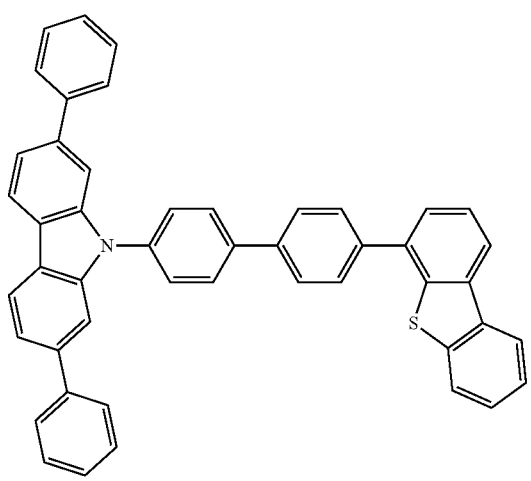

-continued
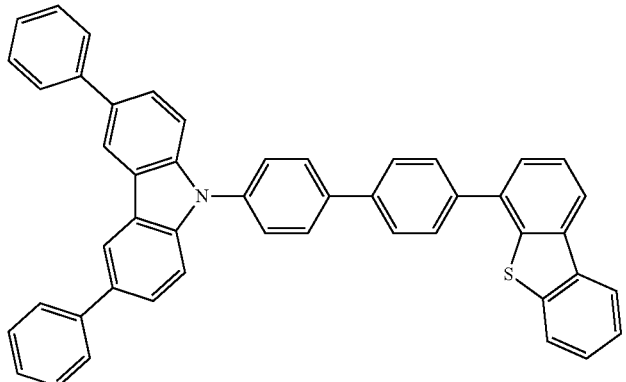
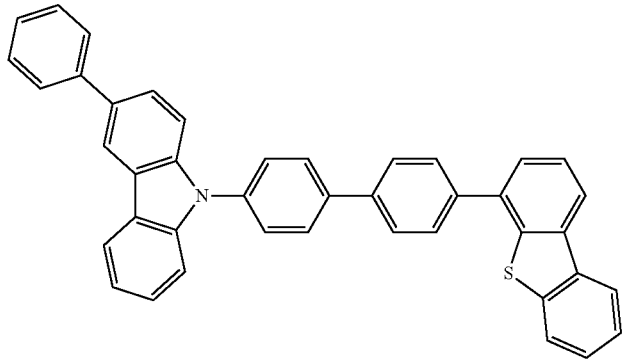
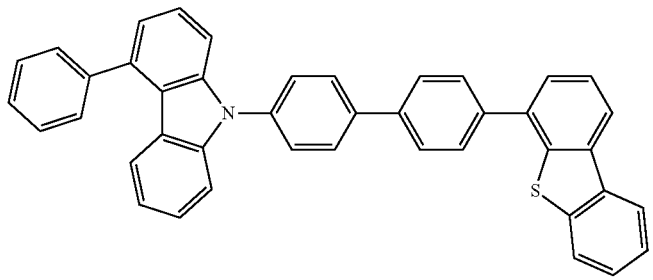
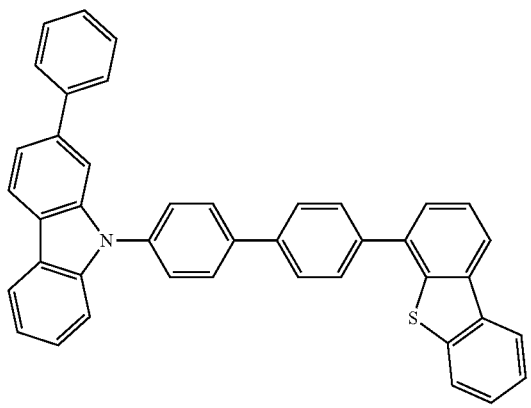
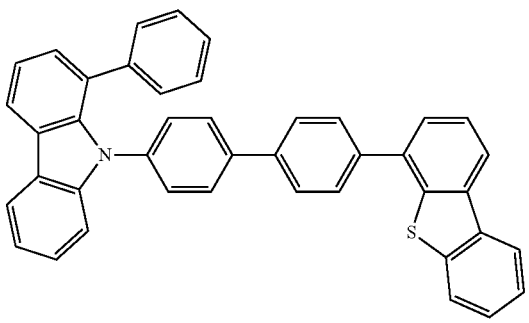
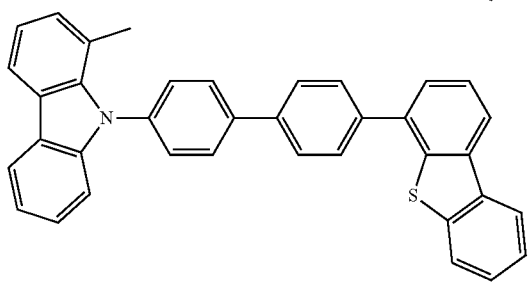
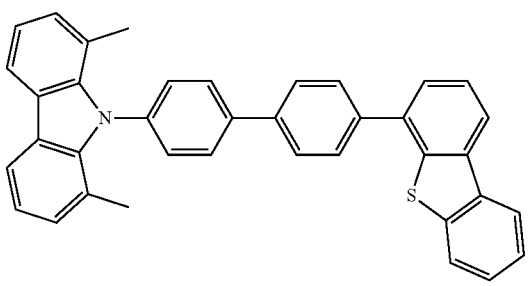

[Formula 48]
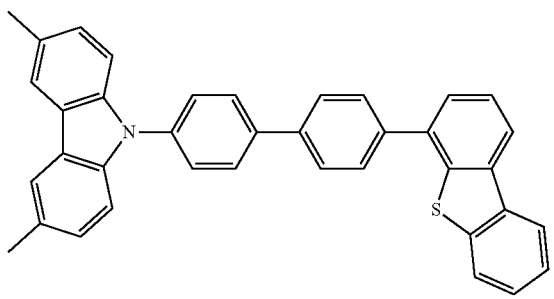
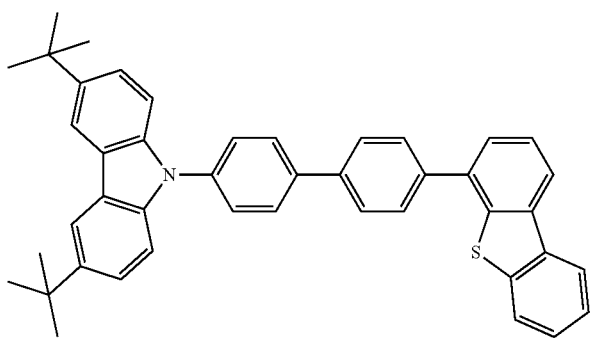
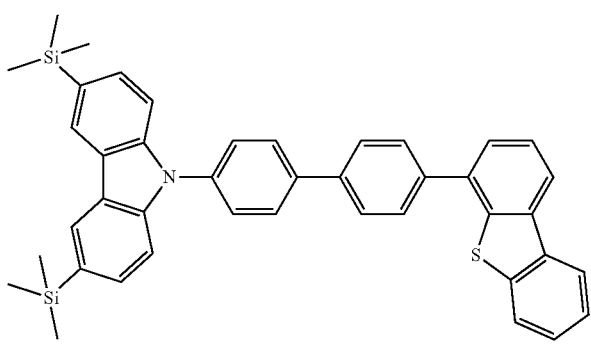
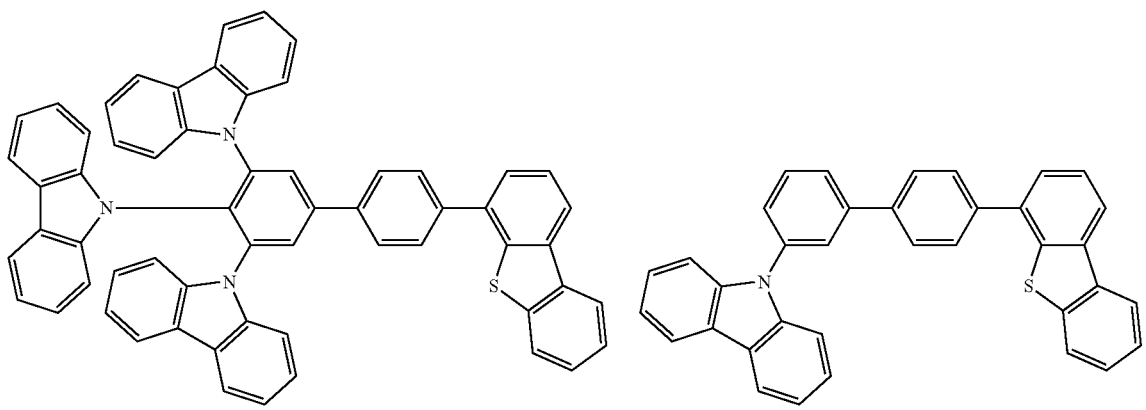

-continued
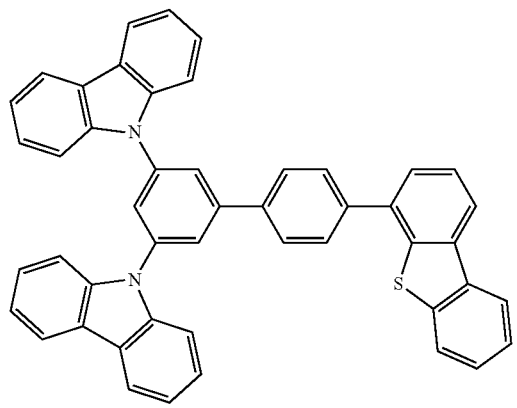
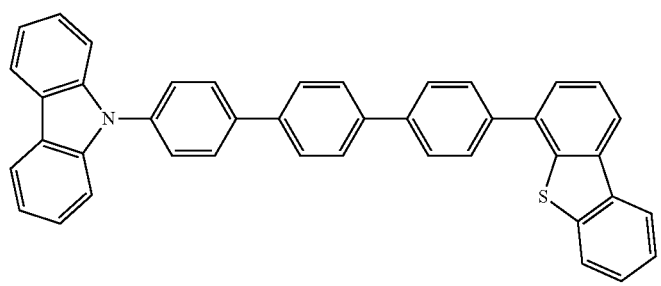
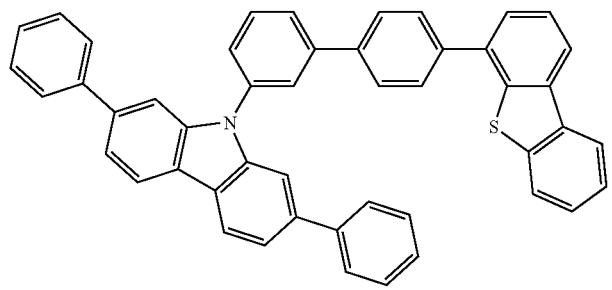
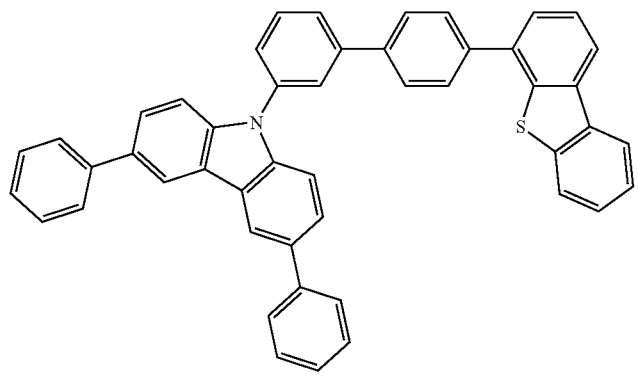

[Formula 49]
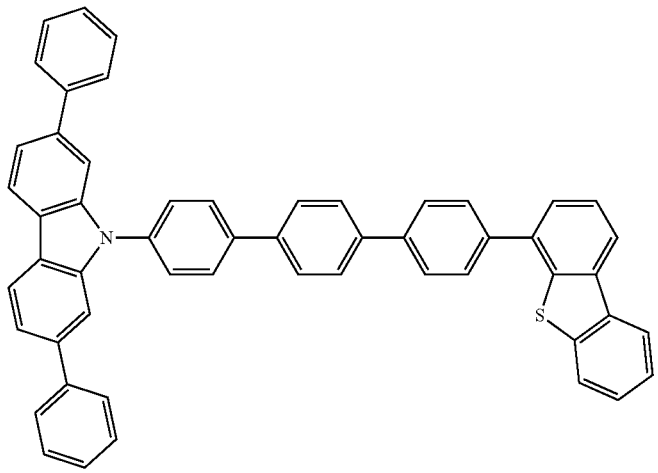
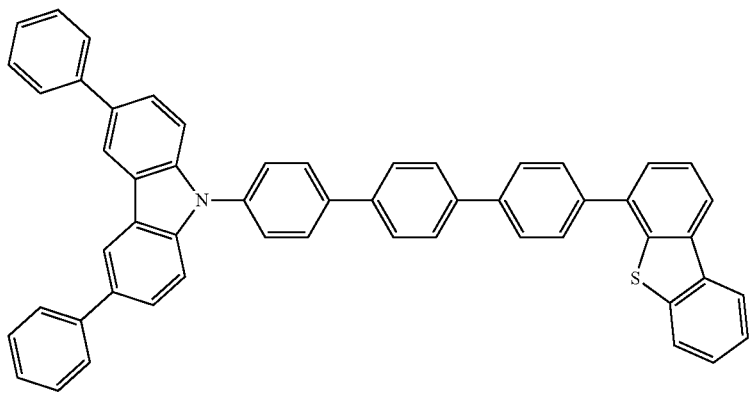
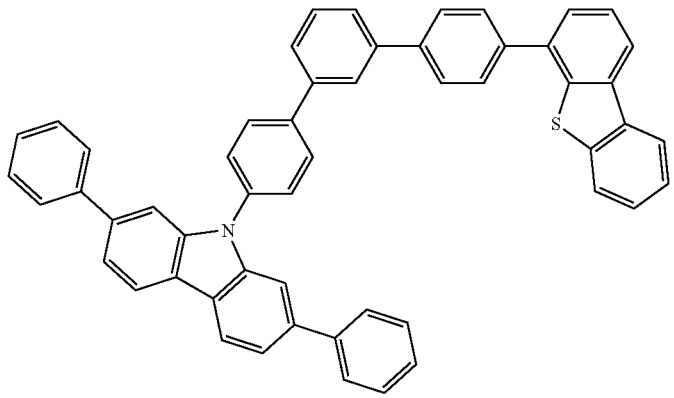
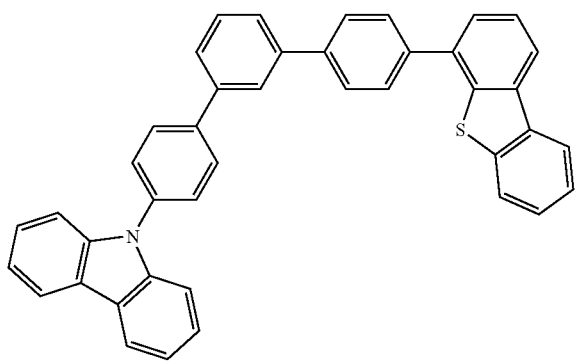

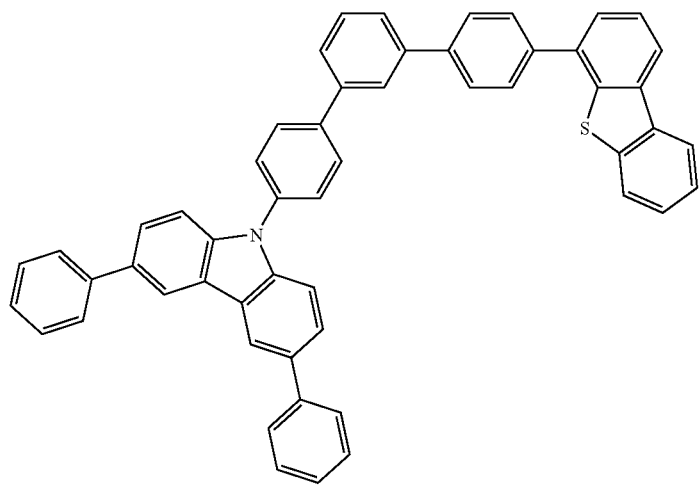
[Formula 50]
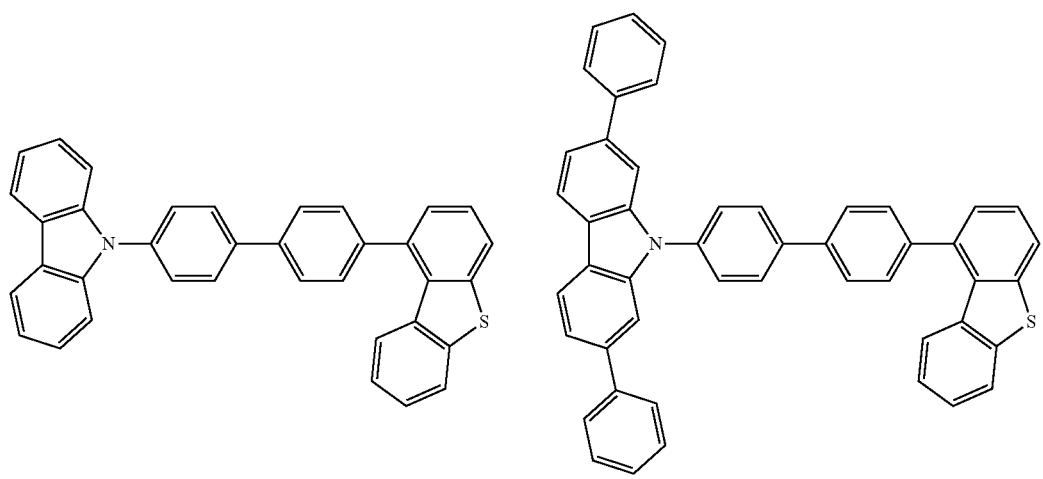
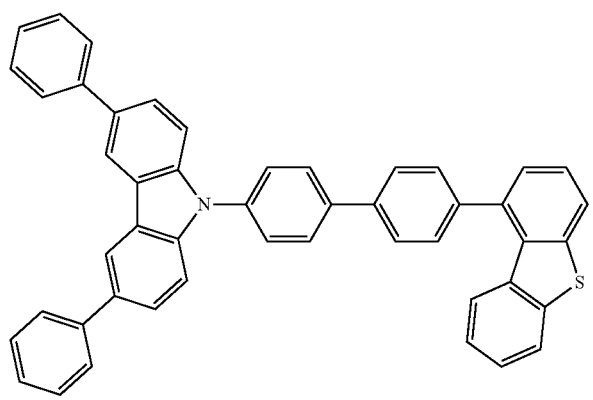

-continued
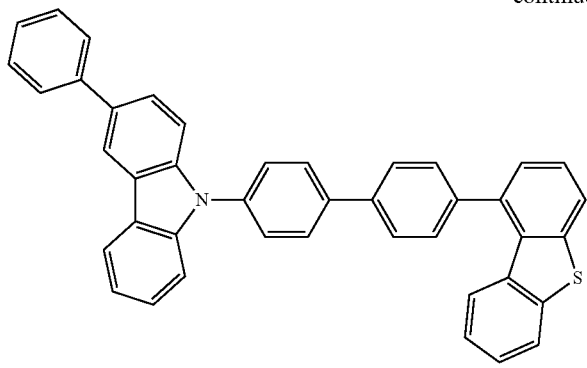
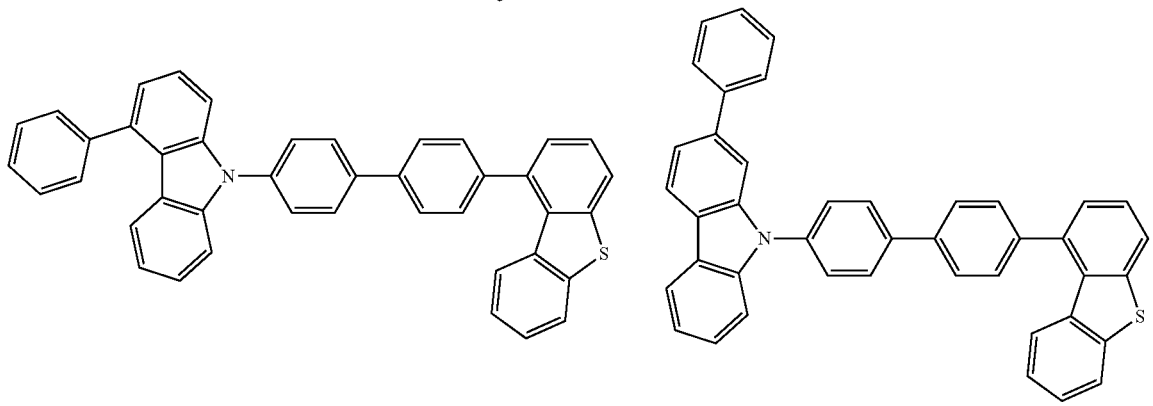
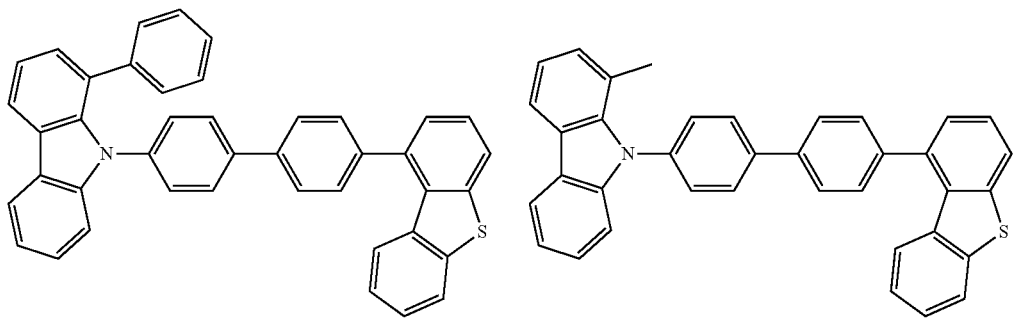
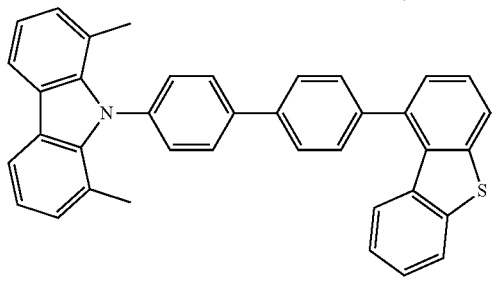
[Formula 51]
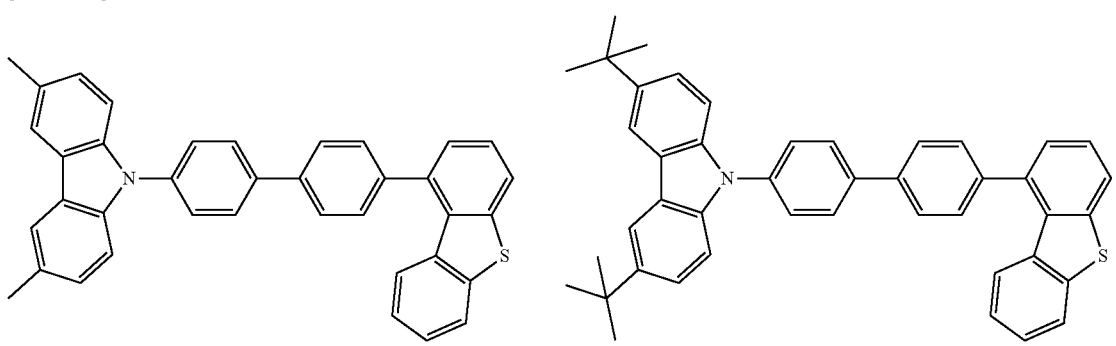

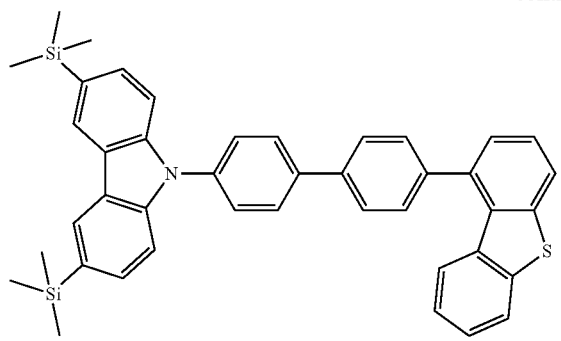
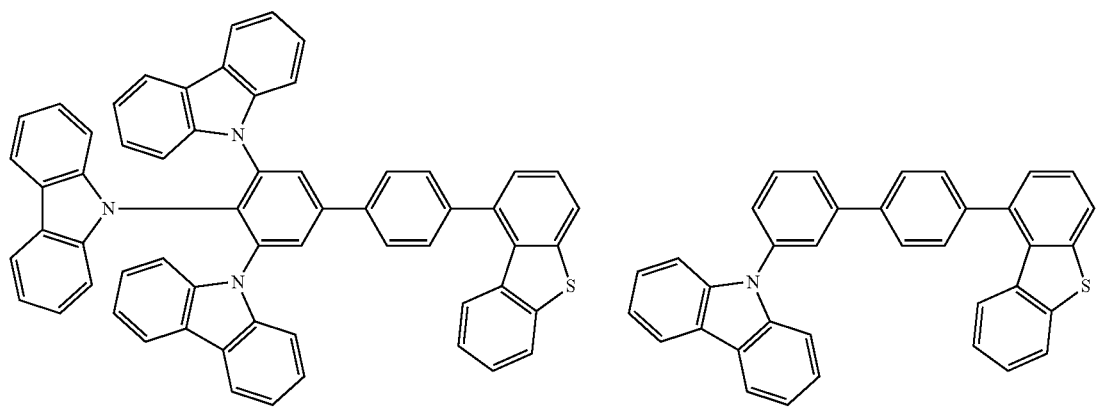
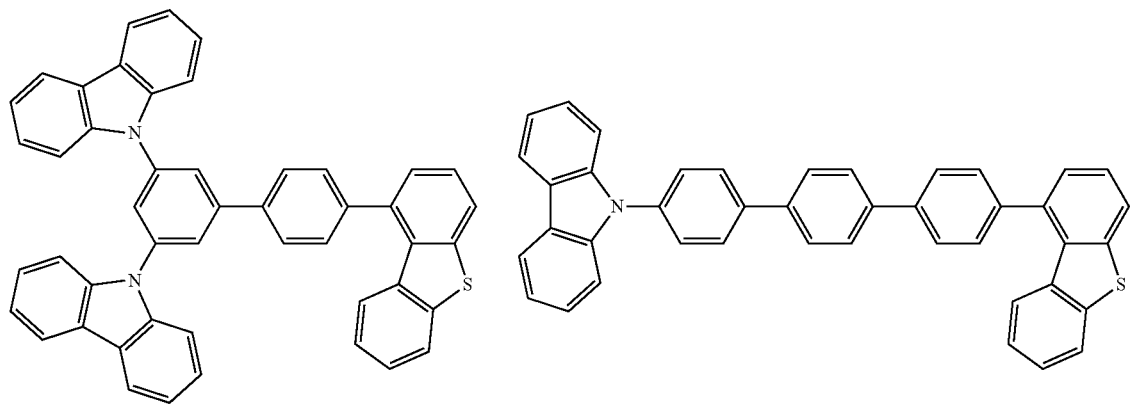
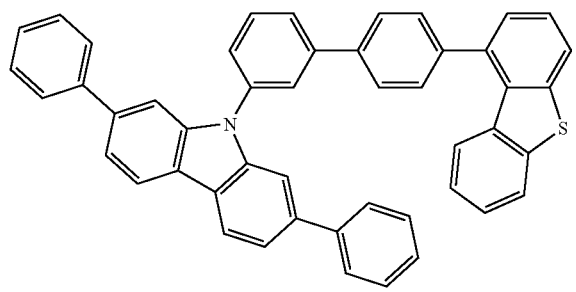

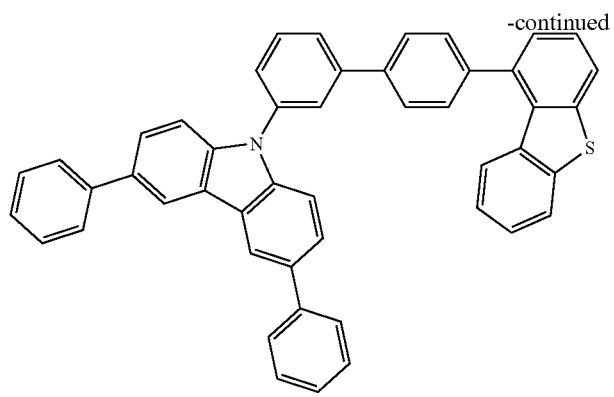
[Formula 52]
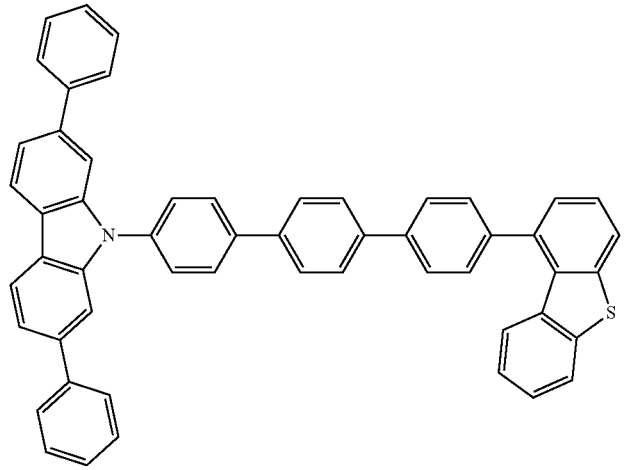
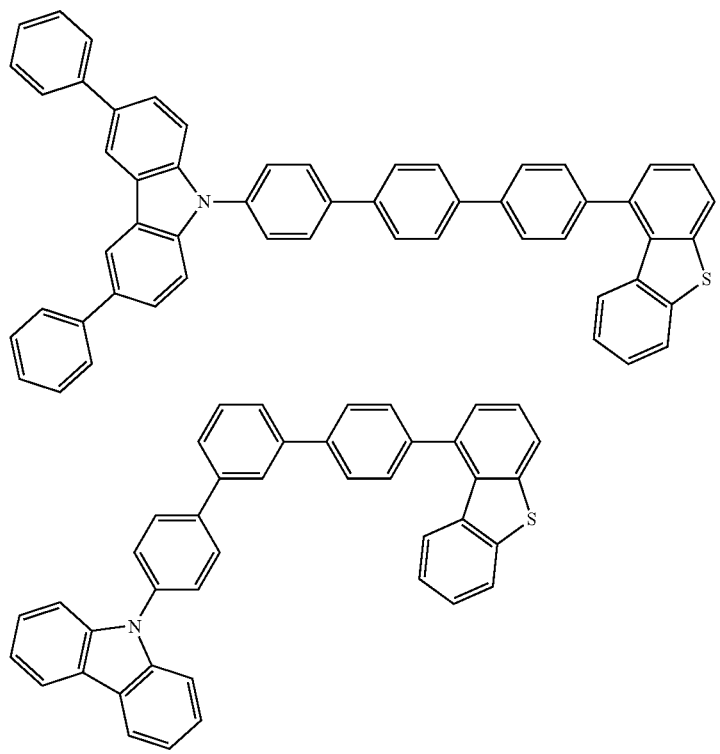

-continued
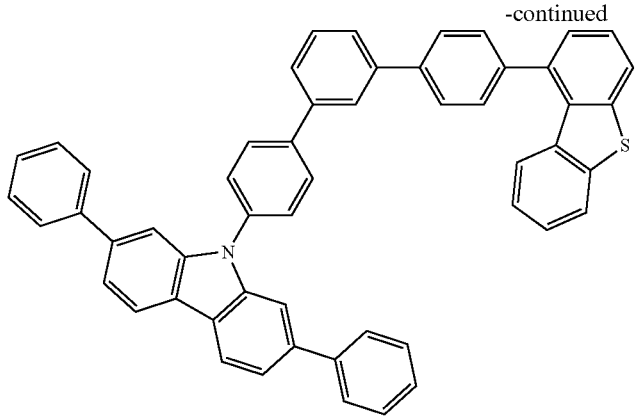
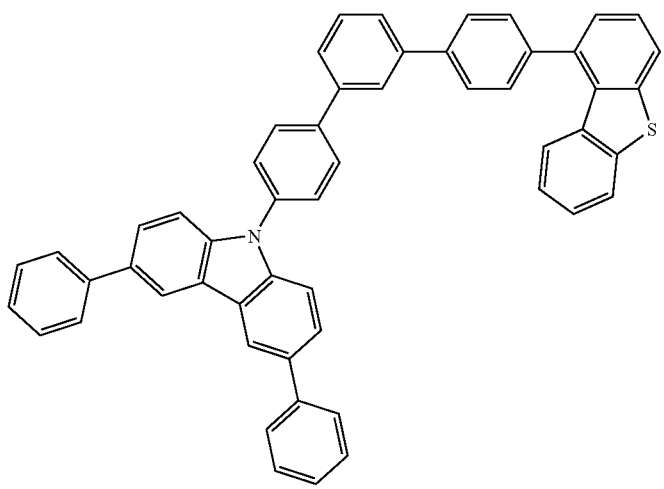
[Formula 53]
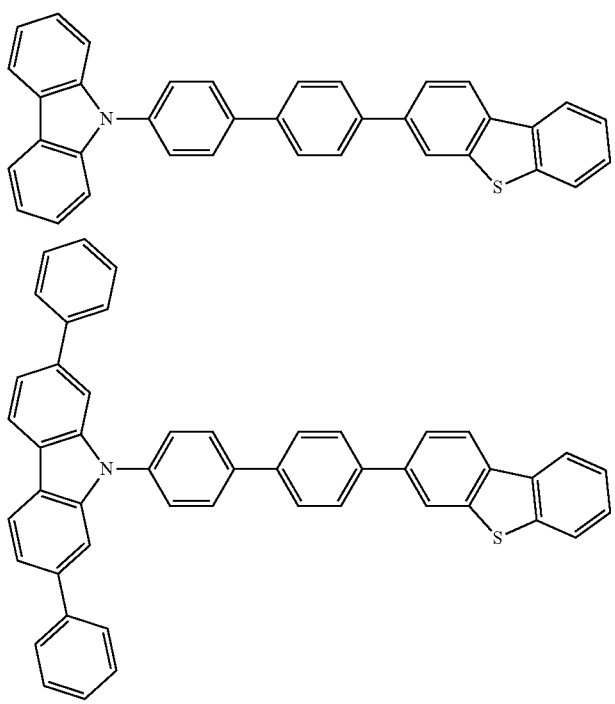

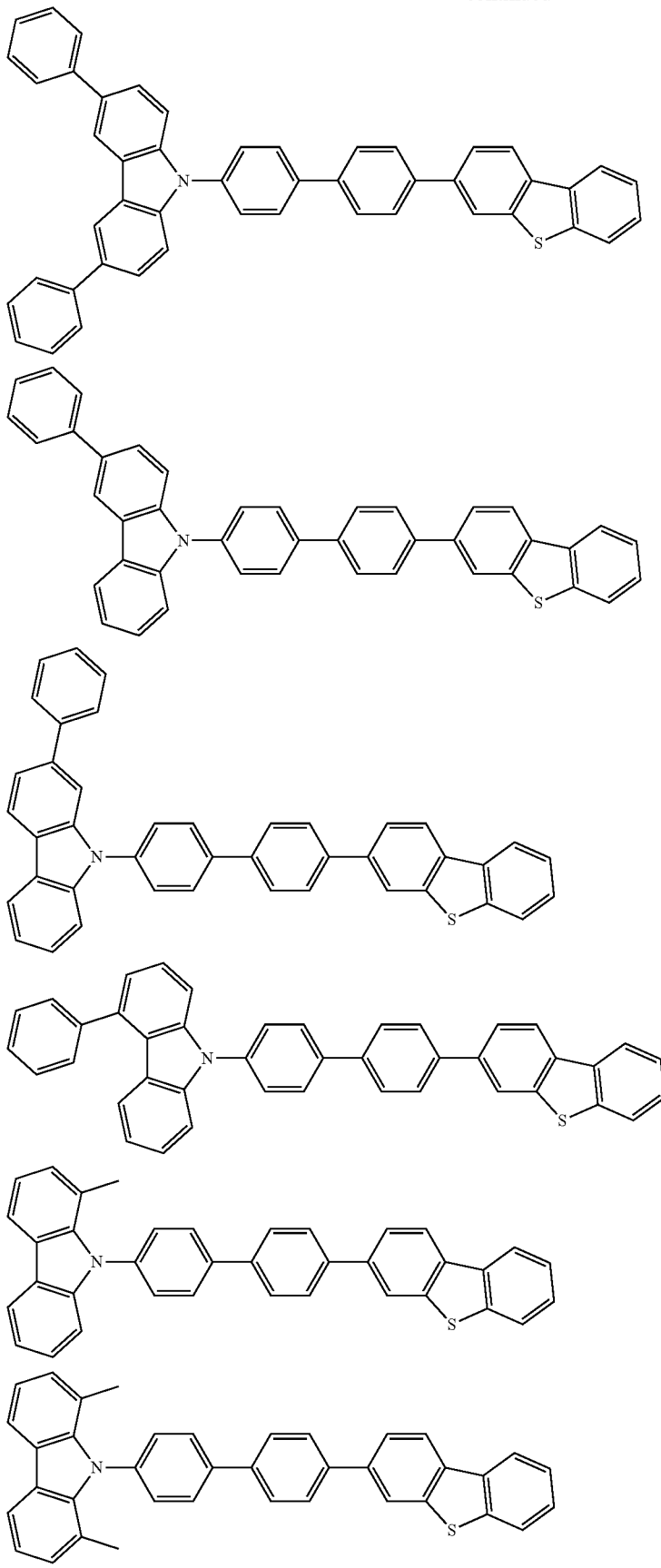

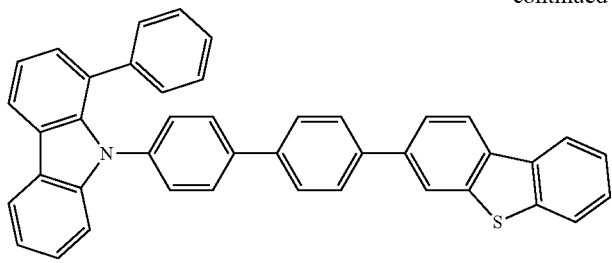
[Formula 54]
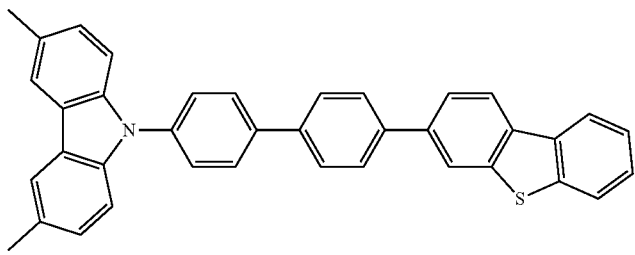
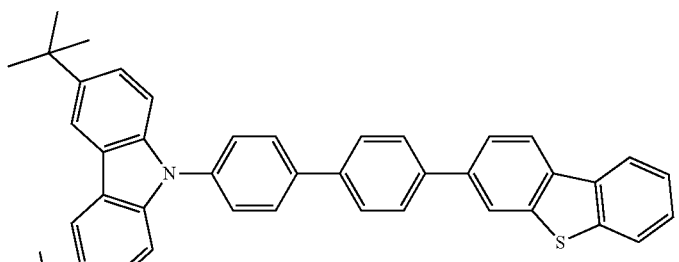
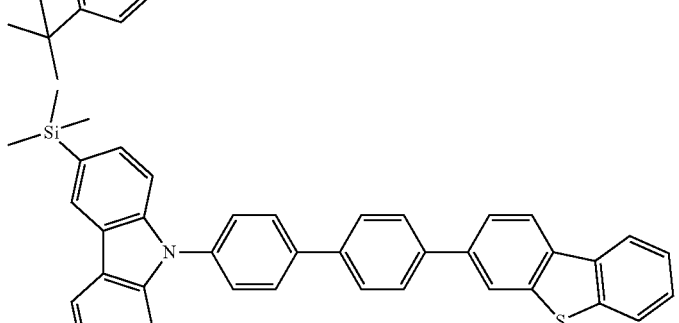
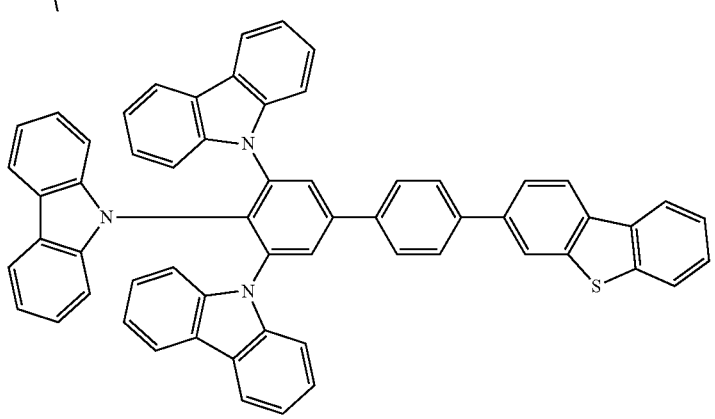

-continued
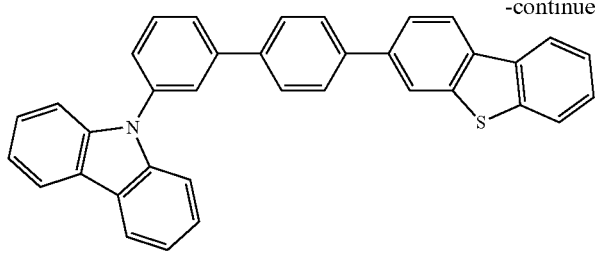
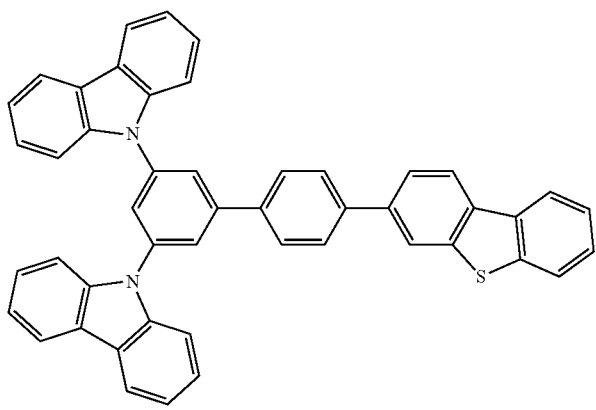
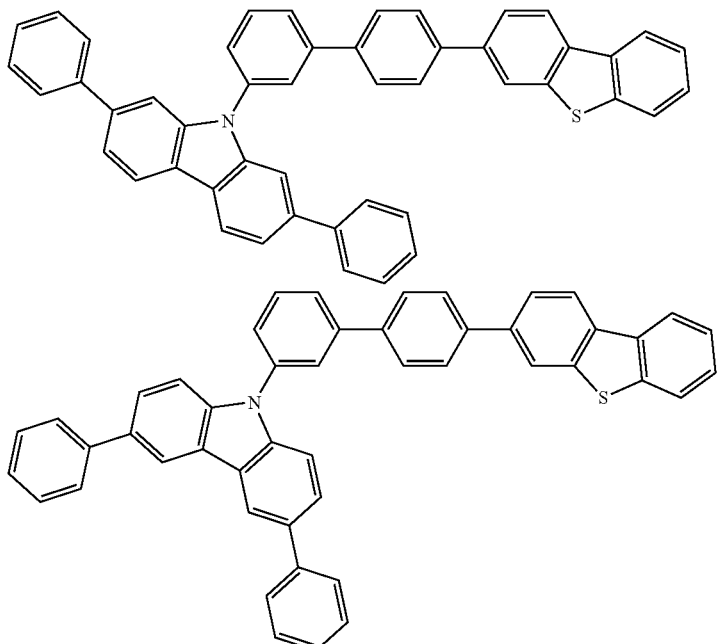
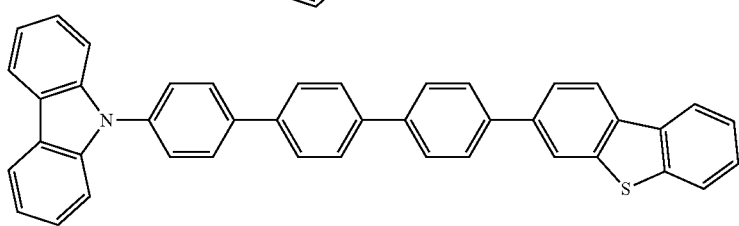

[Formula 55]
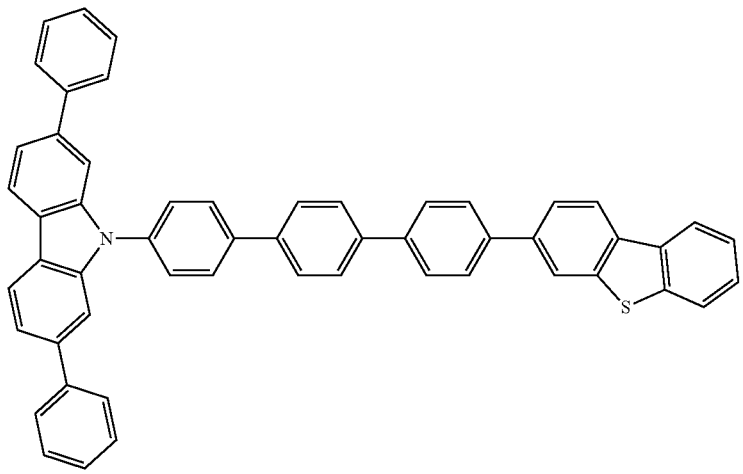
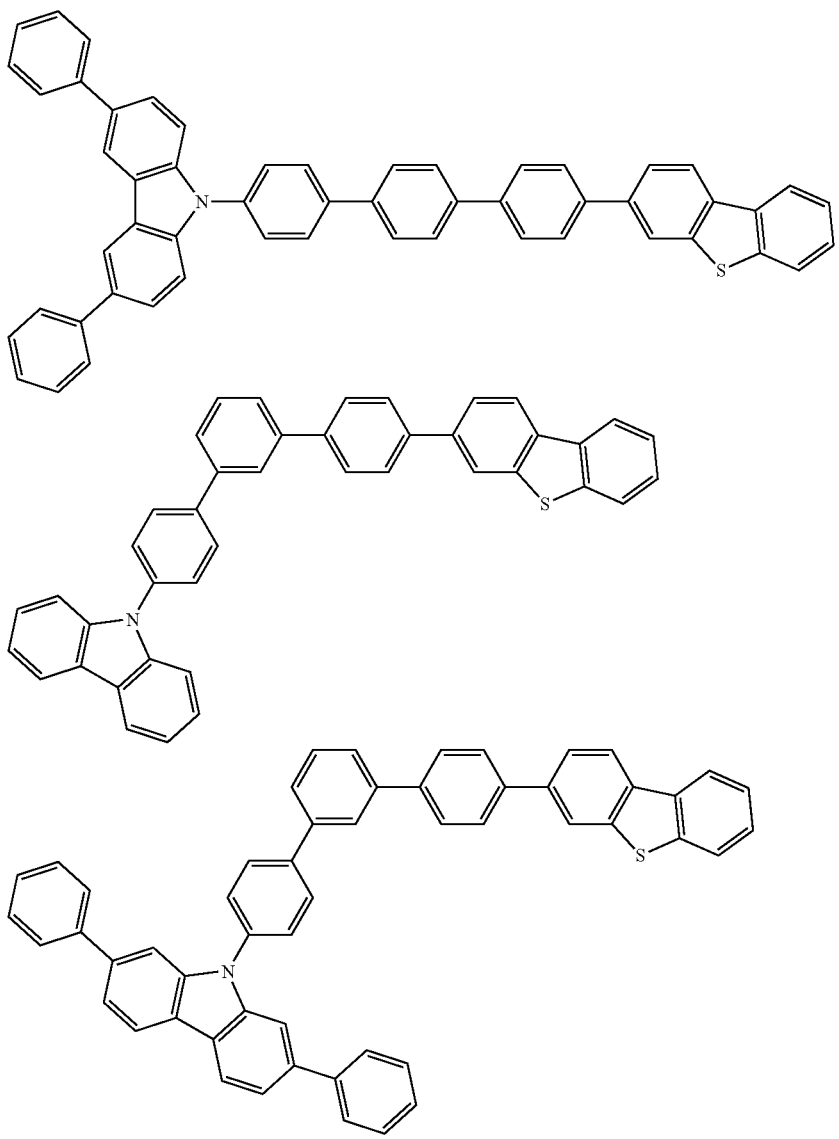

-continued
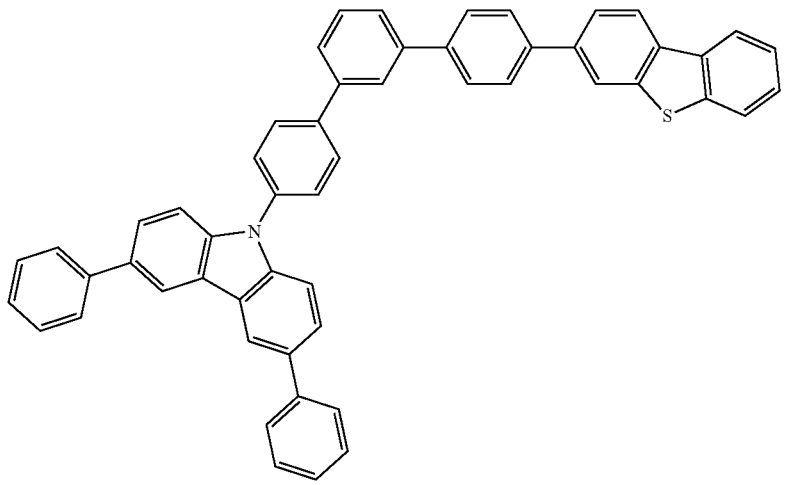
[Formula 56]
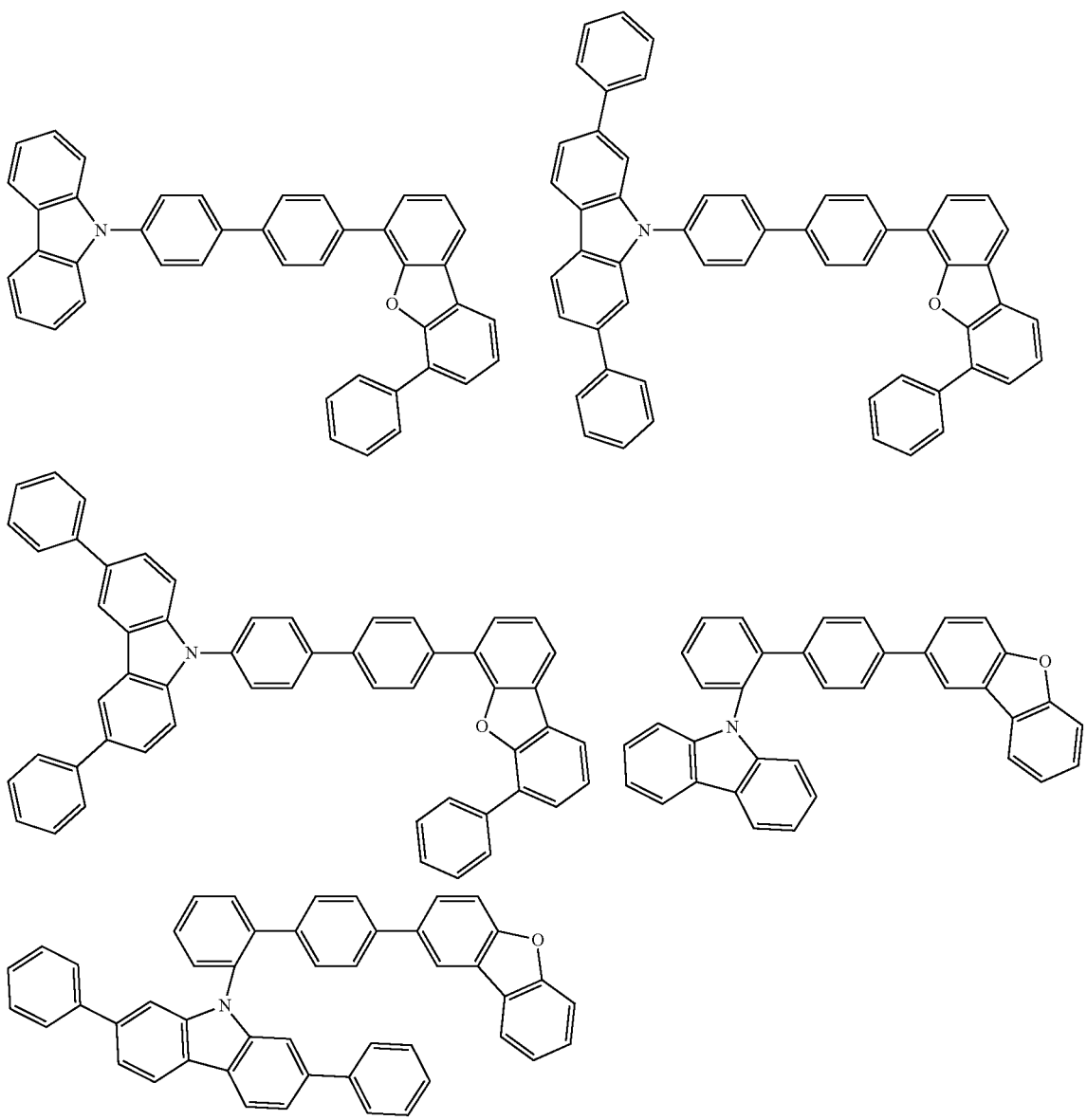

-continued
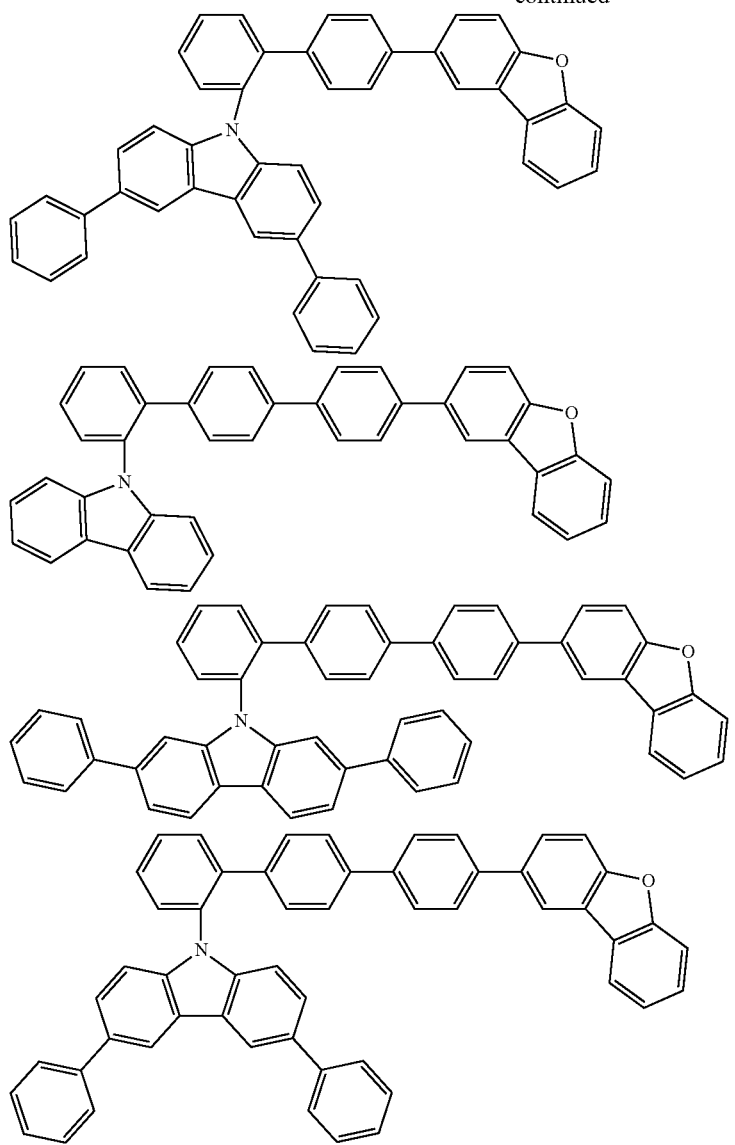
[Formula 57]
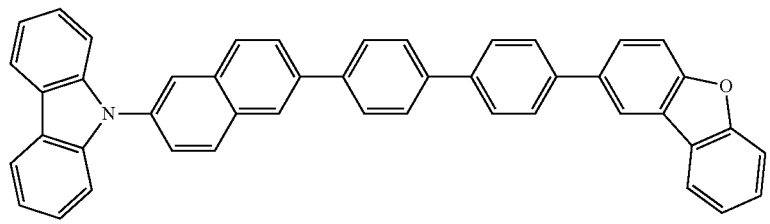
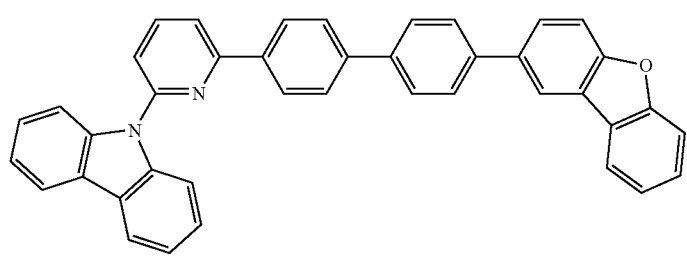

-continued
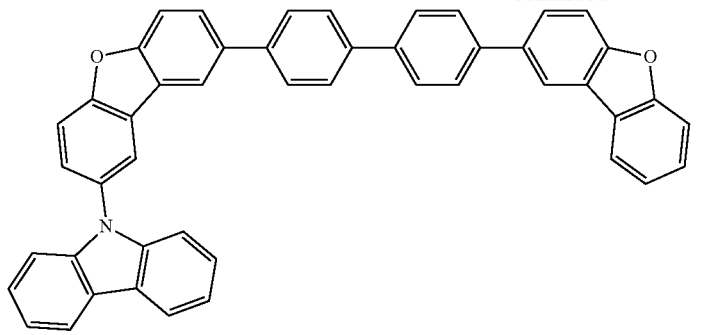
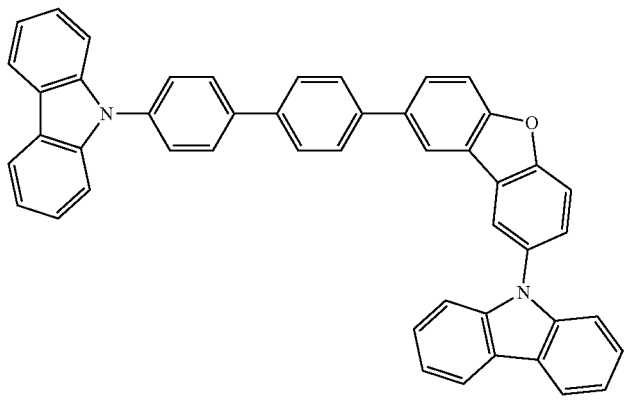
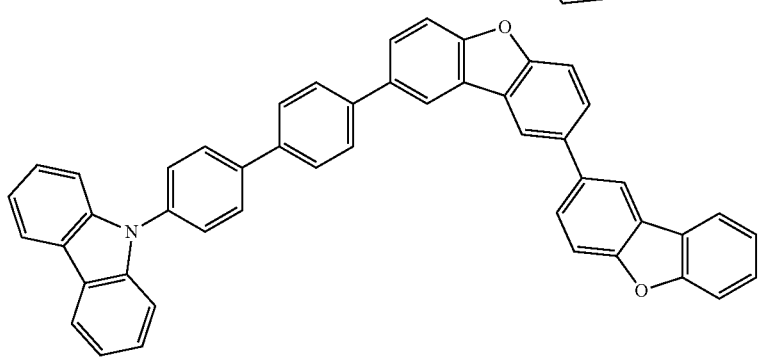
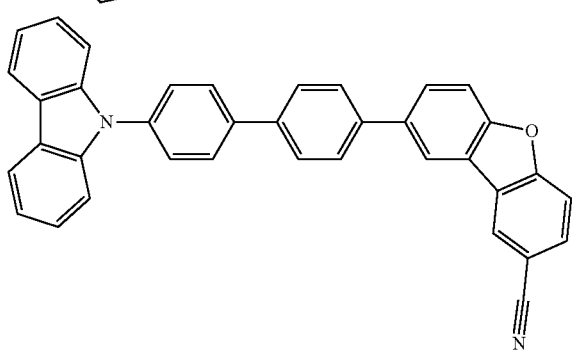
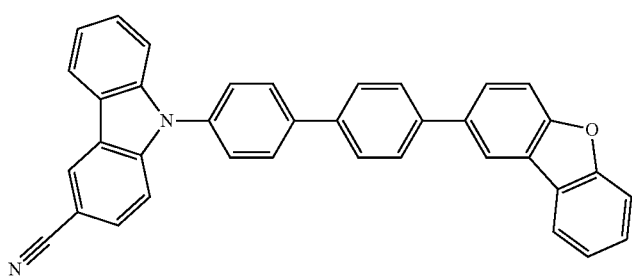

[Formula 58]
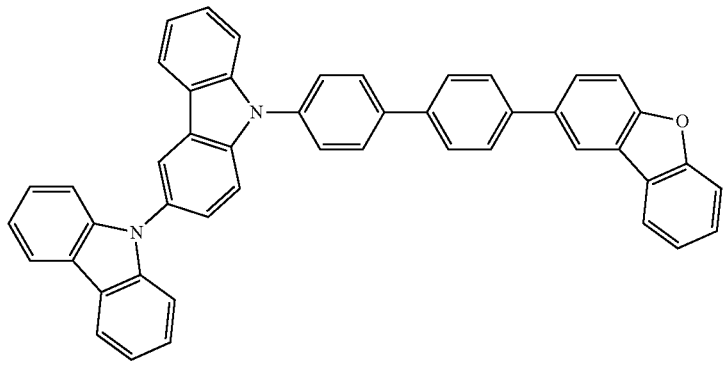
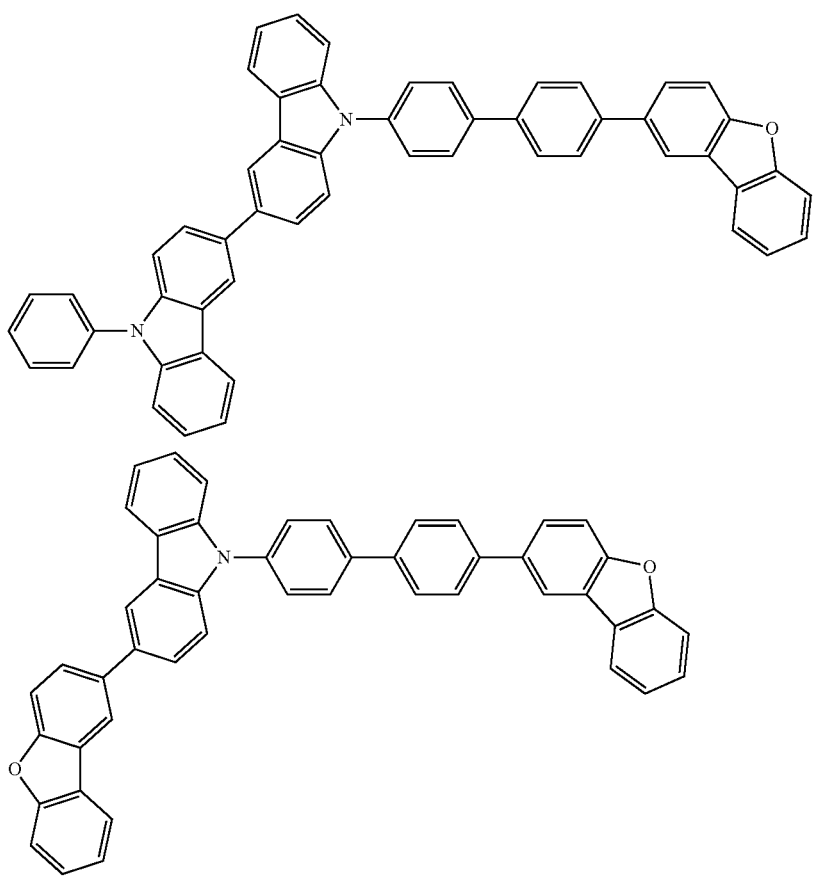
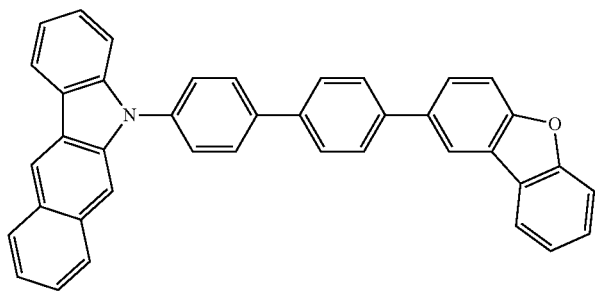

-continued
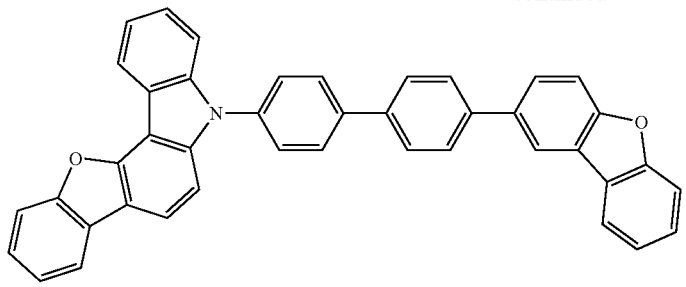
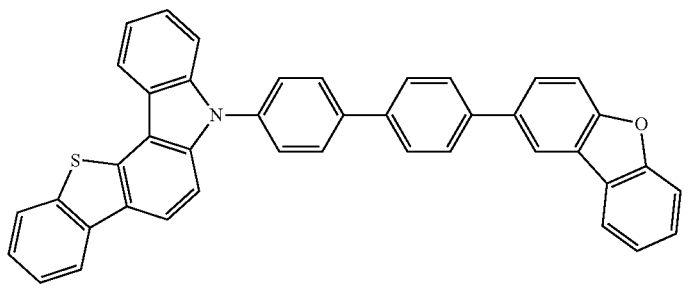
[Formula 59]
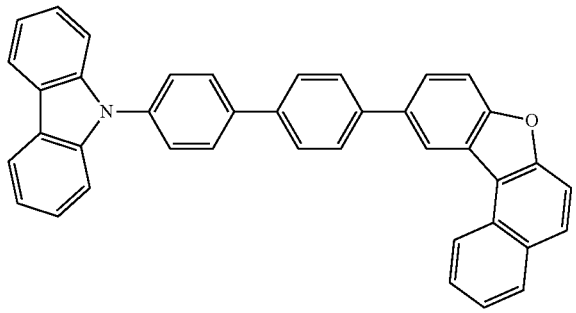
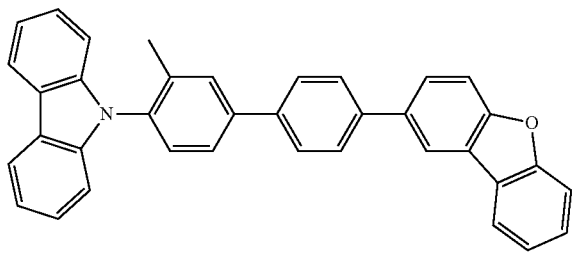
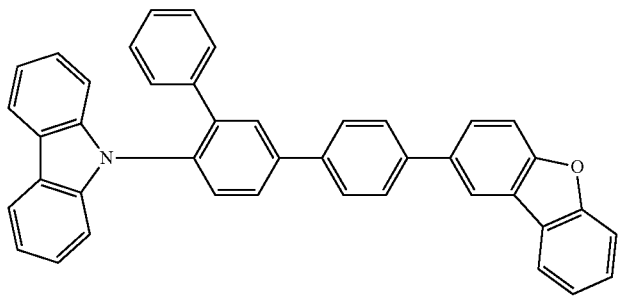

-continued
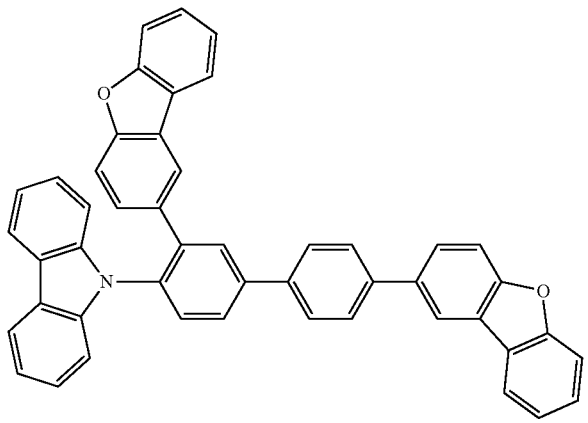
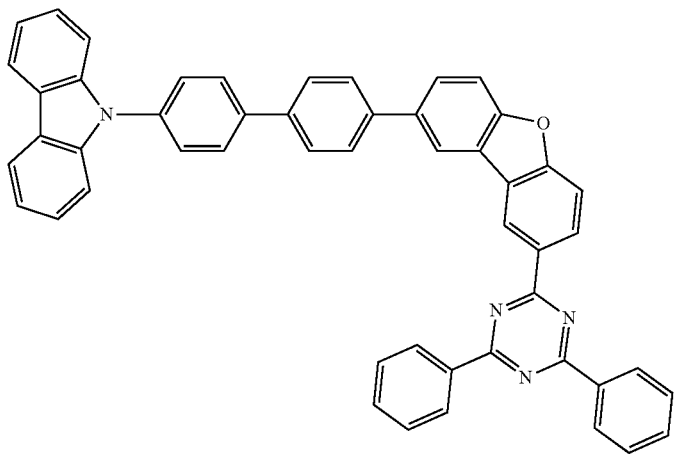
[Formula 60]
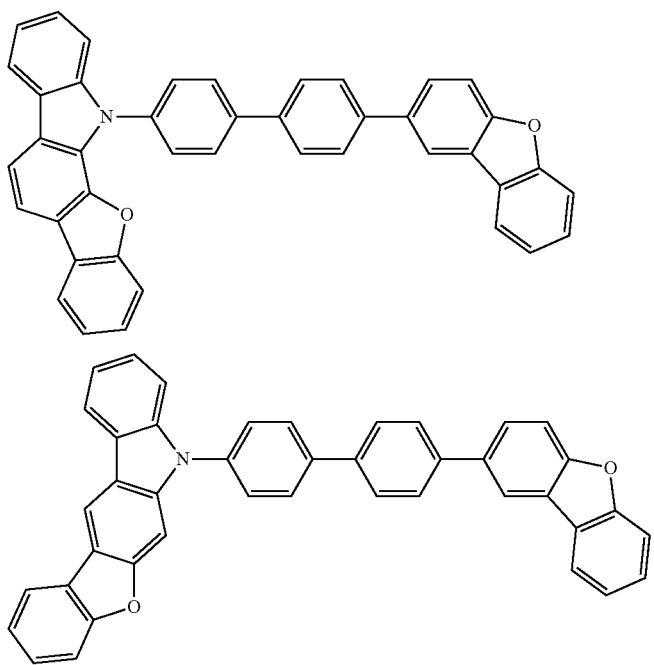

-continued
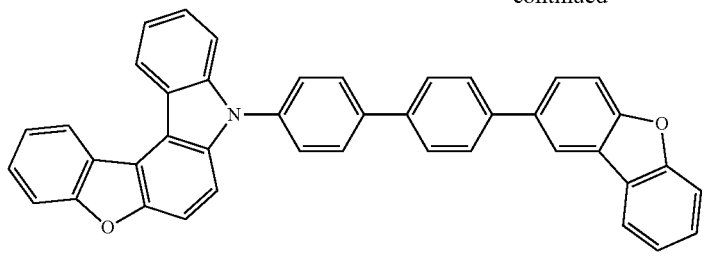
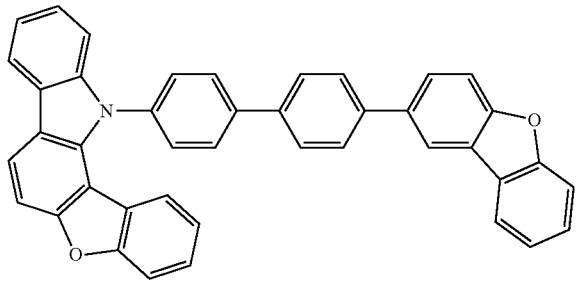
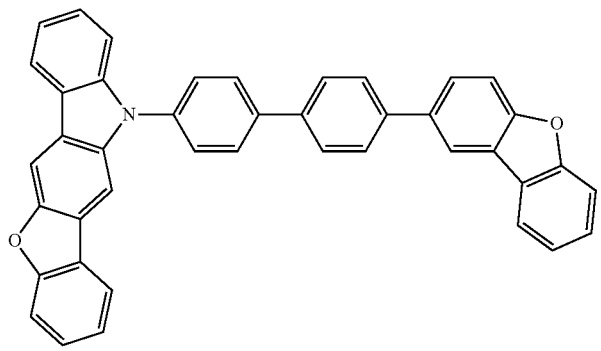
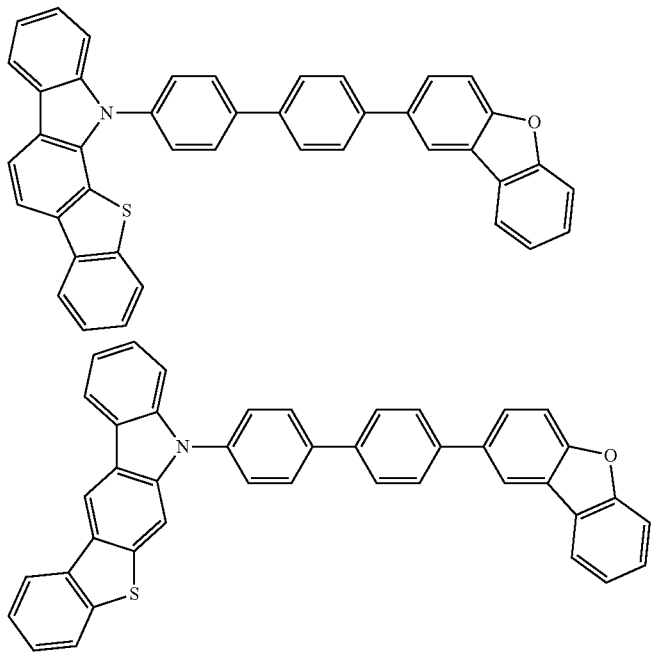

-continued
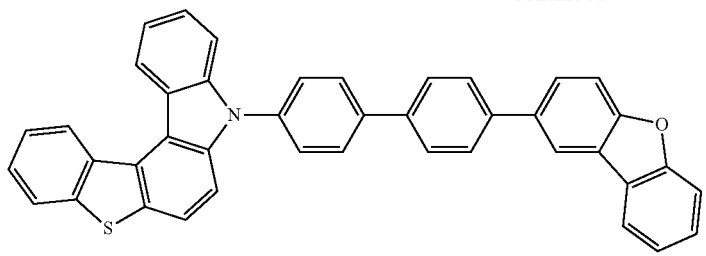
[Formula 61]
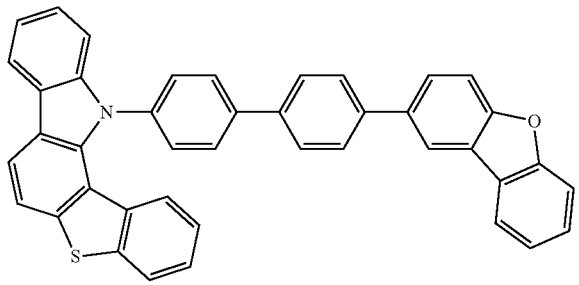
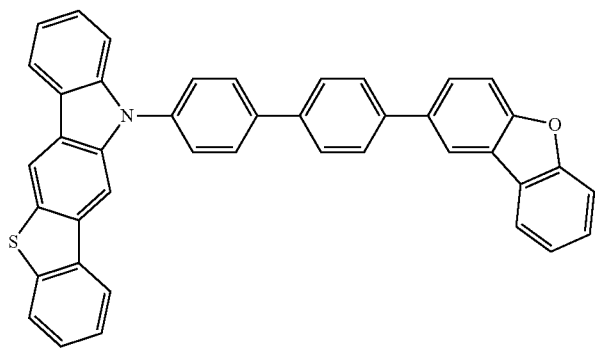
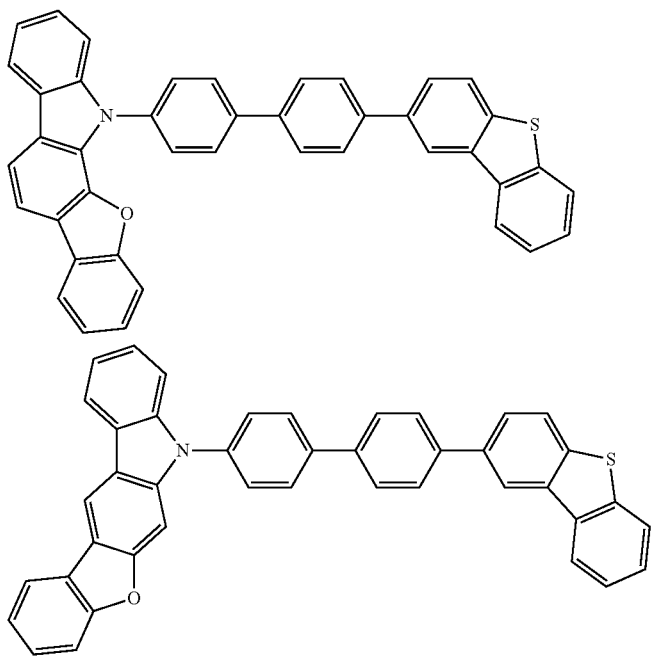

-continued
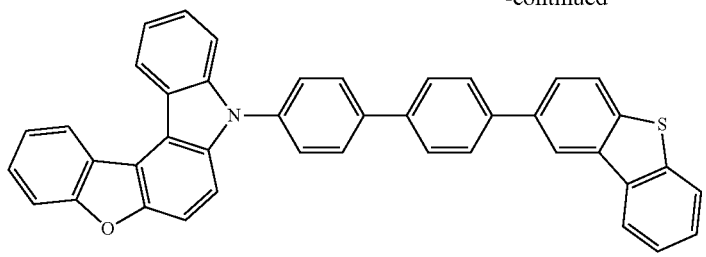
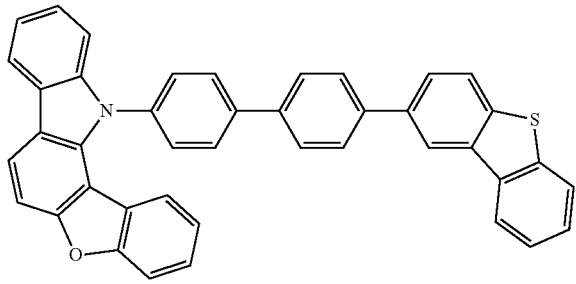
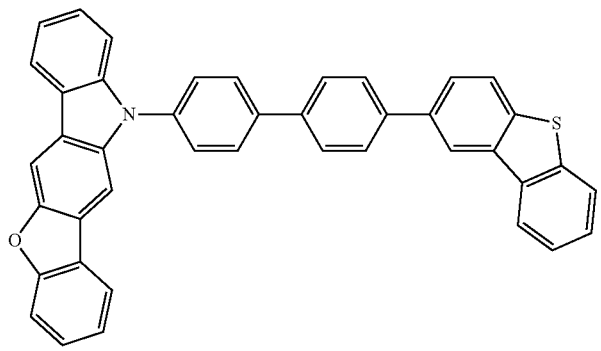
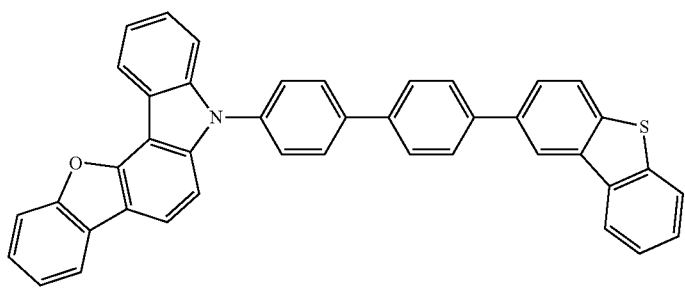
[Formula 62]
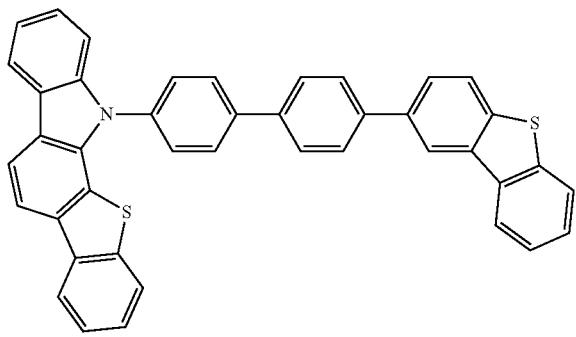

-continued
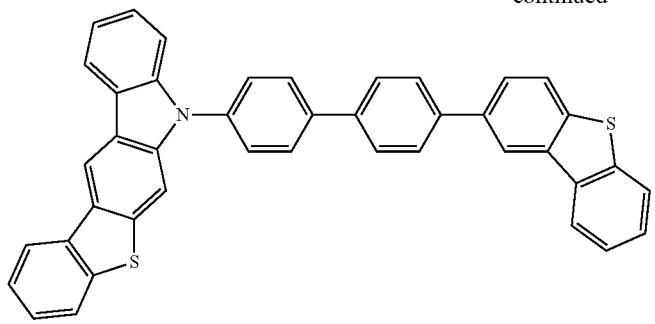
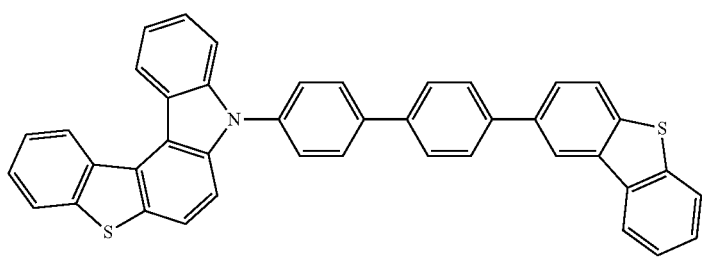
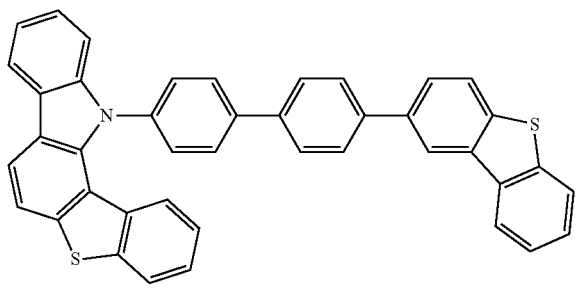
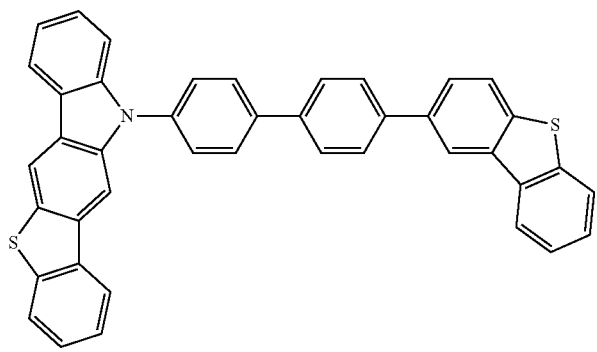
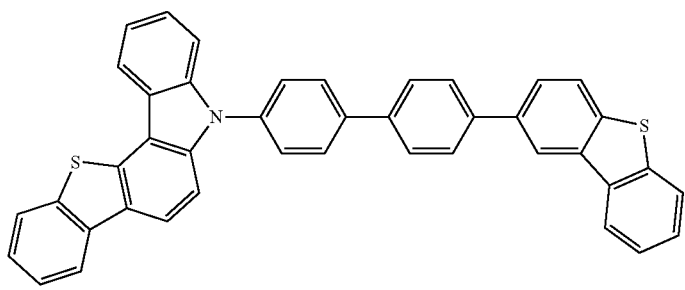

[Formula 63]
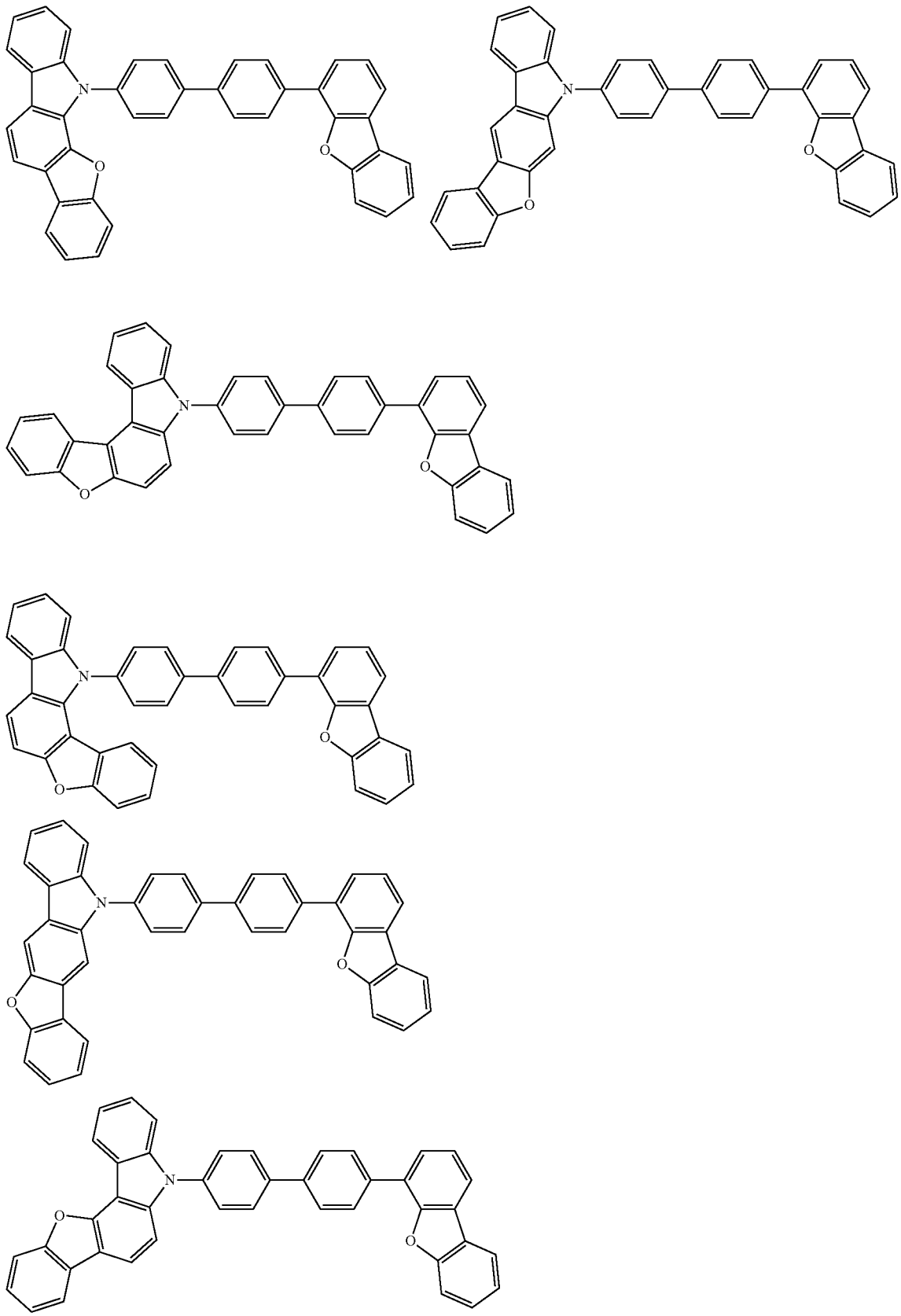

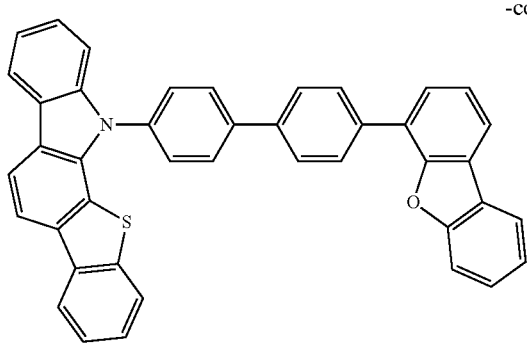
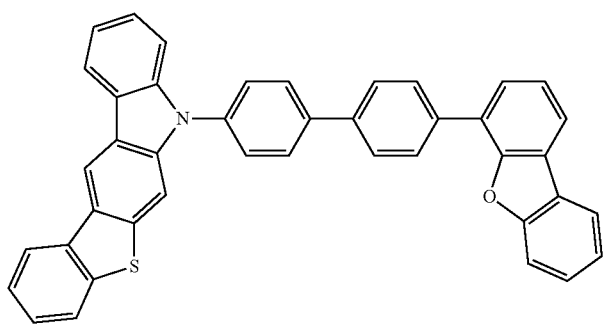
[Formula 64]
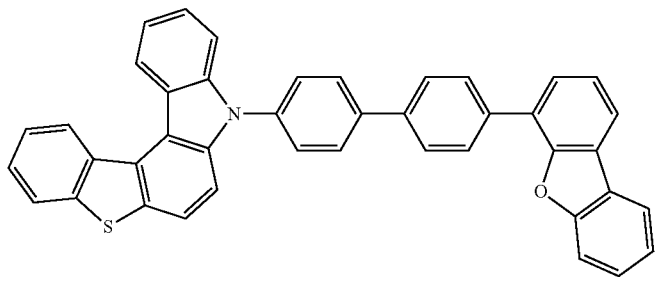
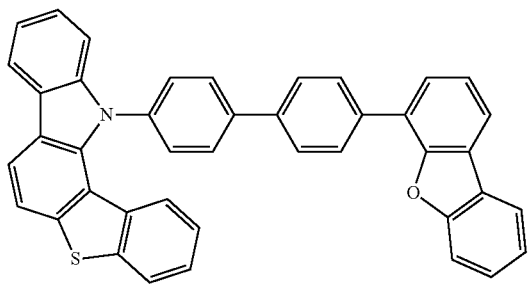
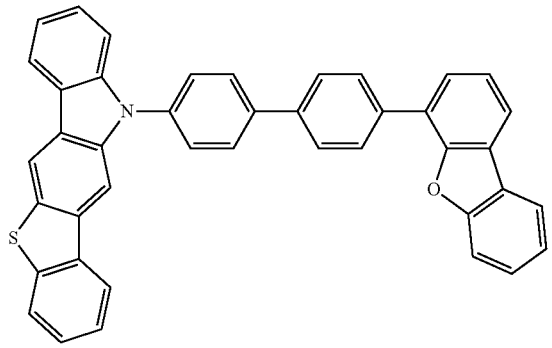

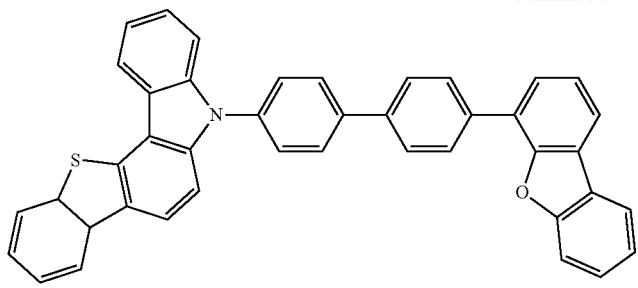
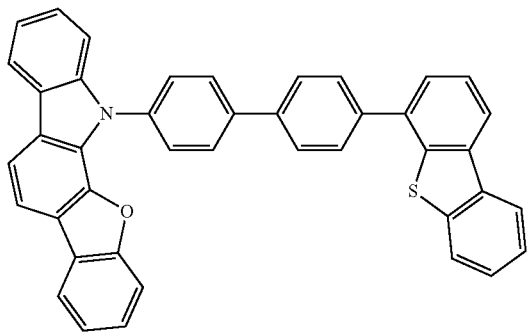
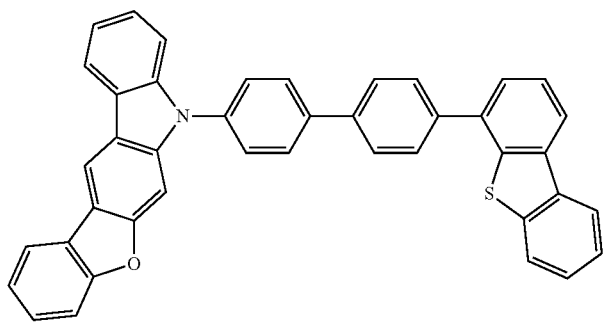
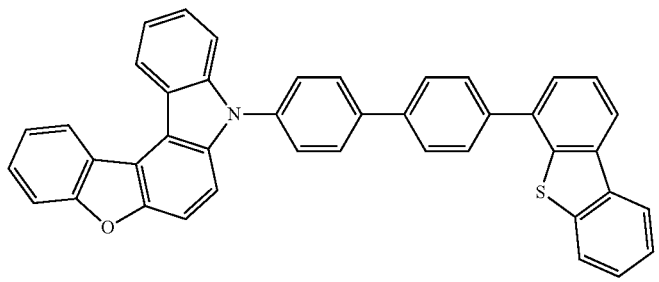
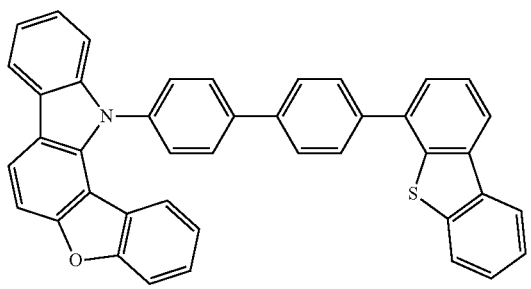

[Formula 65]
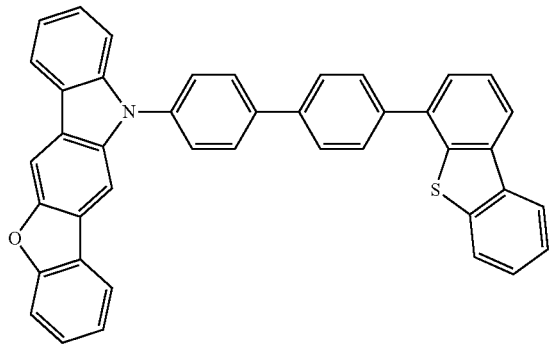
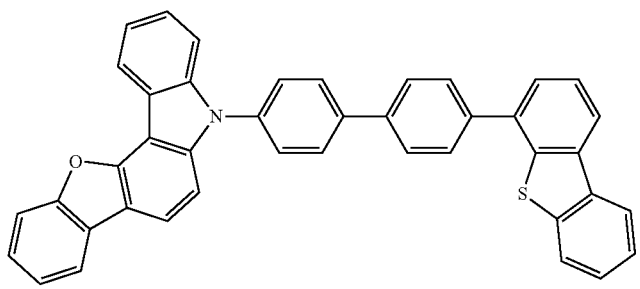
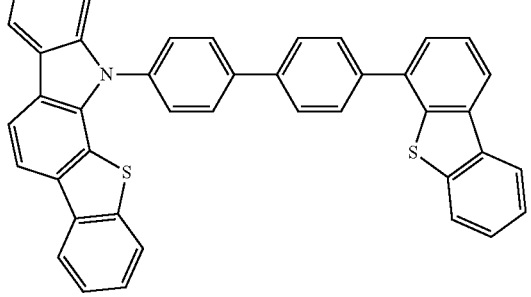
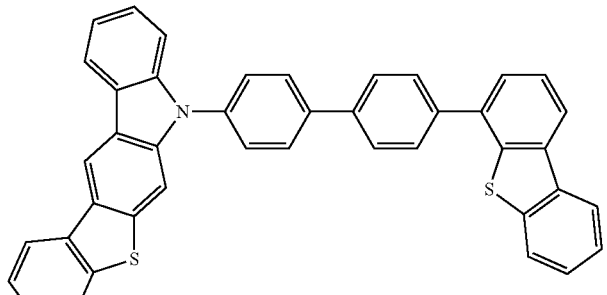
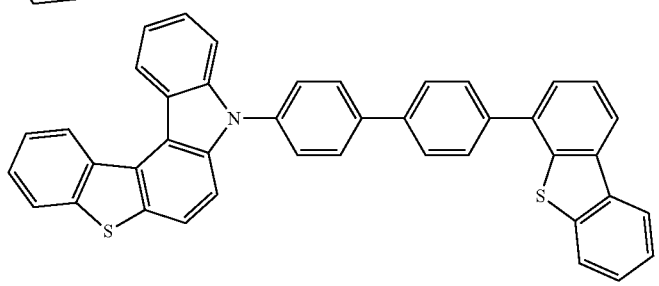

151 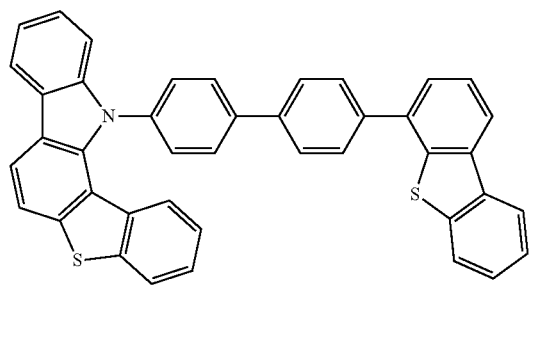 152 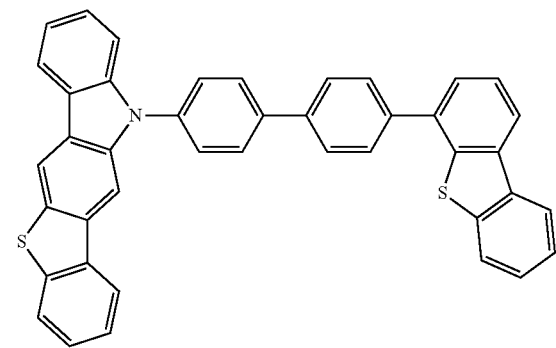
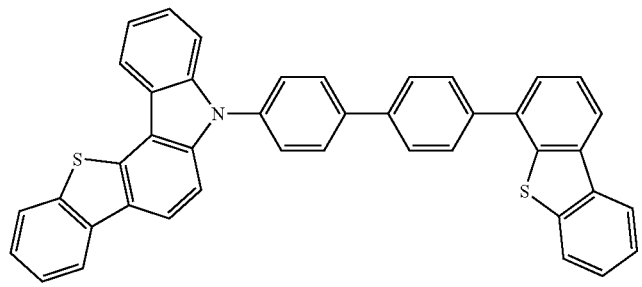
[Formula 66]
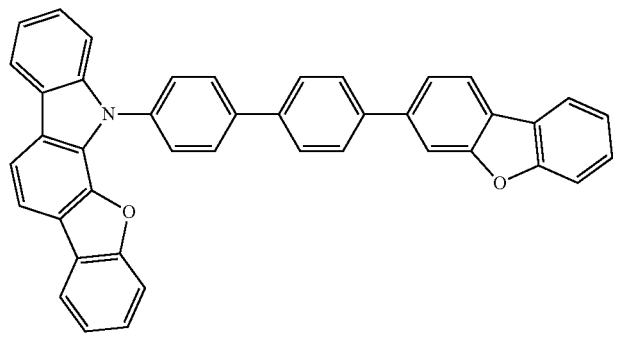  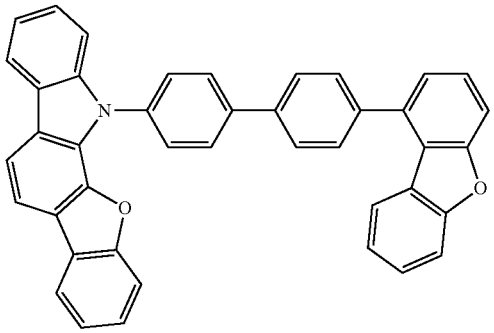
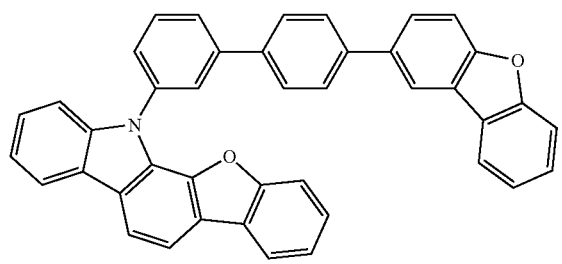
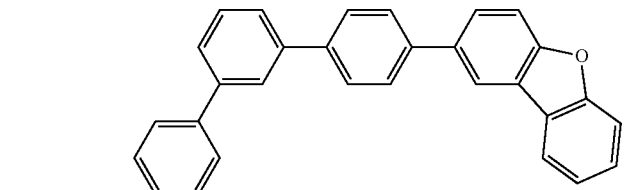
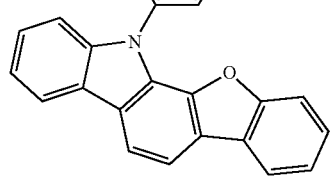

-continued
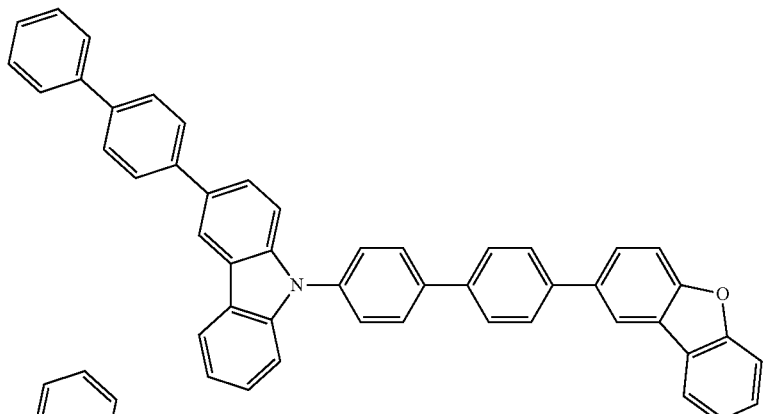
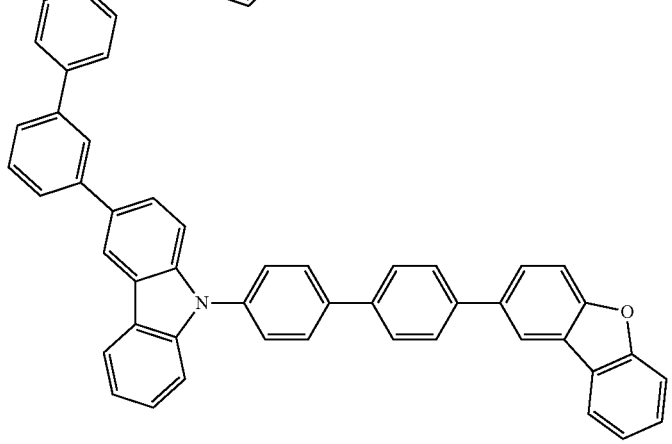
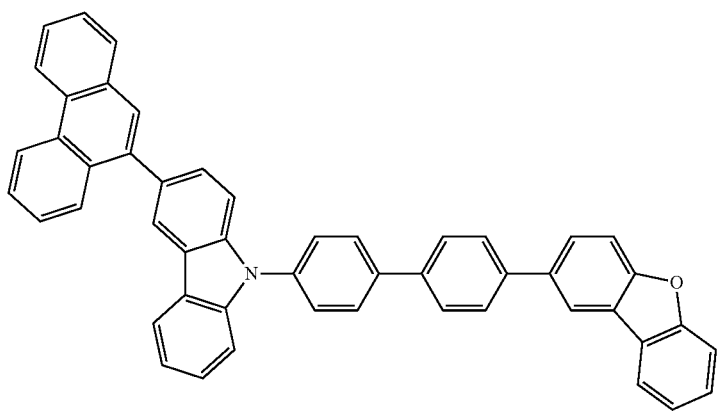
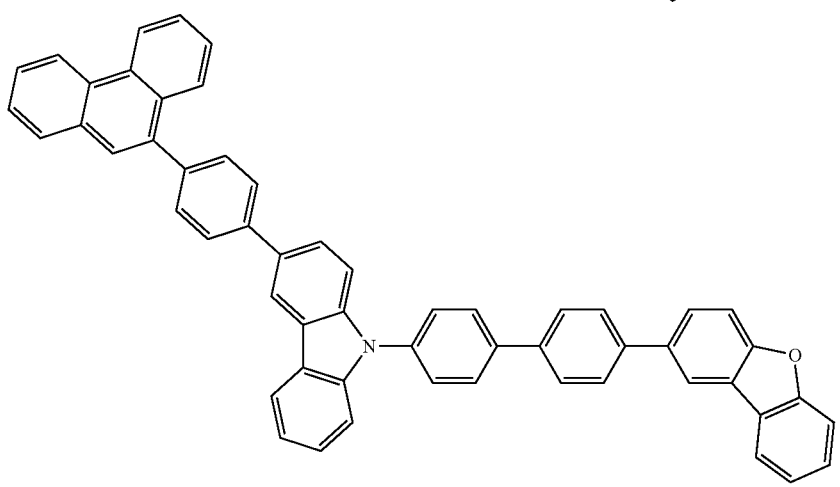

[Formula 67]
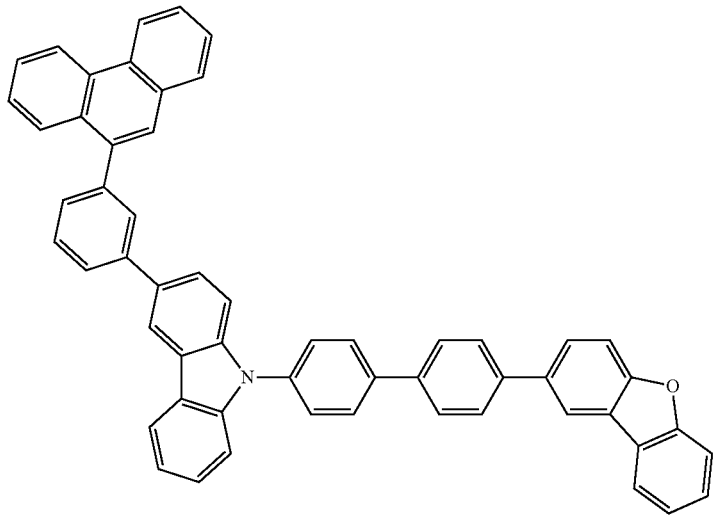
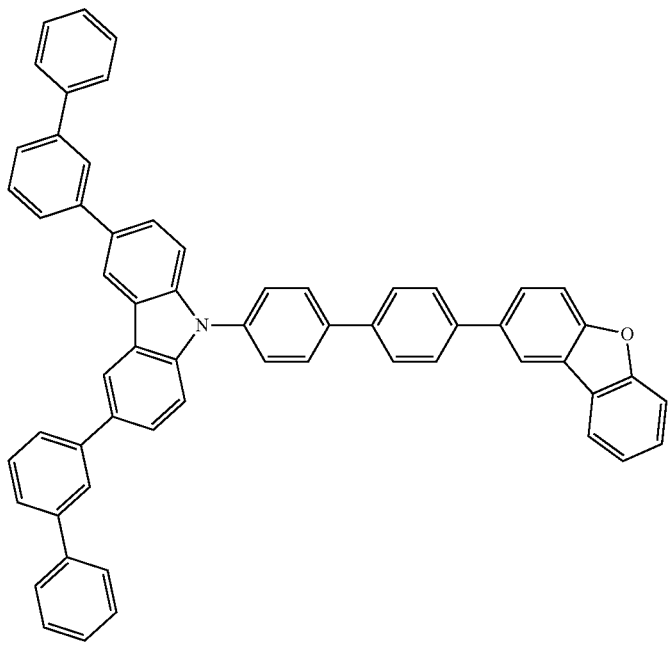
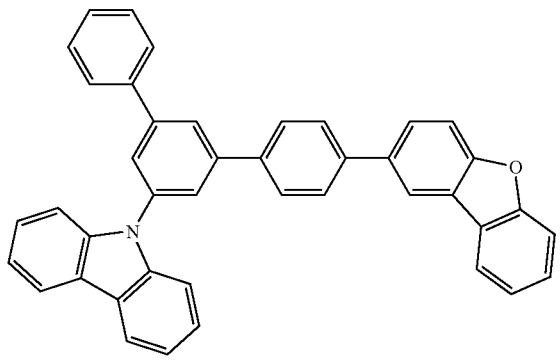

-continued
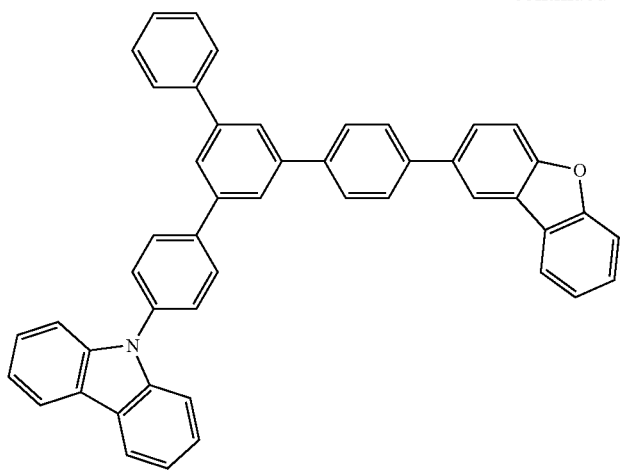
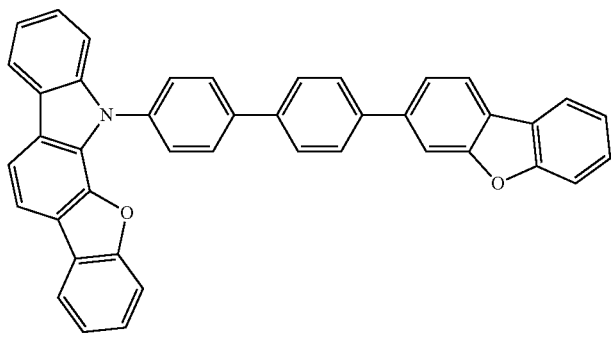
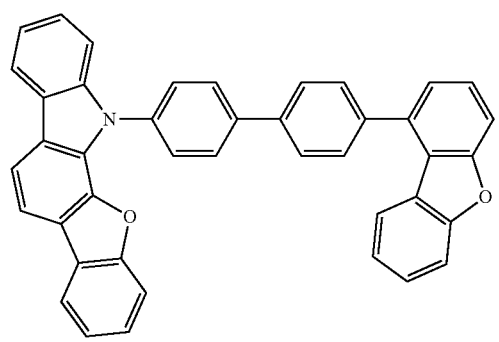
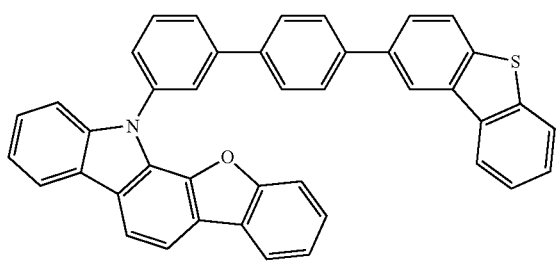
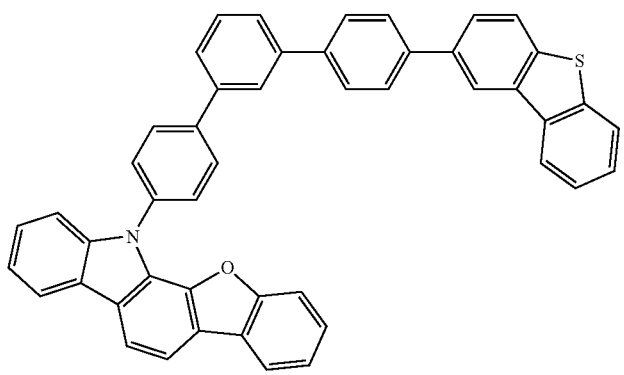

[Formula 68]
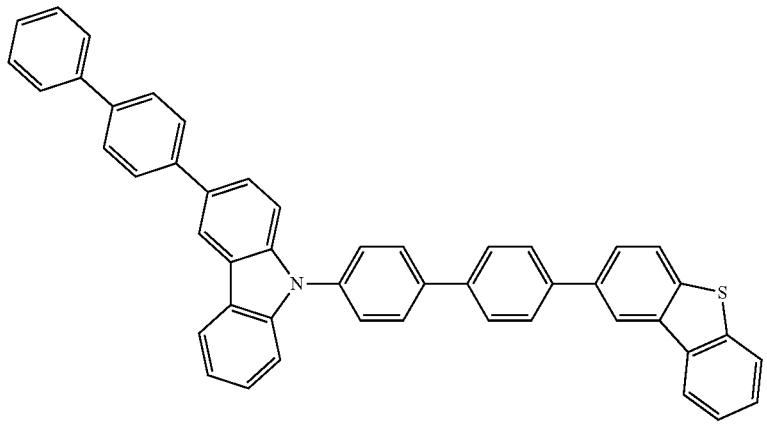
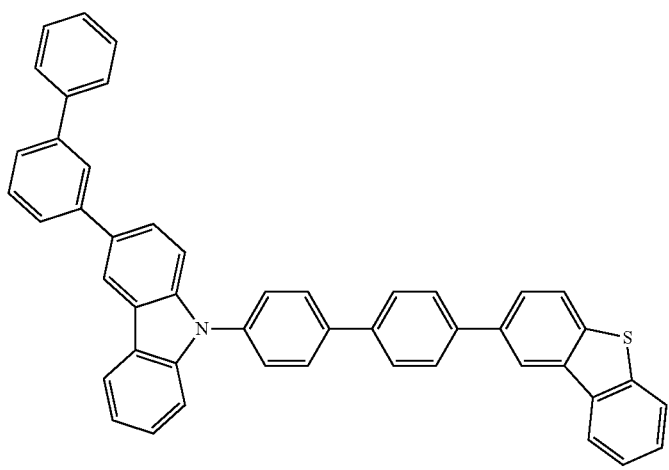
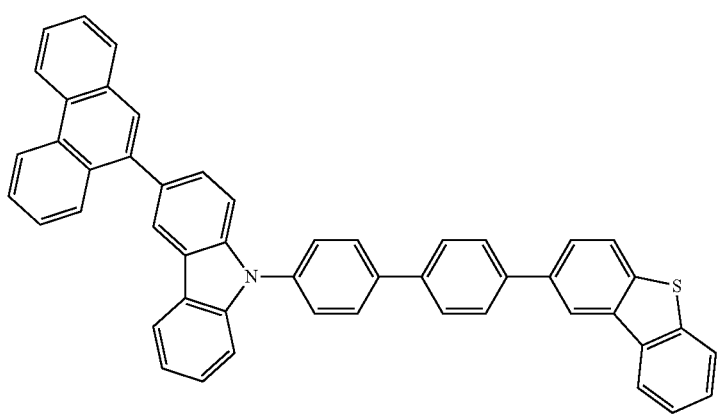

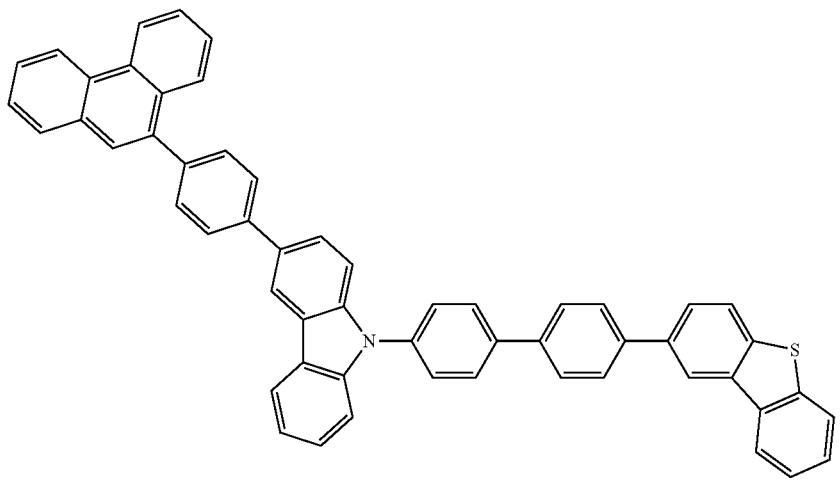
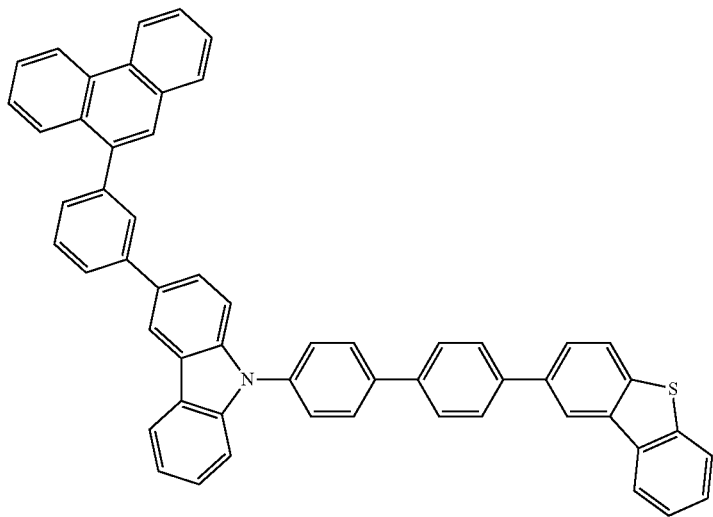
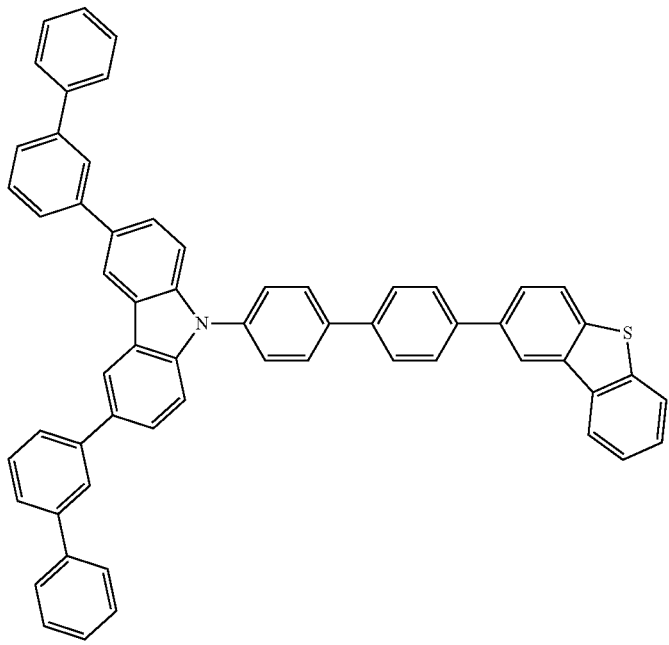

[Formula 69]
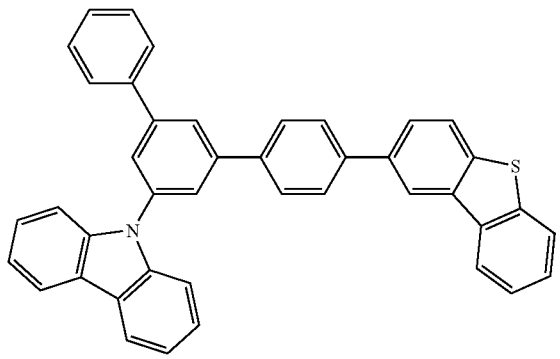
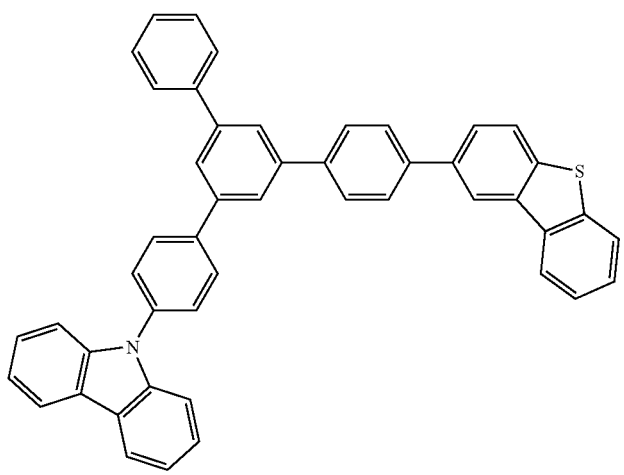
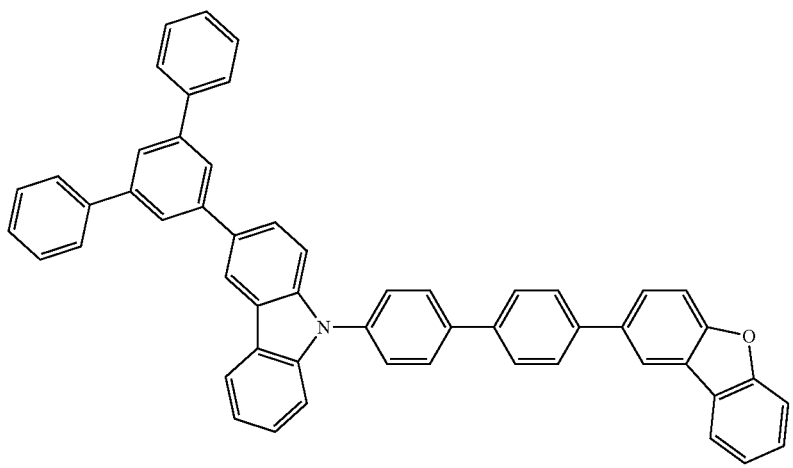

-continued
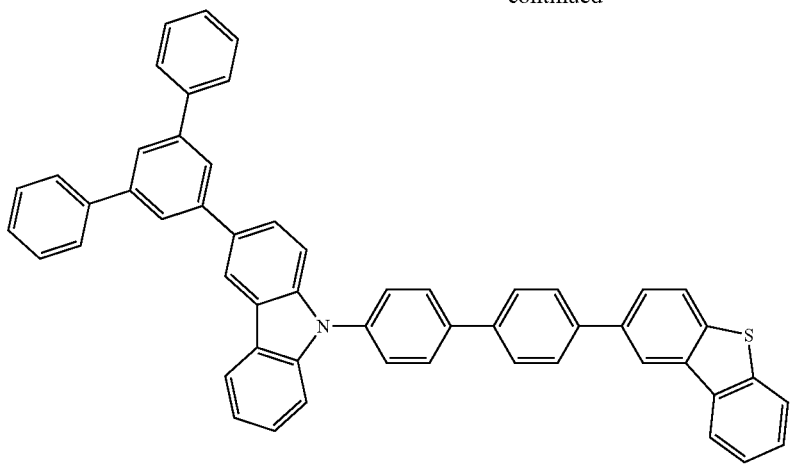
[Formula 70]
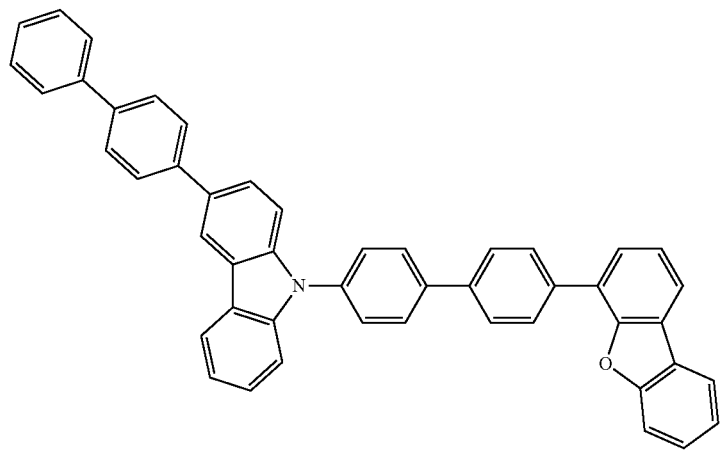
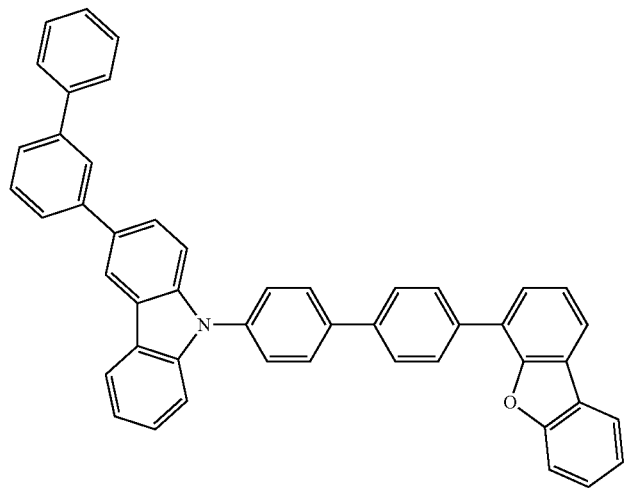

-continued
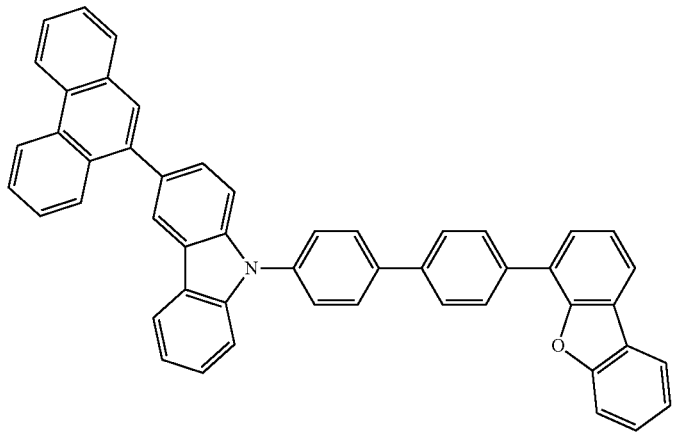
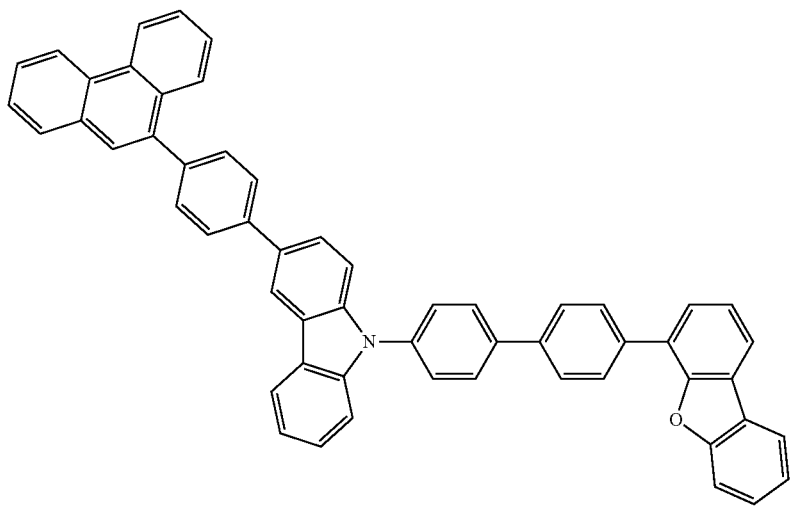
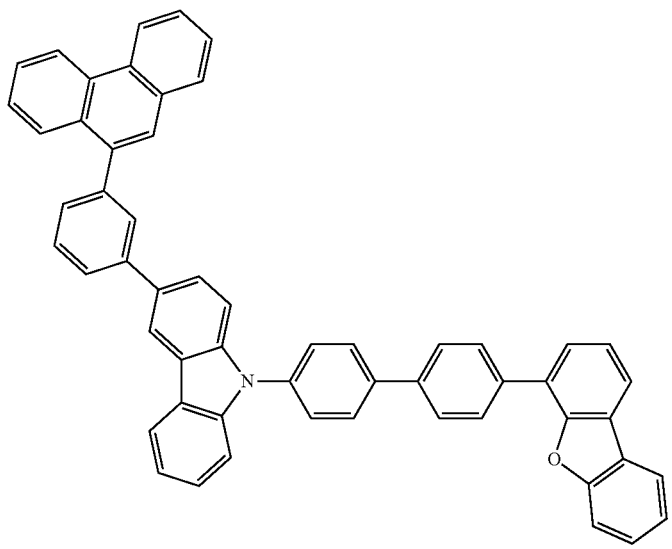

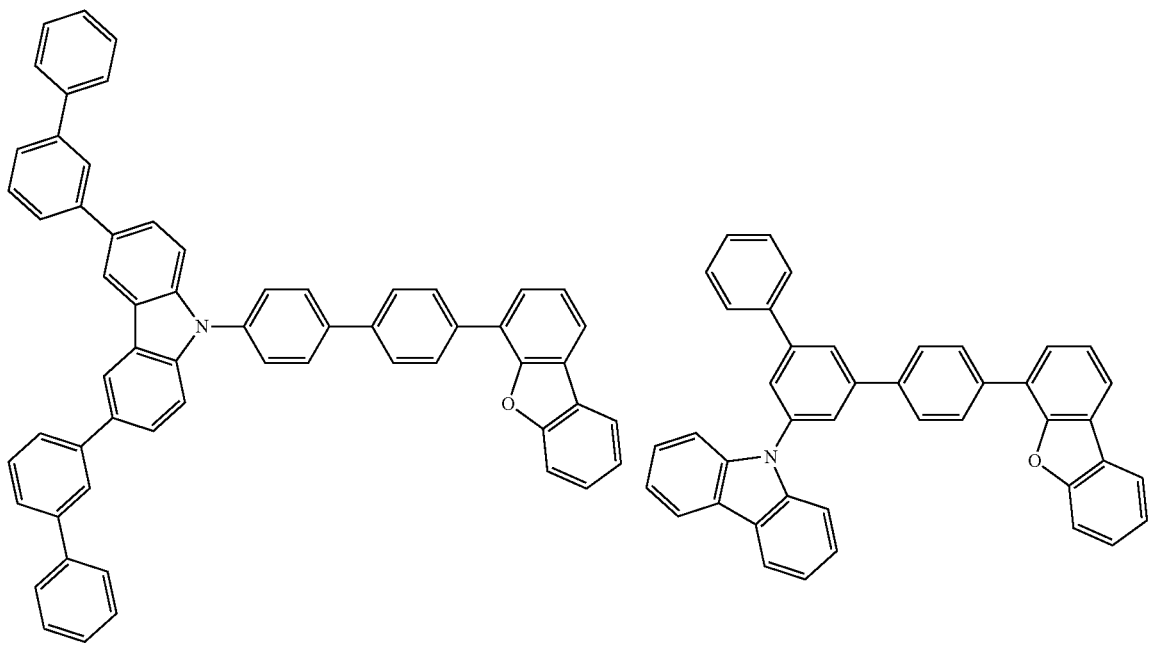
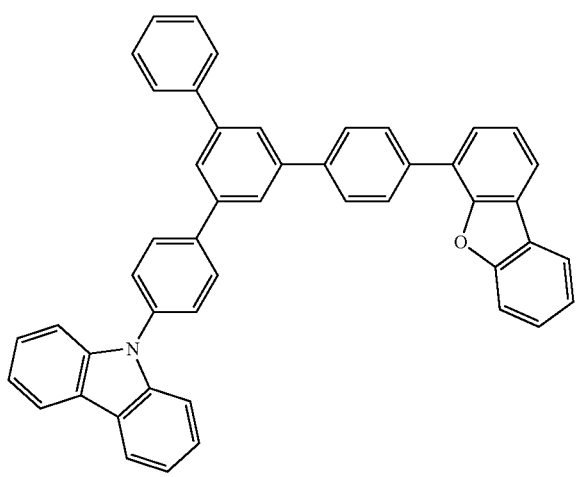
[Formula 71]
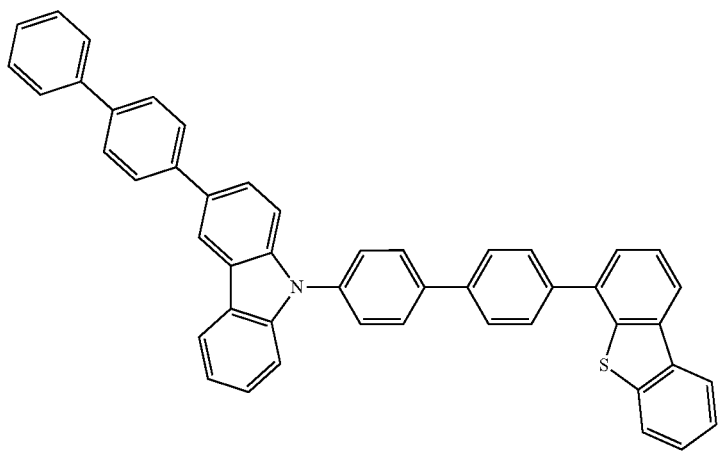

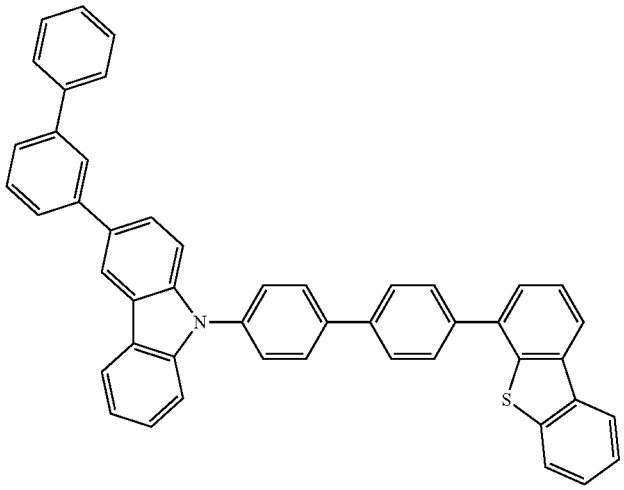
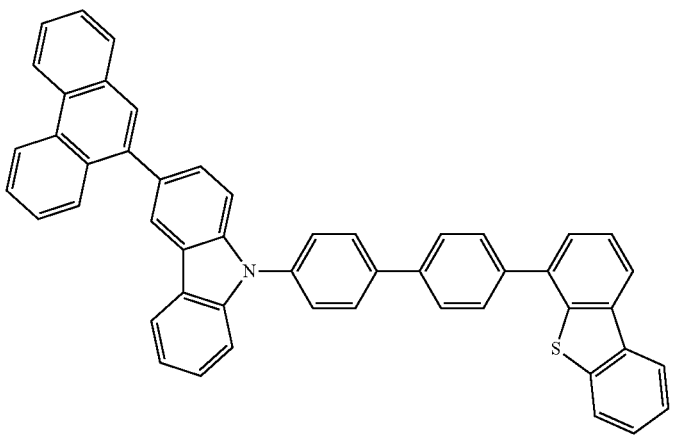
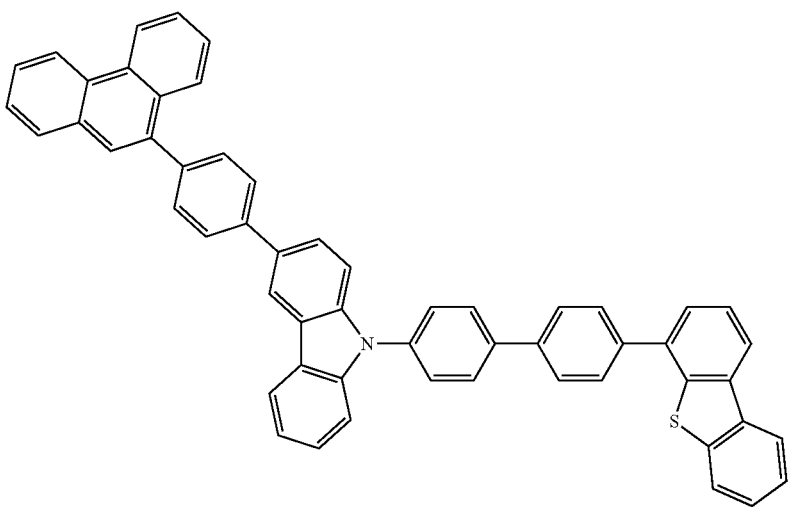

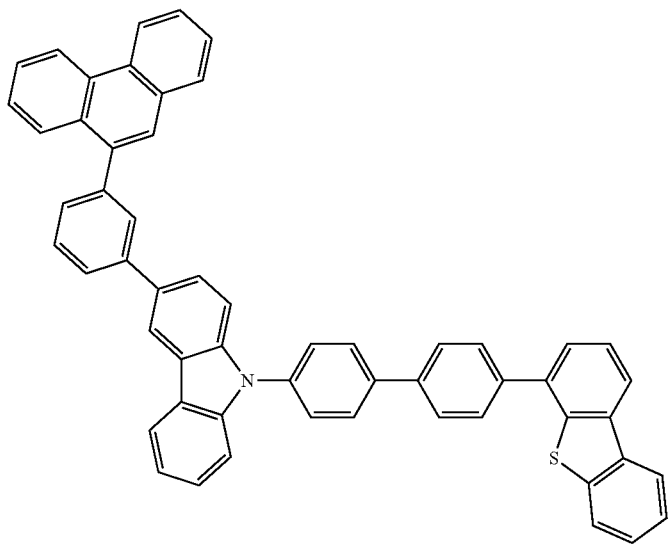
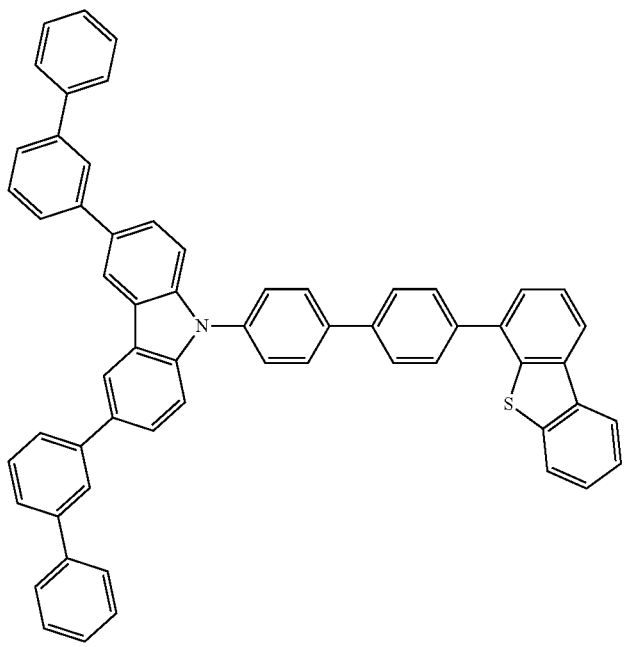
[Formula 72]
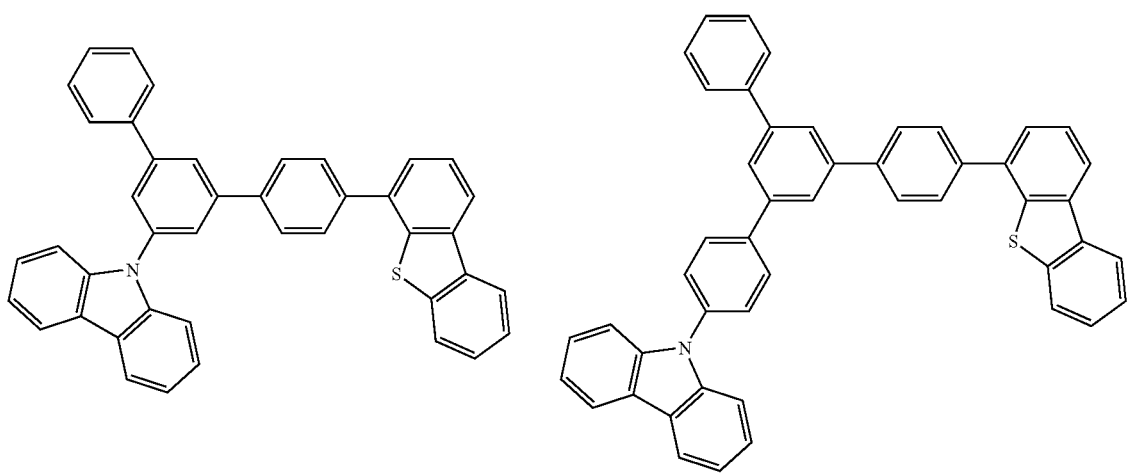

-continued
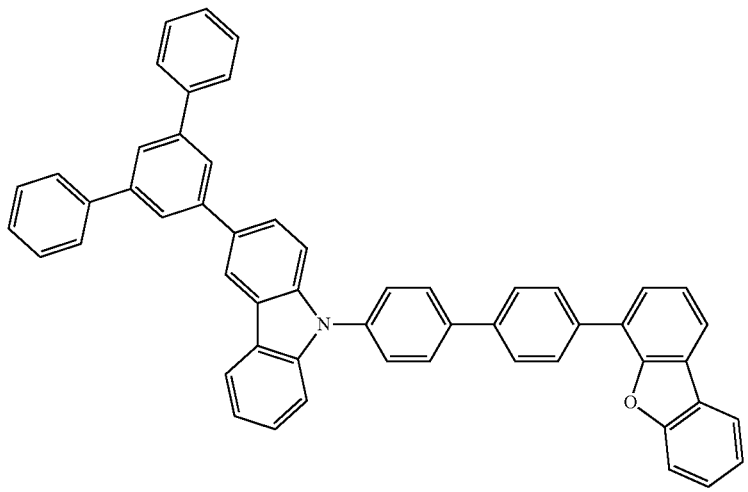
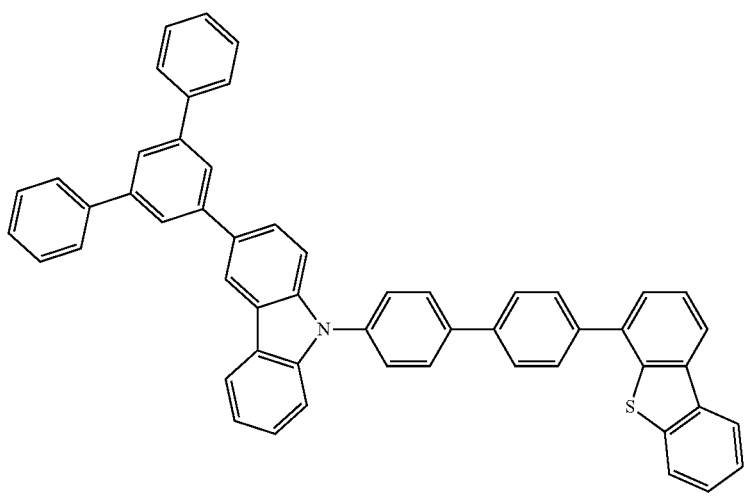
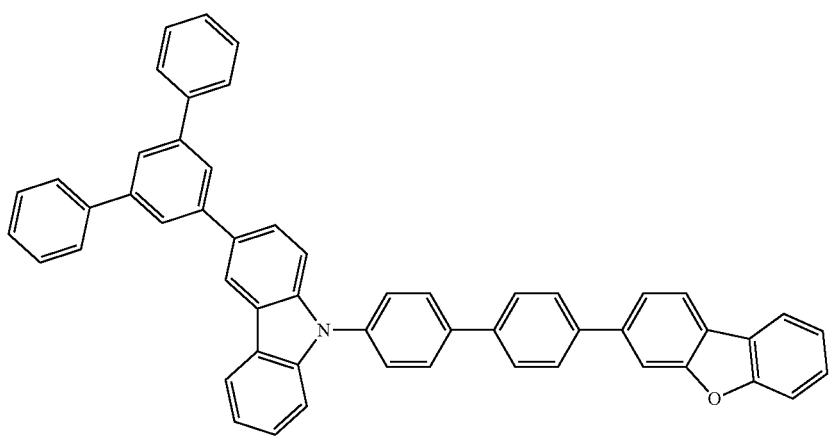

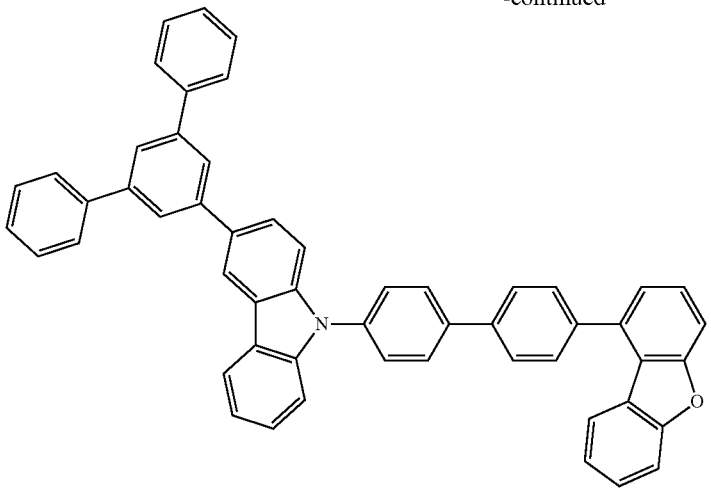

Compound M2

The emitting layer of the exemplary embodiment includes a delayed fluorescent compound M2.

Examples of the delayed fluorescent compound M2 include a compound represented by a formula (1) below.

[Formula 73]

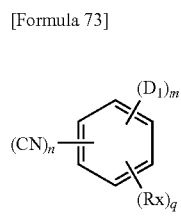

(1)

In the formula (1), n is an integer from 1 to 4, m is an integer from 1 to 4, q is an integer from 0 to 4, and m+n+q=6, CN is a cyano group;

$D_1$ is a group represented by a formula (2), (3) or (3x) below, when a plurality of $D_1$ are present the plurality of $D_1$ are mutually the same or different, Rx is a hydrogen atom or a substituent, or a pair of adjacent ones of Rx are bonded to each other to form a ring, and when a plurality of Rx are present, the plurality of Rx are mutually the same or different, Rx as the substituent is each independently a halogen atom, a substituted or to unsubstituted aryl group having 6 to 30 ring carbon atoms, a substituted or unsubstituted heterocyclic group having 5 to 30 ring atoms, a substituted or unsubstituted amino group, a substituted of unsubstituted carbonyl group, a substituted or unsubstituted alkyl group having 1 to 30 carbon atoms, a substituted or unsubstituted alkyl halide group having 1 to 30 carbon atoms, a substituted or unsubstituted alkylsilyl group having 3 to 30 carbon atoms, or a substituted or unsubstituted arylsilyl group having 6 to 60 ring carbon atoms; CN, $D_1$ and Rx are bonded to respective carbon atoms of a six-membered ring.

[Formula 74]

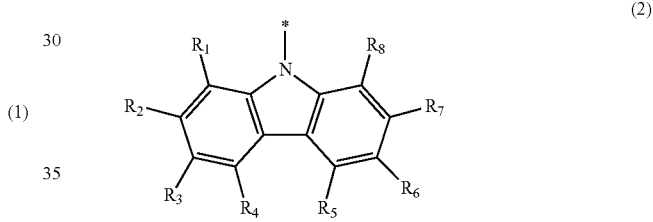

(2)

In the formula (2), $R_1$ to $R_8$ each independently represent a hydrogen atom or a substituent, or at least one pair of a pair of $R_1$ and $R_2$, a pair of $R_2$ and $R_3$, a pair of $R_3$ and $R_4$, a pair of $R_5$ and $R_6$, a pair of $R_6$ and $R_7$, or a pair of $R_7$ and $R_8$ is bonded to each other to form a ring.

$R_1$ to $R_8$ as the substituent are each independently a halogen atom, a substituted or unsubstituted aryl group having 6 to 30 ring carbon atoms, a substituted or unsubstituted heterocyclic group having 5 to 30 ring atoms, a substituted or unsubstituted alky) group having 1 to 30 carbon atoms, a substituted or unsubstituted alkyl halide group having 1 to 30 carbon atoms, a substituted or unsubstituted alkylsilyl group having 3 to 30 carbon atoms, a substituted or unsubstituted arylsilyl group having 6 to 60 ring carbon atoms, a hydroxy group, a substituted or unsubstituted alkoxy group having 1 to 30 carbon atoms, a substituted or unsubstituted alkoxy halide group having 1 to 30 carbon atoms, a substituted or unsubstituted aryloxy group having 6 to 30 ring carbon atoms, a substituted or unsubstituted alkylamino group having 2 to 30 carbon atoms, a substituted or to unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms; and \* represents a bonding position to a carbon atom of a benzene ring in the formula (1)

[Formula 75]

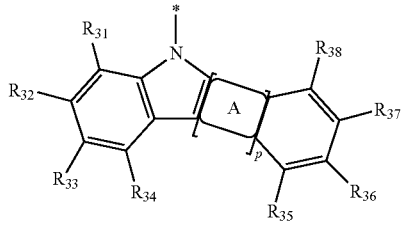

(3)

In the formula (3): $R_{31}$ to $R_{38}$ ere each independently a hydrogen atom or a substituent, or at least one pair of a pair of $R_{31}$ and $R_{32}$, a pair of $R_{32}$ and $R_{33}$, a pair of $R_{33}$ and $R_{34}$, a pair of $R_{35}$ and $R_{36}$, a pair of $R_{36}$ and $R_{37}$, or a pair of $R_{37}$ and $R_{38}$ are mutually bonded to form a ring:

$R_{31}$ to $R_{38}$ as a substituent each independently represent the same as $R_1$ to $R_8$ in the formula (2):

A represents a cyclic structure represented by a formate (131) or (132), the cyclic structure A is fused with any positions of adjacent cyclic structures, p is an integer from 1 to 4, end a plurality of cyclic structures A are mutually the same or different when p is an integer of 2 or more; and * represents a bonding position to a carbon atom of a benzene ring in the formula (1)

[Formula 76]

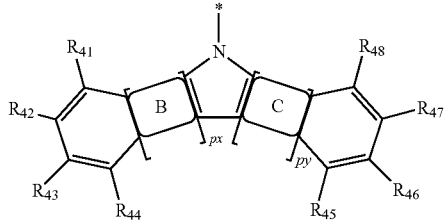

(3X)

In the formula (3X): $R_{41}$ to $R_{48}$ are each independently a hydrogen atom or a substituent, or at least one pair of a pair of $R_{41}$ and $R_{42}$, a pair of $R_{42}$ and $R_{43}$, a pair of $R_{43}$ and $R_{44}$, a pair of $R_{45}$ and $R_{46}$, a pair of $R_{46}$ and $R_{47}$, or a pair of $R_{47}$ and $R_{48}$ are mutually bonded to form a ring;

$R_{41}$ to $R_{48}$ as the substituent each independently represent the same as $R_{31}$ to $R_{38}$ as the substituent in the formula (3):

B represents a cyclic structure represented by the formula (131) or (132) below, the cyclic structure B is fused with any positions of adjacent cyclic structures, px is an integer from 1 to 4, and plurality of cyclic structures B are mutually the same or different when px is an integer of 2 or more;

C represents a cyclic structure represented by the formula (131) or (132) below, the cyclic structure C is fused with any positions of adjacent cyclic structures, py is an integer from 1 to 4, and a plurality of cyclic structures C are mutually the same or different when py is an integer of 2 or more; and * represents a bonding position to a carbon atom of a benzene ring in the formula (1).

[Formula 77]

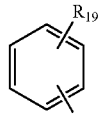

(131)

(132)

In the formula (131). $R_{19}$ and $R_{20}$ are each independently a hydrogen atom, or a substituent, or bonded to a part of an adjacent cyclic structure, or a pair of $R_{19}$ and $R_{20}$ are mutually bonded to form a ring.

In the formula (132): $X_1$ is $CR_{50}R_{51}$, $NR_{52}$, a sulfur atom, or an oxygen atom, $R_{50}$, $R_{51}$ and $R_{52}$ are each independently a hydrogen atom or a substituent or $R_{50}$ and $R_{51}$ are mutually bonded to form a ring, and $R_{19}$, $R_{20}$, $R_{50}$, $R_{51}$ and $R_{52}$ as the substituent each independently represent the same as $R_1$ to $R_8$ as the substituent m the formula (2).

In the formula (131), $R_{19}$ and $R_{20}$ are each independently bonded to a part of an adjacent cyclic structure to form a ring, which specifically means any of (I) to (IV) below.

In the formula (131), a pair of $R_{19}$ and $R_{20}$ are mutually bonded to form a ring, which specifically means (V) below (I) When the cyclic structures represented by the formula (131) are adjacent to each other, between the two adjacent rings, at least one pair of the following are mutually bonded to form a ring. $R_{19}$ of one of the rings and $R_{19}$ of the other of the rings; $R_{19}$ of one of the rings and $R_{20}$ of the other of the rings; and $R_{20}$ of one of the rings and $R_{20}$ of the other of the rings.

(II) When the cyclic structure represented by the formula (131) and the benzene ring having $R_{35}$ to $R_{38}$ in the formula (3) are adjacent to each other, between two adjacent rings, at least one pair of the following are mutually bonded to form a ring; $R_{19}$ of one of the rings and $R_{35}$ of the other of the rings; $R_{19}$ of one erf the rings and $R_{38}$ of the other of the rings; $R_{20}$ of one of the rings and $R_{35}$ of the other of the rings; and $R_{20}$ of one of the rings and $R_{38}$ of the other of the rings.

(III) When the cyclic structure represented by the formula (131) and the benzene ring having $R_{41}$ to $R_{44}$ in the formula (3X) are adjacent to each other, between two adjacent rings, at least one pair of the following are mutually bonded to form a ring: $R_{19}$ of one of the rings and $R_{41}$ of the other of the rings; $R_{19}$ of one of the rings and $R_{44}$ of the other of the rings; $R_{20}$ of one of the rings and $R_{41}$ of the other of the rings; and $R_{20}$ of one of the rings and $R_{44}$ of the other of the rings.

(IV) When the cyclic structure represented by the formula (131) and the benzene ring having $R_{45}$ to $R_{48}$ in the formula (3X) are adjacent to each other, between two adjacent rings, at least one pair of the following are mutually bonded to form a ring: $R_{19}$ of one of the rings and $R_{45}$ of the other of the rings; $R_{19}$ of one of the rings and $R_{48}$ of the other of the rings; $R_{20}$ of one of the rings and $R_{45}$ of the other of the rings; and $R_{20}$ of one of the rings and $R_{48}$ of the other of the rings.

(V) The pair of $R_{19}$ and $R_{20}$ of the cyclic structure represented by the formula (131) are mutually bonded to form a ring. In other words, (V) means that the pair of $R_{19}$ and $R_{20}$ bonded to the same ring are mutually bonded to form a ring.

In the compound M2 of the exemplary embodiment, Rx is a hydrogen atom, an unsubstituted aryl group having 6 to 30 ring carbon atoms, an unsubstituted heterocyclic group having 5 to 30 ring atoms, or an unsubstituted alkyl group having 1 to 30 carbon atoms.

When Rx is an unsubstituted heterocyclic group having 5 to 30 ring atoms, Rx as the unsubstituted heterocyclic group having 5 to 30 ring atoms is preferably a pyridyl group, pyrimidinyl group, triazinyl group, dibenzofuranyl group, or dibenzothienyl group.

Herein, the triazinyl group refers to a group obtained by excluding one hydrogen atom from 1,3,5-triazine, 1,2,4-triazine, or 1,2,3-triazine.

The triazinyl group is preferably a group obtained by excluding one hydrogen atom from 1,3,5-triazine.

In the compound M2 of the exemplary embodiment, Rx is more preferably a hydrogen atom, an unsubstituted aryl group having 6 to 30 ring carbon atoms, an unsubstituted dibenzofuranyl group, or an unsubstituted dibenzothienyl group.

In the compound M2 of the exemplary embodiment, Rx is further preferably a hydrogen atom.

In the compound M2 of the exemplary embodiment, $R_1$ to $R_8$, $R_{31}$ to $R_{36}$, $R_{19}$ to $R_{20}$, $R_{41}$ to $R_{48}$, and $R_{50}$ to $R_{52}$ as a substituent are preferably each independently an unsubstituted aryl group having 6 to 30 ring carbon atoms, an unsubstituted heterocyclic group having 5 to 30 ring atoms, or an unsubstituted alkyl group having 1 to 30 carbon atoms.

The compound M2 of the exemplary embodiment is preferably a compound represented by one of formulae (1-1) to (1-47) below.

[Formula 78]

(1-1)
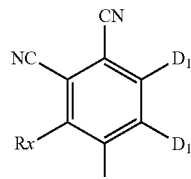

(1-2)
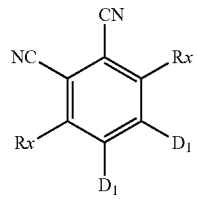

(1-3)
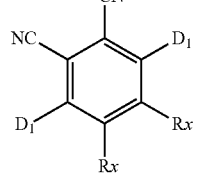

(1-4)
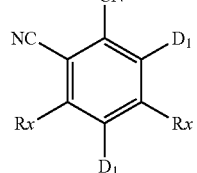

(1-5)
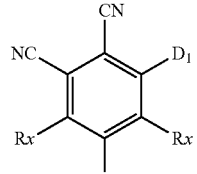

(1-6)
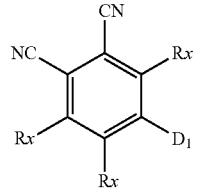

(1-7)
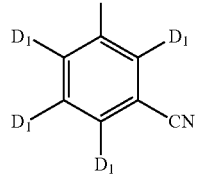

(1-8)
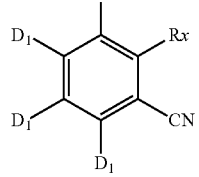

(1-9)
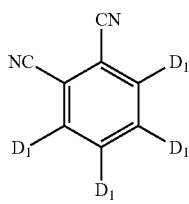

(1-10)
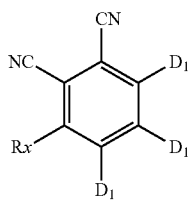

(1-11)
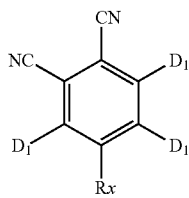

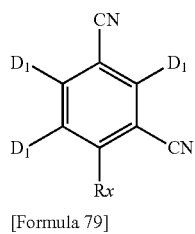
(1-12)
[Formula 79]
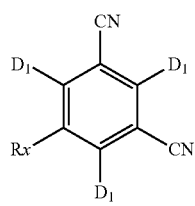
(1-13)
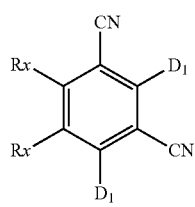
(1-14)
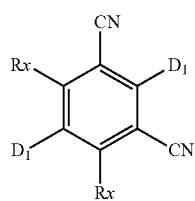
(1-15)
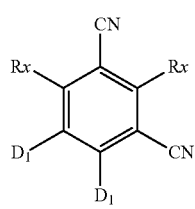
(1-16)
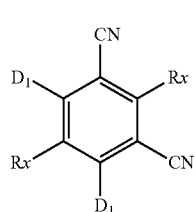
(1-17)
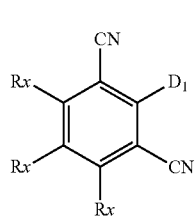
(1-18)
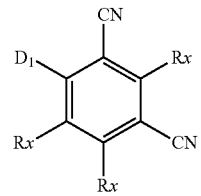
(1-19)
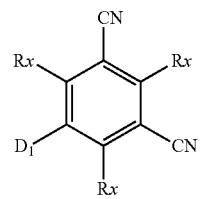
(1-20)
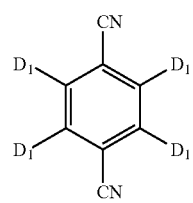
(1-21)
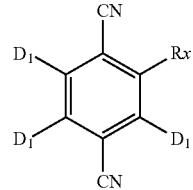
(1-22)
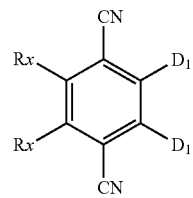
(1-23)
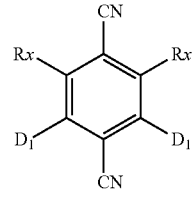
(1-24)
[Formula 80]
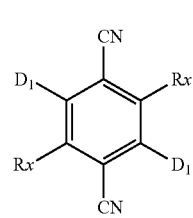
(1-25)

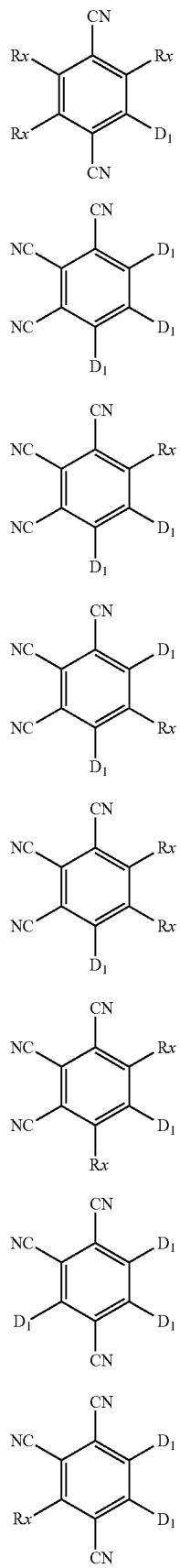
(1-26)
(1-27)
(1-28)
(1-29)
(1-30)
(1-31)
(1-32)
(1-33)
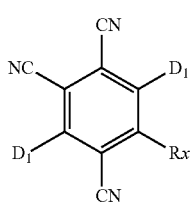
(1-34)
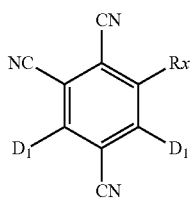
(1-35)
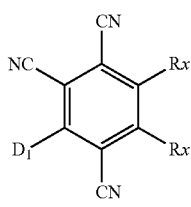
(1-36)
[Formula 81]
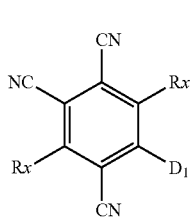
(1-37)
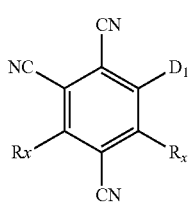
(1-38)
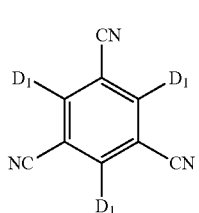
(1-39)
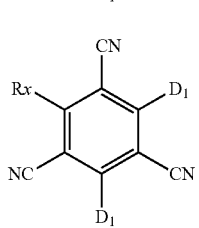
(1-40)

$D_1$ in the formulae (1-1) to (147) each independently represents the same as $D_1$ in the formula (1). Rx each independently represents the same as Rx in the formula (1).

The compound M2 of the exemplary embodiment is preferably a compound represented by one of formulae (14) to (1-7), (1-14) to (1-17) and (1-23) to (1-25).

The compound M2 of the exemplary embodiment is more preferably a compound represented by one of the formulae (1-6), (1-23) and (1-24).

The compound M2 of the exemplary embodiment is further preferably a compound represented by one of formulae (1-6A), (1-23A) and (1-24A).

[Formula 82]

$D_1$ in the formulae (1-6A), (1-23A) and (1-24A) each independently represents the same as $D_1$ in the formula (1).

The compound M2 of the exemplary embodiment is also preferably the compound represented by the formula (1-6).

The compound M2 of the exemplary embodiment is also preferably the to compound represented by the formula (1-23).

The compound M2 of the exemplary embodiment is also preferably the compound represented by the formula (1-24).

The compound M2 of the exemplary embodiment is also preferably a compound represented by one of formulae (1-1), (1-10) and (1-21).

In the compound M2 of the exemplary embodiment, $D_1$ is preferably a group represented by one of formulae (3-1) to (3-12).

[Formula 83]

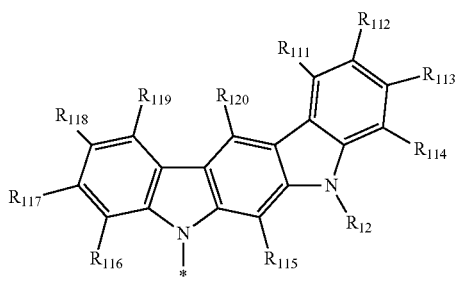

[Formula 84]

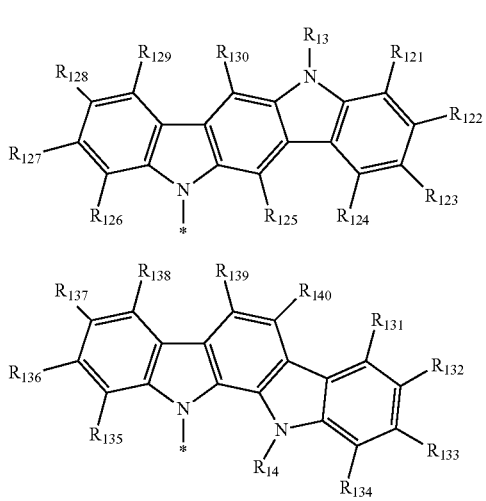

[Formula 85]

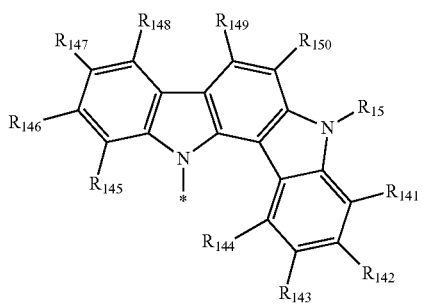

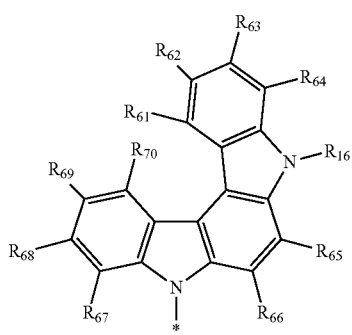

In the formulae (3-1) to (3-6): $R_{11}$ to $R_{16}$ are substituents, $R_{101}$ to $R_{150}$ and $R_{61}$ to $R_{70}$ are each independently a hydrogen atom or a substituent;

$R_{101}$ to $R_{150}$ and $R_{61}$ to $R_{70}$ as the substituent are each independently a substituted or unsubstituted aryl group having 6 to 14 ring carbon atoms, a substituted or unsubstituted heterocyclic group having 5 to 14 ring atoms, a substituted or unsubstituted alky) group having 1 to 6 carbon atoms, a substituted or unsubstituted alkylsilyl group having 3 to 6 carbon atoms, a hydroxy group, a substituted or unsubstituted alkoxy group having 1 to 6 carbon atoms, a substituted or unsubstituted aryloxy group having 6 to 14 ring carbon atoms, a substituted or unsubstituted arylamino group having 6 to 28 ring carbon atoms, a substituted or unsubstituted alkylamino group having 2 to 12 carbon atoms; a thiol group, a substituted or unsubstituted alkylthio group having 1 to 6 carbon atoms, or a substituted or unsubstituted arylthio group having 6 to 14 ring carbon atoms;

$R_{11}$ to $R_{16}$ as the substituent are each independently a substituted or unsubstituted alky) group having 1 to 6 carbon atoms, a substituted or unsubstituted aryl group having 6 to 14 ring carbon atoms, a substituted or unsubstituted heterocyclic group having 5 to 14 ring atoms, a substituted or unsubstituted alkylsilyl group having 3 to 6 carbon atoms, a substituted or unsubstituted aryloxy group having 6 to 14 ring carbon atoms, a substituted or unsubstituted alkylamino group having 2 to 12 carbon atoms, a substituted or unsubstituted alkylthio group having 1 to 6 carbon atoms, or a substituted or unsubstituted arylthio group having 6 to 14 ring carbon atoms; and

* represents a bonding position to a carbon atom of a benzene ring in the formula (1),

[Formula 86]

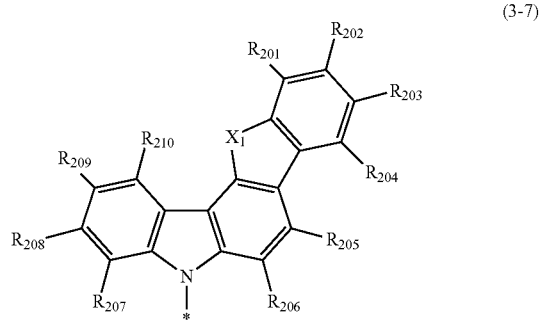

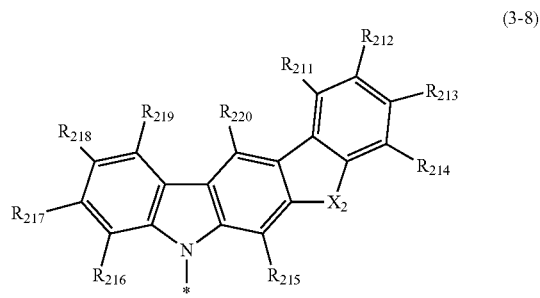

[Formula 87]

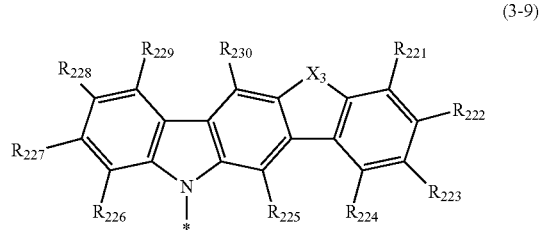

-continued

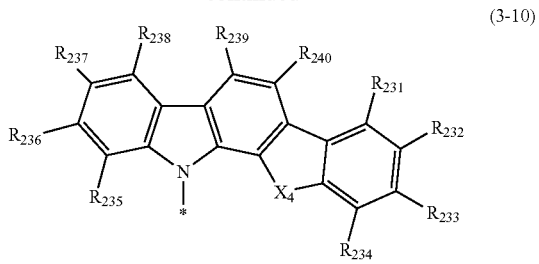

(3-10)

[Formula 88]

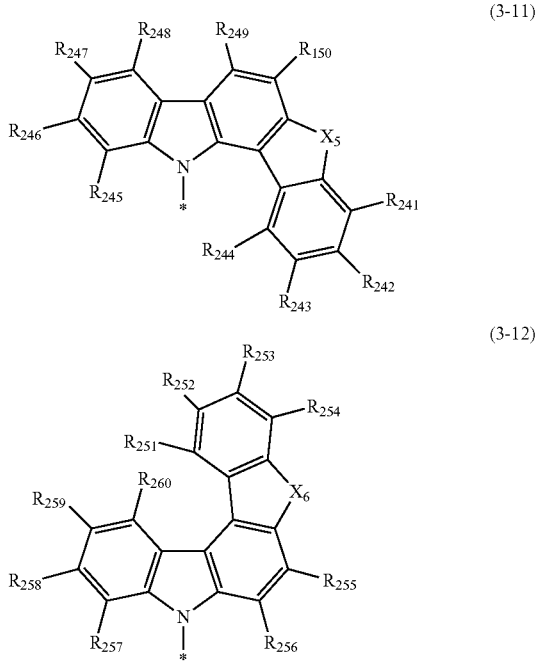

(3-11)

(3-12)

In the formulae (3-7) to (3-12): $X_1$ to $X_6$ each independently represent an oxygen atom, a sulfur atom, or $CR_{151}R_{152}$; $R_{201}$ to $R_{260}$ each independently represent a hydrogen atom or a substituent; and $R_{151}$ and $R_{152}$ each independently represent a hydrogen atom or a substituent or $R_{151}$ and $R_{152}$ are bonded to each other to form a ring;

$R_{201}$ to $R_{260}$, $R_{151}$ and $R_{152}$ as the substituent are each independently a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 6 carbon atoms, a substituted or unsubstituted alkylsilyl group having 3 to 6 carbon atoms, a hydroxy group, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted arylamino group having 6 to 28 ring carbon atoms, a substituted or unsubstituted alkylamino group having 2 to 12 carbon atoms, a thiol group, a substituted or unsubstituted alkylthio group having 1 to 6 carbon atoms, or a substituted or unsubstituted arylthio group having 6 to 14 ring carbon atoms; and

* represents a bonding position to a carbon atom of a benzene ring in the formula (1).

In the compound M2 of the exemplary embodiment, it is also preferable that $D_1$ is a group represented by one of formulae (3-7) to (3-12) and $X_1$ to $X_6$ in the formulae (3-7) to (3-12) are sulfur atoms.

In the compound M2 of the exemplary embodiment, it is also preferable that $D_1$ is a group represented by the formula (3-12) and $X_6$ in the formula (3-12) is a sulfur atom.

In the compound M2 of the exemplary embodiment, it is also preferable that $D_1$ is a group represented by one of formulae (3-7) to (3-12) and $X_1$ to $X_6$ in the formulae (3-7) to (3-12) are oxygen atoms.

In the compound M2 of the exemplary embodiment, it is also preferable that $D_1$ is a group represented by one of formulae (3-7) to (3-12) and $X_1$ to $X_6$ in the formulae (3-7) to (3-12) are $CR_{151}R_{152}$.

In the compound M2 of the exemplary embodiment, $D_1$ is also preferably a group represented by one of the formulae (3-1) to (3-6).

It is also preferable that the compound M2 of the exemplary embodiment is a compound represented by one of the formulae (1-4) to (1-7), (1-14) to (1-17) and (1-23) to (1-25), and $D_1$ is a group represented by one of the formulae (3-1) to (3-12).

It is also preferable that the compound M2 of the exemplary embodiment is a compound represented by one of the formulae (1-4) to (1-7), (1-14) to (1-17) and (1-23) to (1-25), $D_1$ is a group represented by one of the formulae (3-7) to (3-12), and $X_1$ to $X_6$ in the formulae (3-7) to (3-12) are sulfur atoms.

It is also preferable that the compound M2 of the exemplary embodiment is a compound represented by one of the formulae (1-6), (1-23) and (1-24), $D_1$ is a group represented by one of the formulae (3-7) to (3-12), and $X_1$ to $X_6$ in the formulae (3-7) to (3-12) are sulfur atoms.

It is also preferable that the compound M2 of the exemplary embodiment is a compound represented by one of the formulae (1-4) to (1-7), (1-14) to (1-17) and (1-23) to (1-25), $D_1$ is a group represented by one of the formulae (3-7) to (3-12), and $X_1$ to $X_6$ in the formulae (3-7) to (3-12) are oxygen atoms.

It is also preferable that the compound M2 of the exemplary embodiment is a compound represented by one of the formulae (1-6), (1-23) and (1-24), $D_1$ is a group represented by one of the formulae (3-7) to (3-12), and $X_1$ to $X_6$ in the formulae (3-7) to (3-12) are oxygen atoms.

It is also preferable that the compound M2 of the exemplary embodiment is a compound represented by one of the formulae (1-4) to (1-7), (1-14) to (1-17) and (1-23) to (1-25), $D_1$ is a group represented by one of the formulae (3-7) to (3-12), and $X_1$ to $X_6$ in the formulae (3-7) to (3-12) are $CR_{151}R_{152}$.

It is also preferable that the compound M2 of the exemplary embodiment is a compound represented by one of the formulae (1-6), (1-23) and (1-24), $D_1$ is a group represented by one of the formulae (3-7) to (3-12), and $X_1$ to $X_6$ in the formulae (3-7) to (3-12) are $CR_{151}R_{152}$.

It is also preferable that the compound M2 of the exemplary embodiment is a compound represented by one of the formulae (1-4) to (1-7), (1-14) to (1-17) and (1-23) to (1-25), and $D_1$ is a group represented by one of the formulae (3-1) to (3-6).

It is also preferable that the compound M2 of the exemplary embodiment is a compound represented by one of the formulae (1-6), (1-23) and (1-24), and $D_1$ is a group represented by one of the formulae (3-1) to (3-6).

It is preferable that $R_{101}$ to $R_{150}$ and $R_{61}$ to $R_{70}$ as a substituent in the compound M2 of the exemplary embodiment are each independently an unsubstituted aryl group having 6 to 14 ring carbon atoms, an unsubstituted heterocyclic group having 5 to 14 ring atoms, or
an unsubstituted alkyl group having 1 to 6 carbon atoms, and
$R_{11}$ to $R_{16}$ as the substituent are each independently an unsubstituted aryl group having 6 to 14 ring carbon atoms or an unsubstituted heterocyclic group having to 14 ring atoms.

It is also preferable that $R_{101}$ to $R_{150}$ and $R_{61}$ to $R_{70}$ in the compound M2 of the exemplary embodiment are hydrogen atoms, and $R_{11}$ to $R_{16}$ as the substituent are each independently an unsubstituted aryl group having 6 to 14 ring carbon atoms or an unsubstituted heterocyclic group having 5 to 14 ring atoms.

It is preferable that $R_{201}$ to $R_{260}$ as a substituent in the compound M2 of the exemplary embodiment are each independently a halogen atom, an unsubstituted aryl group having 6 to 14 ring carbon atoms, an unsubstituted heterocyclic group having 5 to 14 ring atoms, or an unsubstituted alkyl group having 1 to 6 carbon atoms; and $R_{151}$ and $R_{152}$ as the substituent are each independently an unsubstituted aryl group having 6 to 14 ring carbon atoms or an unsubstituted alkyl group having 1 to 6 carbon atoms.

It is more preferable that $R_{201}$ to $R_{260}$ as a substituent in the compound M2 of the exemplary embodiment are each independently an unsubstituted aryl group having 6 to 14 ring carbon atoms, an unsubstituted heterocyclic group having 5 to 14 ring atoms, or an unsubstituted alkyl group having 1 to 6 carbon atoms; and $R_{151}$ and $R_{152}$ as the substituent are each independently an unsubstituted aryl group having 6 to 14 ring carbon atoms or an unsubstituted alkyl group having 1 to 6 carbon atoms.

It is also preferable that $R_{201}$ to $R_{260}$ in the compound M2 of the exemplary embodiment are hydrogen atoms, and $R_{151}$ and $R_{152}$ as the substituent are each independently an unsubstituted aryl group having 6 to 14 ring carbon atoms or an unsubstituted alkyl group having 1 to 6 carbon atoms.

It is also preferable that $D_1$ in the compound M2 of the exemplary embodiment is a group represented by one of the formulae (2-1), (2-2), (2-3) and (2-4).

[Formula 89]

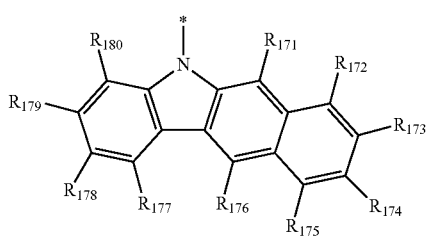

(2-1)

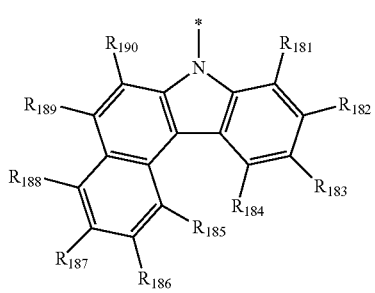

(2-2)

[Formula 90]

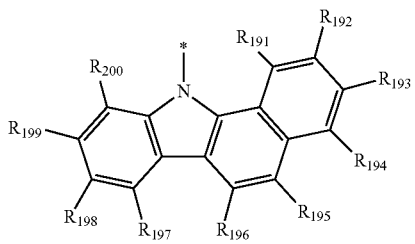

(2-3)

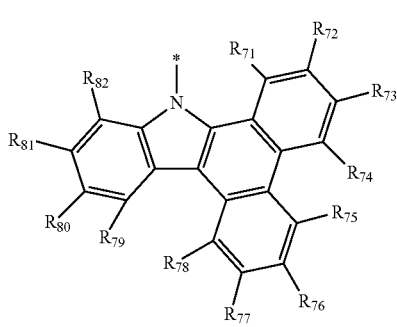

(2-4)

In the formulae (2-1) to (2-4): $R_{171}$ to $R_{200}$ and $R_{71}$ to $R_{82}$ are each independently a hydrogen atom or a substituent, or at least one pair of a pair of $R_{171}$ and $R_{172}$, a pair of $R_{172}$ and $R_{173}$, a pair of $R_{173}$ and $R_{174}$, a pair of $R_{174}$ and $R_{175}$, a pair of $R_{175}$ and $R_{176}$, a pair of $R_{177}$ and $R_{178}$, a pair of $R_{178}$ and $R_{179}$, a pair of $R_{179}$ and $R_{180}$, a pair of $R_{181}$ and $R_{182}$, a pair of $R_{182}$ and $R_{183}$, a pair of $R_{183}$ and $R_{184}$, a pair of $R_{185}$ and $R_{186}$, a pair of $R_{186}$ and $R_{187}$, a pair of $R_{187}$ and $R_{188}$, a pair of $R_{188}$ and $R_{189}$, a pair of $R_{189}$ and $R_{190}$, a pair of $R_{191}$ and $R_{192}$, a pair of $R_{192}$ and $R_{193}$, a pair of $R_{193}$ and $R_{194}$, a pair of $R_{194}$ and $R_{195}$, a pair of $R_{195}$ and $R_{196}$, a pair of $R_{197}$ and $R_{198}$, a pair of $R_{198}$ and $R_{199}$, a pair of $R_{199}$ and $R_{200}$, a pair of $R_{71}$ and $R_{72}$, a pair of $R_{72}$ and $R_{73}$, a pair of $R_{73}$ and $R_{74}$, a pair of $R_{75}$ and $R_{76}$, a pair of $R_{76}$ and $R_{77}$, a pair of $R_{77}$ and $R_{78}$, a pair of $R_{79}$ and $R_{80}$, a pair of $R_{80}$ and $R_{81}$, or a pair of $R_{81}$ and $R_{82}$ are mutually bonded to form a ring;

$R_{171}$ to $R_{200}$ and $R_{71}$ to $R_{82}$ as the substituent are each independently a halogen atom, a substituted or unsubstituted aryl group having 6 to 14 ring carbon atoms, a substituted or unsubstituted heterocyclic group having 5 to 14 ring atoms, a substituted or unsubstituted alkyl group having 1 to 6 carbon atoms, a substituted or unsubstituted alkyl halide group having 1 to 30 carbon atoms, a substituted or unsubstituted alkylsilyl group having 3 to 6 carbon atoms, a hydroxy group, a substituted or unsubstituted alkoxy group having 1 to 6 carbon atoms, a substituted or unsubstituted alkoxy halide group having 1 to 6 carbon atoms, a substituted or unsubstituted aryloxy group having 6 to 14 ring carbon atoms, a substituted or unsubstituted alkylamino group having 2 to 12 carbon atoms, a thiol group, a substituted or unsubstituted alkylthio group having 1 to 6 carbon atoms, or a substituted or unsubstituted arylthio group having 6 to 14 ring carbon atoms; and

* represents a bonding position to a carbon atom of a benzene ring in the formula (1).

It is also more preferable that $D_1$ in the compound M2 of the exemplary embodiment is a group represented by one of the formulae (2-1), (2-3) and (2-4).

195

It is also further preferable that $D_1$ in the compound M2 of the exemplary embodiment is a group represented by one of the formulae (2-1) and (2-3).

It is also preferable that the compound M2 of the exemplary embodiment is a compound represented by one of the formulae (1-1), (1-4) to (1-7), (1-10), (1-14) to (1-17), (1-21), and (1-23) to (1-25), and $D_1$ is a group represented by one of the formulae (2-1), (2-2), (2-3), and (2-4).

It is also preferable that the compound M2 of the exemplary embodiment is a compound represented by one of the formulae (1-6), (1-23), and (1-24), and $D_1$ is a group represented by one of the formulae (2-1), (2-2), (2-3), and (2-4).

It is also preferable that the compound M2 of the exemplary embodiment is a compound represented by one of the formulae (1-1), (1-10), and (1-21), and $D_1$ is a group represented by one of the formulae (2-1), (2-2), (2-3), and (2-4). More preferably, $D_1$ is a group represented by one of the formulae (2-1), (2-3), and (2-4).

It is preferable that $R_{171}$ to $R_{200}$ and $R_{71}$ to $R_{82}$ as a substituent in the compound M2 of the exemplary embodiment are each independently an unsubstituted aryl group having 6 to 14 ring carbon atoms, an unsubstituted heterocyclic group having 5 to 14 ring atoms, or an unsubstituted alkyl group having 1 to 6 carbon atoms.

It is also preferable that $R_{171}$ to $R_{200}$ and $R_{71}$ to $R_{82}$ in the compound M2 of the exemplary embodiment are hydrogen atoms.

Manufacturing Method of Compound M2

The compound M2 can be manufactured by a known method.

Specific examples of the compound M2 of the exemplary embodiment include compounds below. It should however be noted that the invention is not limited to the specific examples of the compound.

[Formula 91]

196

-continued

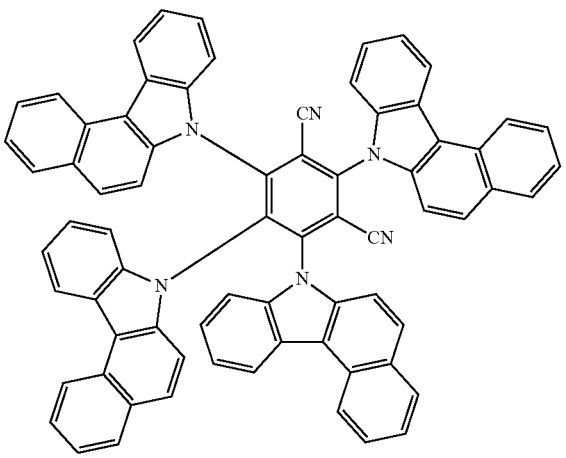

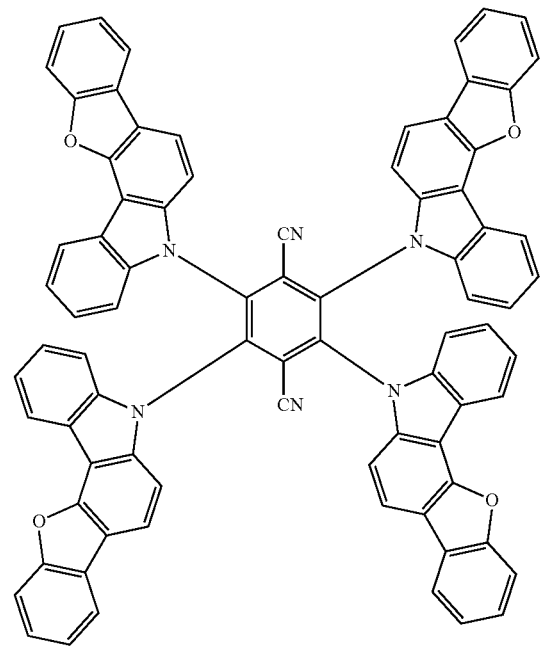

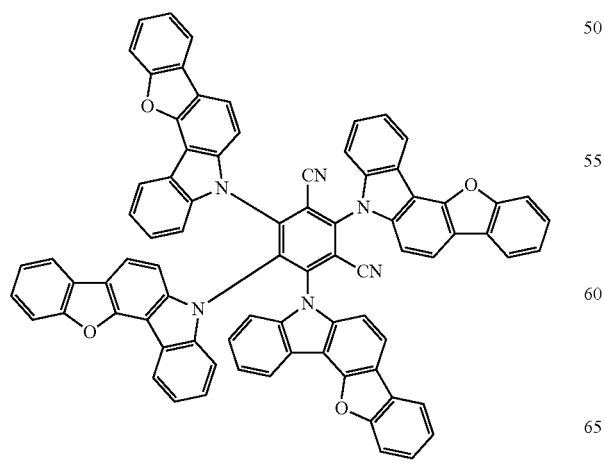

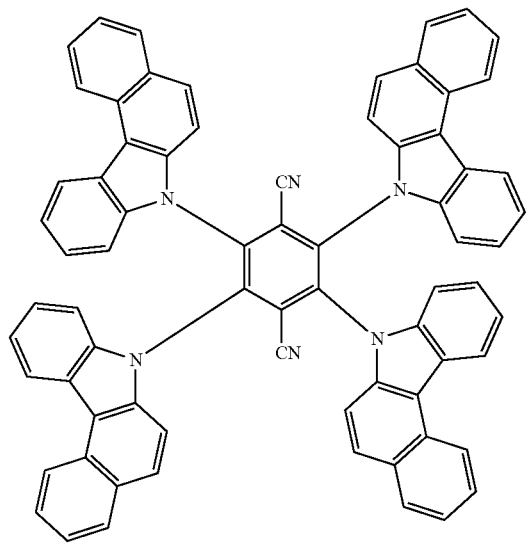

197
-continued
198
-continued
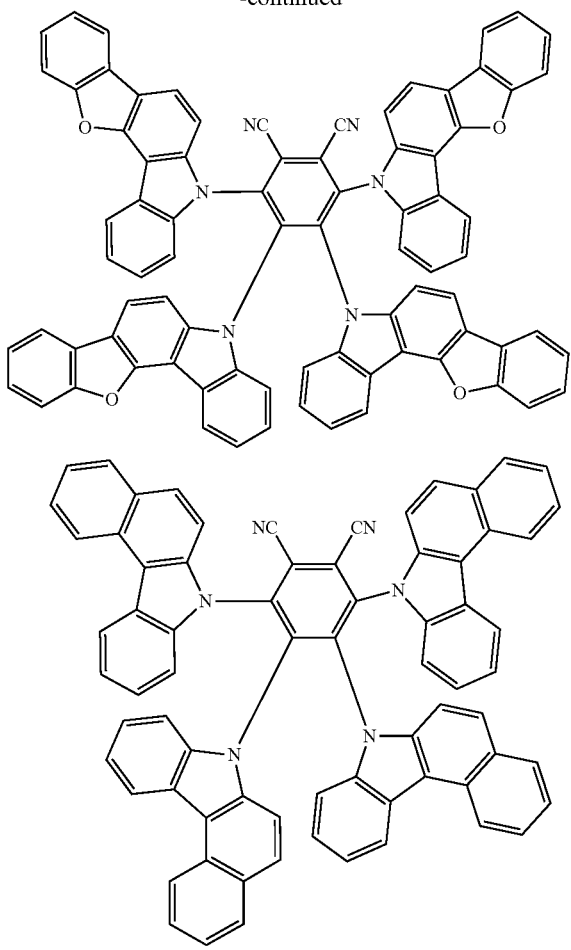
[Formula 92]
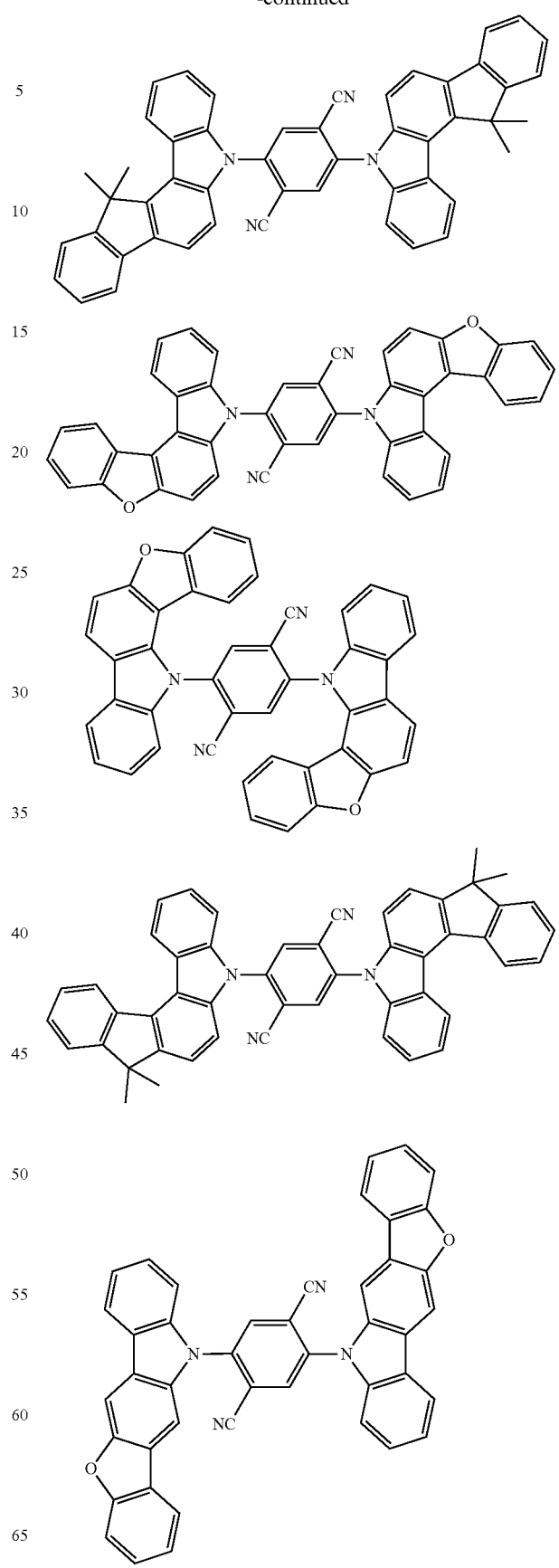

199
-continued
200
-continued
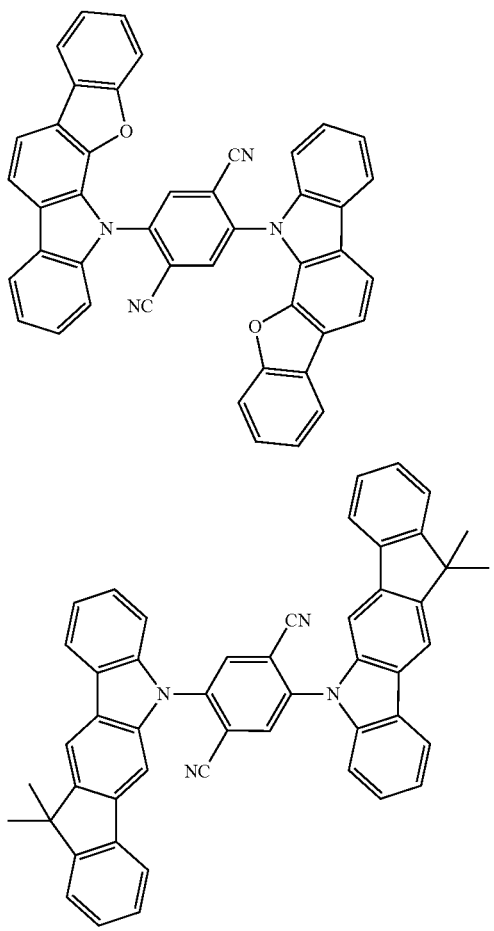
[Formula 93]
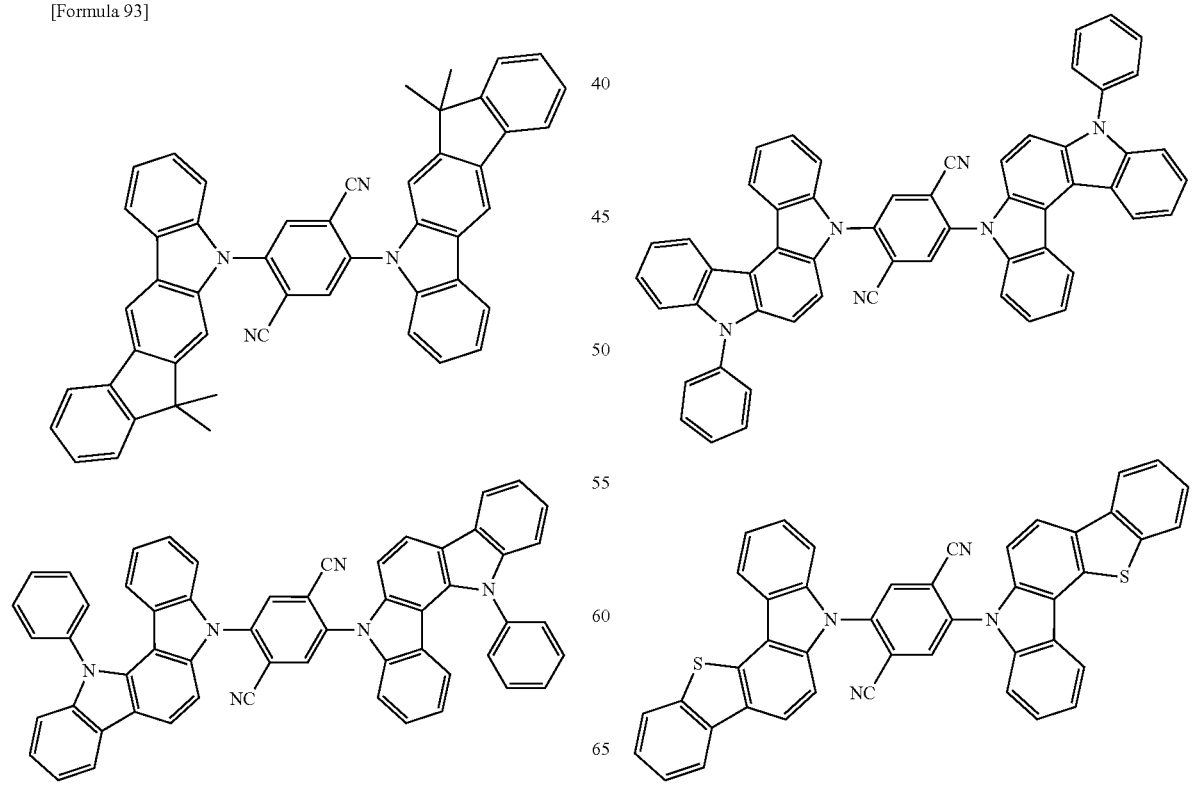

201
-continued
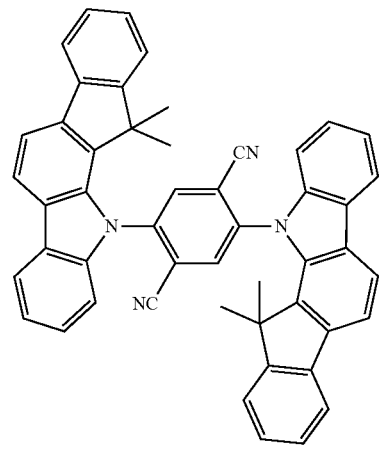
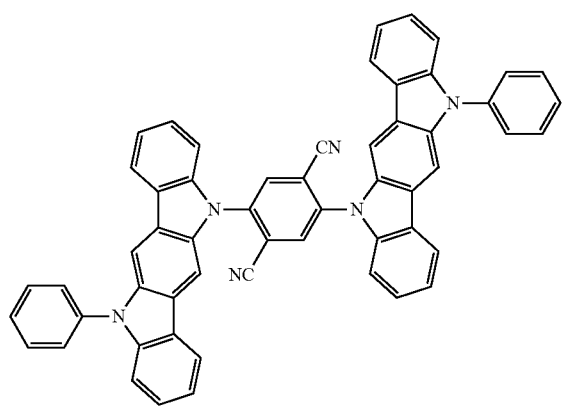
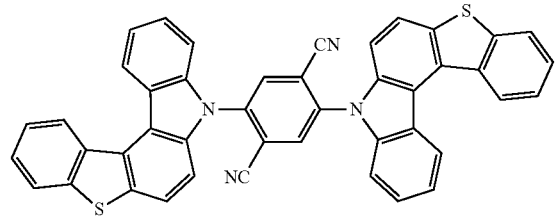
[Formula 94]
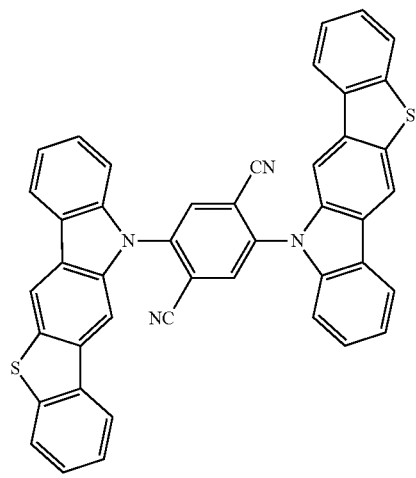
202
-continued
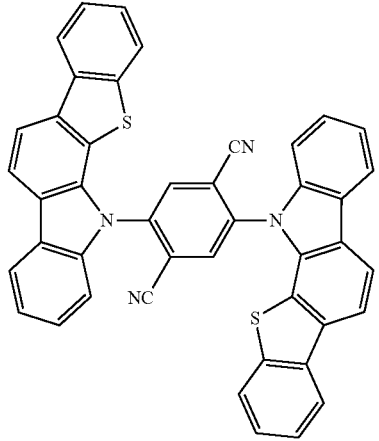
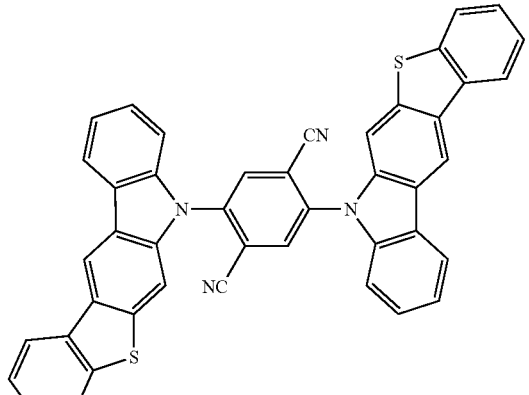
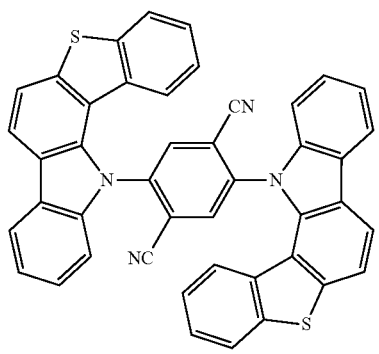
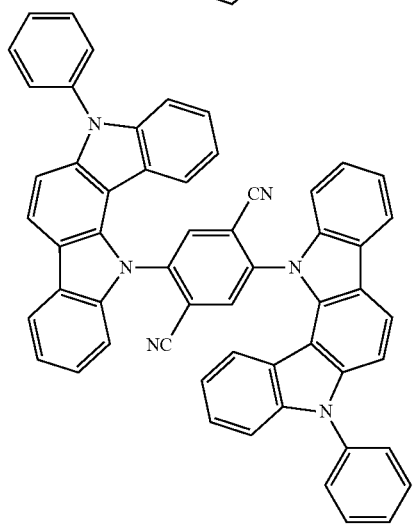

[Formula 95]
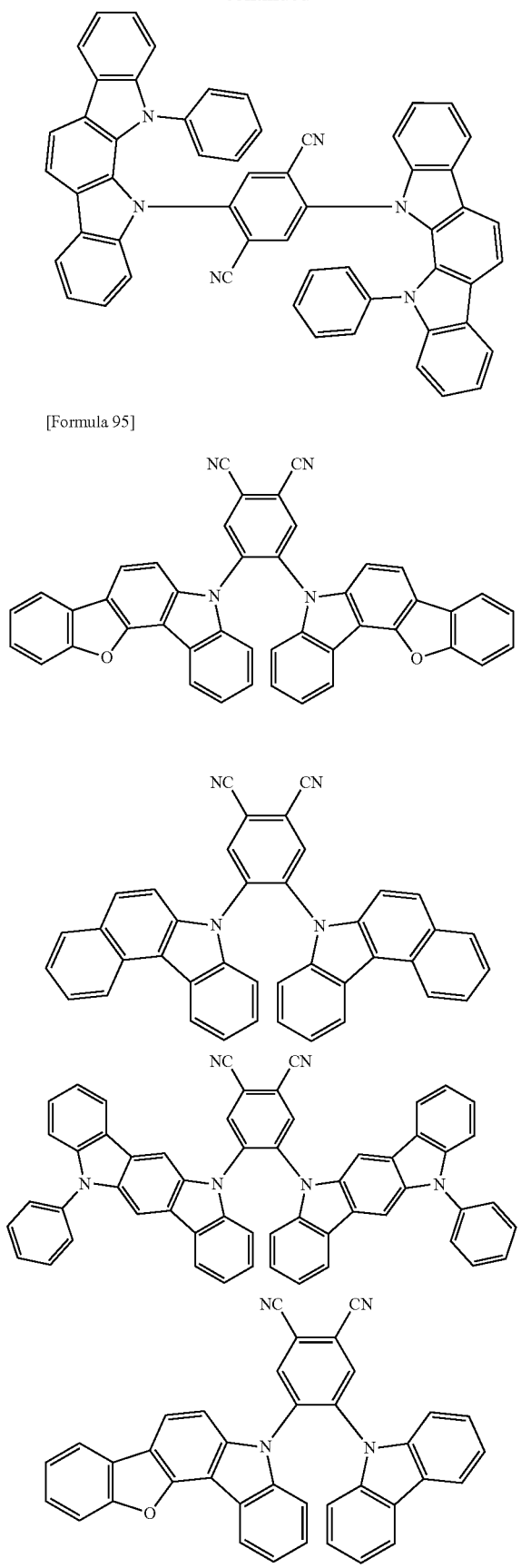
[Formula 96]
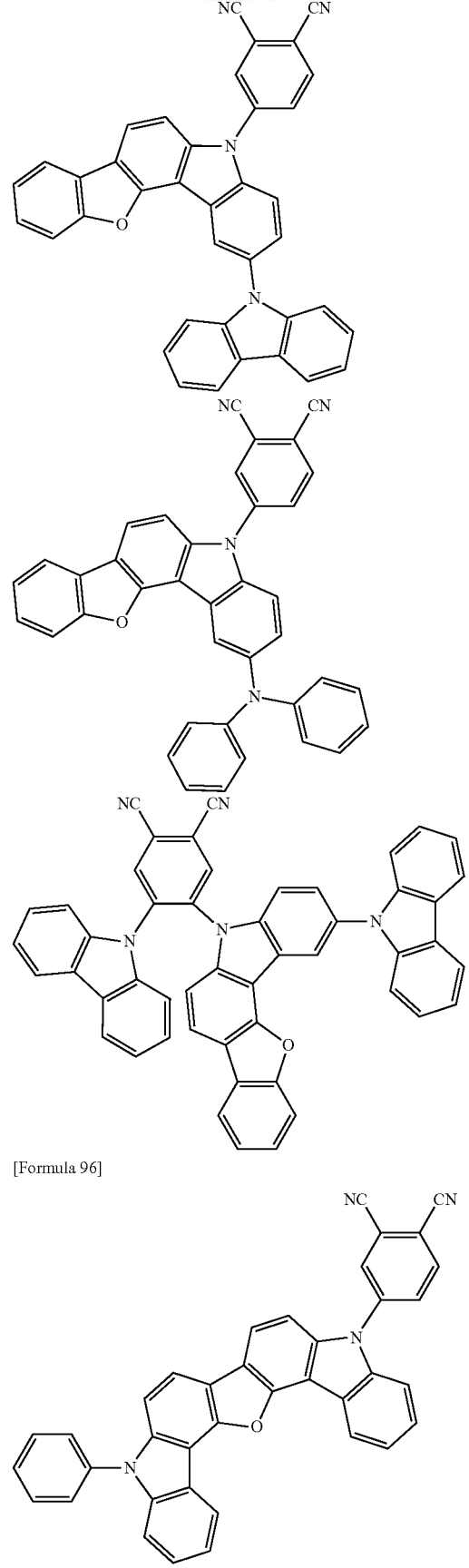

205
-continued
206
-continued
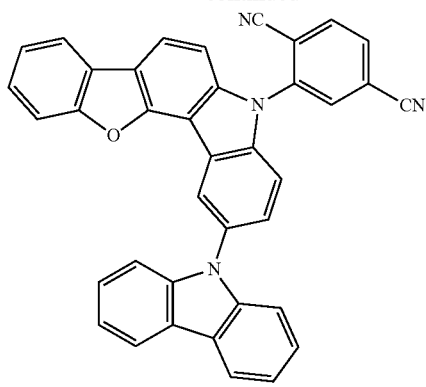
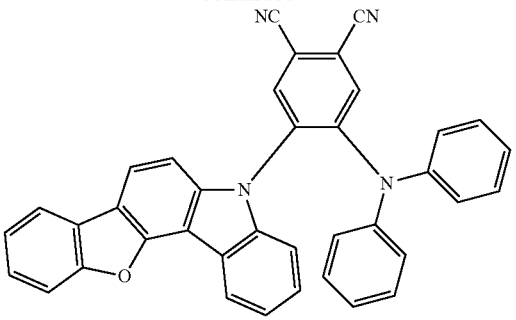
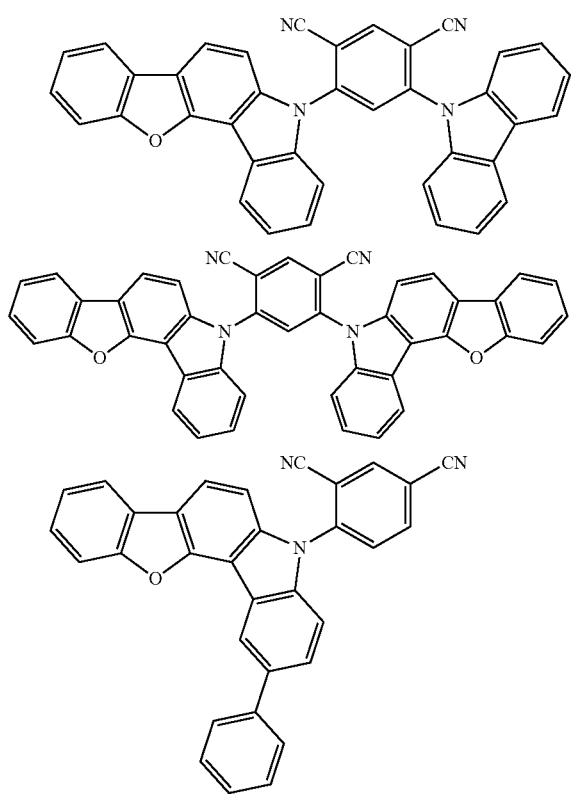
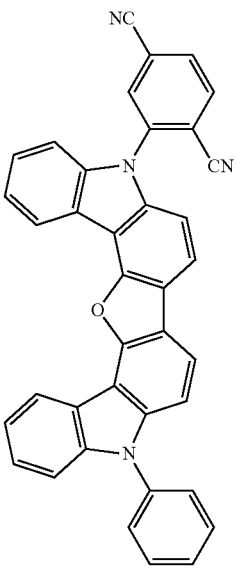
[Formula 97]

207
-continued
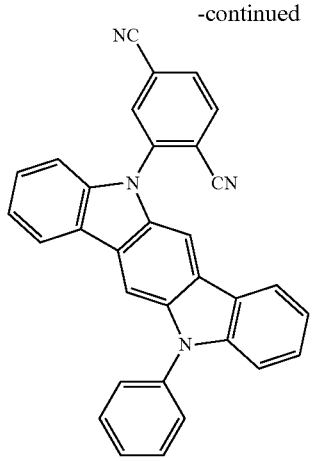
[Formula 98]
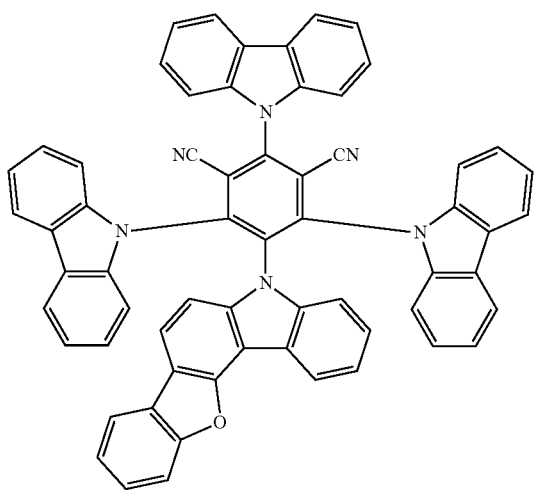
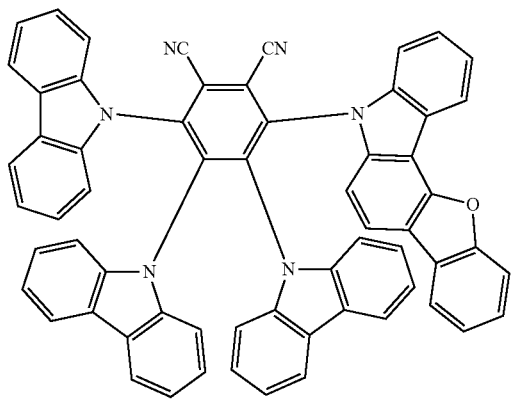
208
-continued
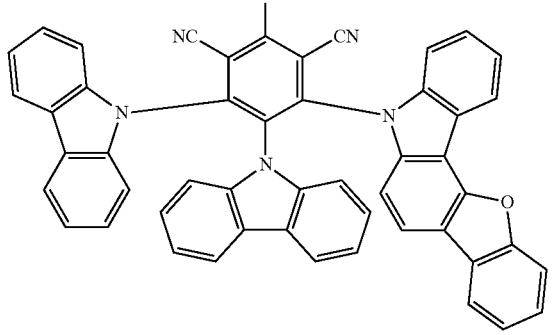
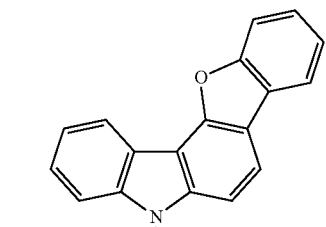
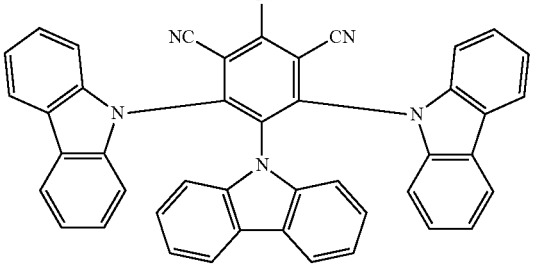
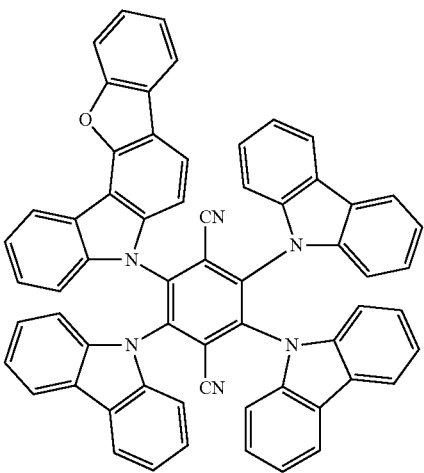

[Formula 99]
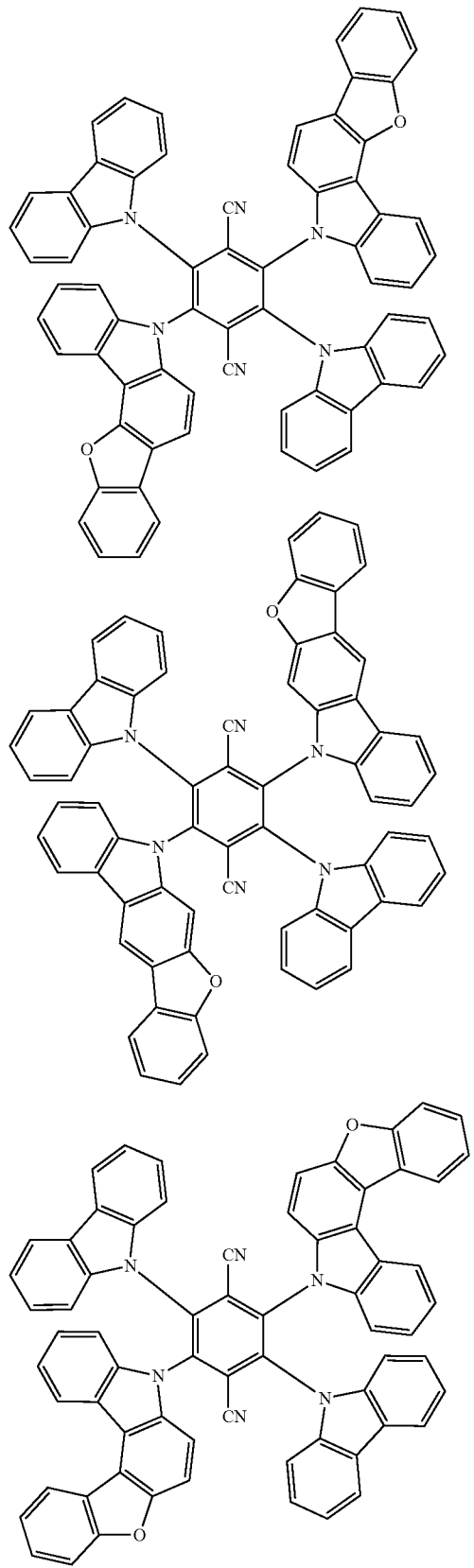
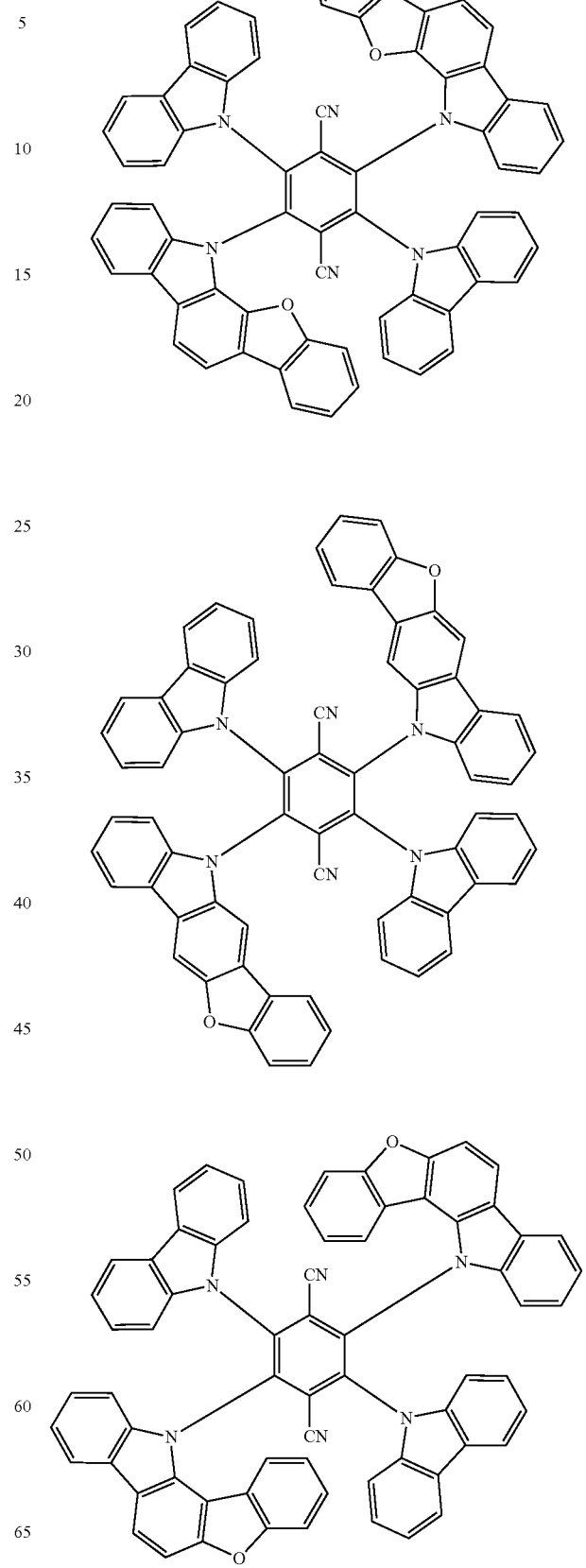

211
-continued
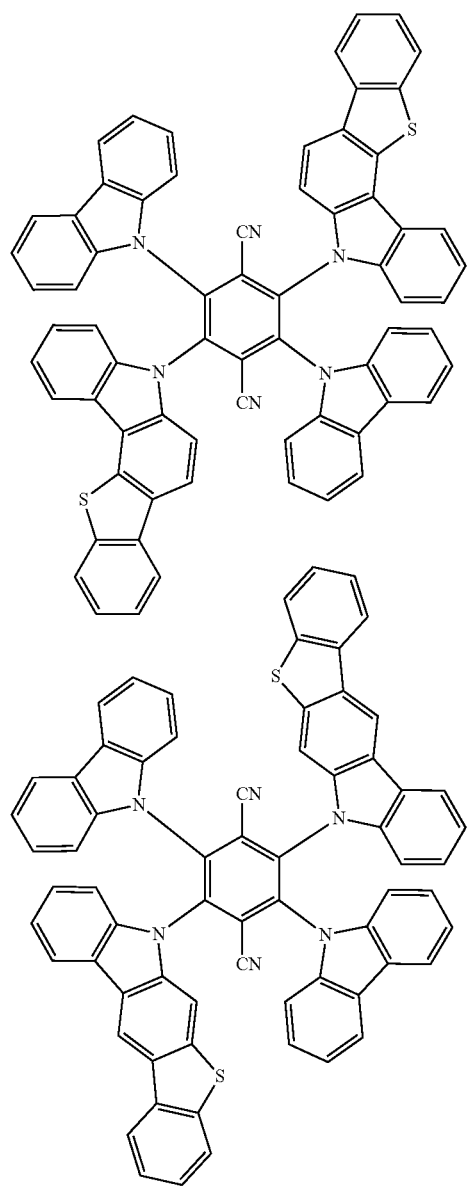
212
-continued
[Formula 100]
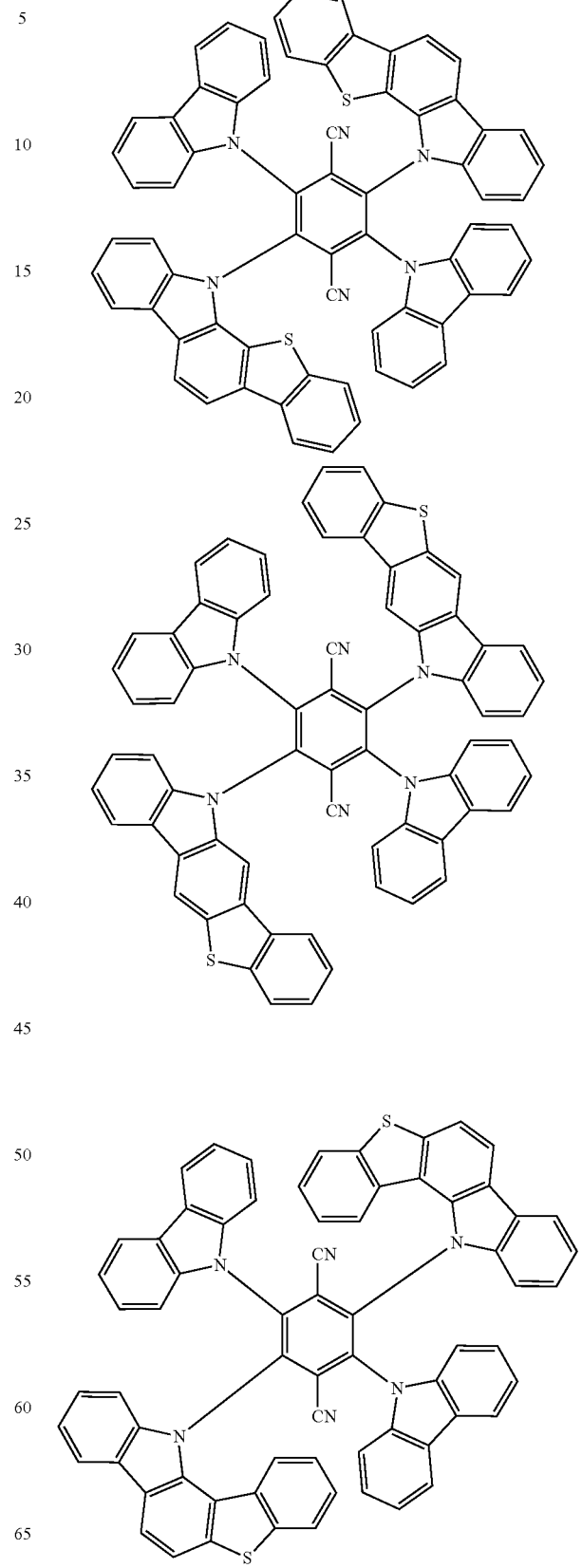

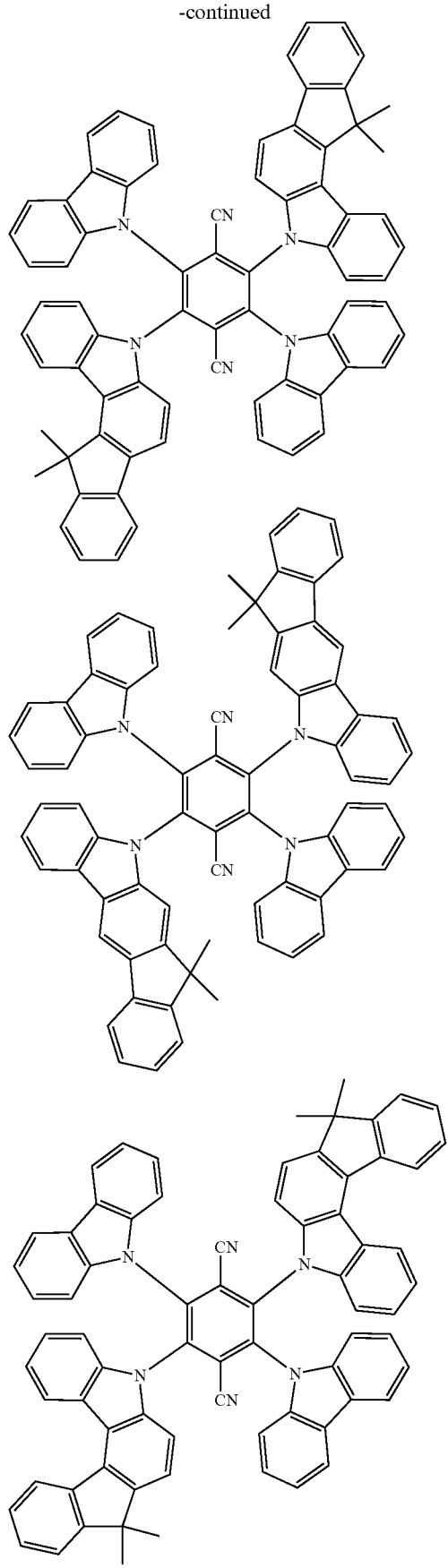
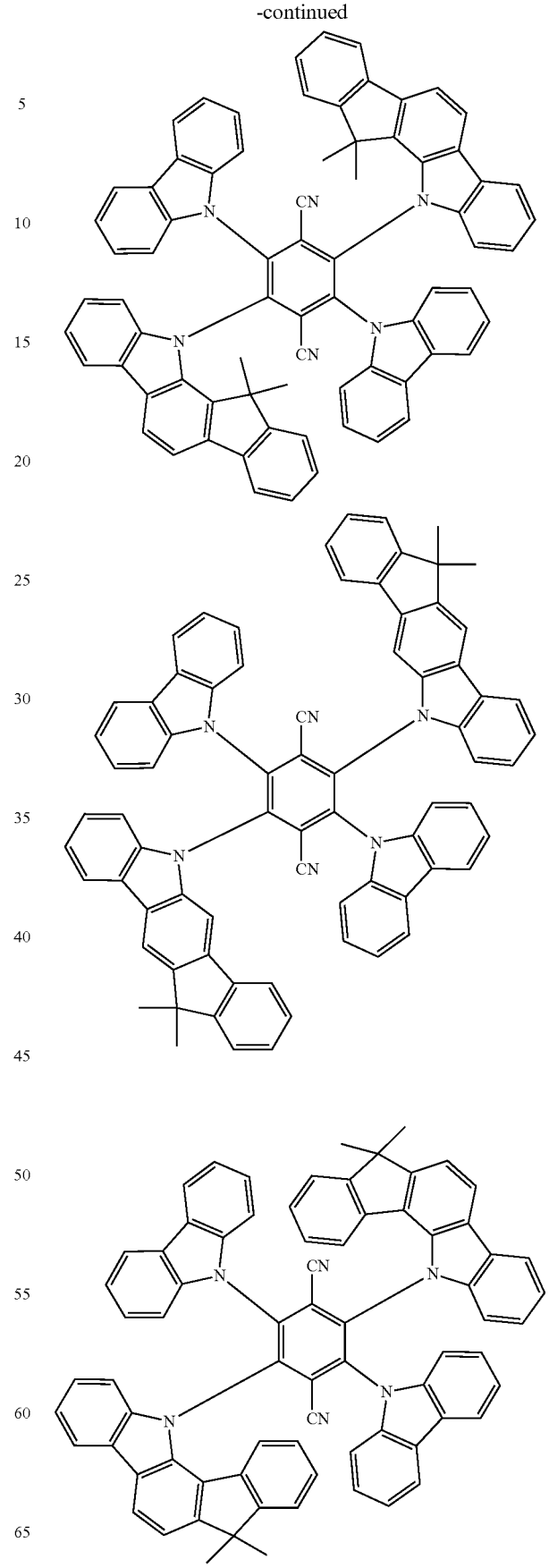

[Formula 101]
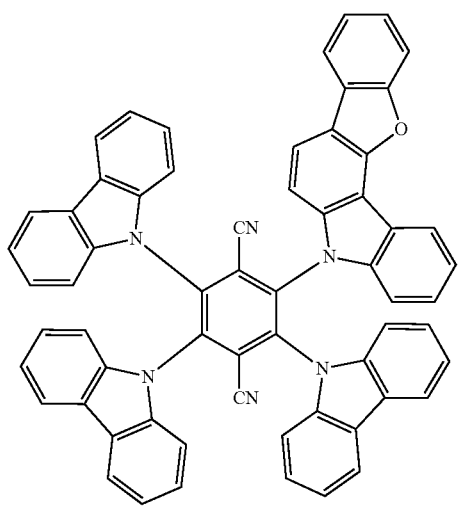
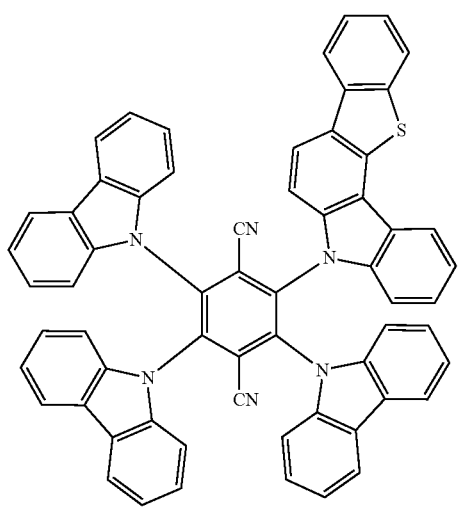
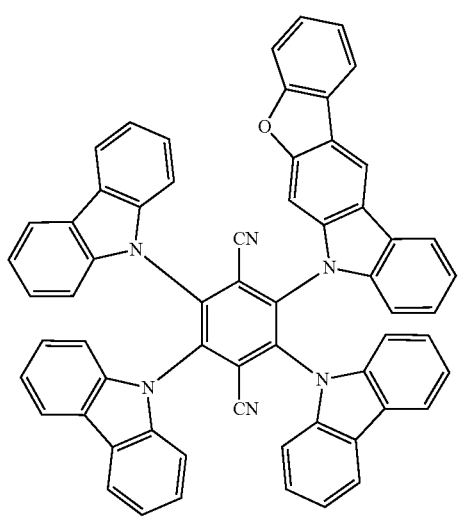
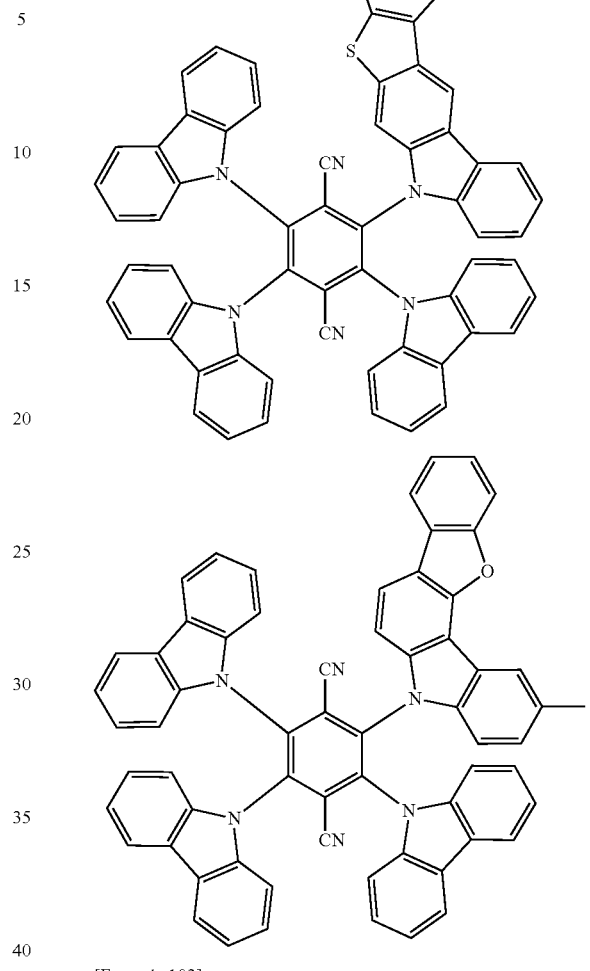
[Formula 102]

217
-continued
218
-continued
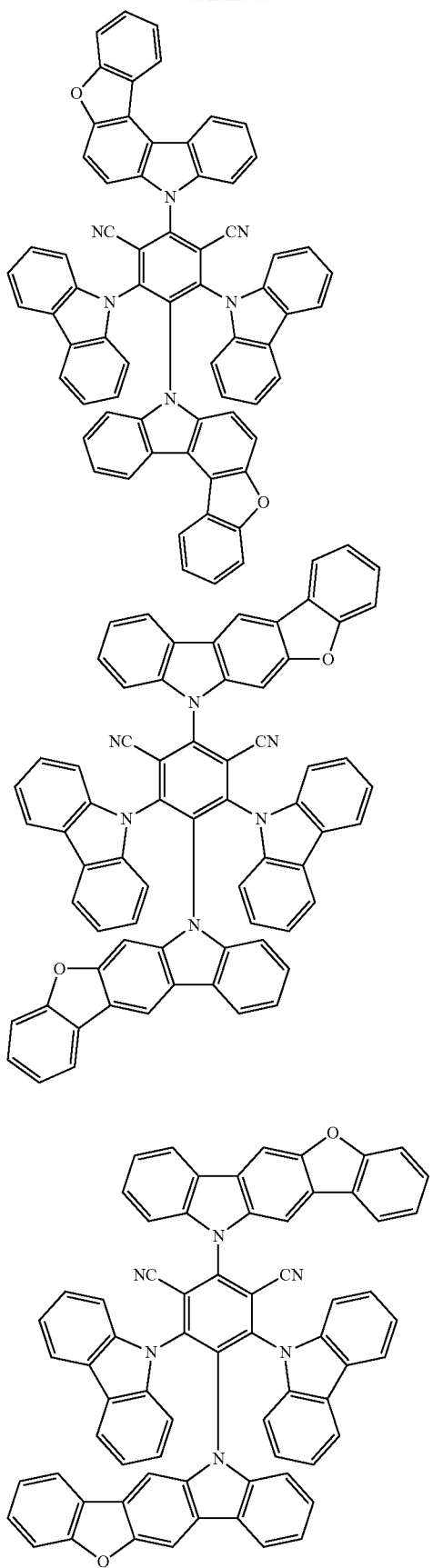
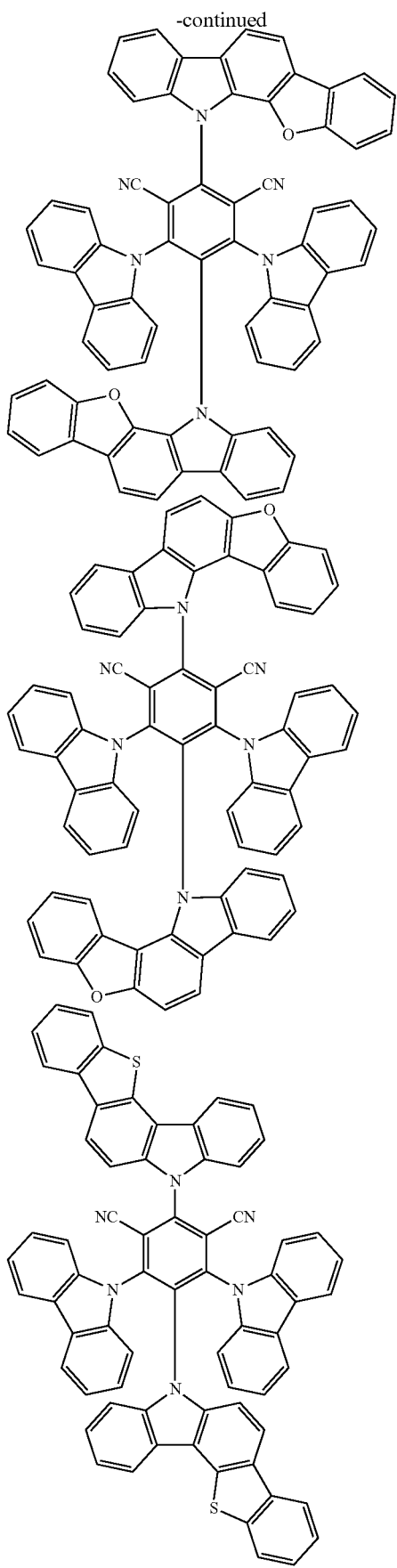

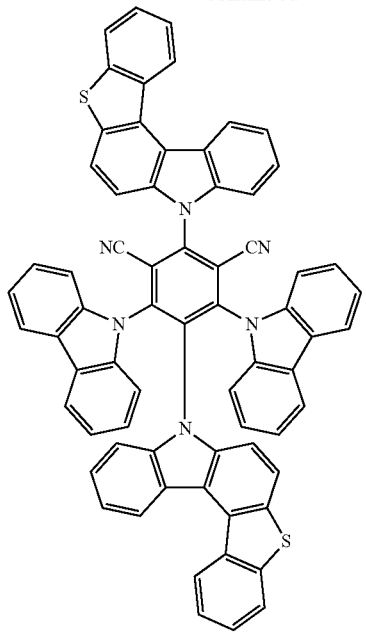
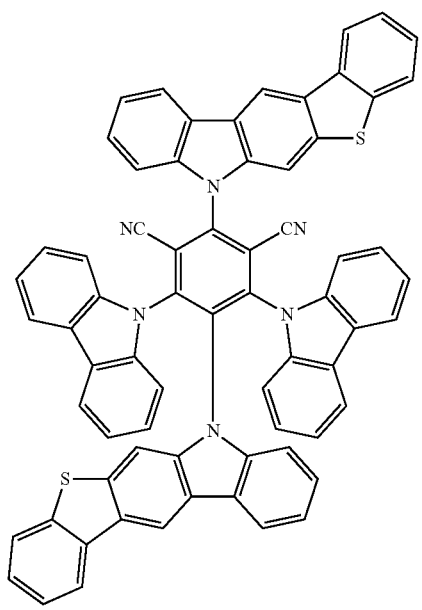
[Formula 103]
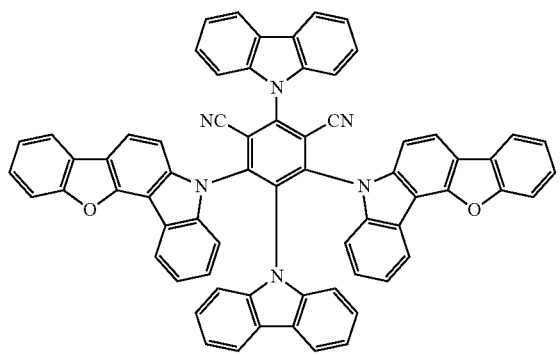
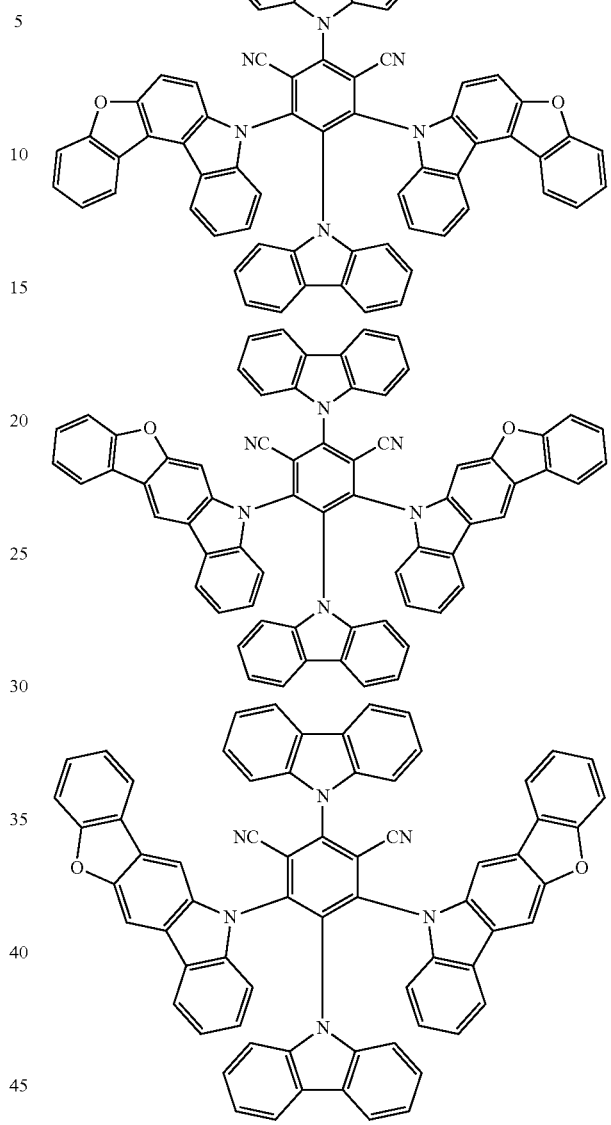
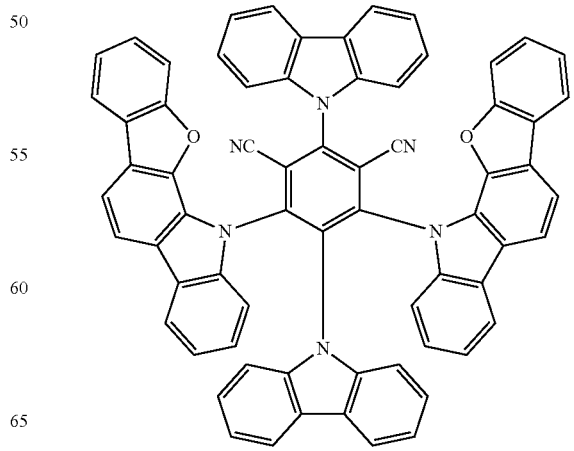

221
-continued
222
-continued
[Formula 104]
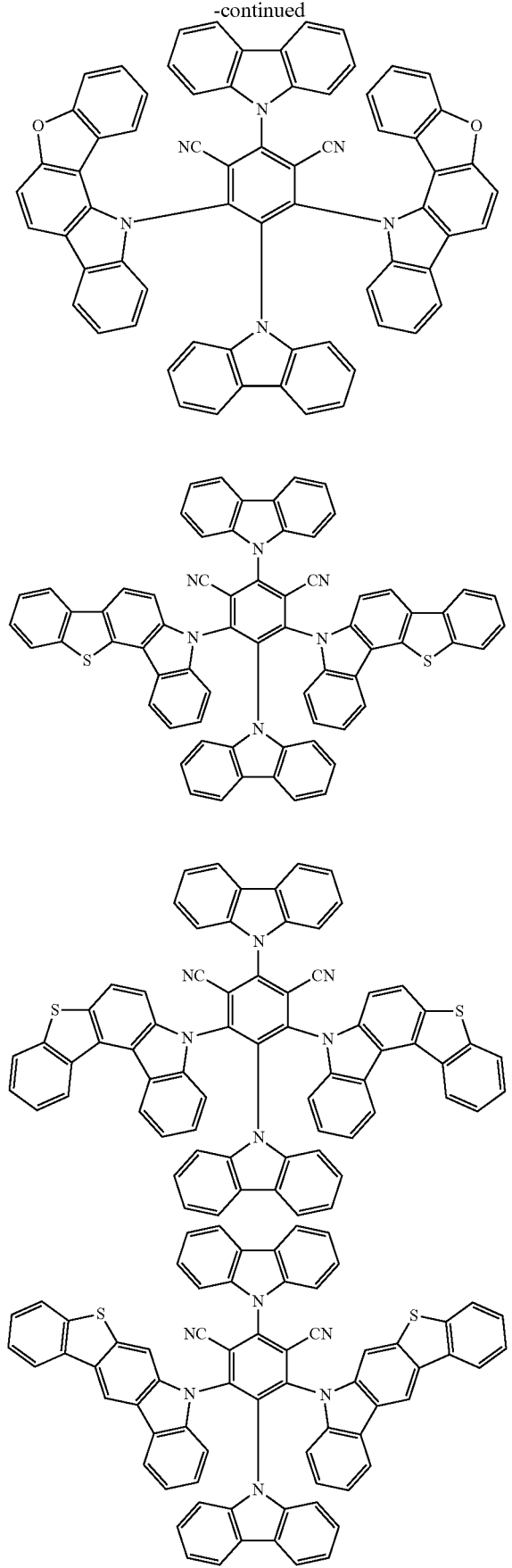
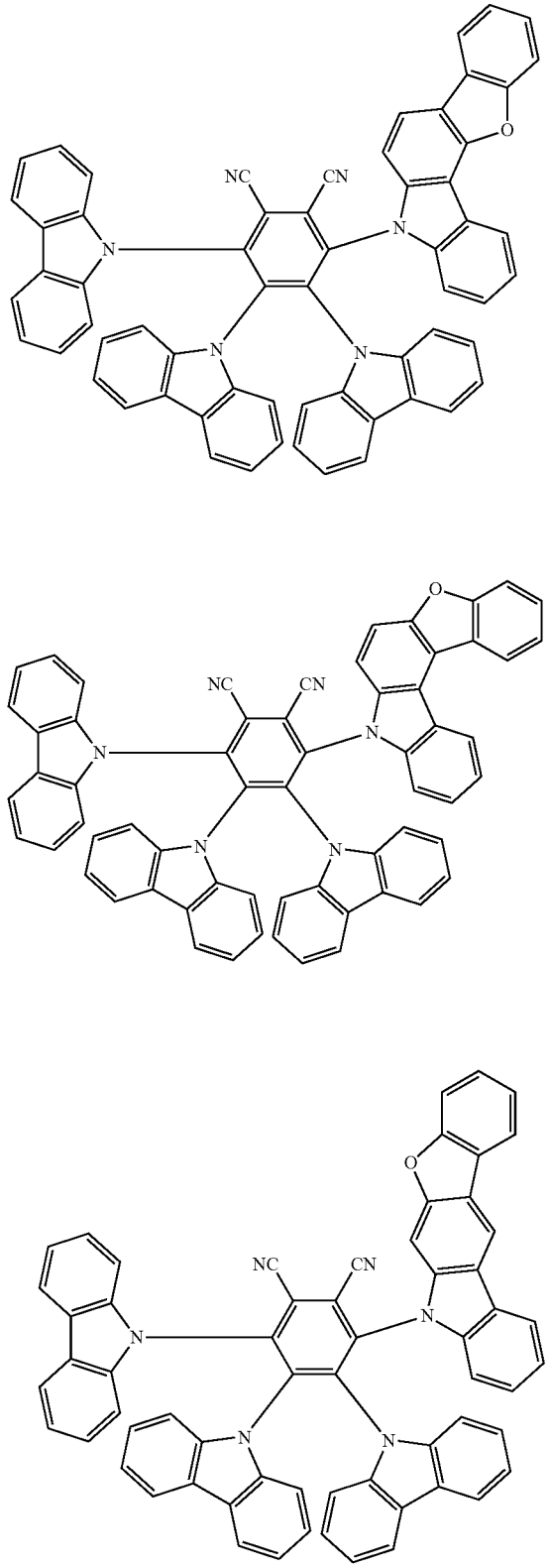

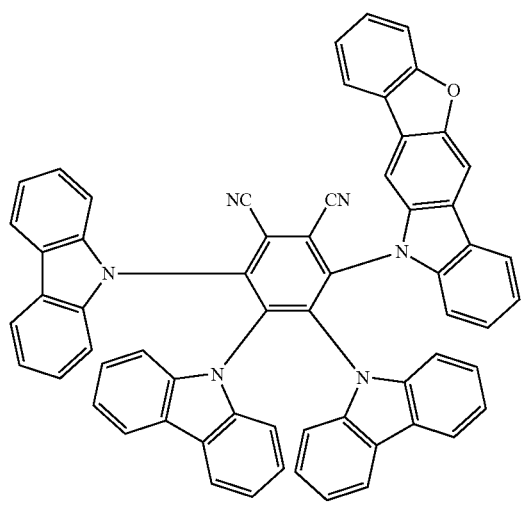
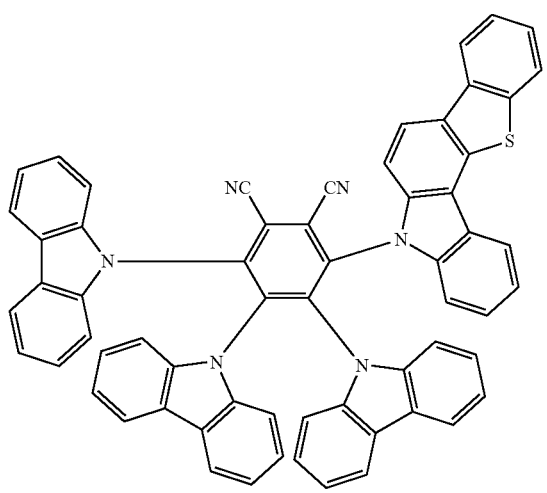
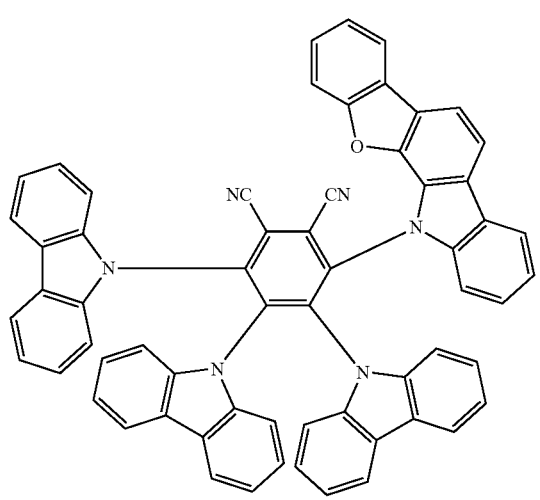
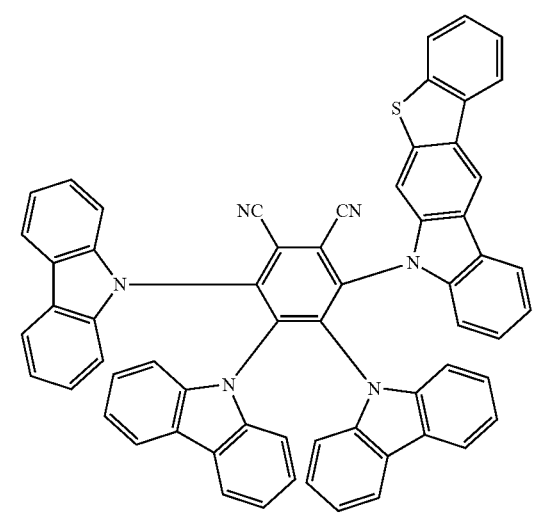
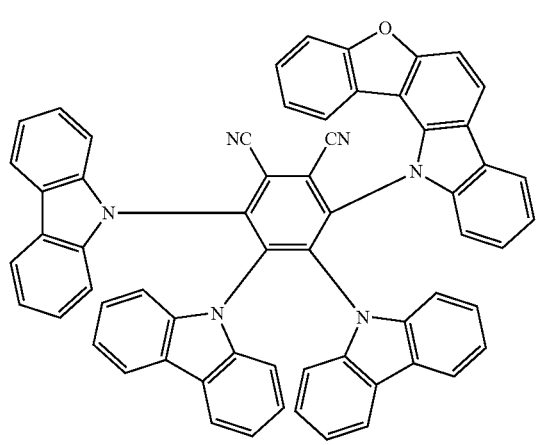

[Formula 105]
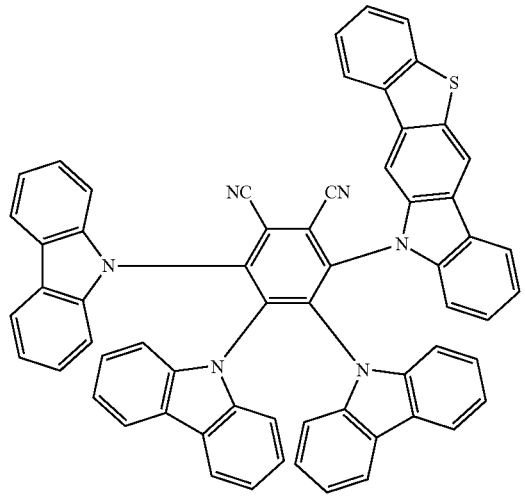
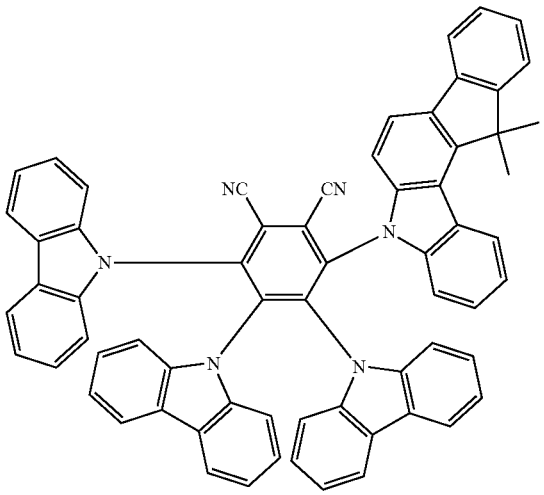
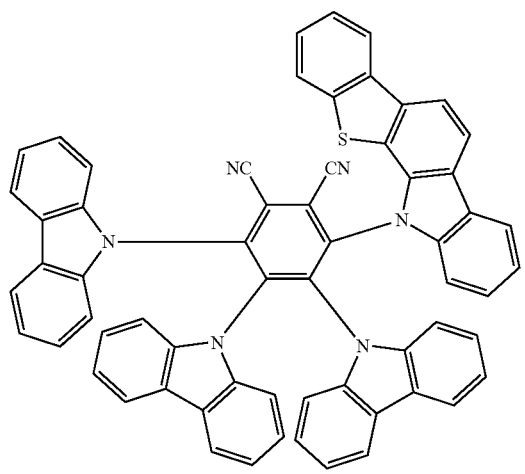
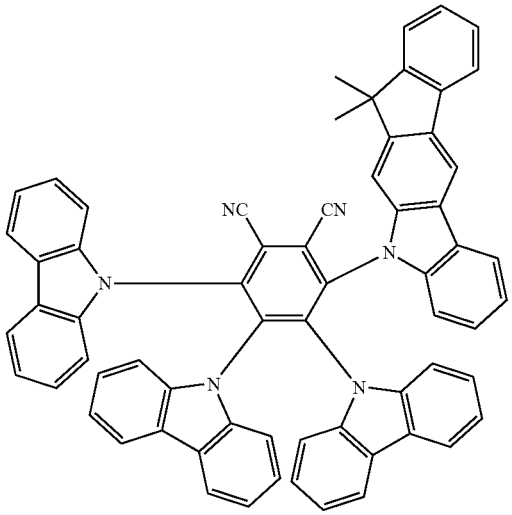
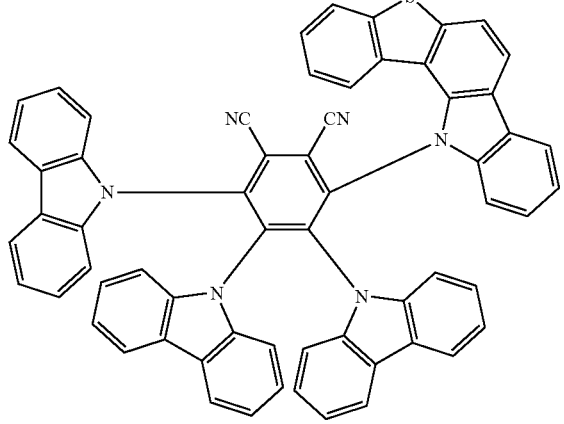

227
-continued
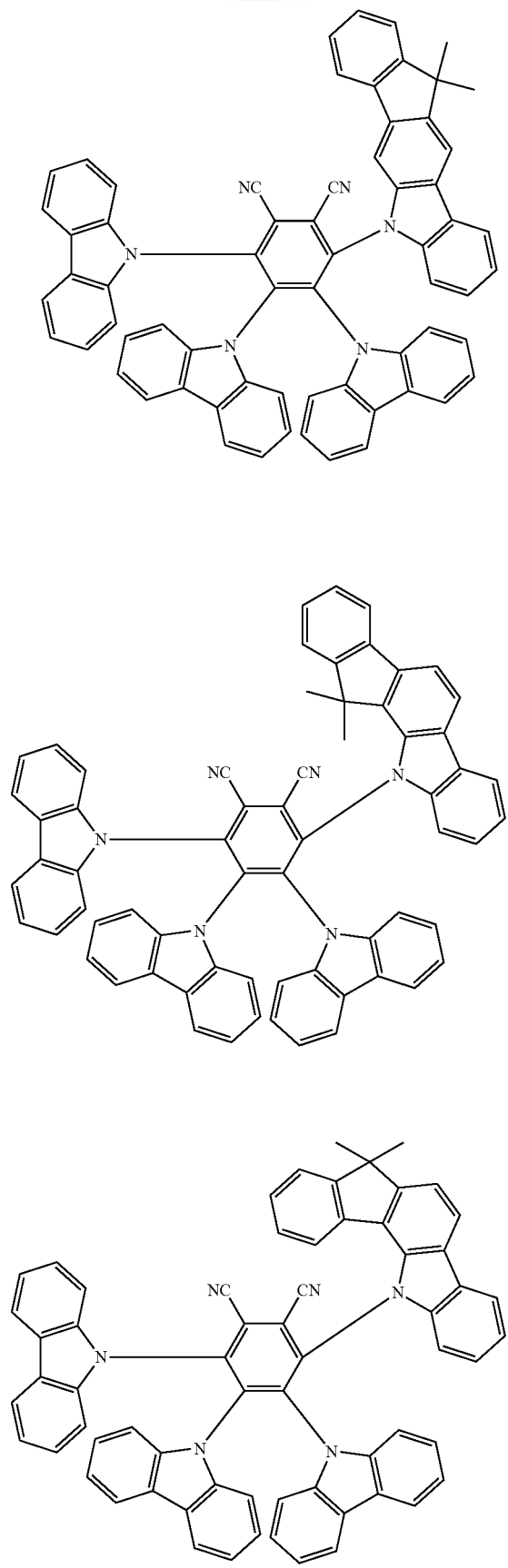
228
-continued
[Formula 106]
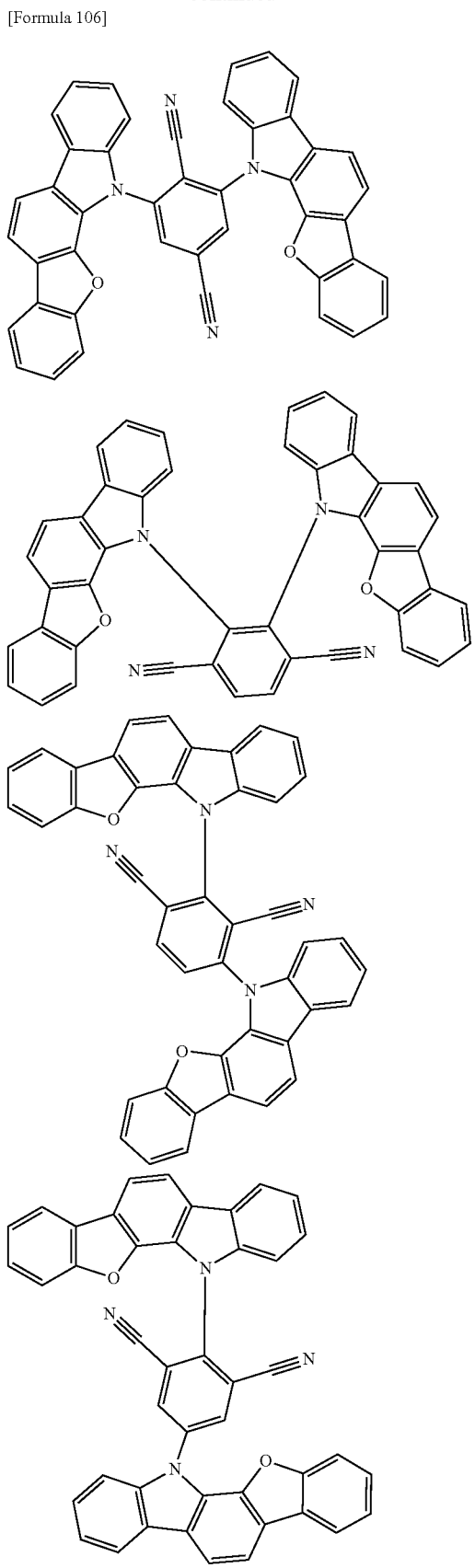

[Formula 107]
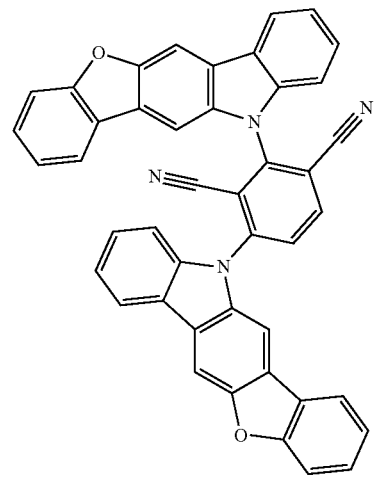
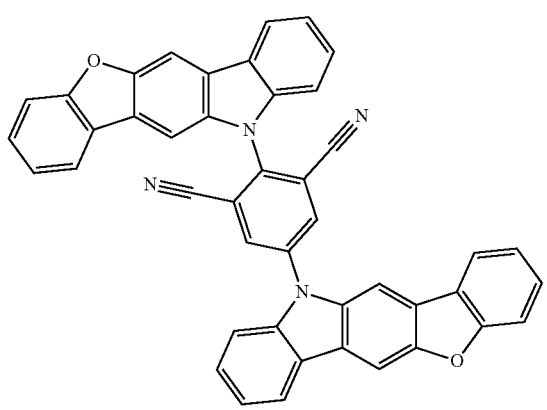
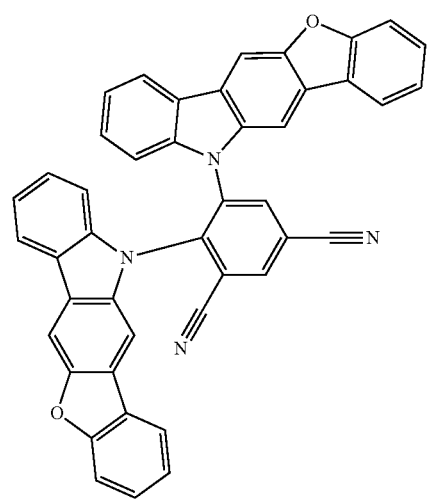
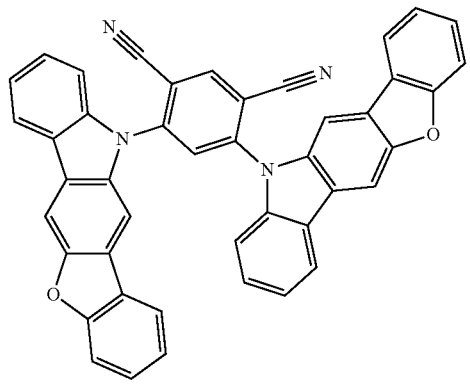
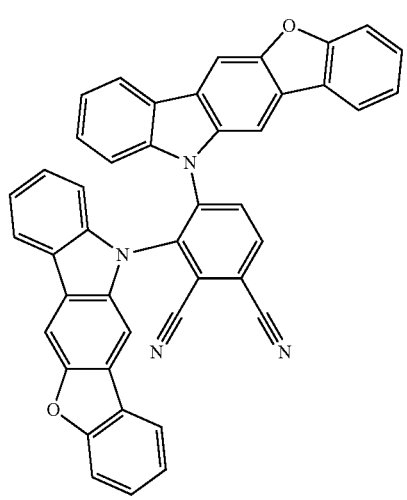
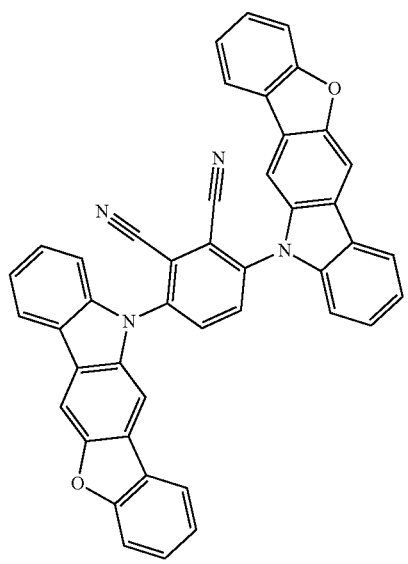

231
-continued
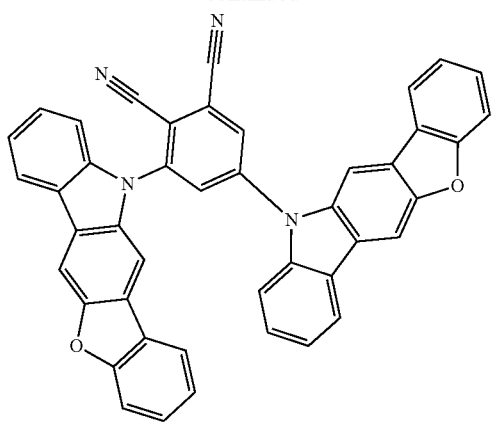
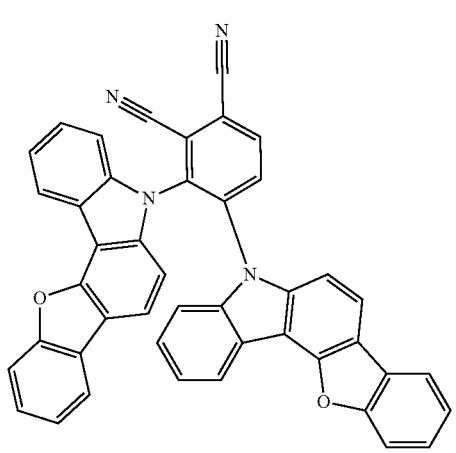
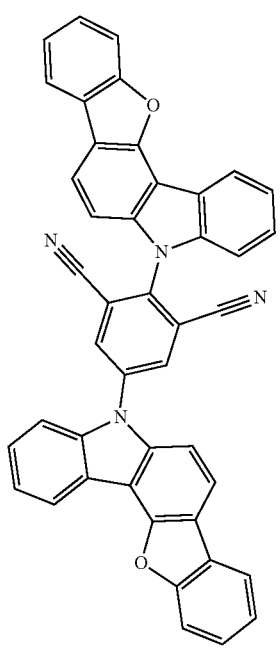
232
-continued
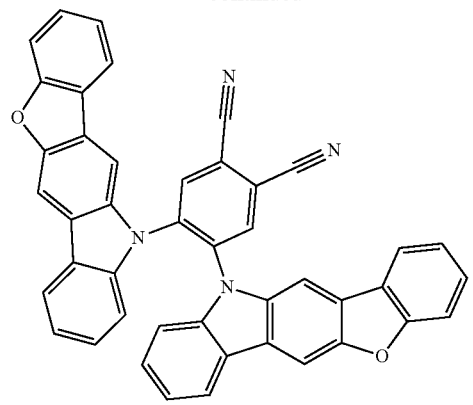
[Formula 108]
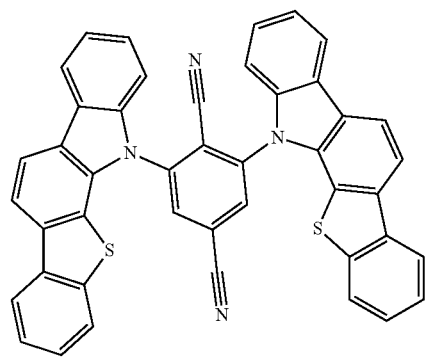
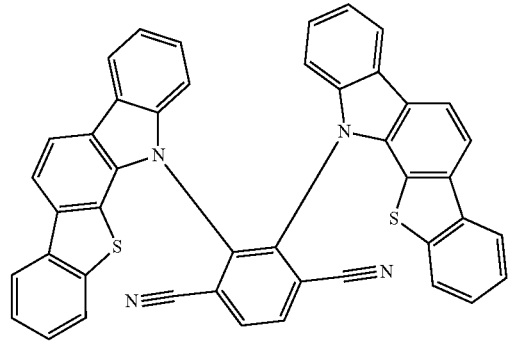
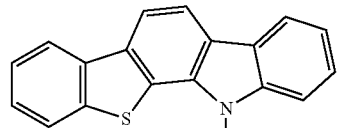
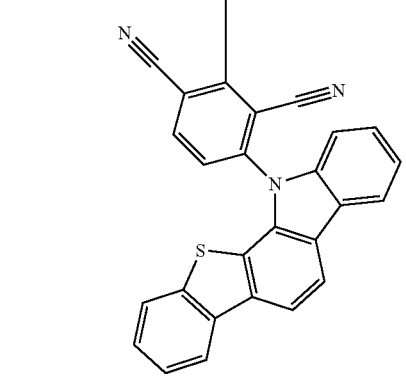

233
-continued
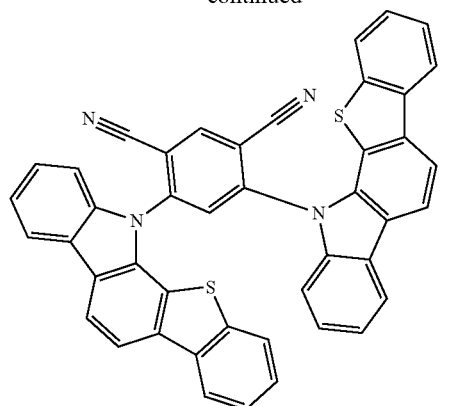
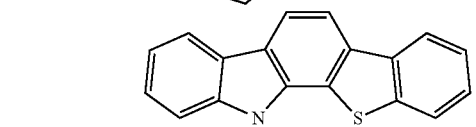
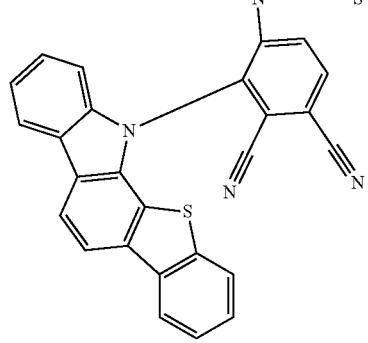
[Formula 109]
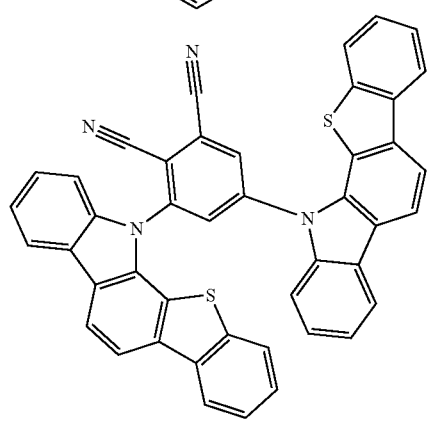
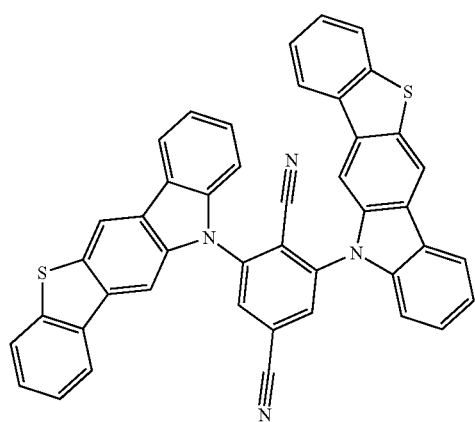
234
-continued
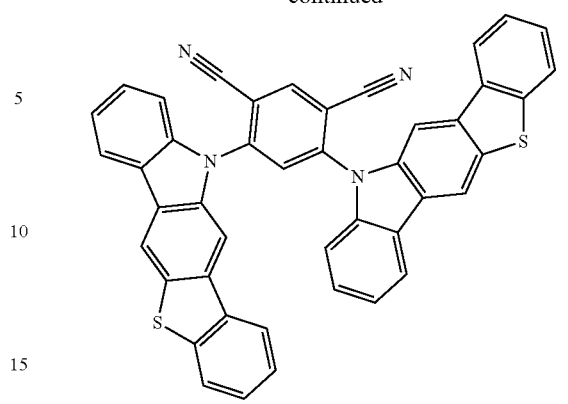
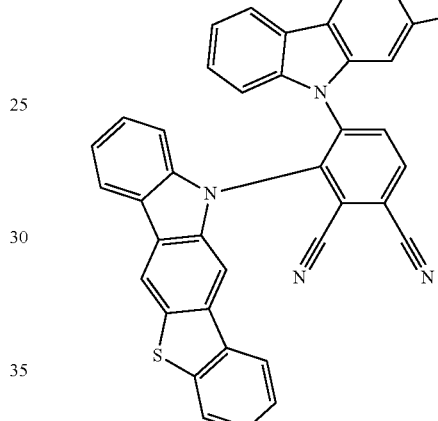
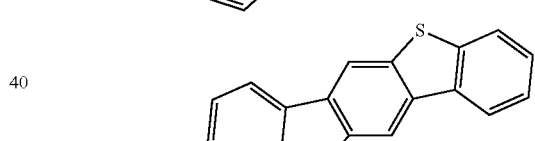
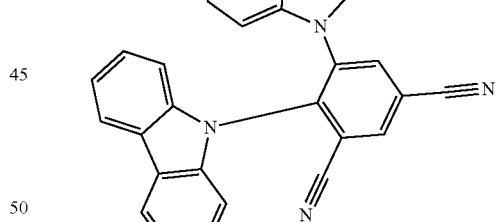
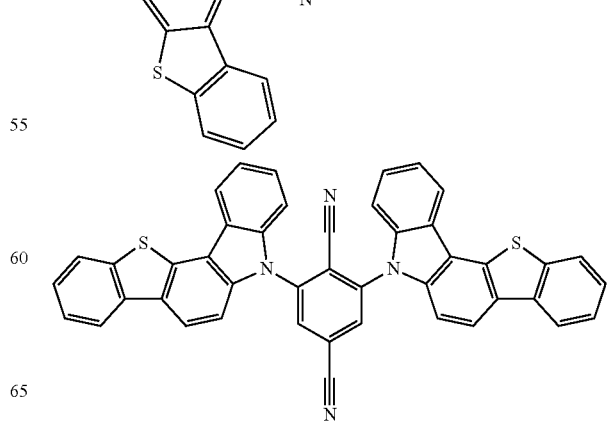

-continued
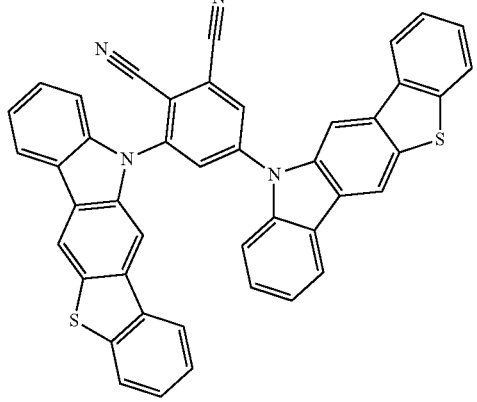
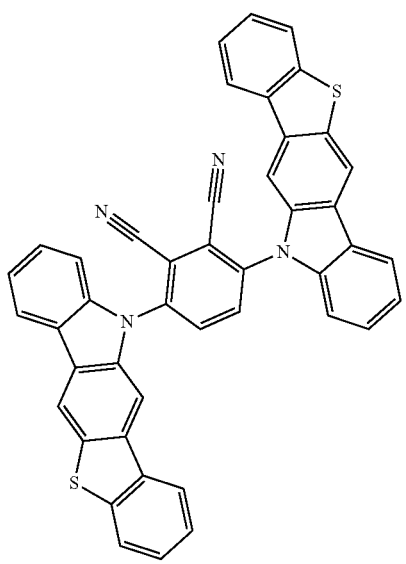
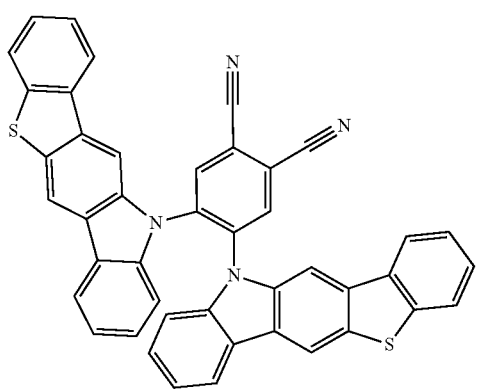
-continued
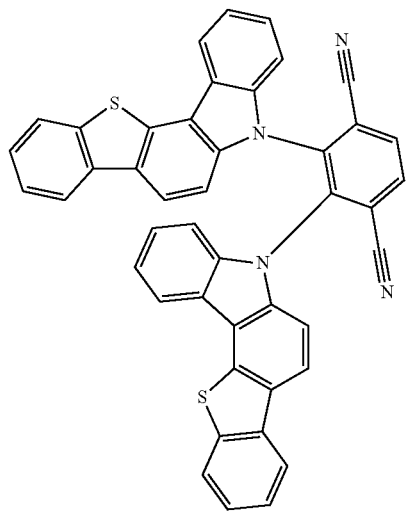
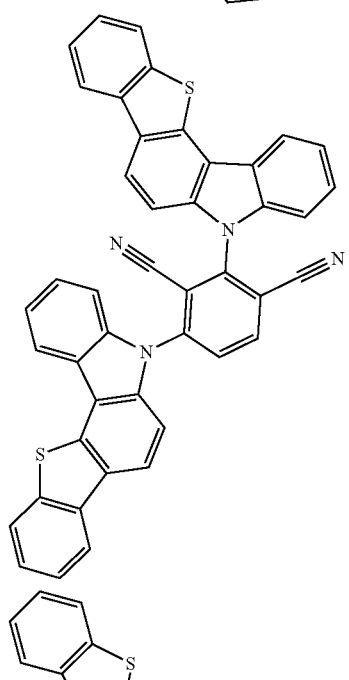
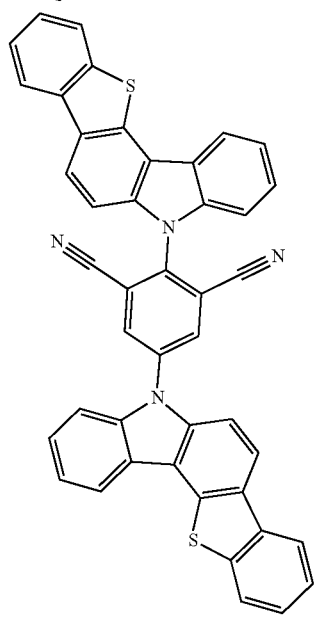

Delayed fluorescence is explained in "Yuki Hando-tai no Debaisu Bussei (Device Physics of Organic Semiconductors)" (edited by ADACHI, Chihaya, published by Kodansha, on pages 261-268). This document describes that, if an energy gap $\Delta E_{13}$ of a fluorescent material between a singlet state and a triplet state is reducible, a reverse energy transfer from the triplet state to the singlet state, which usually occurs at a low transition probability, would occur at a high efficiency to express thermally activated delayed fluorescence (TADF). Further, a mechanism of generating delayed fluorescence is explained in FIG. 10.38 in the document. The compound M2 of the exemplary embodiment is preferably a compound exhibiting thermally activated delayed fluorescence generated by such a mechanism.

In general, emission of delayed fluorescence can be confirmed by measuring the transient PL (Photo Luminescence).

The behavior of delayed fluorescence can also be analyzed based on the decay curve obtained from the transient PL measurement. The transient PL measurement is a method of irradiating a sample with a pulse laser to excite the sample, and measuring the decay behavior (transient characteristics) of PL emission after the irradiation is stopped. PL emission in TADF materials is classified into a light emission component from a singlet exciton generated by the first PL excitation and a light emission component from a singlet exciton generated via a triplet exciton. The lifetime of the singlet exciton generated by the first PL excitation is on the order of nanoseconds and is very short. Therefore, light emission from the singlet exciton rapidly attenuates after irradiation with the pulse laser.

On the other hand, the delayed fluorescence is gradually attenuated due to light emission from a singlet exciton generated via a triplet exciton having a long lifetime. As described above, there is a large temporal difference between the light emission from the singlet exciton generated by the first PL excitation and the light emission from the singlet exciton generated via the triplet exciton. Therefore, the luminous intensity derived from delayed fluorescence can be determined.

FIG. 2 shows a schematic diagram of an exemplary device for measuring the transient PL. An example of a method of measuring a transient PL using FIG. 2 and an example of behavior analysis of delayed fluorescence will be described.

A transient PL measuring device 100 in FIG. 2 includes: a pulse laser 101 capable of radiating a light having a predetermined wavelength; a sample chamber 102 configured to house a measurement sample; a spectrometer 103 configured to divide a light radiated from the measurement sample; a streak camera 104 configured to provide a two-dimensional image; and a personal computer 105 configured to import and analyze the two-dimensional image. A device for measuring the transient PL is not limited to the device described in the exemplary embodiment.

The sample to be housed in the sample chamber 102 is obtained by doping a matrix material with a doping material at a concentration of 12 mass % and forming a thin film on a quartz substrate.

The thin film sample housed in the sample chamber 102 is radiated with a pulse laser from the pulse laser 101 to excite the doping material. Emission is extracted in a direction of 90 degrees with respect to a radiation direction of the excited light. The extracted emission is divided by the spectrometer 103 to form a two-dimensional image in the streak camera 104. As a result, the two-dimensional image is obtainable in which the ordinate axis represents a time, the abscissa axis represents a wavelength, and a bright spot represents a luminous intensity. When this two-dimensional image is taken out at a predetermined time axis, an emission spectrum in which the ordinate axis represents the luminous intensity and the abscissa axis represents the wavelength is obtainable. Moreover, when this two-dimensional image is taken out at the wavelength axis, a decay curve (transient PL) in which the ordinate axis represents a logarithm of the luminous intensity and the abscissa axis represents the time is obtainable.

For instance, a thin film sample A was manufactured as described above from a reference compound H1 as the matrix material and a reference compound D1 as the doping material and was measured in terms of the transient PL.

[Formula 110]

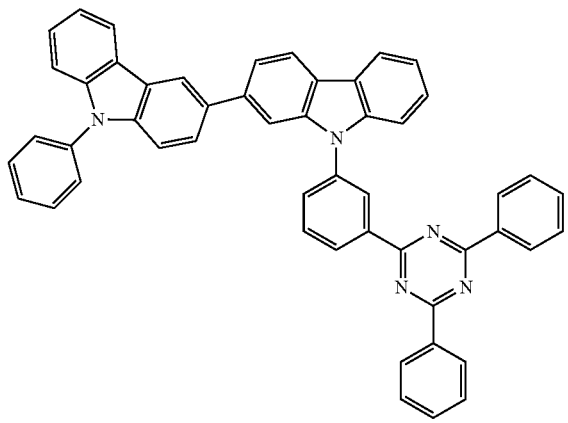

(Reference compound H1)

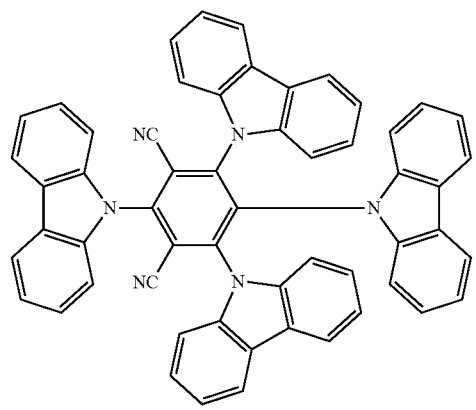

(Reference compound D1)

The decay curve was analyzed with respect to the above thin film sample A and a thin film sample B. The thin film sample B was manufactured in the same manner as described above from a reference compound H2 as the matrix material and the reference compound D1 as the doping material.

FIG. 3 shows decay curves obtained from transient PL obtained by measuring the thin film samples A and B.

[Formula 111]

(Reference compound H2)

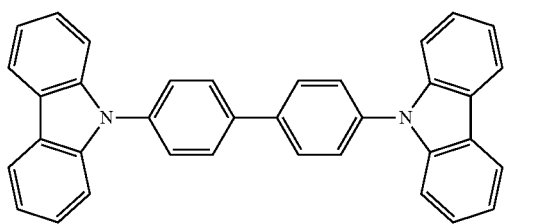

As described above, an emission decay curve in which the ordinate axis represents the luminous intensity and the abscissa axis represents the time can be obtained by the transient PL measurement. Based on the emission decay curve, a fluorescence intensity ratio between fluorescence emitted from a singlet state generated by photo-excitation and delayed fluorescence emitted from a singlet state generated by inverse energy transfer via a triplet state can be estimated. In a delayed fluorescent material, a ratio of the intensity of the slowly decaying delayed fluorescence to the intensity of the promptly decaying fluorescence is relatively large.

Specifically, Prompt emission and Delay emission are present as emission from the delayed fluorescent material. Prompt emission is observed promptly when the excited state is achieved by exciting the compound of the exemplary embodiment with a pulse beam (i.e., a beam emitted from a pulse laser) having a wavelength absorbable by the delayed fluorescent material. Delay emission is observed not promptly when the excited state is achieved but after the excited state is achieved.

An amount of Prompt emission, an amount of Delay emission and a ratio between the amounts thereof can be obtained according to the method as described in "Nature 492, 234-238, 2012" (Reference Document 1). The amount of Prompt emission and the amount of Delay emission may be calculated using a device different from one described in Reference Document 1 or one shown in FIG. 2.

Herein, a sample manufactured by a method shown below is used for measuring delayed fluorescence of the compound M2. For instance, the compound M2 is dissolved in toluene to prepare a dilute solution with an absorbance of 0.05 or less at the excitation wavelength to eliminate the contribution of self-absorption. In order to prevent quenching due to oxygen, the sample solution is frozen and degassed and then sealed in a cell with a lid under an argon atmosphere to obtain an oxygen-free sample solution saturated with argon.

The fluorescence spectrum of the sample solution is measured with a spectrofluorometer FP-8600 (manufactured by JASCO Corporation), and the fluorescence spectrum of a 9,10-diphenylanthracene ethanol solution is measured under the same conditions. Using the fluorescence area intensities of both spectra, the total fluorescence quantum yield is calculated by an equation (1) in Morris et al. J. Phys. Chem. 80 (1976) 969.

An amount of Prompt emission, an amount of Delay emission and a ratio between the amounts thereof can be obtained according to the method as described in "Nature 492, 234-238, 2012" (Reference Document 1). The amount of Prompt emission and the amount of Delay emission may be calculated using a device different from one described in Reference Document 1 or one shown in FIG. 2.

In the exemplary embodiment, provided that an amount of Prompt emission of a measurement target compound (compound M2) is denoted by $X_P$ and the amount of Delay emission is denoted by $X_D$, the delayed fluorescence means that a value of $X_D/X_P$ is 0.05 or more.

The amounts of Prompt emission and Delay emission and a ratio of the amounts thereof in compounds other than the compound M2 herein are measured in the same manner as those of the compound M2.

Relationship Between Compound M3 and Compound M2 in Emitting Layer

In the organic EL device of the exemplary embodiment, the singlet energy $S_1(M2)$ of the compound M2 and a singlet energy $S_1(M3)$ of the compound M3 satisfy a relationship of a numerical formula (Numerical Formula 1) below.

$$S_1(M3) > S_1(M2) \qquad \text{(Numerical Formula 1)}$$

An energy gap $T_{77K}(M3)$ at 77K of the compound M3 is preferably larger than an energy gap $T_{77K}(M2)$ at 77K of the compound M2. In other words, a relationship of the following numerical formula (Numerical Formula 11) is preferably satisfied.

$$T_{77K}(M3) > T_{77K}(M2) \qquad \text{(Numerical Formula 11)}$$

When the organic EL device of the exemplary embodiment emits light, it is preferable that the compound M3 does not mainly emit light in the emitting layer.

Relationship Between Triplet Energy and Energy Gap at 77 [K]

Here, a relationship between a triplet energy and an energy gap at 77 [K] will be described. In the exemplary embodiment, the energy gap at 77 [K] is different from a typical triplet energy in some aspects.

The triplet energy is measured as follows. Firstly, a solution in which a compound (measurement target) is dissolved in an appropriate solvent is encapsulated in a quartz glass tube to prepare a sample. A phosphorescent spectrum (ordinate axis: phosphorescent luminous intensity, abscissa axis: wavelength) of the sample is measured at a low temperature (77 [K]). A tangent is drawn to the rise of the phosphorescent spectrum close to the short-wavelength region. The triplet energy is calculated by a predetermined conversion equation based on a wavelength value at an intersection of the tangent and the abscissa axis.

Here, the thermally activated delayed fluorescent compound among the compounds of the exemplary embodiment is preferably a compound having a small ΔST. When ΔST is small, intersystem crossing and inverse intersystem crossing are likely to occur even at a low temperature (77 [K]), so that the singlet state and the triplet state coexist. As a result, the spectrum to be measured in the same manner as the above includes emission from both the singlet state and the triplet state. Although it is difficult to distinguish the emission from the singlet state from the emission from the triplet state, the value of the triplet energy is basically considered dominant.

Accordingly, in the exemplary embodiment, the triplet energy is measured by the same method as a typical triplet energy T, but a value measured in the following manner is referred to as an energy gap $T_{77K}$ in order to differentiate the measured energy from the typical triplet energy in a strict meaning. The measurement target compound is dissolved in EPA (diethylether:isopentane:ethanol=5:5:2 in volume ratio) at a concentration of 10 μmol/L, and the obtained solution is encapsulated in a quartz cell to provide a measurement sample. A phosphorescent spectrum (ordinate axis: phosphorescent luminous intensity, abscissa axis: wavelength) of the sample is measured at a low temperature (77 [K]). A tangent is drawn to the rise of the phosphorescent spectrum close to the short-wavelength region. An energy amount is calculated by a conversion equation below based on a wavelength value $\lambda_{edge}$ [nm] at an intersection of the tangent and the abscissa axis and is defined as an energy gap $T_{77K}$ at 77 [K].

$$T_{77K}[eV]=1239.85/\lambda\text{edge} \quad \text{Conversion Equation (F1):}$$

The tangent to the rise of the phosphorescence spectrum close to the short-wavelength region is drawn as follows. While moving on a curve of the phosphorescence spectrum from the short-wavelength region to the maximum spectral value closest to the short-wavelength region among the maximum spectral values, a tangent is checked at each point on the curve toward the long-wavelength of the phosphorescence spectrum. An inclination of the tangent is increased along the rise of the curve (i.e., a value of the ordinate axis is increased). A tangent drawn at a point of the maximum inclination (i.e., a tangent at an inflection point) is defined as the tangent to the rise of the phosphorescence spectrum close to the short-wavelength region.

The maximum with peak intensity being 15% or less of the maximum peak intensity of the spectrum is not included in the above-mentioned maximum closest to the short-wavelength region. The tangent drawn at a point of the maximum spectral value being closest to the short-wavelength region and having the maximum inclination is defined as a tangent to the rise of the phosphorescence spectrum close to the short-wavelength region.

For phosphorescence measurement, a spectrophotofluorometer body F-4500 (manufactured by Hitachi High-Technologies Corporation) is usable. Any device for phosphorescence measurement is usable. A combination of a cooling unit, a low temperature container, an excitation light source and a light-receiving unit may be used for phosphorescence measurement.

Singlet Energy S1

A method of measuring a singlet energy $S_1$ with use of a solution (occasionally referred to as a solution method) is exemplified by a method below.

A toluene solution in which a measurement target compound is dissolved at a concentration of 10 μmol/L is prepared and is encapsulated in a quartz cell to provide a measurement sample. Absorption spectrum (ordinate axis: absorption intensity, abscissa axis: wavelength) of the sample is measured at the normal temperature (300K). A tangent is drawn to the fall of the absorption spectrum on the long-wavelength side, and a wavelength value λedge (nm) at an intersection of the tangent and the abscissa axis is assigned to a conversion equation (F2) below to calculate singlet energy.

$$S_1[eV]=1239.85/\lambda\text{edge} \quad \text{Conversion Equation (F2):}$$

Any device for measuring absorption spectrum is usable. For instance, a spectrophotometer (U3310 manufactured by Hitachi, Ltd.) is usable.

The tangent to the fall of the absorption spectrum on the long-wavelength side is drawn as follows. While moving on a curve of the absorption spectrum from the maximum spectral value closest to the long-wavelength side in a long-wavelength direction, a tangent at each point on the curve is checked. An inclination of the tangent is decreased and increased in a repeated manner as the curve falls (i.e., a value of the ordinate axis is decreased). A tangent drawn at a point of the minimum inclination closest to the long-wavelength side (except when absorbance is 0.1 or less) is defined as the tangent to the fall of the absorption spectrum on the long-wavelength side.

The maximum absorbance of 0.2 or less is not included in the above-mentioned maximum absorbance on the long-wavelength side.

In the exemplary embodiment, a difference $(S_1-T_{77K})$ between the singlet energy $S_1$ and the energy gap $T_{77K}$ at 77 [K] is defined as ΔST.

In the exemplary embodiment, a difference ΔST(M2) between the singlet energy $S_1$(M2) of the compound M2 and the energy gap $T_{77K}$(M2) at 77K of the compound M2 is preferably less than 0.3 eV, more preferably less than 0.2 eV, further preferably less than 0.1 eV, more further preferably less than 0.01 eV. In other words, ΔST(M2) preferably satisfies a relationship of one of numerical formulae (Numerical Formula 1A to Numerical Formula 1D).

$$\Delta ST(M2)=S_1(M2)-T_{77K}(M2)<0.3 \text{ eV} \quad \text{(Numerical Formula 1A)}$$

$$\Delta ST(M2)=S_1(M2)-T_{77K}(M2)<0.2 \text{ eV} \quad \text{(Numerical Formula 1B)}$$

$$\Delta ST(M2)=S_1(M2)-T_{77K}(M2)<0.1 \text{ eV} \quad \text{(Numerical Formula 1C)}$$

$$\Delta ST(M2)=S_1(M2)-T_{77K}(M2)<0.01 \text{ eV} \quad \text{(Numerical Formula 1D)}$$

Film Thickness of Emitting Layer

A film thickness of the emitting layer of the organic EL device in the exemplary embodiment is preferably in a range of 5 nm to 50 nm, more preferably in a range of 7 nm to 50 nm, most preferably in a range of 10 nm to 50 nm. When the film thickness of the emitting layer is 5 nm or more, the formation of the emitting layer and the adjustment of the chromaticity are easy. When the film thickness of the emitting layer is 50 nm or less, an increase in the drive voltage is likely to be reducible.

Content Ratios of Compounds in Emitting Layer

Content ratios of the compounds M2 and M3 in the emitting layer preferably fall, for instance, within a range below.

The content ratio of the compound M2 is preferably in a range from 10 mass % to 80 mass %, more preferably in a range from 10 mass % to 60 mass %, further preferably in a range from 20 mass % to 60 mass %.

The content ratio of the compound M3 is preferably in a range from 20 mass % to 90 mass %, more preferably in a range from 40 mass % to 90 mass %, further preferably in a range from 40 mass % to 80 mass %.

It should be noted that the emitting layer of the exemplary embodiment may further contain material(s) other than the compounds M2 and M3.

The emitting layer may include a single type of the compound M2 or may include two or more types of the compound M2. The emitting layer may include a single type of the compound M3 or may include two or more types of the compound M3.

FIG. 4 shows a relationship in energy level and energy transfer between the compound M3 and the compound M2 in the emitting layer. In FIG. 4, S0 represents a ground state. S1(M2) represents the lowest singlet state of the compound M2. T1(M2) represents the lowest triplet state of the compound M2. S1(M3) represents the lowest singlet state of the compound M3. T1(M3) represents the lowest triplet state of the compound M3. Dashed arrows in FIG. 4 show energy transfer between the excited states. An energy transfer occurs by Förster transfer from the lowest singlet state S1 of the compound M3 to the lowest singlet state S1 of the compound M2 or an energy transfer occurs by Dexter transfer from the lowest triplet state T1 of the compound M3 to the lowest triplet state T1 of the compound M2. Further, when a material having a small ΔST(M2)) is used as the compound M2, inverse intersystem crossing can be caused by a heat energy from the lowest triplet state T1 to the lowest singlet state S1 in the compound M2. Consequently, fluorescence from the lowest singlet state S1 of the compound M2 can be observed. It is inferred that the internal quantum efficiency can be theoretically raised up to 100% also by using delayed fluorescence by the TADF mechanism.

The organic EL device according to the exemplary embodiment contains the delayed fluorescent compound M2, the compound M3 (the compound M3 represented by the formula (100)) having the singlet energy larger than that of the compound M2 in the emitting layer.

The organic EL device according to the exemplary embodiment is applicable to an electronic device such as a display device and a light-emitting device.

An arrangement of an organic EL device will be further described below.

Substrate

The substrate is used as a support for the organic EL device. For instance, glass, quartz, plastics and the like are usable for the substrate. A flexible substrate is also usable. The flexible substrate is a bendable substrate, which is exemplified by a plastic substrate. Examples of the material for the plastic substrate include polycarbonate, polyarylate, polyethersulfone, polypropylene, polyester, polyvinyl fluoride, polyvinyl chloride, polyimide, and polyethylene naphthalate. Moreover, an inorganic vapor deposition film is also usable.

Anode

Metal having a large work function (specifically, 4.0 eV or more), an alloy, an electrically conductive compound and a mixture thereof are preferably used as the anode formed on the substrate. Specific examples of the material include ITO (Indium Tin Oxide), indium oxide-tin oxide containing silicon or silicon oxide, indium oxide-zinc oxide, indium oxide containing tungsten oxide and zinc oxide, and graphene. In addition, gold (Au), platinum (Pt), nickel (Ni), tungsten (W), chrome (Cr), molybdenum (Mo), iron (Fe), cobalt (Co), copper (Cu), palladium (Pd), titanium (Ti), and nitrides of a metal material (e.g., titanium nitride) are usable.

The material is typically formed into a film by a sputtering method. For instance, the indium oxide-zinc oxide can be formed into a film by the sputtering method using a target in which zinc oxide in a range from 1 mass % to 10 mass % is added to indium oxide. Moreover, for instance, the indium oxide containing tungsten oxide and zinc oxide can be formed by the sputtering method using a target in which tungsten oxide in a range from 0.5 mass % to 5 mass % and zinc oxide in a range from 0.1 mass % to 1 mass % are added to indium oxide. In addition, the anode may be formed by a vacuum deposition method, a coating method, an inkjet method, a spin coating method or the like.

Among the organic layers formed on the anode, since the hole injecting layer adjacent to the anode is formed of a composite material into which holes are easily injectable irrespective of the work function of the anode, a material usable as an electrode material (e.g., metal, an alloy, an electroconductive compound, a mixture thereof, and the elements belonging to the group 1 or 2 of the periodic table) is also usable for the anode.

A material having a small work function such as elements belonging to Groups 1 and 2 in the periodic table of the elements, specifically, an alkali metal such as lithium (Li) and cesium (Cs), an alkaline earth metal such as magnesium (Mg), calcium (Ca) and strontium (Sr), alloys (e.g., MgAg and AlLi) including the alkali metal or the alkaline earth metal, a rare earth metal such as europium (Eu) and ytterbium (Yb), and alloys including the rare earth metal are also usable for the anode. It should be noted that the vacuum deposition method and the sputtering method are usable for forming the anode using the alkali metal, alkaline earth metal and the alloy thereof. Further, when a silver paste is used for the anode, the coating method and the inkjet method are usable.

Cathode

It is preferable to use metal, an alloy, an electroconductive compound, and a mixture thereof, which have a small work function (specifically, 3.8 eV or less) for the cathode. Examples of the material for the cathode include elements belonging to Groups 1 and 2 in the periodic table of the elements, specifically, the alkali metal such as lithium (Li) and cesium (Cs), the alkaline earth metal such as magnesium (Mg), calcium (Ca) and strontium (Sr), alloys (e.g., MgAg and AlLi) including the alkali metal or the alkaline earth metal, the rare earth metal such as europium (Eu) and ytterbium (Yb), and alloys including the rare earth metal.

It should be noted that the vacuum deposition method and the sputtering method are usable for forming the cathode using the alkali metal, alkaline earth metal and the alloy thereof. Further, when a silver paste is used for the cathode, the coating method and the inkjet method are usable.

By providing the electron injecting layer, various conductive materials such as Al, Ag, ITO, graphene, and indium oxide-tin oxide containing silicon or silicon oxide may be used for forming the cathode regardless of the work function. The conductive materials can be formed into a film using the sputtering method, inkjet method, spin coating method and the like.

Hole Injecting Layer

The hole injecting layer is a layer containing a substance exhibiting a high hole injectability. Examples of the substance exhibiting a high hole injectability include molybdenum oxide, titanium oxide, vanadium oxide, rhenium oxide, ruthenium oxide, chrome oxide, zirconium oxide, hafnium oxide, tantalum oxide, silver oxide, tungsten oxide, and manganese oxide.

In addition, the examples of the highly hole-injectable substance further include: an aromatic amine compound, which is a low-molecule organic compound, such as 4,4', 4''-tris(N,N-diphenylamino)triphenylamine (abbreviation: TDATA), 4,4',4''-tris[N-(3-methylphenyl)-N-phenylamino] triphenylamine (abbreviation: MTDATA), 4,4'-bis[N-(4-diphenylaminophenyl)-N-phenylamino]biphenyl (abbreviation: DPAB), 4,4'-bis(N-{4-[N'-(3-methylphenyl)-N'-phenylamino]phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazole-3-yl)-N-phenylamino]-9-phenylcarbazole (abbreviation: PCzPCA1), 3,6-bis[N-(9-phenylcarbazole-3-yl)-N-phenylamino]-9-phenylcarbazole (abbreviation: PCzPCA2), and 3-[N-(1-naphthyl)-N-(9-phenylcarbazole-3-yl)amino]-9-phenylcarbazole (abbreviation: PCzPCN1); and dipyrazino[2,3-f:20,30-h]quinoxaline-2,3,6,7,10,11-hexacarbonitrile (HAT-CN).

In addition, a high polymer compound (e.g., oligomer, dendrimer and polymer) is usable as the substance exhibiting a high hole injectability. Examples of the high-molecule compound include poly(N-vinylcarbazole) (abbreviation: PVK), poly(4-vinyltriphenylamine) (abbreviation: PVTPA), poly[N-(4-{N'-[4-(4-diphenylam ino)phenyl]phenyl-N'-phenylam ino}phenyl)methacrylam ide](abbreviation:

PTPDMA), and poly[N,N'-bis(4-butylphenyl)-N,N'-bis(phenyl)benzidine] (abbreviation: Poly-TPD). Moreover, an acid-added high polymer compound such as poly(3,4-ethylenedioxythiophene)/poly(styrene sulfonic acid) (PEDOT/PSS) and polyaniline/poly(styrene sulfonic acid) (PAni/PSS) are also usable.

Hole Transporting Layer

The hole transporting layer is a layer containing a highly hole-transporting substance. An aromatic amine compound, carbazole derivative, anthracene derivative and the like are usable for the hole transporting layer. Specific examples of a material for the hole transporting layer include an aromatic amine compound such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluoren-2-yl)-N-phenylamino]biphenyl (abbreviation: DFLDPBi), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluoren-2-yl)-N-phenylamino]biphenyl (abbreviation: BSPB). The above-described substances mostly have a hole mobility of $10^{-6}$ cm$^2$/(V·s) or more.

For the hole transporting layer, a carbazole derivative such as CBP, 9-[4-(N-carbazolyl)]phenyl-10-phenylanthracene (CzPA), and 9-phenyl-3-[4-(10-phenyl-9-anthryl)phenyl]-9H-carbazole (PCzPA) and an anthracene derivative such as t-BuDNA, DNA, and DPAnth may be used. A high polymer compound such as poly(N-vinylcarbazole) (abbreviation: PVK) and poly(4-vinyltriphenylamine) (abbreviation: PVTPA) is also usable.

However, in addition to the above substances, any substance exhibiting a higher hole transportability than an electron transportability may be used. It should be noted that the layer containing the substance exhibiting a high hole transportability may be not only a single layer but also a laminate of two or more layers formed of the above substance(s).

When the hole transporting layer includes two or more layers, one of the layers with a larger energy gap is preferably provided closer to the emitting layer. An example of the material with a larger energy gap is HT-2 used in later-described Examples.

Electron Transporting Layer

The electron transporting layer is a layer containing a highly electron-transporting substance. For the electron transporting layer, 1) a metal complex such as an aluminum complex, beryllium complex, and zinc complex, 2) a hetero aromatic compound such as imidazole derivative, benzimidazole derivative, azine derivative, carbazole derivative, and phenanthroline derivative, and 3) a high polymer compound are usable. Specifically, as a low-molecule organic compound, a metal complex such as Alq, tris(4-methyl-8-quinolinato)aluminum (abbreviation: Almq$_3$), bis(10-hydroxybenzo[h]quinolinato)beryllium (abbreviation: BeBq$_2$), BAlq, Znq, ZnPBO and ZnBTZ is usable. In addition to the metal complex, a heteroaromatic compound such as 2-(4-biphenylyl)-5-(4-tert-butylphenyl)-1,3,4-oxadiazole (abbreviation: PBD), 1,3-bis[5-(ptert-butylphenyl)-1,3,4-oxadiazole-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), and 4,4'-bis(5-methylbenzoxazole-2-yl)stilbene (abbreviation: BzOs) is usable.

In the exemplary embodiment, a benzimidazole compound is preferably usable. The above-described substances mostly have an electron mobility of $10^{-6}$ cm$^2$/(V·s) or more. It should be noted that any substance other than the above substance may be used for the electron transporting layer as long as the substance exhibits a higher electron transportability than the hole transportability. The electron transporting layer may be provided in the form of a single layer or a laminate of two or more layers of the above substance(s).

Moreover, a high polymer compound is usable for the electron transporting layer. For instance, poly[(9,9-dihexylfluorene-2,7-diyl)-co-(pyridine-3,5-diyl)](abbreviation: PF-Py), poly[(9,9-dioctylfluorene-2,7-diyl)-co-(2,2'-bipyridine-6,6'-diyl)] (abbreviation: PF-BPy) and the like are usable.

Electron Injecting Layer

The electron injecting layer is a layer containing a highly electron-injectable substance. Examples of a material for the electron injecting layer include an alkali metal, alkaline earth metal and a compound thereof, examples of which include lithium (Li), cesium (Cs), calcium (Ca), lithium fluoride (LiF), cesium fluoride (CsF), calcium fluoride (CaF$_2$), and lithium oxide (LiOx). In addition, the alkali metal, alkaline earth metal or the compound thereof may be added to the substance exhibiting the electron transportability in use. Specifically, for instance, magnesium (Mg) added to Alq may be used. In this case, the electrons can be more efficiently injected from the cathode.

Alternatively, the electron injecting layer may be provided by a composite material in a form of a mixture of the organic compound and the electron donor. Such a composite material exhibits excellent electron injectability and transportability since electrons are generated in the organic compound by the electron donor. In this case, the organic compound is preferably a material excellent in transporting the generated electrons. Specifically, the above examples (e.g., the metal complex and the hetero aromatic compound) of the substance forming the electron transporting layer are usable. As the electron donor, any substance exhibiting electron donating property to the organic compound is usable. Specifically, the electron donor is preferably alkali metal, alkaline earth metal and rare earth metal such as lithium, cesium, magnesium, calcium, erbium and ytterbium. The electron donor is also preferably alkali metal oxide and alkaline earth metal oxide such as lithium oxide, calcium oxide, and barium oxide. Moreover, a Lewis base such as magnesium oxide is usable. Further, the organic compound such as tetrathiafulvalene (abbreviation: TTF) is usable.

Layer Formation Method

A method for forming each layer of the organic EL device in the third exemplary embodiment is subject to no limitation except for the above particular description. However, known methods of dry film-forming such as vacuum deposition, sputtering, plasma or ion plating and wet film-forming such as spin coating, dipping, flow coating or ink jet printing are applicable.

Film Thickness

A thickness of each of the organic layers in the organic EL device according to the third exemplary embodiment is not limited except for the above particular description. In general, the thickness preferably ranges from several nanometers to 1 μm because excessively small film thickness is likely to cause defects (e.g. pin holes) and excessively large thickness leads to the necessity of applying high voltage and consequent reduction in efficiency.

Second Exemplary Embodiment

An arrangement of an organic EL device according to a second exemplary embodiment will be described below. In the description of the second exemplary embodiment, the same components as those in the first exemplary embodiment are denoted by the same reference signs and names to simplify or omit an explanation of the components. In the second exemplary embodiment, any materials and compounds that are not specified may be the same as those in the first exemplary embodiment.

The organic EL device according to the second exemplary embodiment is different from the organic EL device according to the first exemplary embodiment in that the emitting layer further includes the fluorescent compound M1. The second exemplary embodiment is the same as the first exemplary embodiment in other respects.

In other words, in the second exemplary embodiment, the emitting layer contains the compound M3 represented by the formula (100), the delayed fluorescent compound M2, and the fluorescent compound M1.

In this arrangement, the compound M1 is preferably a dopant material, the compound M2 is preferably a host material, and the compound M3 is preferably a host material. One of the compound M2 and the compound M3 may be referred to as a first host material, and the other may be referred to as a second host material.

Compound M1

The emitting layer of the exemplary embodiment includes the fluorescent compound M1.

The compound M1 of the exemplary embodiment is not a phosphorescent metal complex. The compound M1 of the exemplary embodiment is preferably not a heavy metal complex. The compound M1 of the exemplary embodiment is preferably not a metal complex.

A fluorescent material is usable as the compound M1 of the exemplary embodiment. Specific examples of the fluorescent material include a bisarylaminonaphthalene derivative, aryl-substituted naphthalene derivative, bisarylaminoanthracene derivative, aryl-substituted anthracene derivative, bisarylaminopyrene derivative, aryl-substituted pyrene derivative, bisarylamino chrysene derivative, aryl-substituted chrysene derivative, bisarylaminofluoranthene derivative, aryl-substituted fluoranthene derivative, indenoperylene derivative, acenaphthofluoranthene derivative, compound including a boron atom, pyromethene boron complex compound, compound having a pyromethene skeleton, metal complex of the compound having a pyromethene skeleton, diketopyrrolopyrrole derivative, perylene derivative, and naphthacene derivative.

The compound M1 of the exemplary embodiment is preferably a compound represented by a formula (20) below.

[Formula 112]

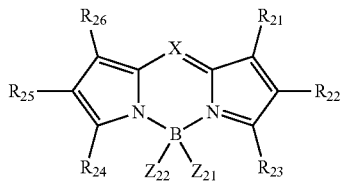

(20)

In the formula (20): X is a nitrogen atom, or a carbon atom bonded to Y;

Y is a hydrogen atom or a substituent; $R_{21}$ to $R_{26}$ are each independently a hydrogen atom or a substituent, or at least one of a pair of $R_{21}$ and $R_{22}$, a pair of $R_{22}$ and $R_{23}$, a pair of $R_{24}$ and $R_{26}$, or a pair of $R_{25}$ and $R_{26}$ are mutually bonded to form a ring.

Y and $R_{21}$ to as the substituent are each independently selected from the group consisting of a substituted or unsubstituted alkyl group having 1 to 30 carbon atoms, a substituted or unsubstituted alkyl halide group having 1 to 30 carbon atoms, a substituted or unsubstituted cycloalkyl group having 3 to 30 ring carbon atoms, a substituted or unsubstituted aryl group having 6 to 30 ring carbon atoms, a substituted or unsubstituted alkoxy group having 1 to 30 carbon atoms a substituted or unsubstituted alkoxy halide group having 1 to 30 carbon atoms, a substituted or unsubstituted alkylthio group having 1 to 30 carbon atoms; a substituted or unsubstituted aryloxy group having 6 to 30 ring carbon atoms, a substituted or unsubstituted arylthio group having 6 to 30 ring carbon atoms, a substituted or unsubstituted alkenyl group having 2 to 30 carbon atoms, a substituted or unsubstituted aralkyl group having 7 to 30 carbon atoms, a substituted or unsubstituted heteroaryl group having 5 to 30 ring atoms, a halogen atom, a carboxy group, a substituted or unsubstituted ester group, a substituted or unsubstituted carbamoyl group, a substituted or unsubstituted amino group, a nitro group, a cyano group, a substituted or unsubstituted silyl group, and a substituted or unsubstituted silolanyl group;

$Z_{21}$ and $Z_{22}$ are each independently a substituent, or ere mutually bonded to form a ring, and $Z_{21}$ and $Z_{22}$ as the substituent are each independently selected from the group consisting of a halogen atom, a substituted or unsubstituted alkyl group having 1 to 30 carbon atoms, a substituted or unsubstituted alkyl halide group having 1 to carbon atoms, a substituted or unsubstituted aryl group having 6 to 30 ring carbon atoms, a substituted or unsubstituted alkoxy group having 1 to 30 carbon atoms, a substituted or unsubstituted alkoxy halide group having 1 to 30 carbon atoms, and a substituted or unsubstituted aryloxy group having 6 to 30 ring carbon atoms.

In the formula (20), for instance, when a pair of $R_{25}$ and $R_{26}$ are mutually bonded to form a ring, the compound M1 is represented by a formula (21) below.

[Formula 113]

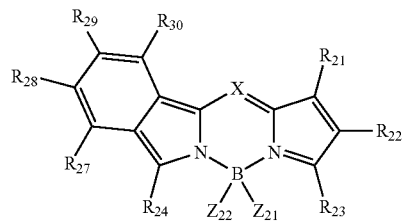

(21)

In the formula (21), X, Y, $R_{21}$ to $R_{24}$, $Z_{21}$ and $Z_{22}$ respectively represent the same as X, Y, $R_{21}$ to $R_{24}$, $Z_{21}$ and $Z_{22}$ in the formula (20). $R_{27}$ to $R_{30}$ each independently represent a hydrogen atom or a substituent. When $R_{27}$ to $R_{30}$ are each independently the substituent, the substituent represents the same as the substituents for $R_{21}$ to $R_{24}$.

In the formula (20), when $Z_{21}$ and $Z_{22}$ are mutually bonded to form a ring, the compound M1 is represented by, for instance, a formula (20A) or a formula (20B) below. However, a structure of the compound M1 is not limited to structures below.

[Formula 114]

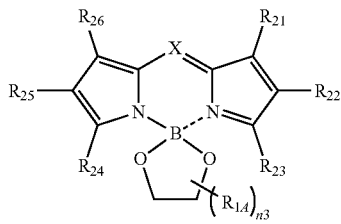
(20A)

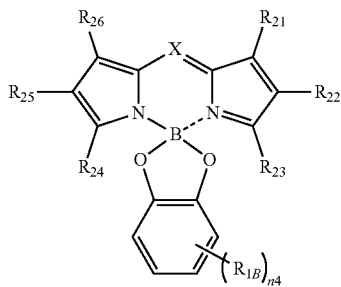
(20B)

In the formula (20A), X, Y and $R_{21}$ to $R_{26}$ respectively represent the same as X, Y and $R_{21}$ to $R_{26}$ in the formula (20). $R_{1A}$ each independently represent a hydrogen atom or a substituent. When $R_{1A}$ is the substituent: the substituent represents the same as the substituents for $R_{21}$ to $R_{25}$, n3 is 4.

In the formula (20B), X, Y and $R_{21}$ to $R_{26}$ respectively represent the same as X, Y and $R_{21}$ to $R_{26}$ in the formula (20). $R_{1B}$ each independently represent a hydrogen atom or a substituent. When $R_{1B}$ is the substituent, the substituent represents the same as the substituents for $R_{21}$ to $R_{26}$, n4 is 4.

It is preferable that at least one of $Z_{21}$ or $Z_{22}$ (preferably both of $Z_{21}$ and $Z_{22}$) is a group selected from the group consisting of a substituted or unsubstituted alkyl group having 1 to 30 carbon atoms, substituted or unsubstituted alkyl halide group having 1 to 30 carbon atoms, substituted or unsubstituted aryl group having 6 to 30 ring carbon atoms, substituted or unsubstituted alkoxy group having 1 to 30 carbon atoms, substituted or unsubstituted alkoxy halide group having 1 to 30 carbon atoms, and substituted or unsubstituted aryloxy group having 6 to 30 ring carbon atoms.

It is more preferable that at least one of $Z_{21}$ or $Z_{22}$ is a group selected from the group consisting of a fluorine-substituted alkoxy group having 1 to 30 carbon atoms, a fluorine-substituted aryloxy group having 6 to 30 ring carbon atoms, and an aryloxy group having 6 to 30 ring carbon atoms and substituted with a fluoroalkyl group having 1 to 30 carton atoms.

Further preferably, at feast one of $Z_{21}$ or $Z_{22}$ is a fluorine-substituted alkoxy group having 1 to 30 carbon atoms. Further more preferably, both of $Z_{21}$ and $Z_{22}$ are a fluorine-substituted alkoxy group having 1 to 30 carbon atoms.

It is also preferable that both of $Z_{21}$ and $Z_{22}$ are the same to each other.

Meanwhile, H is also preferable diet at least one of $Z_{21}$ or $Z_{22}$ is a fluorine atom. It is also more preferable that both of $Z_{21}$ and $Z_{22}$ are fluorine atoms.

It is also preferable that at least one of $Z_{21}$ or $Z_{22}$ is a group represented by a formula (20a) below

[Formula 115]

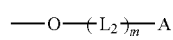
(20a)

In the formula (20a) A represents a substituted or unsubstituted alkyl group having 1 to 6 carbon atoms, substituted or unsubstituted alkyl halide group having 1 to 6 carbon atoms, or substituted or unsubstituted aryl group having 6 to 12 ring carbon atoms; $L_2$ represents a substituted or unsubstituted alkylene group having 1 to 6 carbon atoms, or substituted or unsubstituted arylene group having 6 to 12 ring carbon atoms; and m is 0, 1, 2, 3, 4, 5, 6 or 7. When m is 2, 3, 4, 5, 6 or 7 a plurality of $L_2$ are mutually the same or different m is preferably 0.1 or 2 When m is 0. A is directly bonded to O (oxygen atom).

When $Z_{31}$ and $Z_{22}$ in the formula (20) are each the group represented by the formula (20a) the compound M1 is represented by a formula (22) below.

The compound M1 is also preferably a compound represented by a formula (22) below.

[Formula 116]

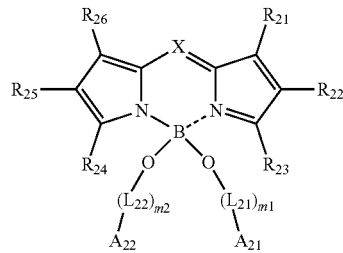
(22)

In the formula (22), X, Y bonded to a carbon atom as X, and $R_{21}$ to $R_{26}$ represent the same as X, Y and $R_{21}$ to $R_{26}$ in the formula (20). $A_{21}$ and $A_{22}$ represent the same as A in the formula (20a) and may be mutually the same or different. $L_{21}$ and $L_{22}$ represent the same as $L_2$ in the formula (20a) and may be mutually the same or different, m1 and m2 are each independently 0, 1, 2, 3, 4, 5, 6 or 7, preferably 0, 1 or 2. When m1 is 2, 3, 4, 5, 6 or 7, a plurality of $L_{31}$ are mutually the same or different. When m2 is 2, 3, 4, 5, 6 or 7, a plurality of $L_{22}$ are mutually the same or different. When m1 is 0, $A_{21}$ is directly bonded to O (oxygen atom). When m2 is 0, $A_{22}$ is directly bonded to O (oxygen atom).

At least one of A or $L_2$ in the formula (20a) is preferably substituted with a halogen atom, more preferably substituted with a fluorine atom.

A in the formula (20a) is more preferably a perfluoroalkyl group having 1 to 6 carbon atoms or a perfluoroaryl group having 6 to 12 carbon atoms, further preferably a perfluoroalkyl group having 1 to 6 carbon atoms.

$L_2$ in the formula (20a) is more preferably a perfluoroalkylene group having 1 to 6 carbon atoms or a perfluoroarylene group having 6 to 12 carbon atoms, further preferably a perfluoroalkylene group having 1 to 6 carbon atoms.

In other words, the compound M1 is also preferably a compound represented by a formula (22a) below.

[Formula 117]

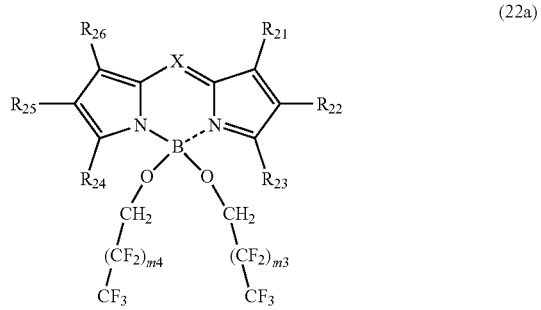

(22a)

In the formula (22a): X represents the same as X in the formula (20); Y bonded to a carbon atom as X represents the same as Y in the formula (20); $R_{21}$ to $R_{26}$ each independently represent the same as $R_{21}$ to $R_{26}$ in the formula (20); m3 is in a range from 0 to 4; m4 is in a range from Q to 4; and m3 and m4 are mutually the same or different.

In the formulae (20), (21), (22) and (22a), X is a carbon atom bonded to Y; and Y is a hydrogen atom or a substituent.

Y as the substituent is preferably a substituent selected from the group consisting of a substituted or unsubstituted alkyl group having 1 to 30 carbon atoms, substituted or unsubstituted alkyl halide group having 1 to 30 carbon atoms and substituted or unsubstituted aryl group having 6 to 30 ring carbon atoms, more preferably a substituted or unsubstituted aryl group having 6 to 30 ring carbon atoms.

In the formulae (20), (21), (22) and (22a), it is more preferable that: X is a carbon atom bonded to Y; Y is a hydrogen atom or a substituent; Y as the substituent is a substituted or unsubstituted aryl group having 6 to 30 ring carbon atoms; and when Y as the substituent is an aryl group having 6 to 30 ring carbon atoms having a substituent, the substituent is a substituted or unsubstituted alkyl group having 1 to 30 carbon atoms, a substituted or unsubstituted alkyl halide group having 1 to 30 carbon atoms, a substituted or unsubstituted alkoxy group having 1 to 30 carbon atoms, a substituted or unsubstituted alkoxy halide group having 1 to 30 carbon atoms, or an aryl group having 6 to 30 ring carbon atoms and substituted by an alkyl group having 1 to 30 carbon atoms.

In the compound M1, $Z_{21}$ and $Z_{22}$ may be mutually bonded to form a ring. However, it is preferable that $Z_{21}$ and $Z_{22}$ are not mutually bonded.

In the formulae (20), (22) and (22a), at least one of $R_{21}$, $R_{23}$, $R_{24}$ or $R_{26}$ is preferably a substituted or unsubstituted alkyl group having 1 to 30 carbon atoms or a substituted or unsubstituted alkyl halide group having 1 to 30 carbon atoms.

In the formulae (20), (22) and (22a), $R_{21}$, $R_{23}$, $R_{24}$ and $R_{26}$ are more preferably each a substituted or unsubstituted alkyl group having 1 to 30 carbon atoms or a substituted or unsubstituted alkyl halide group having 1 to 30 carbon atoms. In this case, $R_{22}$ and $R_{25}$ are preferably hydrogen atoms.

In the formulae (20), (22) and (22a), at least one of $R_{21}$, $R_{23}$, $R_{24}$ or $R_{26}$ is preferably a substituted or unsubstituted aryl group having 6 to 30 ring carbon atoms.

In the formulae (20), (22) and (22a), $R_{21}$, $R_{23}$, $R_{24}$ and $R_{26}$ are more preferably each a substituted or unsubstituted aryl group having 6 to 30 ring carbon atoms. In this case, $R_{22}$ and $R_{25}$ are preferably hydrogen atoms.

In the formulae (20), (22) and (22a), it is more preferable that: $R_{21}$, $R_{23}$, $R_{24}$ and $R_{26}$ are each independently a substituted or unsubstituted alkyl group having 1 to 30 carbon atoms (preferably 1 to 6 carbon atoms), a substituted or unsubstituted alkyl halide group having 1 to 30 carbon atoms (preferably 1 to 6 carbon atoms), or an aryl group having 6 to 30 ring carbon atoms (preferably 6 to 12 ring carbon atoms) and substituted with an alkyl group having 1 to 30 carbon atoms; and $R_{22}$ and $R_{25}$ are hydrogen atoms.

In the formula (21), at least one of $R_{21}$, $R_{23}$ or $R_{24}$ is preferably a substituted or unsubstituted alkyl group having 1 to 30 carbon atoms or a substituted or unsubstituted alkyl halide group having 1 to 30 carbon atoms.

In the formula (21), $R_{21}$, $R_{23}$ and $R_{24}$ are more preferably a substituted or unsubstituted alkyl group having 1 to 30 carbon atoms or a substituted or unsubstituted alkyl halide group having 1 to 30 carbon atoms. In this case, $R_{22}$ is preferably a hydrogen atom.

In the formula (21), at least one of $R_{21}$, $R_{23}$ or $R_{24}$ is preferably a substituted or unsubstituted aryl group having 6 to 30 ring carbon atoms.

In the formula (21), $R_{21}$, $R_{23}$ and $R_{24}$ are more preferably a substituted or unsubstituted aryl group having 6 to 30 ring carbon atoms. In this case, $R_{22}$ is preferably a hydrogen atom.

In the formula (21), it is more preferable that: $R_{21}$, $R_{23}$, and $R_{24}$ are each independently a substituted or unsubstituted alkyl group having 1 to 30 carbon atoms (preferably 1 to 6 carbon atoms), a substituted or unsubstituted alkyl halide group having 1 to 30 carbon atoms (preferably 1 to 6 carbon atoms), or an aryl group having 6 to 30 ring carbon atoms (preferably 6 to 12 ring carbon atoms) and substituted with an alkyl group having 1 to 30 carbon atoms; and $R_{22}$ is a hydrogen atom.

In the compound M1, examples of the fluorine-substituted alkoxy group include 2,2,2-trifluoroethoxy group, 2,2-difluoroethoxy group, 2,2,3,3,3-pentafluoro-1-propoxy group, 2,2,3,3-tetrafluoro-1-propoxy group, 1,1,1,3,3,3-hexafluoro-2-propoxy group, 2,2,3,3,4,4,4-heptafluoro-1-butyloxy group, 2,2,3,3,4,4-hexafluoro-1-butyloxy group, nonafluoro-tertiary-butyloxy group, 2,2,3,3,4,4,5,5,5-nonafluoropentanoxy group, 2,2,3,3,4,4,5,5,6,6,6-undecafluorohexanoxy group, 2,3-bis(trifluoromethyl)-2,3-butanedioxy group, 1,1,2,2-tetra(trifluoromethyl)ethylene glycoxy group, 4,4,5,5,6,6,6-heptafluorohexane-1,2-dioxy group, and 4,4,5,5,6,6,7,7,8,8,9,9,9-tridecafluorononane-1,2-dioxy group.

In the compound M1, examples of the fluorine-substituted aryloxy group or the aryloxy group substituted with a fluoroalkyl group include a pentafluorophenoxy group, 3,4,5-trifluorophenoxy group, 4-trifluoromethylphenoxy group, 3,5-bistrifluoromethylphenoxy group, 3-fluoro-4-trifluoromethylphenoxy group, 2,3,5,6-tetrafluoro-4-trifluoromethylphenoxy group, 4-fluorocatecholato group, 4-trifluoromethylcatecholato group, and 3,5-bistrifluoromethylcatecholato group.

When the compound M1 is a fluorescent compound, the compound M1 preferably emits light having a main peak wavelength in a range from 400 nm to 700 nm.

Herein, the main peak wavelength means a peak wavelength of an emission spectrum exhibiting a maximum luminous intensity among fluorescence spectra measured in a toluene solution in which a measurement target compound is dissolved at a concentration ranging from $10^{-6}$ mol/l to $10^{-5}$ mol/l. A spectrophotofluorometer (F-7000 manufactured by Hitachi High-Tech Science Corporation) is used as a measurement device.

The compound M1 preferably exhibits red or green light emission.

Herein, the red light emission refers to a light emission in which a main peak wavelength of fluorescence spectrum is in a range from 600 nm to 660 nm.

When the compound M1 is a red fluorescent compound, the main peak wavelength of the compound M1 is preferably in a range from 600 nm to 660 nm, more preferably in a range from 600 nm to 640 nm, further preferably in a range from 610 nm to 630 nm.

Herein, the green light emission refers to a light emission in which a main peak wavelength of fluorescence spectrum is in a range from 500 nm to 560 nm.

When the compound M1 is a green fluorescent compound, the main peak wavelength of the compound M1 is preferably in a range from 500 nm to 560 nm, more preferably in a range from 500 nm to 540 nm, further preferably in a range from 510 nm to 540 nm.

Herein, the blue light emission refers to a light emission in which a main peak wavelength of fluorescence spectrum is in a range from 430 nm to 480 nm.

When the compound M1 is a blue fluorescent compound, the main peak wavelength of the compound M1 is preferably in a range from 430 nm to 480 nm, more preferably in a range from 440 nm to 480 nm.

A main peak wavelength of light from an organic EL device is measured as follows.

Voltage is applied on the organic EL devices such that a current density becomes 10 mA/cm², where spectral radiance spectrum is measured by a spectroradiometer CS-2000 (manufactured by Konica Minolta, Inc.).

A peak wavelength of an emission spectrum, at which the luminous intensity of the resultant spectral radiance spectrum is at the maximum, is measured and defined as the main peak wavelength (unit: nm).

Manufacturing Method of Compound M1

The compound M1 can be manufactured by a known method.

Specific examples of the compound M1 according to the exemplary embodiment are shown below. It should however be noted that the invention is not limited to the specific examples of the compound.

A coordinate bond between a boron atom and a nitrogen atom in a pyrromethene skeleton is shown by various means such as a solid line, a broken line, an arrow, and omission. Herein, the coordinate bond is shown by a solid line or a broken line, or the description of the coordinate bond is omitted.

[Formula 118]

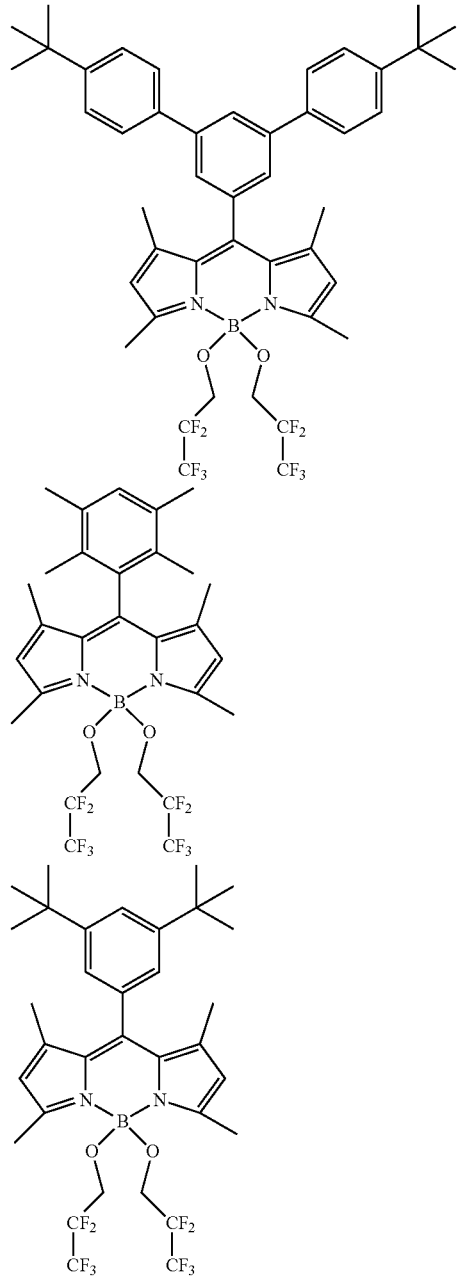

[Formula 119]

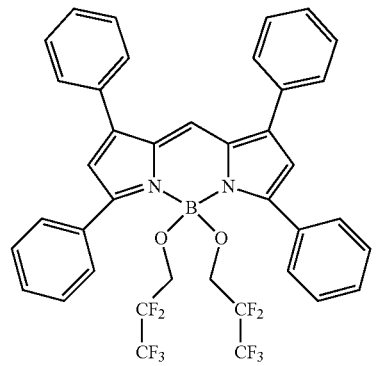

255
-continued
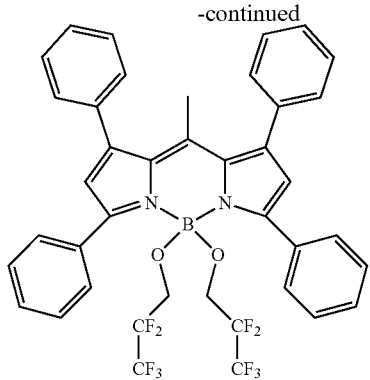
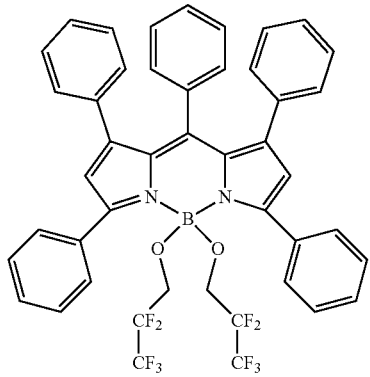
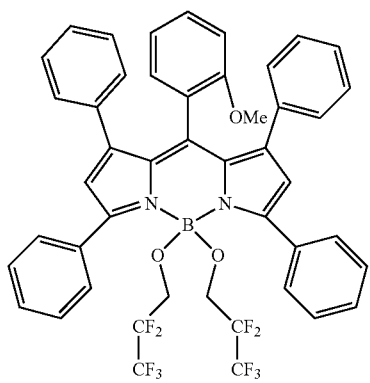
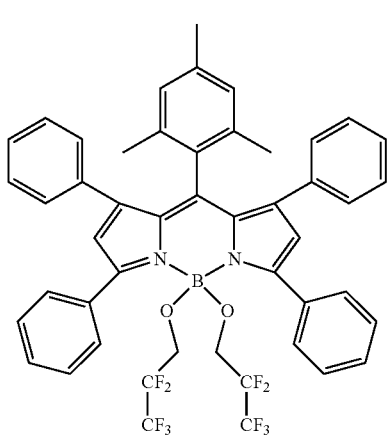
256
-continued
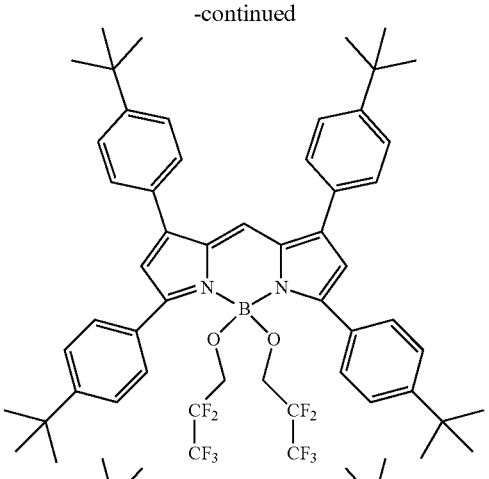
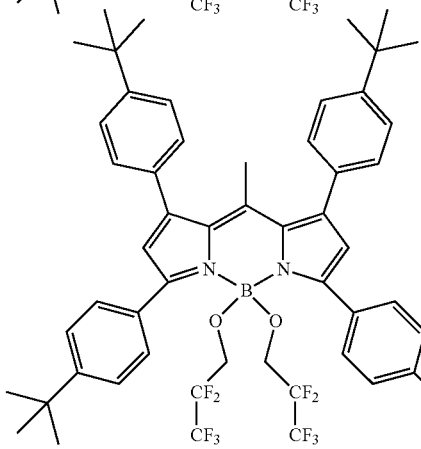
[Formula 120]
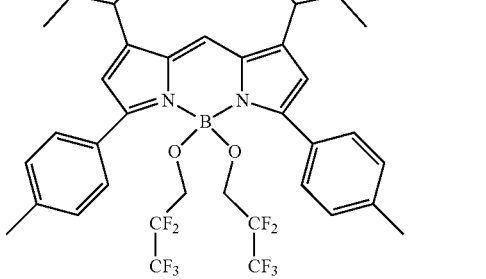

257
-continued
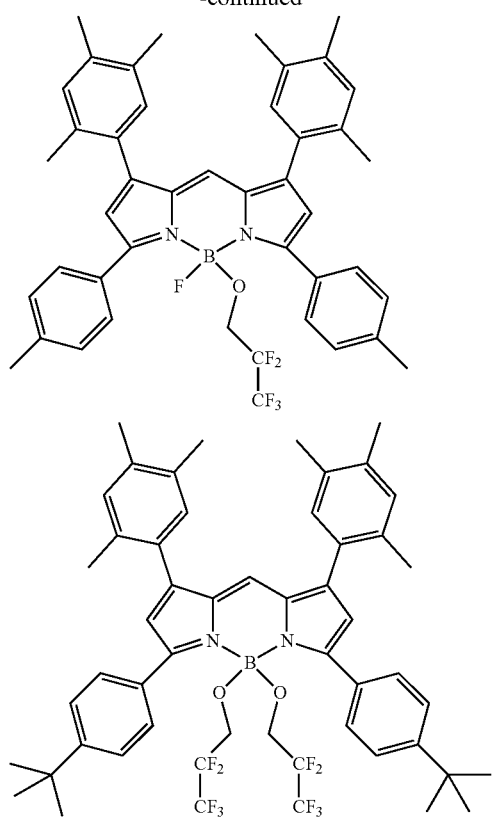
[Formula 121]
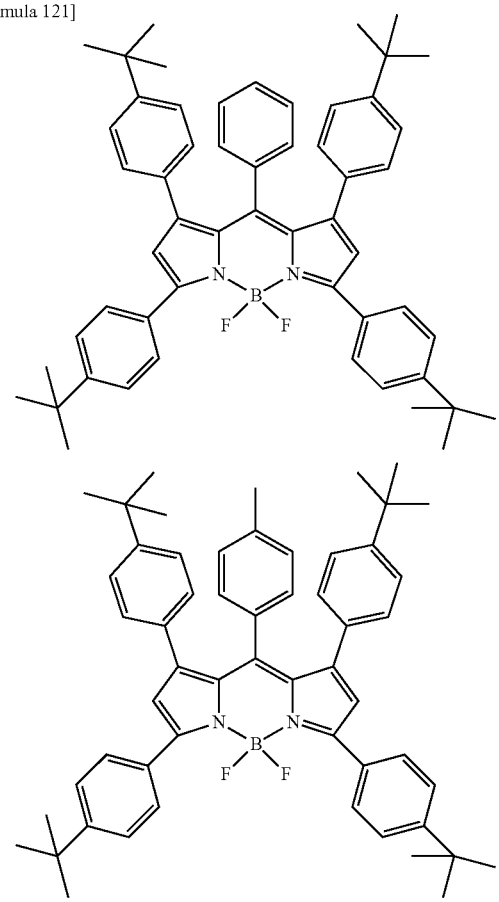
258
-continued
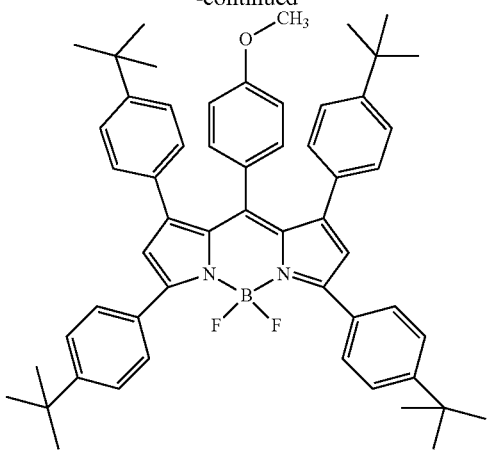
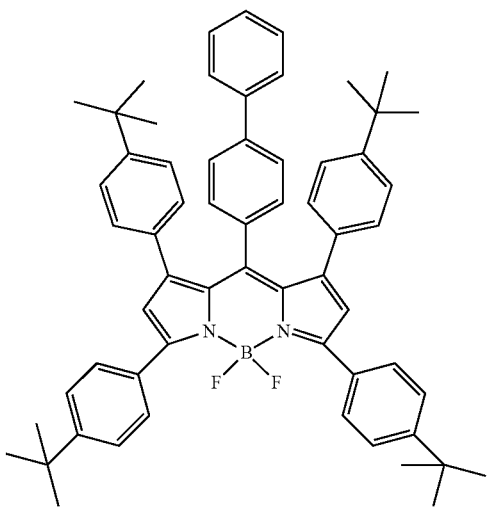
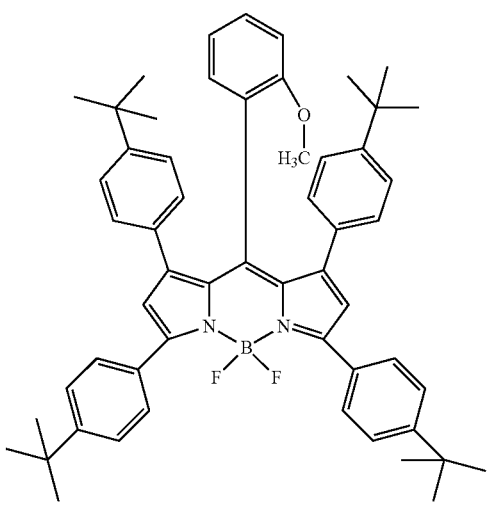

[Formula 122]
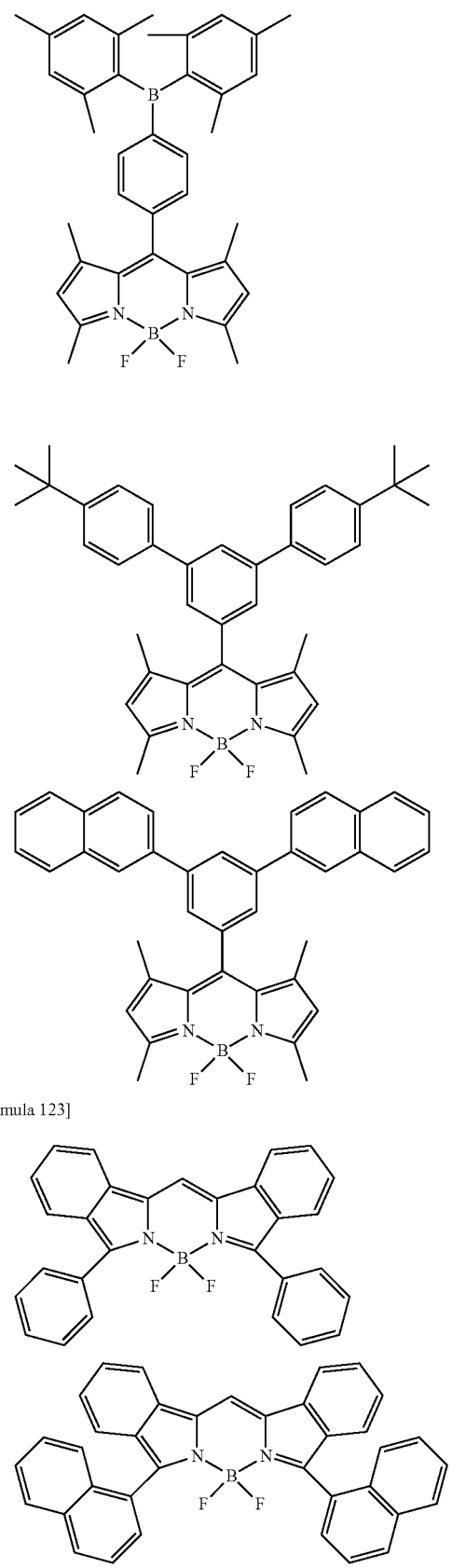
[Formula 123]
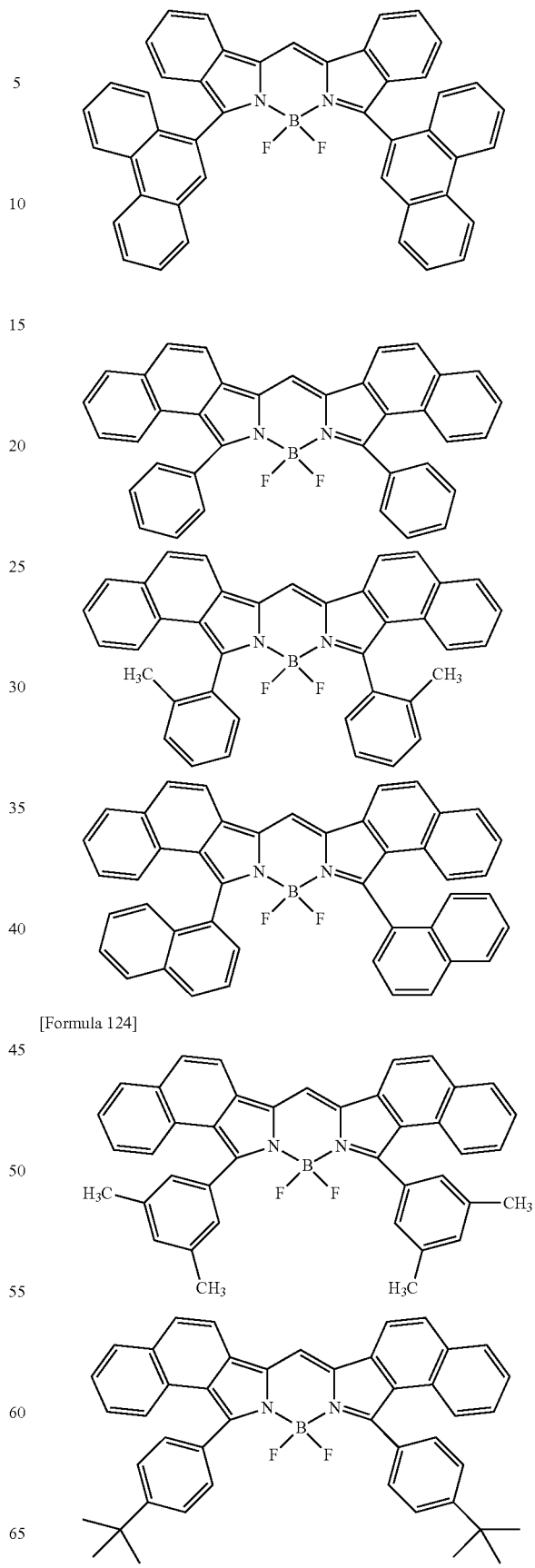
[Formula 124]

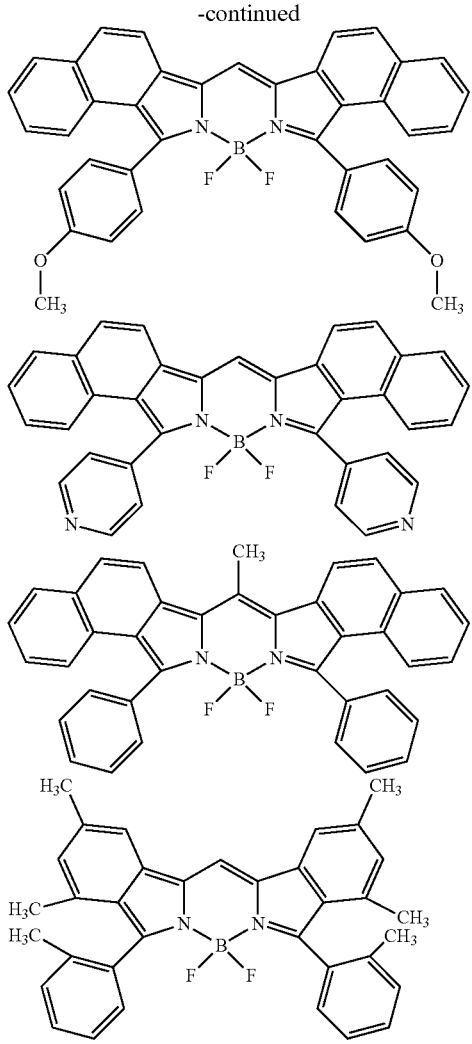

Relationship Between Compound M3, Compound M2 and Compound M1 in Emitting Layer

In the organic EL device of the exemplary embodiment, the singlet energy $S_1(M2)$ of the compound M2 and a singlet energy $S_1(M1)$ of the compound M1 no preferably satisfy a relationship of a numerical formula (Numerical Formula 2) below.

$$S_1(M2) > S_1(M1) \quad \text{(Numerical Formula 2)}$$

The singlet energy $S_1(M3)$ of the compound M3 is preferably larger than the singlet energy $S_1(M1)$ of the compound M1.

The singlet energy $S_1(M3)$ of the compound M3, the singlet energy $S_1(M2)$ of the compound M2, and the singlet energy $S_1(M1)$ of the compound M1 preferably satisfy a relationship of a numerical formula (Numerical Formula 2A) below.

$$S_1(M3) > S_1(M2) > S_1(M1) \quad \text{(Numerical Formula 2A)}$$

When the organic EL device of the exemplary embodiment emits light, it is preferable that the fluorescent compound M1 in the emitting layer mainly emits light.

The organic EL device of the exemplary embodiment preferably emits red light or green light.

Content Ratios of Compounds in Emitting Layer

Content ratios of the compounds M3, M2 and M1 in the emitting layer preferably fall within, for instance, the following range.

The content ratio of the compound M3 is preferably in a range from 10 mass % to 80 mass %.

The content ratio of the compound M2 is preferably in a range from 10 mass % to 80 mass %, more preferably in a range from 10 mass % to 60 mass %, further preferably in a range from 20 mass % to 60 mass %.

The content ratio of the compound M1 is preferably in a range from 0.01 mass % to 10 mass %, more preferably in a range from 0.01 mass % to 5 mass %, further preferably in a range from 0.01 mass % to 1 mass %.

An upper limit of the total of the respective content ratios of the compounds M3, M2 and M1 in the emitting layer is 100 mass %. It should be noted that the emitting layer of the exemplary embodiment may further contain material(s) other than the compounds M3, M2 and M1.

The emitting layer may include a single type of the compound M3 or may include two or more types of the compound M3. The emitting layer may include a single type of the compound M2 or may include two or more types of the compound M2. The emitting layer may include a single type of the compound M1 or may include two or more types of the compound M1.

FIG. 5 shows an example of a relationship between energy levels of the compounds M3, M2 and M1 in the emitting layer. In FIG. 5, S0 represents a ground state. S1(M1) represents the lowest singlet state of the compound M1. T1(M1) represents the lowest triplet state of the compound M1. S1 (M2) represents the lowest singlet state of the compound M2. T1(M2) represents the lowest triplet state of the compound M1. S1(M3) represents the lowest singlet state of the compound M3. T1(M3) represents the lowest triplet state of the compound M3. A dashed arrow directed from S1 (M2) to S1 (M1) in FIG. 5 represents Förster energy transfer from the lowest singlet state of the compound M2 to the lowest singlet state of the compound M1.

As shown in FIG. 5, when a compound having a small ΔST(M2) is used as the compound M2, inverse intersystem crossing from the lowest triplet state T1(M2) to the lowest singlet state S1(M2) can be caused by a heat energy. Subsequently, Förster energy transfer from the lowest singlet state S1 (M2) of the compound M2 to the compound M1 occurs to generate the lowest singlet state S1 (M1). Consequently, fluorescence from the lowest singlet state S1(M1) of the compound M1 can be observed. It is inferred that the internal quantum efficiency can be theoretically raised up to 100% also by using delayed fluorescence by the TADF mechanism.

The organic EL device according to the second exemplary embodiment contains the delayed fluorescent compound M2, the compound M3 (the compound M3 represented by the formula (100)) having the singlet energy larger than that of the compound M2, and the compound M1 having the singlet energy smaller than that of the delayed fluorescent compound M2 in the emitting layer.

According to the second exemplary embodiment, an organic EL device having high-performance, for instance, an organic EL device emitting light with a long lifetime can be achieved.

The organic EL device according to the second exemplary embodiment is applicable to an electronic device such as a display device and a light-emitting device.

Third Exemplary Embodiment

Electronic Device

An electronic device according to the present exemplary embodiment is installed with any one of the organic EL devices according to the above exemplary embodiments. Examples of the electronic device include a display device and a light-emitting device. Examples of the display device include a display component (e.g., an organic EL panel module), TV, mobile phone, tablet and personal computer. Examples of the light-emitting unit include an illuminator and a vehicle light.

Fourth Exemplary Embodiment

Compound

The compound of the fourth exemplary embodiment is a compound represented by a formula (201), a formula (202), or a formula (203) below.

[Formula 125]

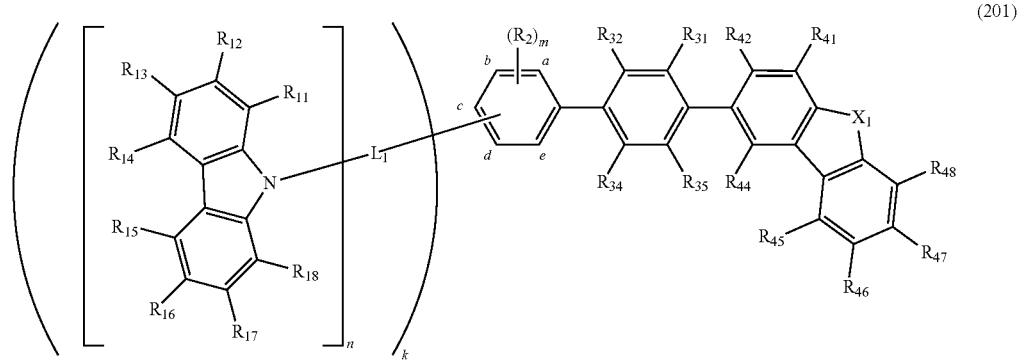

(201)

In the formula (201): $X_1$ is an oxygen atom or a sulfur atom.

n is 1, 2 or 3, k is 1, 2 or 3, m is 2, 3 or 4, k+m=5, $R_{11}$ to $R_{18}$ are each independently a hydrogen atom or a substituent, a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ are not mutually bonded, when at least one of n or k is 2 or more, a plurality of $R_{11}$ are mutually the same or different, a plurality of $R_{12}$ are mutually the same or different, a plurality of $R_{13}$ are mutually the same or different, a plurality of $R_{14}$ are mutually the same or different, a plurality of $R_{15}$ are mutually the same or different, a plurality of $R_{16}$ are mutually the same or different, a plurality of $R_{17}$ are mutually the same or different, and a plurality of $R_{18}$ are mutually the same or different, $L_1$ is a single bond or a linking group, when $L_1$ is a single bond, n is 1, when k is 2 or more, a plurality of $L_1$ are mutually the same or different, $L_1$ as a linking group is a group derived from a substituted or unsubstituted aryl group having 6 to 30 ring carbon atoms, a group derived from a substituted or unsubstituted heterocyclic group having 5 to 30 ring atoms, or a group in which two groups selected from the group consisting of a group derived from a substituted or unsubstituted aryl group having 6 to 30 ring carbon atoms and a group derived from a substituted or unsubstituted heterocyclic group having 5 to 30 ring atoms are bonded, when k is 1 and m is 4, four $R_2$ are respectively bonded to carbon atoms at any ones of positions of a, b, c, d and e shown in the formula (201), and one $L_1$ is bonded to a carbon atom at the position of a, b, c, d or e which is not bonded to $R_2$, when k is 2 and m is 3, three $R_2$ are respectively bonded to carbon atoms at any ones of positions of a, b, c, d and e shown in the formula (201), and two $L_1$ are respectively bonded to carbon atoms at any ones of positions of a, b, c, d and e which are not bonded to $R_2$, when k is 3 and m is 2, two $R_2$ are respectively bonded to carbon atoms at any ones of positions of a, b, c, d and e shown in the formula (201), and three $L_1$ are respectively bonded to carbon atoms at the positions of a, b, c, d and e which are not bonded to $R_2$, $R_2$, $R_{31}$, $R_{32}$, $R_{34}$ and $R_{35}$ are each independently a hydrogen atom or a substituent, a plurality of $R_2$ are mutually the same or different when m is 2 or more, $R_{41}$, $R_{42}$, $R_{44}$ and $R_{45}$ to $R_{48}$ are each independently a hydrogen atom or a substituent, or at least one pair of a pair of $R_{41}$ and $R_{42}$, a pair of $R_{45}$ and $R_{46}$, a pair of $R_{46}$ and $R_{47}$, or a pair of $R_{47}$ and $R_{48}$ are mutually bonded to form a ring, $R_{11}$ to $R_{18}$, $R_2$, $R_{31}$, $R_{32}$, $R_{34}$, $R_{35}$, $R_{41}$, $R_{42}$, $R_{44}$ and $R_{45}$ to $R_{48}$ as the substituent are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms, and at least one of $R_{11}$ to $R_{16}$ is an unsubstituted aryl group having 6 to 30 ring carbon atoms.

[Formula 126]

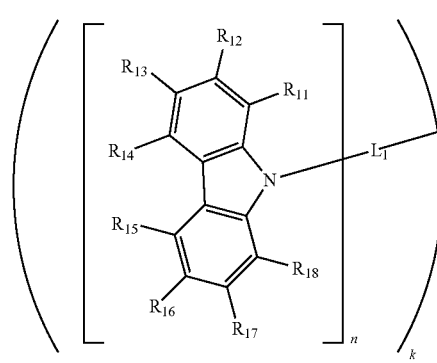
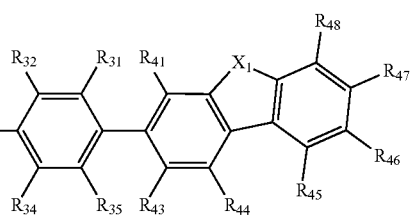

(202)

In the formula (202): $X_1$ is an oxygen atom or a sulfur atom, n is 1, 2 or 3, k is 1, 2 or 3, m is 2, 3 or 4, k+m=5, $R_{11}$ to $R_{18}$ are each independently a hydrogen atom or a substituent, a pair of $R_{11}$ and $R_{12}$, a pair of $R_{12}$ and $R_{13}$, a pair of $R_{13}$ and $R_{14}$, a pair erf $R_{15}$ and $R_{16}$, a pair of $R_{16}$ and $R_{17}$, and a pair of $R_{17}$ and $R_{18}$ are not mutually bonded, when at least one of n or k is 2 or more, a plurality of $R_{11}$ are mutually the same or different, a plurality of $R_{12}$ are mutually the same or different, a plurality of $R_{13}$ are mutually the same or different, a plurality of $R_{14}$ are mutually the same or different, a plurality of $R_{15}$ are mutually the same or different, a plurality of $R_{16}$ are mutually the same or different, a plurality of $R_{17}$ are mutually the same or different, and a plurality of $R_{18}$ are mutually the same or different, $L_1$ is a single bond or a linking group, when $L_1$ is a single bond, n is 1, when k is 2 or more, a plurality of $L_1$ are mutually the same or different, $L_1$ as a linking group is a group derived from a substituted or unsubstituted aryl group having 6 to 30 ring carbon atoms, a group derived from a substituted or unsubstituted heterocyclic group having 5 to 30 ring atoms, or a group in which two groups selected from the group consisting of a group derived from a substituted or unsubstituted aryl group having 6 to 30 ring carbon atoms and a group derived from a substituted or unsubstituted heterocyclic group having 5 to 30 ring atoms are bonded, when k is 1 and m is 4, four $R_2$ are respectively bonded to carbon atoms at any ones of positions of a, b, c, d and e shown in the formula (202), and one $L_1$ is bonded to a carbon atom at the position of a, b, c, d or e which is not bonded to $R_2$, when k is 2 and m is 3, three $R_2$ are respectively bonded to carbon atoms at any ones of positions of a, b, c, d and e shown in the formula (202), and two $L_1$ are respectively bonded to carbon atoms at the positions of a, b, c, d and e which are not bonded to $R_2$, when k is 3 and m is 2, two $R_2$ are respectively bonded to carbon atoms at any ones of positions of a, b, c, d and e shown in the formula (202), and three $L_1$ are respectively bonded to carbon atoms at the positions of a, b, c, d and e which are not bonded to $R_2$, $R_2$, $R_{31}$, $R_{32}$, $R_{34}$ and $R_{35}$ are each independently a hydrogen atom or a substituent, a plurality of $R_2$ are mutually the same or different when m is 2 or more, $R_{41}$, $R_{43}$, $R_{44}$ and $R_{45}$ to $R_{48}$ are each independently a hydrogen atom or a substituent, or at least one pair of a pair of $R_{43}$ and $R_{44}$, a pair of $R_{45}$ and $R_{46}$, a pair of $R_{46}$ and $R_{47}$, or a pair of $R_{47}$ and $R_{48}$ are mutually bonded to form a ring, $R_{11}$ to $R_{18}$, $R_2$, $R_{31}$, $R_{32}$, $R_{34}$, $R_{35}$, $R_{41}$, $R_{43}$, $R_{44}$ and $R_{45}$ to $R_{48}$ as the substituent are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted akylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms, and at least one of $R_{11}$ to $R_{18}$ is an unsubstituted aryl group having 6 to 30 ring carbon atoms.

[Formula 127]

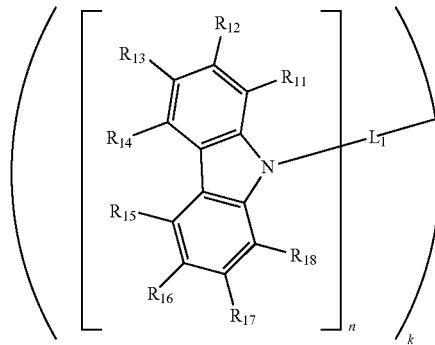

(203)

In the formula (203): $X_1$ is an oxygen atom or a sulfur atom, n is 1, 2 or 3, k is 1, 2 or 3.

m is 2, 3 or 4, k+m=5, $R_{11}$ to $R_{18}$ are each independently a hydrogen atom or a substituent, a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, and a pair of $R_{17}$ and $R_{18}$ are not mutually bonded, when at least one of n or k is 2 or more, a plurality of $R_{11}$ are mutually the same or different, a plurality of $R_{12}$ are mutually the same or different, a plurality of $R_{13}$ are mutually the same or different, a plurality of $R_{14}$ are mutually the same or different, a plurality of $R_{15}$ are mutually the same or different, a plurality of $R_{16}$ are mutually the same or different, a plurality of $R_{17}$ are mutually the same or different, and a plurality of $R_{18}$ are mutually the same or different, $L_1$ is a single bond or a linking group, when $L_1$ is a single bond, n is 1, when k is 2 or more, a plurality of $L_1$ are mutually the same or different, $L_1$ as a linking group is a group derived from a substituted or unsubstituted aryl group having 6 to 30 ring carbon atoms, a group derived from a substituted or unsubstituted heterocyclic group having 5 to 30 ring atoms, or a group in which two groups selected from the group consisting of a group derived from a substituted or unsubstituted aryl group having 6 to 30 ring carbon atoms and a group derived from a substituted or unsubstituted heterocyclic group having 5 to 30 ring atoms are bonded, when k is 1 and m is 4, four $R_2$ are respectively bonded to carbon atoms at any ones of positions of a, b, c, d and e shown in the formula (203), and one $L_1$ is bonded to a carbon atom at the position of a, b, c, d or e which is not bonded to $R_2$, when k is 2 and m is 3, three $R_2$ are respectively bonded to carbon atoms at any ones of positions of a, b, c, d and e shown in the formula (203), and two $L_1$ are respectively bonded to carbon atoms at the positions of a, b, c, d and e which are not bonded to $R_2$, when k is 3 and m is 2, two $R_2$ are respectively bonded to carbon atoms at any ones of positions of a, b, c, d and e shown in the formula (203), and three $L_1$ are respectively bonded to carbon atoms at the positions of a, b, c, d and e which are not bonded to $R_2$, $R_2$, $R_{31}$, $R_{32}$, $R_{34}$ and $R_{35}$ are each independently a hydrogen atom or a substituent, a plurality of $R_2$ are mutually the same or different when m is 2 or more, $R_{42}$ to $R_{44}$ and $R_{45}$ to $R_{48}$ are each independently a hydrogen atom or a substituent, or at least one pair of a pair of $R_{42}$ and $R_{43}$, a pair of $R_{43}$ and $R_{44}$, a pair of $R_{45}$ and $R_{46}$, a pair of $R_{46}$ and $R_{47}$, and a pair of $R_{47}$ and $R_{48}$ are mutually bonded to form a ring, $R_{11}$ to $R_{18}$, $R_2$, $R_{31}$, $R_{32}$, $R_{34}$, $R_{35}$, $R_{42}$ to $R_{44}$ and $R_{45}$ to $R_{48}$ as the substituent are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms, and at least one of $R_{11}$ to $R_{18}$ is an unsubstituted aryl group having 6 to 30 ring carbon atoms.

Organic EL Device

An organic EL device in an arrangement of the fourth exemplary embodiment is an organic EL device in which the compound M3 in the organic EL device of the first exemplary embodiment is replaced by the compound of the fourth exemplary embodiment (the compound represented by one of the formulae (201) to (203)).

For instance, the compounds represented by the formulae (201) to (203) respectively represent the same as the compounds represented by the formulae (201A) to (203A), which are shown as an example of the compound M3 in the first exemplary embodiment.

Specifically, in the formula (201), $X_1$, $R_{11}$ to $R_{18}$, n, K, m, $L_1$, $R_2$, $R_{31}$, $R_{32}$, $R_{34}$, $R_{35}$, $R_{41}$, $R_{42}$, $R_{44}$ and $R_{45}$ to $R_{48}$ respectively represent the same as $X_1$, $R_{11}$ to $R_{18}$, n, k, m, $L_1$, $R_2$, $R_{31}$, $R_{32}$; $R_{34}$, $R_{35}$, $R_{41}$, $R_{42}$, $R_{44}$ and $R_{45}$ to $R_{48}$ the formula (201A).

In the formula (202), $X_1$, $R_{11}$ to $R_{18}$, n, k, m, $L_1$, $R_2$, $R_{31}$, $R_{32}$, $R_{34}$, $R_{35}$, $R_{41}$, $R_{43}$, $R_{44}$ and $R_{45}$ to $R_{48}$ respectively represent the same as $X_1$, $R_{11}$ to $R_{18}$, n, k, m, $L_1$, $R_2$, $R_{31}$, $R_{32}$, $R_{34}$, $R_{35}$, $R_{41}$, $R_{43}$, $R_{44}$ and $R_{45}$ to $R_{48}$ in the formula (202A).

In the formula (203), $X_1$, $R_{11}$ to $R_{18}$, n, k, m, $L_1$, $R_2$, $R_{31}$, $R_{32}$, $R_{34}$, $R_{35}$, $R_{42}$ to $R_{44}$ and $R_{45}$ to $R_{48}$ respectively represent the same as $X_1$, $R_{11}$ to $R_{18}$, n, k, m, $L_1$, $R_2$, $R_{31}$, $R_{32}$, $R_{34}$, $R_{35}$, $R_{42}$ to $R_{44}$ and $R_{45}$ to $R_{48}$ in the formula (203A).

The compound according to the fourth exemplary embodiment is a compound capable of achieving a high-performance organic EL device, for instance, an organic EL device configured to emit light with a long lifetime.

Accordingly, an organic EL device in the arrangement of the fourth exemplary embodiment also has high performance, for instance, emits light with a long lifetime.

Fifth Exemplary Embodiment

Compound

The compound of the fifth exemplary embodiment is a compound represented by a formula (300) below:

[Formula 128]

(300)

In the formula (300): $X_1$ is an oxygen atom or a sulfur atom, n is 1, 2 or 3, k is 1, 2 or 3, m is 2, 3 or 4, k+m=5, $R_{11}$ to $R_{18}$ are each independently a hydrogen atom or a substituent, at least one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ are mutually bonded to each other to form a ring, when at least one of n or k is 2 or more, a plurality of $R_{11}$ are mutually the same or different, a plurality of $R_{12}$ are mutually the same or different, a plurality of $R_{13}$ are mutually the same or different, a plurality of $R_{14}$ are mutually the same or different, a plurality of $R_{15}$ are mutually the same or different, a plurality of $R_{16}$ are mutually the same or different, a plurality of $R_{17}$ are mutually the same or different, and a plurality of $R_{18}$ are mutually the same or different, $L_1$ is a single bond or a linking group, when k is 2 or more, a plurality of $L_1$ are mutually the same or different, when $L_1$ is a single bond, n is 1, $L_1$ as a linking group is a group derived from a substituted or unsubstituted aryl group having 6 to 30 ring carbon atoms, a group derived from a substituted or unsubstituted heterocyclic group having 5 to 30 ring atoms, or a group in which two groups selected from the group consisting of a group derived from a substituted or unsubstituted aryl group having 6 to 30 ring carbon atoms and a group derived from a substituted or unsubstituted heterocyclic group having 5 to 30 ring atoms are bonded, when k is 1 and m is 4, four $R_2$ are respectively bonded to carbon atoms at any ones of positions of a, b, c, d and e shown in the formula (300), and one $L_1$ is bonded to a carbon atom at the position of a, b, c, d or e which is not bonded to $R_2$, when k is 2 and m is 3, three $R_2$ are respectively bonded to carbon atoms at any ones of positions of a, b, c, d and e shown in the formula (300), and two $L_1$ are respectively bonded to carbon atoms at the positions of a, b, c, d and e which are not bonded to $R_2$, when k is 3 and m is 2, two $R_2$ are respectively bonded to carbon atoms at any ones of positions of a, b, c, d and e shown in the formula (300), and three $L_1$ are respectively bonded to carbon atoms at the positions of a, b, c, d and e which are not bonded to $R_2$, $R_2$, $R_{31}$, $R_{32}$, $R_{34}$ and $R_{35}$ are each independently a hydrogen atom or a substituent, a plurality of $R_2$ are mutually the same or different when m is 2 or more, $R_{41}$, $R_{42}$, $R_{43}$ and $R_{45}$ to $R_{48}$ are each independently a hydrogen atom or a substituent, or at least one pair of a pair of $R_{41}$ and $R_{42}$, a pair of $R_{42}$ and $R_{43}$, a pair of $R_{45}$ and $R_{46}$, a pair of $R_{46}$ and $R_{47}$, or a pair of $R_{47}$ and $R_{48}$ are mutually bonded to form a ring, and $R_{11}$ to $R_{18}$, $R_2$, $R_{31}$, $R_{32}$, $R_{34}$, $R_{35}$, $R_{41}$, $R_{42}$, $R_{43}$ and $R_{45}$ to $R_{48}$ as the substituent are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms.

Organic EL Device

An organic EL device in an arrangement of the fifth exemplary embodiment is an organic EL device in which the compound M3 in the organic EL device of the first exemplary embodiment is replaced by the compound of the fifth exemplary embodiment (the compound represented by the formula (300)).

For instance, the compound represented by the formula (300) represents the same as the compound represented by the formula (300A), which is shown as an example of the compound M3 in the first exemplary embodiment.

Specifically, in the formula (300), $X_1$, $R_{11}$ to $R_{18}$, n, k, m, $L_1$, $R_2$, $R_{31}$, $R_{32}$, $R_{34}$, $R_{35}$, $R_{41}$ to $R_{43}$ and $R_{45}$ to $R_{48}$ respectively represent the same as $X_1$, $R_{11}$ to $R_{18}$, n, k, m, $L_1$, $R_2$, $R_{31}$, $R_{32}$, $R_{34}$, $R_{35}$, $R_{41}$ to $R_{43}$ and $R_{45}$ to $R_{48}$ in the formula (300A).

The compound according to the fifth exemplary embodiment is a compound capable of achieving a high-performance organic EL device, for instance, an organic EL device configured to emit light with a long lifetime.

Accordingly, an organic EL device in the arrangement of the fifth exemplary embodiment also has high-performance, for instance, emits light with a long lifetime.

Preferable arrangements of the compounds according to the fourth and fifth exemplary embodiments will be described below.

In the compounds of the fourth and fifth exemplary embodiments, it is preferable that at least one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ are mutually bonded to form a ring, and that a pair of $R_{41}$ and $R_{42}$, a pair of $R_{42}$ and $R_{43}$, a pair of $R_{43}$ and $R_{44}$, a pair of $R_{45}$ and $R_{46}$, a pair of $R_{46}$ and $R_{47}$, and a pair of $R_{47}$ and $R_{48}$ are not mutually bonded.

In the compounds of the fourth and fifth exemplary embodiments, it is preferable that a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, and a pair of $R_{17}$ and $R_{18}$, a pair of $R_{41}$ and $R_{42}$, a pair of $R_{42}$ and $R_{43}$, a pair of $R_{43}$ and $R_{44}$, a pair of $R_{45}$ and $R_{46}$, a pair of $R_{46}$ and $R_{47}$, and a pair of $R_{47}$ and $R_{48}$ are not mutually bonded.

In the compounds of the fourth and fifth exemplary embodiments, it is preferable that $R_2$, $R_{31}$, $R_{32}$, $R_{34}$, and $R_{35}$ are hydrogen atoms, and $L_1$ is a single bond, or a group derived from an unsubstituted aryl group having 6 to 30 ring carbon atoms or a group derived from an unsubstituted heterocyclic group having 5 to 30 ring atoms.

In the compounds of the fourth and fifth exemplary embodiments, n is preferably 1 or 2, and n is more preferably 1.

In the compounds of the fourth and fifth exemplary embodiments, k is preferably 1 or 2.

In the compounds of the fourth and fifth exemplary embodiments, it is more preferable that n is 1 or 2, and k is 1 or 2.

In the compounds of the fourth and fifth exemplary embodiments, it is preferable that $R_{11}$ to $R_{18}$ and $R_{41}$ to $R_{48}$ are each independently a hydrogen atom, a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms.

In the compounds of the fourth and fifth exemplary embodiments, it is more preferable that $R_{11}$ to $R_{18}$ and $R_{41}$ to $R_{48}$ are each independently a hydrogen atom, a substituted or unsubstituted aryl group having 6 to 30 ring carbon atoms, or a substituted or unsubstituted heterocyclic group having 5 to 30 ring atoms.

In the compounds of the fourth and fifth exemplary embodiments, it is further preferable that $R_{11}$ to $R_{18}$ and $R_{41}$ to $R_{48}$ are each independently a hydrogen atom, or a substituted or unsubstituted aryl group having 6 to 30 ring carbon atoms.

In the compounds of the fourth and fifth exemplary embodiments, it is further more preferable that $R_{11}$ to $R_{18}$ and $R_{41}$ to $R_{48}$ are each independently a hydrogen atom, or a substituted or unsubstituted phenyl group.

In the compounds of the fourth and fifth exemplary embodiments, it is preferable that $R_{11}$ to $R_{18}$ are each independently a hydrogen atom, or a substituted or unsubstituted phenyl group, and $R_{41}$ to $R_{48}$ are each independently a hydrogen atom.

In the compounds of the fourth and fifth exemplary embodiments, it is preferable that $L_1$ is a single bond or a group derived from an unsubstituted aryl group having 6 to 30 ring carbon atoms.

In the compounds of the fourth and fifth exemplary embodiments, it is more preferable that $L_1$ is a single bond or a group derived from an unsubstituted benzene ring.

In the compounds of the fourth and fifth exemplary embodiments, it is more preferable that $L_1$ is a single bond.

In the compounds of the fourth and fifth exemplary embodiments, it is preferable that $X_1$ is an oxygen atom.

In the compound of the fourth exemplary embodiment, it is preferable that $R_2$, $R_{31}$, $R_{32}$, $R_{34}$ and $R_{35}$ are hydrogen atoms, n is 1 or 2, k is 1 or 2, $R_{11}$ to $R_{18}$ and $R_{41}$ to $R_{48}$ are each independently a hydrogen atom, or a substituted or unsubstituted aryl group having 6 to 30 ring carbon atoms, a pair of $R_{41}$ and $R_{42}$, a pair of $R_{42}$ and $R_{43}$, a pair of $R_{43}$ and $R_{44}$, a pair of $R_{45}$ and $R_{46}$, a pair of $R_{46}$ and $R_{47}$, and a pair of $R_{47}$ and $R_{48}$ are not mutually bonded, and $L_1$ is a single bond or a group derived from an unsubstituted aryl group having 6 to 30 ring carbon atoms.

In the compound of the fourth exemplary embodiment, it is also preferable that $R_2$, $R_{31}$, $R_{32}$, $R_{34}$ and $R_{35}$ are hydrogen atoms, n is 1 or 2, k is 1 or 2, $R_{11}$ to $R_{18}$ are each independently a hydrogen atom, or a substituted or unsubstituted phenyl group, $R_{41}$ to $R_{48}$ are hydrogen atoms, and $L_1$ is a single bond.

In the compound of the fifth exemplary embodiment, it is preferable that $R_2$, $R_{31}$, $R_{32}$, $R_{34}$ and $R_{35}$ are hydrogen atoms, n is 1 or 2, k is 1 or 2, $R_{11}$ to $R_{18}$, $R_{41}$ to $R_{43}$ and $R_{45}$ to $R_{48}$ are each independently a hydrogen atom, or a substituted or unsubstituted aryl group having 6 to 30 ring carbon atoms, a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, a pair of $R_{17}$ and $R_{18}$, a pair of $R_{41}$ and $R_{42}$, a pair of $R_{42}$ and $R_{43}$, a pair of $R_{45}$ and $R_{46}$, a pair of $R_{46}$ and $R_{47}$, and a pair of $R_{47}$ and $R_{48}$ are not mutually bonded, and $L_1$ is a single bond or a group derived from an unsubstituted aryl group having 6 to 30 ring carbon atoms.

In the compound of the fifth exemplary embodiment, it is also preferable that $R_2$, $R_{31}$, $R_{32}$, $R_{34}$ and $R_{35}$ are hydrogen atoms, n is 1 or 2, k is 1 or 2, $R_{11}$ to $R_{18}$ are each independently a hydrogen atom, or a substituted or unsubstituted phenyl group, a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, and a pair of $R_{17}$ and $R_{18}$ are not mutually bonded, $R_{41}$ to $R_{43}$ and $R_{45}$ to $R_{48}$ are hydrogen atoms, and $L_1$ is a single bond.

Fifth Exemplary Embodiment A

Compound

A compound of a fifth exemplary embodiment A is a compound represented by one of formulae (501) to (514) below.

[Formula 129]

(501)

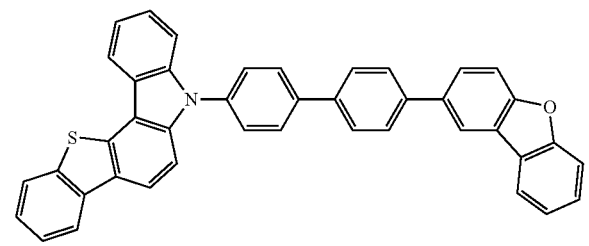

(502)

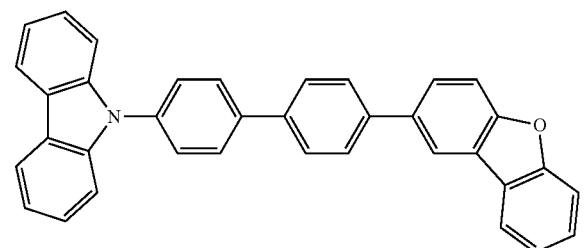

(503)

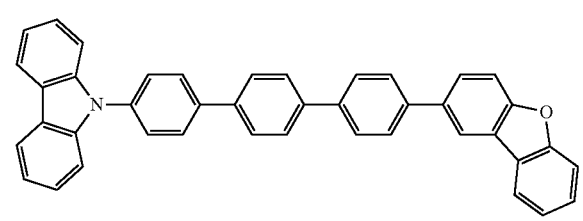

(504)

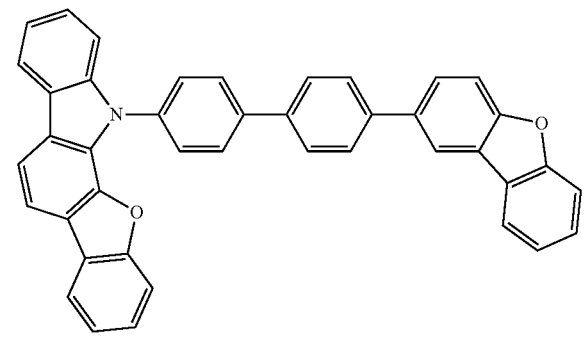

(505)

(506)

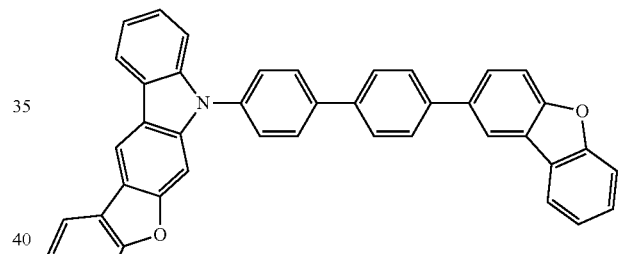

[Formula 130]

(507)

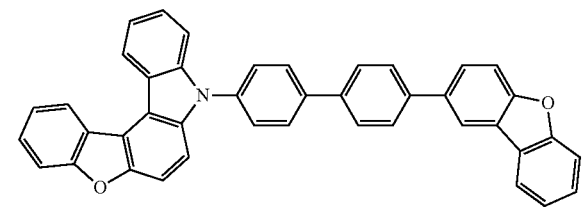

(508)

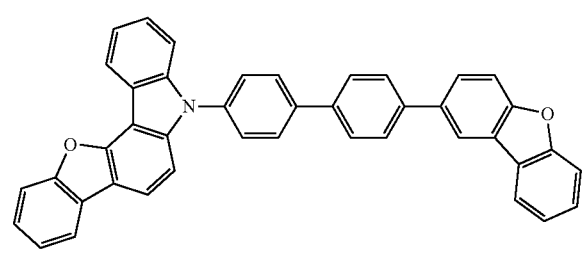

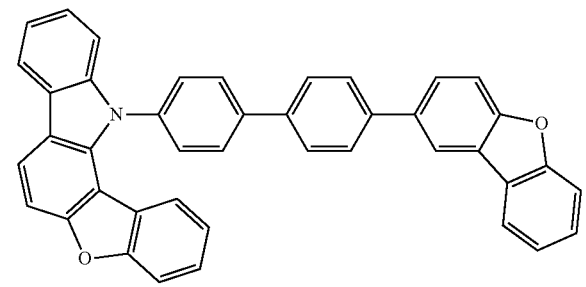

(509)
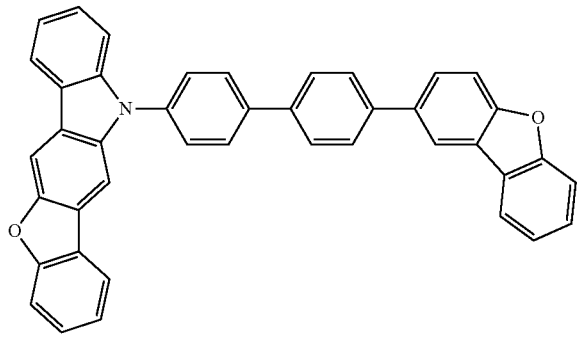

(510)
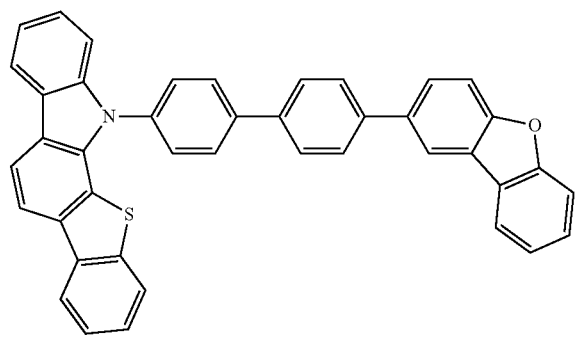

(511)
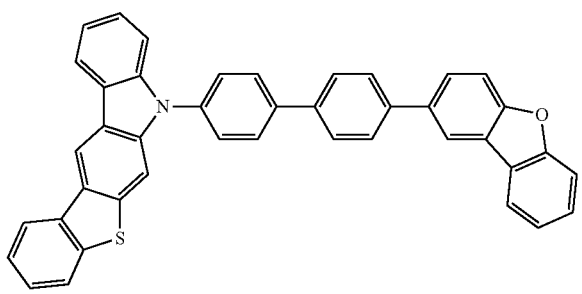

(512)
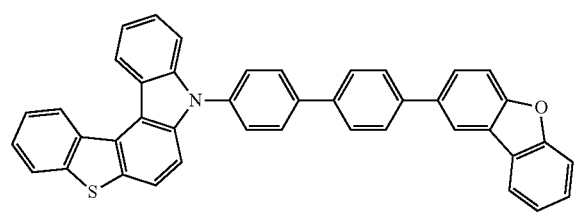

(513)
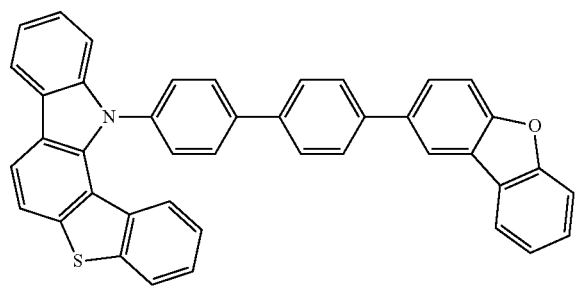

(514)
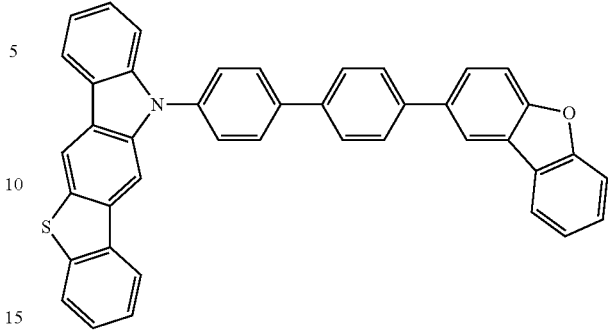

Organic EL Device

An organic EL device in an arrangement of the fifth exemplary embodiment A is an organic EL device in which the compound M3 in the organic EL device of the first exemplary embodiment is replaced by the compound of the fifth exemplary embodiment A (the compound represented by one of the formulae (501) to (514)).

The compound represented by one of the formulae (501) to (514) is an example of the compound M3 in the first exemplary embodiment.

The compound according to the fifth exemplary embodiment A is a compound capable of achieving a high-performance organic EL device, for instance, an organic EL device configured to emit light with a long lifetime.

Accordingly, an organic EL device in the arrangement of the fifth exemplary embodiment A also has high performance, for instance, emits light with a long lifetime.

Sixth Exemplary Embodiment

Organic-EL-Device Material

An organic-EL-device material of a sixth exemplary embodiment contains at least one of the compound of the fourth exemplary embodiment, the compound of the fifth exemplary embodiment or the compound of the fifth exemplary embodiment A.

Specifically, the organic-EL-device material of the sixth exemplary embodiment contains at least one of the compounds represented by the formulae (201) to (203), (300) and (501) to (514).

According to the organic-EL-device material of the sixth exemplary embodiment, a high-performance organic EL device, for instance, an organic EL device configured to emit light with a long lifetime and an electronic device including the organic EL device can be achieved.

The organic-EL-device material according to the sixth exemplary embodiment may further contain an additional compound. When the organic-EL-device material according to the sixth exemplary embodiment further contains the additional compound, the additional compound may be solid or liquid.

Modification of Embodiment(s)

The scope of the invention is not limited by the above-described exemplary embodiments but includes any modification and improvement as long as such modification and improvement are compatible with the invention.

For instance, the emitting layer is not limited to a single layer, but may be provided by laminating a plurality of emitting layers. When the organic EL device has a plurality of emitting layers, it is only required that at least one of the emitting layers satisfies the conditions described in the above exemplary embodiments. The rest of the emitting layers is, for instance, a fluorescent emitting layer or a phosphorescent emitting layer with use of emission caused by electron transfer from the triplet excited state directly to the ground state, in an exemplary embodiment.

When the organic EL device includes a plurality of emitting layers, these emitting layers are mutually adjacently provided, or form a so-called tandem organic EL device, in which a plurality of emitting units are layered via an intermediate layer.

For instance, in an exemplary embodiment, a blocking layer is provided adjacent to at least one of a side near the anode and a side near the cathode of the emitting layer. The blocking layer is preferably provided in contact with the emitting layer to block at least any of holes, electrons, and excitons.

For instance, when the blocking layer is provided in contact with the cathode-side of the emitting layer, the blocking layer permits transport of electrons, and blocks holes from reaching a layer provided near the cathode (e.g., the electron transporting layer) beyond the blocking layer. When the organic EL device includes the electron transporting layer, the blocking layer is preferably disposed between the emitting layer and the electron transporting layer.

When the blocking layer is provided in contact with the anode-side of the emitting layer, the blocking layer permits transport of holes, but blocks electrons from reaching a layer provided near the anode (e.g., the hole transporting layer) beyond the blocking layer. When the organic EL device includes the hole transporting layer, the blocking layer is preferably disposed between the emitting layer and the hole transporting layer.

Alternatively, the blocking layer may be provided adjacent to the emitting layer so that the excitation energy does not leak out from the emitting layer toward neighboring layer(s). The blocking layer blocks excitons generated in the emitting layer from being transferred to a layer(s) (e.g., the electron transporting layer and the hole transporting layer) closer to the electrode(s) beyond the blocking layer.

The emitting layer is preferably bonded with the blocking layer.

Specific structure, shape and the like of the components in the invention may be designed in any manner as long as an object of the invention can be achieved.

Herein, numerical ranges represented by "x to y" represents a range whose lower limit is the value (x) recited before "to" and whose upper limit is the value (y) recited after "to."

Rx and Ry are mutually bonded to form a ring, which means herein, for instance, that Rx and Ry contain a carbon atom, a nitrogen atom, an oxygen atom, a sulfur atom or a silicon atom, the atom (a carbon atom, a nitrogen atom, an oxygen atom, a sulfur atom or a silicon atom) contained in Rx and the atom (a carbon atom, a nitrogen atom, an oxygen atom, a sulfur atom or a silicon atom) contained in Ry are mutually bonded via a single bond, a double bond, a triple bond or a divalent linking group to form a ring having 5 or more ring atoms (specifically, a heterocyclic ring or an aromatic hydrocarbon ring), x represents a number, a character or a combination of a number and a character, y represents a number, a character or a combination of a number and a character.

The divalent linking group is not particularly limited and is exemplified by —O—, —CO—, —CO$_2$—, —S—, —SO—, —SO$_2$—, —NH—, —NRa—, and a group obtained by combining two or more linking groups of those.

Specific examples of the heterocyclic ring include a cyclic structure (heterocyclic ring) obtained by removing a bond from a "heteroaryl group Sub$_2$" exemplarily shown in the later-described "Description of Each Substituent in Formula." The heterocyclic ring may have a substituent.

Specific examples of the heterocyclic ring include cyclic structures (heterocyclic rings) obtained by removing a bond from an "aryl group Sub$_1$" exemplarily shown in the later-described "Description of Each Substituent in Formula." The aromatic hydrocarbon ring may have a substituent.

Examples of Ra include a substituted or unsubstituted alkyl group Sub$_3$ having 1 to 30 carbon atoms, a substituted or unsubstituted aryl group Sub$_1$ having 6 to 30 ring carbon atoms, and a substituted or unsubstituted heteroaryl group Sub$_2$ having 5 to 30 ring atoms, which are exemplarily shown in the later-described "Description of Each Substituent in Formula."

Rx and Ry are mutually bonded to form a ring, which means, for instance, that: an atom contained in Rx$_1$ and an atom contained in Ry$_1$ in a molecular structure represented by a formula (E1) below form a ring (cyclic structure) E represented by a formula (E2); an atom contained in Rx$_1$ and an atom contained in Ry$_1$ in a molecular structure represented by a formula (F1) below form a ring (cyclic structure) F represented by a formula (F2); an atom contained in Rx$_1$ and an atom contained in Ry$_1$ in a molecular structure represented by a formula (G1) below form a ring (cyclic structure) G represented by a formula (G2); an atom contained in Rx$_1$ and an atom contained in Ry$_1$ in a molecular structure represented by a formula (H1) below form a ring (cyclic structure) H represented by a formula (H2); and an atom contained in Rx$_1$ and an atom contained in Ry$_1$ in a molecular structure represented by a formula (I1) below form a ring (cyclic structure) I represented by a formula (I2).

In the formulae (E1) to (I1), * each independently represents a bonding position to another atom in a molecule. Two * in the formula (E1) correspond one-to-one to two * in the formula (E2). Two * in the formula (F1) correspond one-to-one to two * in the formula (F2). Two. * in the formula (G1) correspond one-to-one to two * in the formula (G2). Two * in the formula (H1) correspond one-to-one to two * In the formula (H2). Two * in the formula (I1) correspond one-to-one to two * in the formula (I2).

[Formula 131]

(E1)

(F1)

(G1)

(H1)

-continued (I1)

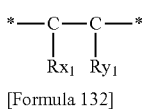

[Formula 132]

(E2)

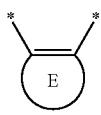

(F2)

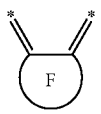

(G2)

(H2)

(I2)

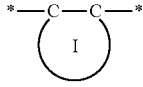

In the molecular structures represented by the respective formulae (E2) to (I2), E to I each represent a cyclic structure (the ring having 5 or more ring atoms), in the formulae (E2) to (I2), * each independently represents a bonding position to another atom in a molecule. Two * in the formula (E2) correspond one-to-one to two * in the formula (E1). Similarly, two * in each of the formulae (F2) to (I2) correspond one-to-one to two * in in each of the formulae (Ft) to (I1).

For instance, when in the formula (E1). $Rx_1$ and $Ry_1$ are mutually bonded to form the ring E m the formula (E2) and the ring E is an unsubstituted benzene ring, the molecular structure represented by the formula (E1) is a molecular structure represented by a formula (E3) below. Herein, two * in the formula (E3) each independently correspond to two * in the formula (E2) and the formula (E1).

For instance, when in the formula (E1), $Rx_1$ and $Ry_1$ are mutually bonded to form the ring E in the formula (E2) and the ring E is an unsubstituted pyrrole ring, the molecular structure represented by the formula (E1) is a molecular structure represented by a formula (E4) below. Herein, two in the formula (E4) each independently correspond to two * In the formula (62) and the formula (E1) In the formulae (E3) and (E4), * each independently represents a bonding position to another atom in a molecule.

[Formula 133]

(E3)

(E4)

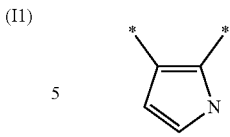

Herein, the ring carbon atoms refer to the number of carbon atoms among atoms forming a ring of a compound (e.g., a monocyclic compound, fused-ring compound, crosslinking compound, carbon ring compound, and heterocyclic compound) in which the atoms are bonded to each other to form the ring. When the ring is substituted by a substituents), carbon atoms) contained in the substituent(s) is not counted in the ring carbon atoms. Unless specifically described, the same to applies to the "ring carbon atoms" described later. For instance, a benzene ring has 6 ring carbon atoms, a naphthalene ring has 10 ring carbon atoms, a pyridinyl group has 5 ring carbon atoms, and a furanyl group has A ring carbon atoms. When a benzene ring and/or a naphthalene ring is substituted by a substituent (e.g., an alkyl group), the number of carbon atoms of the alkyl group is not counted in the number of the ring carbon atoms. When a fluorene ring is substituted by a substituent (e.g., a fluorene ring) (i.e., a spirofluorene ring is included), the number of carbon atoms of the fluorene ring as the substituent is not counted in the number of the ring carbon atoms of the fluorene ring.

Herein, the ring atoms refer to the number of atoms forming a ring of a compound (e.g., a monocyclic compound, fused-ring compound, crosslinking compound, carbon ring compound, and heterocyclic compound) in which the atoms are bonded to each other to form the ring (e.g., monocyclic ring, fused ring, ring assembly). Atom(s) not forming a ring and atom(s) included in a substituent when the ring is substituted by the substituent are not counted in the number of the ring atoms. Unless specifically described, the same applies to the "ring atoms" described later; For instance, a pyridine ring has six ring atoms, a quinazoline ring has ten ring atoms, and a furan ring has five ring atoms. A hydrogen atom(s) and/or an atom(s) of a substituent which are bonded to carbon atoms of a pyridine ring and/or quinazoline ring are not counted in the ring atoms. When a fluorene ring is substituted by a substituent (e.g., a fluorene ring) (i.e., a spirofluorene ring is included), the number of atoms of the fluorene ring as the substituent is not counted in the number of the ring atoms of the fluorene ring.

Description of Each Substituent in Formula Herein

The aryl group (occasionally referred to as an aromatic hydrocarbon group) herein is exemplified by an aryl group $Sub_1$. The aryl group $Sub_1$ is at least one group selected from the group consisting of a phenyl group, biphenyl group, terphenyl group, naphthyl group, anthryl group, phenanthryl group, fluorenyl group, pyrenyl group, chrysenyl group, fluoranthenyl group, benz[a]anthryl group, benzo[c] phenanthryl group, triphenylenyl group, benzo[k]fluoranthenyl group, benzo[g]chrysenyl group, benzo[b]triphenylenyl group, picenyl group, and perylenyl group.

Herein, the aryl group $Sub_1$ preferably has 6 to 30 ring carbon atoms, more preferably 6 to 20 ring carbon atoms, further preferably 6 to 14 ring carbon atoms, further more preferably 6 to 12 ring carbon atoms. Among the aryl group $Sub_1$, a phenyl group, biphenyl group, naphthyl group, phenanthryl group, terphenyl group and fluorenyl group are preferable. A carbon atom in a position 9 of each of 1-fluorenyl group, 2-fluorenyl group, 3-fluorenyl group and 4-fluorenyl group is preferably substituted by a substituted or unsubstituted alkyl group $Sub_3$ or a substituted or unsubstituted aryl group $Sub_1$ described later herein.

The heteroaryl group (occasionally referred to as a heterocyclic group, heteroaromatic ring group or aromatic heterocyclic group) herein is exemplified by a heterocyclic group $Sub_2$. The heterocyclic group $Sub_2$ is a group containing, as a hetero atom(s), at least one atom selected from the group consisting of nitrogen, sulfur, oxygen, silicon, selenium atom and germanium atom. The heterocyclic group $Sub_2$ preferably contains, as a hetero atom(s), at least one atom selected from the group consisting of nitrogen, sulfur and oxygen.

The heterocyclic group $Sub_2$ herein are, for instance, at least one group selected from the group consisting of a pyridyl group, pyrimidinyl group, pyrazinyl group, pyridazinyl group, triazinyl group, quinolyl group, isoquinolinyl group, naphthyridinyl group, phthalazinyl group, quinoxalinyl group, quinazolinyl group, phenanthridinyl group, acridinyl group, phenanthrolinyl group, pyrrolyl group, imidazolyl group, pyrazolyl group, triazolyl group, tetrazolyl group, indolyl group, benzimidazolyl group, indazolyl group, imidazopyridinyl group, benzotriazolyl group, carbazolyl group, furyl group, thienyl group, oxazolyl group, thiazolyl group, isoxazolyl group, isothiazolyl group, oxadiazolyl group, thiadiazolyl group, benzofuranyl group, benzothienyl group, benzoxazolyl group, benzothiazolyl group, benzisoxazolyl group, benzisothiazolyl group, benzoxadiazolyl group, benzothiadiazolyl group, dibenzofuranyl group, dibenzothienyl group, piperidinyl group, pyrrolidinyl group, piperazinyl group, morpholyl group, phenazinyl group, phenothiazinyl group, and phenoxazinyl group.

Herein, the heterocyclic group $Sub_2$ preferably has 5 to 30 ring atoms, more preferably 5 to 20 ring atoms, further preferably 5 to 14 ring atoms. Among the above heterocyclic group $Sub_2$, a 1-dibenzofuranyl group, 2-dibenzofuranyl group, 3-dibenzofuranyl group, 4-dibenzofuranyl group, 1-dibenzothienyl group, 2-dibenzothienyl group, 3-dibenzothienyl group, 4-dibenzothienyl group, 1-carbazolyl group, 2-carbazolyl group, 3-carbazolyl group, 4-carbazolyl group, and 9-carbazolyl group are further more preferable. A nitrogen atom in position 9 of 1-carbazolyl group, 2-carbazolyl group, 3-carbazolyl group and 4-carbazolyl group is preferably substituted by the substituted or unsubstituted aryl group $Sub_1$ or the substituted or unsubstituted heterocyclic group $Sub_2$ described herein.

Herein, the heterocyclic group $Sub_2$ may be a group derived from any one of moieties represented by formulae (XY-1) to (XY-18) below.

[Formula 134]

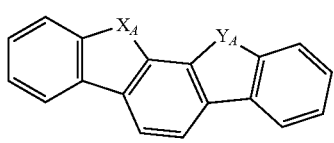
(XY-1)

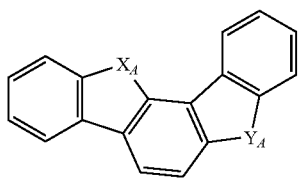
(XY-2)

-continued

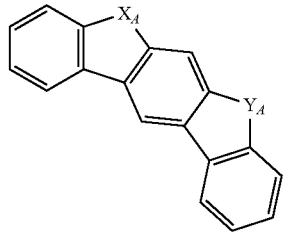
(XY-3)

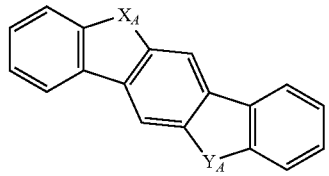
(XY-4)

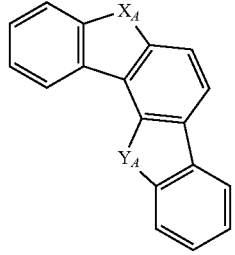
(XY-5)

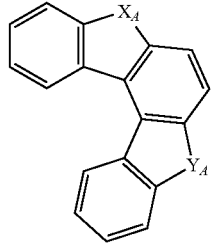
(XY-6)

[Formula 135]

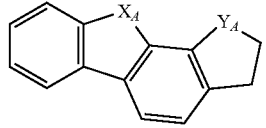
(XY-7)

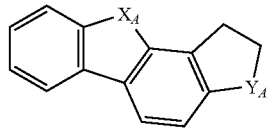
(XY-8)

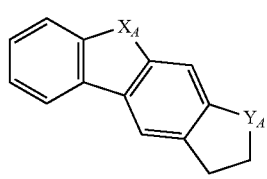
(XY-9)

(XY-10)
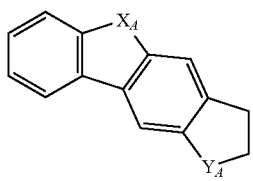

(XY-11)
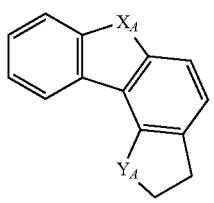

(XY-12)
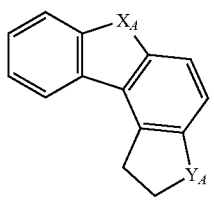

[Formula 136]

(XY-13)
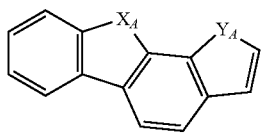

(XY-14)
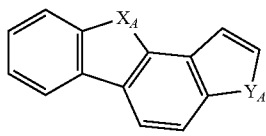

(XY-15)
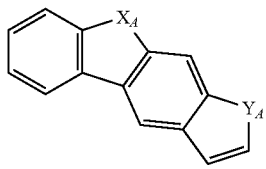

(XY-16)
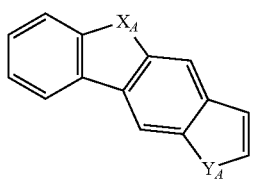

(XY-17)
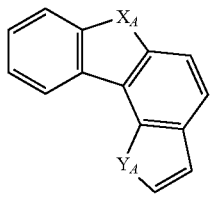

(XY-18)
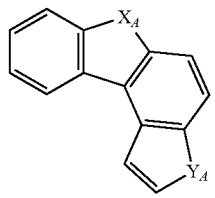

In the formulae (XY-1) to (XY-18), $X_A$ and $Y_A$ each independently represent a hetero atom, and preferably represent an oxygen atom, sulfur atom, selenium atom, silicon atom or germanium atom. Each of the moieties represented by the respective formulae (XY-1) to (XY-18) has a bond at any position to provide a heterocyclic group. The heterocyclic group may be substituted.

Herein, the heterocyclic group $Sub_2$ may be a group represented by one of formulae (XY-19) to (XY-22) below. Moreover, the position of the bond may be changed as needed

[Formula 137]

(XY-19)
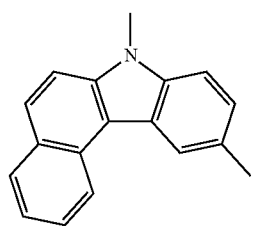

(XY-20)
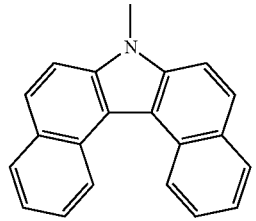

(XY-21)
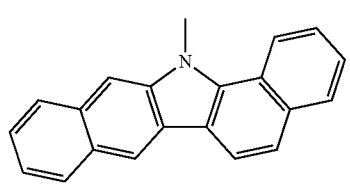

(XY-22)
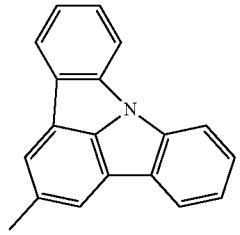

The alkyl group herein may be any one of a linear alkyl group, branched alkyl group and cyclic alkyl group.

The alkyl group herein is exemplified by an alkyl group $Sub_3$.

The linear alkyl group herein is exemplified by a linear alkyl group $Sub_{31}$.

The branched alkyl group herein is exemplified by a branched alkyl group $Sub_{32}$.

The cyclic alkyl group herein is exemplified by a cyclic alkyl group $Sub_{33}$.

For instance, the alkyl group $Sub_3$ is at least one group selected from the group consisting of the linear alkyl group $Sub_{31}$, branched alkyl group $Sub_{32}$, and cyclic alkyl group $Sub_{33}$.

The linear alkyl group $Sub_{31}$ or branched alkyl group $Sub_{32}$ is exemplified by at least one group selected from the group consisting of a methyl group, ethyl group, n-propyl group, isopropyl group, n-butyl group, s-butyl group, isobutyl group, t-butyl group, n-pentyl group, n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, neopentyl group, amyl group, isoamyl group, 1-methylpentyl group, 2-methylpentyl group, 1-pentylhexyl group, 1-butylpentyl group, 1-heptyloctyl group, and 3-methylpentyl group.

Herein, the linear alkyl group $Sub_{31}$ or branched alkyl group $Sub_{32}$ preferably has 1 to 30 carbon atoms, more preferably 1 to 20 carbon atoms, further preferably 1 to 10 carbon atoms, further more preferably 1 to 6 carbon atoms. The linear alkyl group $Sub_{31}$ or branched alkyl group $Sub_{32}$ is further more preferably a methyl group, ethyl group, propyl group, isopropyl group, n-butyl group, s-butyl group, isobutyl group, t-butyl group, n-pentyl group, n-hexyl group, amyl group, isoamyl group and neopentyl group.

Herein, the cyclic alkyl group $Sub_{33}$ is exemplified by a cycloalkyl group $Sub_{331}$.

The cycloalkyl group $Sub_{331}$ herein is exemplified by at least one group selected from the group consisting of a cyclopropyl group, cyclobutyl group, cyclopentyl group, cyclohexyl group, 4-methylcyclohexyl group, adamantyl group and norbornyl group. The cycloalkyl group $Sub_{331}$ preferably has 3 to 30 ring carbon atoms, more preferably 3 to 20 ring carbon atoms, further preferably 3 to 10 ring carbon atoms, further more preferably 5 to 8 ring carbon atoms. Among the cycloalkyl group $Sub_{331}$, a cyclopentyl group and a cyclohexyl group are further more preferable.

Herein, an alkyl halide group is exemplified by an alkyl halide group $Sub_4$. The alkyl halide group $Sub_4$ is provided by substituting the alkyl group $Sub_3$ with at least one halogen atom, preferably at least one fluorine atom.

Herein, the alkyl halide group $Sub_4$ is exemplified by at least one group selected from the group consisting of a fluoromethyl group, difluoromethyl group, trifluoromethyl group, fluoroethyl group, trifluoromethylmethyl group, trifluoroethyl group, and pentafluoroethyl group.

Herein, a substituted silyl group is exemplified by a substituted silyl group $Sub_5$. The substituted silyl group $Sub_5$ is exemplified by at least one group selected from the group consisting of an alkylsilyl group $Sub_{51}$ and an arylsilyl group $Sub_{52}$.

Herein, the alkylsilyl group $Sub_{51}$ is exemplified by a trialkylsilyl group $Sub_{511}$ having the above-described alkyl group $Sub_3$.

The trialkylsilyl group $Sub_{511}$ is exemplified by at least one group selected from the group consisting of a trimethylsilyl group, triethylsilyl group, tri-n-butylsilyl group, tri-n-octylsilyl group, triisobutylsilyl group, dimethylethylsilyl group, dimethylisopropylsilyl group, dimethyl-n-propylsilyl group, dimethyl-n-butylsilyl group, dimethyl-t-butylsilyl group, diethylisopropylsilyl group, vinyl dimethylsilyl group, propyldimethylsilyl group, and triisopropylsilyl group. Three alkyl groups $Sub_3$ in the trialkylsilyl group $Sub_{511}$ may be mutually the same or different.

Herein, the arylsilyl group $Sub_{52}$ is exemplified by at least one group selected from the group consisting of a dialkylarylsilyl group $Sub_{521}$, alkyldiarylsilyl group $Sub_{522}$ and triarylsilyl group $Sub_{523}$.

The dialkylarylsilyl group $Sub_{521}$ is exemplified by a dialkylarylsilyl group including two alkyl groups $Sub_3$ and one aryl group $Sub_1$. The dialkylarylsilyl group $Sub_{521}$ preferably has 8 to 30 carbon atoms.

The alkyldiarylsilyl group $Sub_{522}$ is exemplified by an alkyldiarylsilyl group including one alkyl group $Sub_3$ and two aryl groups $Sub_1$. The alkyldiarylsilyl group $Sub_{522}$ preferably has 13 to 30 carbon atoms.

The triarylsilyl group $Sub_{523}$ is exemplified by a triarylsilyl group including three aryl groups $Sub_1$. The triarylsilyl group $Sub_{523}$ preferably has 18 to 30 carbon atoms.

Herein, a substituted or unsubstituted alkyl sulfonyl group is exemplified by an alkyl sulfonyl group $Sub_6$. The alkyl sulfonyl group $Sub_6$ is represented by $-SO_2R_w$. $R_w$ in $-SO_2R_w$ represents a substituted or unsubstituted alkyl group $Sub_3$ described above.

Herein, an aralkyl group (occasionally referred to as an arylalkyl group) is exemplified by an aralkyl group $Sub_7$. An aryl group in the aralkyl group $Sub_7$ includes, for instance, at least one of the above-described aryl group $Sub_1$ and the above-described heteroaryl group $Sub_2$.

The aralkyl group $Sub_7$ herein is preferably a group having the aryl group $Sub_1$ and is represented by $-Z_3-Z_4$. $Z_3$ is exemplified by an alkylene group corresponding to the above alkyl group $Sub_3$. $Z_4$ is exemplified by the above aryl group $Sub_1$. In this aralkyl group $Sub_7$, an aryl moiety has 6 to 30 carbon atoms (preferably 6 to 20 carbon atoms, more preferably 6 to 12 carbon atoms) and an alkyl moiety has 1 to 30 carbon atoms (preferably 1 to 20 carbon atoms, more preferably 1 to 10 carbon atoms, further preferably 1 to 6 carbon atoms). The aralkyl group $Sub_7$ is exemplified by at least one group selected from the group consisting of a benzyl group, 2-phenylpropane-2-yl group, 1-phenylethyl group, 2-phenylethyl group, 1-phenylisopropyl group, 2-phenylisopropyl group, phenyl-t-butyl group, α-naphthylmethyl group, 1-α-naphthylethyl group, 2-α-naphthylethyl group, 1-α-naphthylisopropyl group, 2-α-naphthylisopropyl group, β-naphthylmethyl group, 1-β-naphthylethyl group, 2-β-naphthylethyl group, 1-β-naphthyl isopropyl group, and 2-β-naphthylisopropyl group.

The alkoxy group herein is exemplified by an alkoxy group $Sub_8$. The alkoxy group $Sub_8$ is represented by $-OZ_1$. $Z_1$ is exemplified by the above alkyl group $Sub_3$. The alkoxy group $Sub_8$ is exemplified by at least one group selected from the group consisting of a methoxy group, ethoxy group, propoxy group, butoxy group, pentyloxy group and hexyloxy group. The alkoxy group $Sub_8$ preferably has 1 to 30 carbon atoms, more preferably 1 to 20 carbon atoms.

Herein, an alkoxy halide group is exemplified by an alkoxy halide group $Sub_9$. The alkoxy halide group $Sub_9$ is provided by substituting the alkoxy group $Sub_8$ with at least one halogen atom, preferably at least one fluorine atom.

Herein, an aryloxy group (occasionally referred to as an arylalkoxy group) is exemplified by an arylalkoxy group $Sub_{10}$. An aryl group in the arylalkoxy group $Sub_{10}$ includes at least one of the aryl group $Sub_1$ and the heteroaryl group $Sub_2$.

The arylalkoxy group $Sub_{10}$ herein is represented by $-OZ_2$. $Z_2$ is exemplified by the aryl group $Sub_1$ or the heteroaryl group $Sub_2$. The arylalkoxy group $Sub_{10}$ preferably has 6 to 30 ring carbon atoms, more preferably 6 to 20 ring carbon atoms. The arylalkoxy group $Sub_{10}$ is exemplified by a phenoxy group.

Herein, a substituted amino group is exemplified by a substituted amino group $Sub_{11}$. The substituted amino group $Sub_{11}$ is exemplified by at least one group selected from the group consisting of an arylamino group $Sub_{111}$ and an alkylamino group $Sub_{112}$.

The arylamino group $Sub_{111}$ is represented by $-NHR_{V1}$ or $-N(R_{V1})_2$. $R_{V1}$ is exemplified by the aryl group $Sub_1$. Two $R_{V1}$ in $-N(R_{V1})_2$ are mutually the same or different.

The alkylamino group $Sub_{112}$ is represented by $-NHR_{V2}$ or $-N(R_{V2})_2$. $R_{V2}$ is exemplified by the alkyl group $Sub_3$. Two $R_{V2}$ in $-N(R_{V2})_2$ are mutually the same or different.

Herein, the alkenyl group is exemplified by an alkenyl group $Sub_{12}$. The alkenyl group $Sub_{12}$, which is linear or branched, is exemplified by at least one group selected from the group consisting of a vinyl group, propenyl group, butenyl group, oleyl group, eicosapentaenyl group, docosahexaenyl group, styryl group, 2,2-diphenylvinyl group, 1,2,2-triphenylvinyl group, and 2-phenyl-2-propenyl group.

The alkynyl group herein is exemplified by an alkynyl group $Sub_{13}$. The alkynyl group $Sub_{13}$ may be linear or branched and is at least one group selected from the group consisting of an ethynyl group, a propynyl group and a 2-phenylethynyl group.

The alkylthio group herein is exemplified by an alkylthio group $Sub_{14}$.

The alkylthio group $Sub_{14}$ is represented by $-SR_{v3}$. $R_{v3}$ is exemplified by the alkyl group $Sub_3$. The alkylthio group $Sub_{14}$ preferably has 1 to 30 carbon atoms, more preferably 1 to 20 carbon atoms.

The arylthio group herein is exemplified by an arylthio group $Sub_{15}$.

The arylthio group $Sub_{15}$ is represented by $-SR_{V4}$. $R_{V4}$ is exemplified by the aryl group $Sub_1$. The arylthio group $Sub_{15}$ preferably has 6 to 30 ring carbon atoms, more preferably 6 to 20 ring carbon atoms.

Herein, examples of the halogen atom include a fluorine atom, a chlorine atom, a bromine atom and an iodine atom, among which a fluorine atom is preferable.

A substituted phosphino group herein is exemplified by a substituted phosphino group $Sub_{16}$. The substituted phosphino group $Sub_{16}$ is exemplified by a phenyl phosphanyl group.

An arylcarbonyl group herein is exemplified by an arylcarbonyl group $Sub_{17}$. The arylcarbonyl group $Sub_{17}$ is represented by $-COY'$. Y' is exemplified by the aryl group $Sub_1$. Herein, the arylcarbonyl group $Sub_{17}$ is exemplified by at least one group selected from the group consisting of a phenyl carbonyl group, diphenyl carbonyl group, naphthyl carbonyl group, and triphenyl carbonyl group.

An acyl group herein is exemplified by an acyl group $Sub_{18}$. The acyl group $Sub_{18}$ is represented by $-COR'$. R' is exemplified by the alkyl group $Sub_3$. The acyl group $Sub_{15}$ herein is exemplified by at least one group selected from the group consisting of an acetyl group and a propionyl group.

A substituted phosphoryl group herein is exemplified by a substituted phosphoryl group $Sub_{19}$. The substituted phosphoryl group $Sub_{19}$ is represented by a formula (P) below.

[Formula 138]

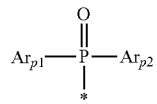

(P)

In the formula (P), $Ar_{P1}$ anti $Ar_{P2}$ are any one substituent selected from the group consisting of the above alkyl group $Sub_3$ and the above aryl group $Sub_1$.

An eater group herein is exemplified by an eater group $Sub_{20}$. The ester group $Sub_{20}$ is exemplified by an alkyl ester group.

An alkyl aster group herein is exemplified by an alkyl ester group $Sub_{201}$. The alkyl ester group $Sub_{201}$ is represented by $-C(=O)OR^E$. $R^E$ is exemplified by a substituted or unsubstituted alkyl group $Sub_3$ described above.

A siloxanyl group herein is exemplified by a siloxanyl group $Sub_{21}$. The siloxanyl group $Sub_{21}$ is a silicon compound group through an ether bond. The siloxanyl group $Sub_{21}$ is exemplified by a trimethylsiloxanyl group.

A carbamoyl group herein is represented by $-CONH_2$.

A substituted carbamoyl group herein is exemplified by a carbamoyl group $Sub_{22}$. The carbamoyl group $Sub_{22}$ is represented by $-CONH-Ar^C$ or $-CONH-R^C$. $Ar^C$ is exemplified by at least one group selected from the group consisting of a substituted or unsubstituted aryl group $Sub_1$ (preferably 5 to 10 ring carbon atoms) and a substituted or unsubstituted heteroaryl group $Sub_2$ (preferably 5 to 14 ring atoms). $Ar^C$ may be a group formed by bonding the aryl group $Sub_1$ and the heteroaryl group $Sub_2$.

$R^C$ is exemplified by a substituted or unsubstituted alkyl group $Sub_3$ described above (preferably having 1 to 6 carbon atoms).

Herein, "carbon atoms forming a ring (ring carbon atoms)" mean carbon atoms forming a saturated ring, unsaturated ring, or aromatic ring. "Atoms forming a ring (ring atoms)" mean carbon atoms and hetero atoms forming a ring including a saturated ring, unsaturated ring, or aromatic ring.

Herein, a hydrogen atom includes isotope having different numbers of neutrons, specifically, protium, deuterium and tritium.

Hereinafter, an alkyl group $Sub_3$ means at least one group of a linear alkyl group $Sub_{31}$, a branched alkyl group $Sub_{32}$, and a cyclic alkyl group $Sub_{33}$ described in "Description of Each Substituent."

Similarly, a substituted silyl group $Sub_5$ means at least one group of an alkylsilyl group $Sub_{51}$ and an arylsilyl group $Sub_{52}$.

Similarly, a substituted amino group $Sub_{11}$ means at least one group of an arylamino group $Sub_{111}$ and an alkylamino group $Sub_{112}$.

Herein, a substituent for a "substituted or unsubstituted" group is exemplified by a substituent $R_{F1}$. The substituent $R_{F1}$ is at least one group selected from the group consisting of an aryl group $Sub_1$, heteroaryl group $Sub_2$, alkyl group $Sub_3$, alkyl halide group $Sub_4$, substituted silyl group $Sub_5$, alkylsulfonyl group $Sub_6$, aralkyl group $Sub_7$, alkoxy group $Sub_8$, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, arylcarbonyl group $Sub_{17}$, acyl group $Sub_{18}$, substituted phosphoryl group $Sub_{19}$, ester group $Sub_{20}$, siloxanyl group $Sub_{21}$, carbamoyl group $Sub_{22}$, unsubstituted amino group, unsubstituted silyl group, halogen atom, cyano group, hydroxy group, nitro group, and carboxy group.

Herein, the substituent $R_{F1}$ for a "substituted or unsubstituted" group may be a diaryl boron group ($Ar_{B1}Ar_{B2}B$—). $Ar_{B1}$ and $Ar_{B2}$ are exemplified by the above-described aryl group $Sub_1$. $Ar_{B1}$ and $Ar_{B2}$ in $Ar_{B1}Ar_{B2}B$— are the same or different.

Specific examples and preferable examples of the substituent $R_{F1}$ are the same as those of the substituents described in "Description of Each Substituent" (e.g., an aryl group $Sub_1$, heteroaryl group $Sub_2$, alkyl group $Sub_3$, alkyl halide group $Sub_4$, substituted silyl group $Sub_5$, alkylsulfonyl group $Sub_6$, aralkyl group $Sub_7$, alkoxy group $Sub_8$, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, arylcarbonyl group $Sub_{17}$, acyl group $Sub_{18}$, substituted phosphoryl group $Sub_{19}$, ester group $Sub_{20}$, siloxanyl group $Sub_{21}$, and carbamoyl group $Sub_{22}$).

The substituent $R_{F1}$ for a "substituted or unsubstituted" group may be further substituted by at least one group (hereinafter, also referred to as a substitutent $R_{F2}$) selected from the group consisting of an aryl group $Sub_1$, heteroaryl group $Sub_2$, alkyl group $Sub_3$, alkyl halide group $Sub_4$, substituted silyl group $Sub_5$, alkylsulfonyl group $Sub_6$, aralkyl group $Sub_7$, alkoxy group $Sub_8$, alkoxy halide group $Sub_9$, arylalkoxy group $Sub_{10}$, substituted amino group $Sub_{11}$, alkenyl group $Sub_{12}$, alkynyl group $Sub_{13}$, alkylthio group $Sub_{14}$, arylthio group $Sub_{15}$, substituted phosphino group $Sub_{16}$, arylcarbonyl group $Sub_{17}$, acyl group $Sub_{18}$, substituted phosphoryl group $Sub_{19}$, ester group $Sub_{20}$, siloxanyl group $Sub_{21}$, carbamoyl group $Sub_{22}$, unsubstituted amino group, unsubstituted silyl group, halogen atom, cyano group, hydroxy group, nitro group, and carboxy group. Moreover, a plurality of substituents $R_{F2}$ may be bonded to each other to form a ring.

"Unsubstituted" for a "substituted or unsubstituted" group means that a group is not substituted by the above-described substituent $R_{F1}$ but bonded with a hydrogen atom.

Herein, "XX to YY carbon atoms" in the description of "substituted or unsubstituted ZZ group having XX to YY carbon atoms" represent carbon atoms of an unsubstituted ZZ group and do not include carbon atoms of the substituent $R_{F1}$ of the substituted ZZ group.

Herein, "XX to YY atoms" in the description of "substituted or unsubstituted ZZ group having XX to YY atoms" represent atoms of an unsubstituted ZZ group and do not include atoms of the substituent $R_{F1}$ of the substituted ZZ group.

The same description as the above applies to "substituted or unsubstituted" in compounds or moieties thereof described herein.

Herein, when the substituents are bonded to each other to form a ring, the ring is structured to be a saturated ring, an unsaturated ring, an aromatic hydrocarbon ring or a hetero ring.

Herein, examples of the aromatic hydrocarbon group in the linking group include a divalent or multivalent group obtained by eliminating one or more atoms from the above monovalent aryl group $Sub_1$.

Herein, examples of the heterocyclic group in the linking group include a divalent or multivalent group obtained by eliminating one or more atoms from the above monovalent heteroaryl group $Sub_2$.

EXAMPLES

Example(s) of the invention will be described below. However, the invention is not limited to Example(s).

Compounds

Compounds used for manufacturing organic EL devices in Examples 1 to 16 and compounds synthesized in Synthesis Examples 1 to 16 are shown below.

Compounds 1 to 16 are each the compound M3 represented by the formula (100).

The compounds 3 to 4 and the compounds 14 to 15 each also fall under the compound represented by the formula (201).

The compound 9 also falls under the compound represented by the formula (300).

The compound 10 also falls under the compound represented by the formula (202).

The compound 11 also falls under the compound represented by the formula (203).

[Formula 139]

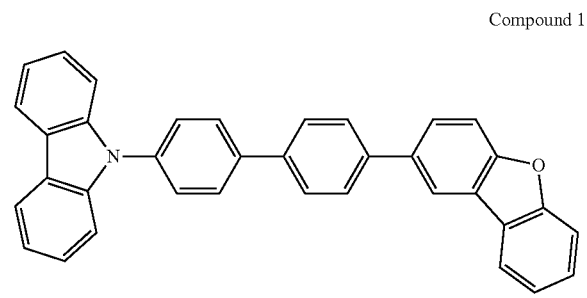

Compound 1

Compound 2

[Formula 140]
Compound 3
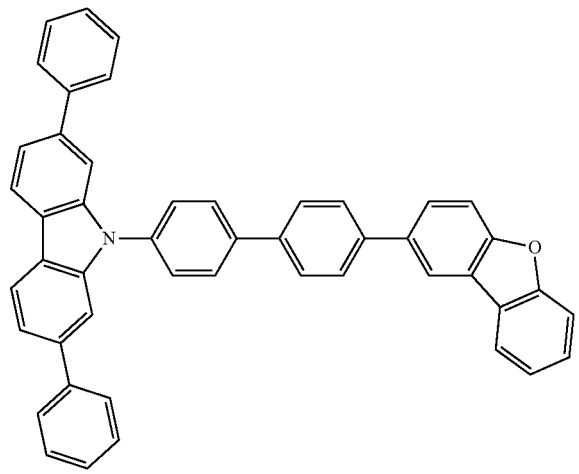
Compound 4
[Formula 141]
Compound 5
Compound 6
[Formula 142]
Compound 7
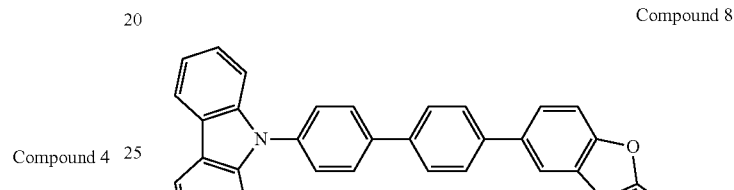
[Formula 143]
Compound 8
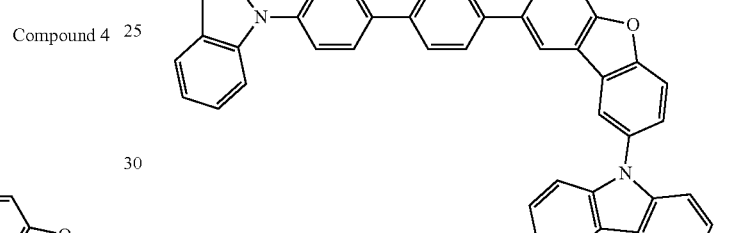
Compound 9
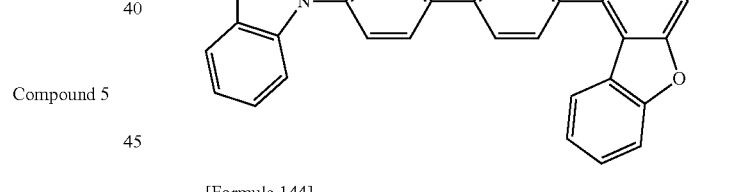
[Formula 144]
Compound 10
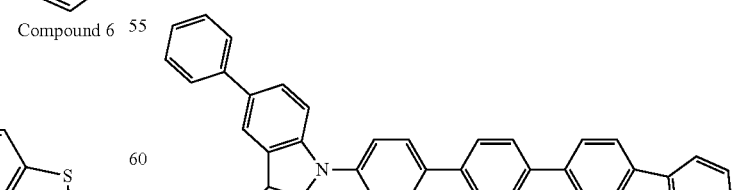

Compound 11
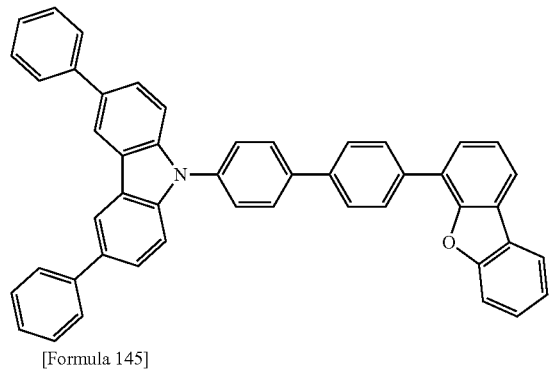
[Formula 145]
Compound 12
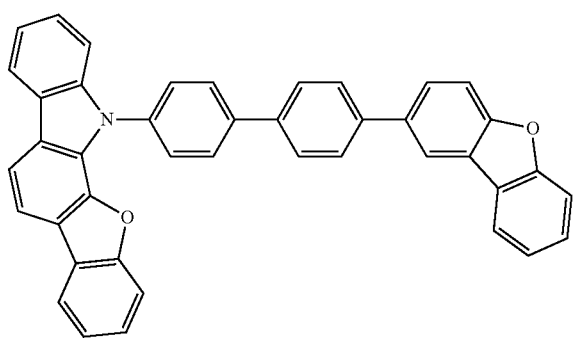
Compound 13
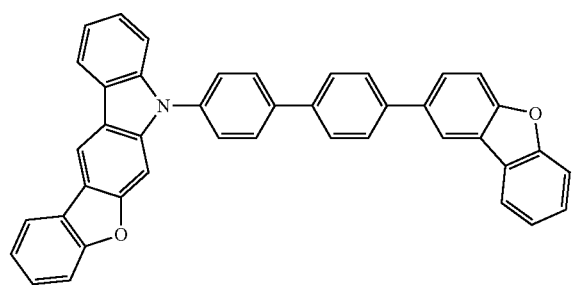
Compound 14
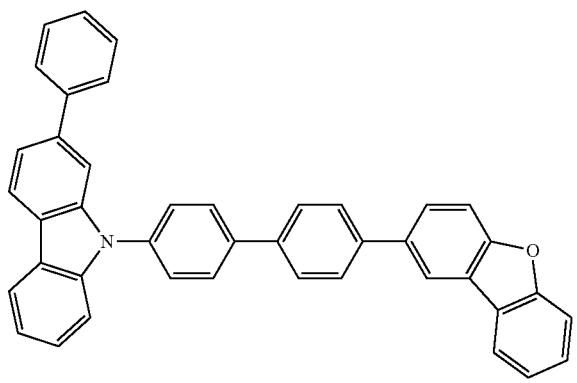
Compound 15
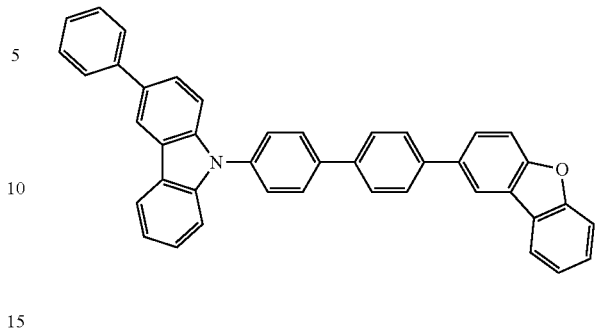
Compound 16
Comparative compounds Ref-1 and Ref-2 used for manufacturing organic EL devices in Comparatives 1 to 6 are shown below.
[Formula 146]
Ref-1
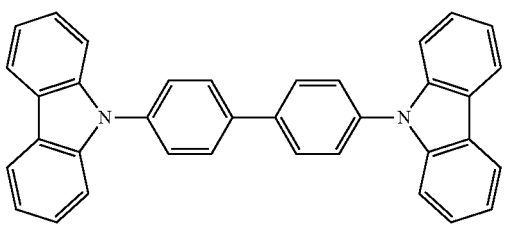
Ref-2
Other compounds used for manufacturing the organic EL devices in Examples 1 to 16 and Comparatives 1 to 6 are shown below.

[Formula 147]
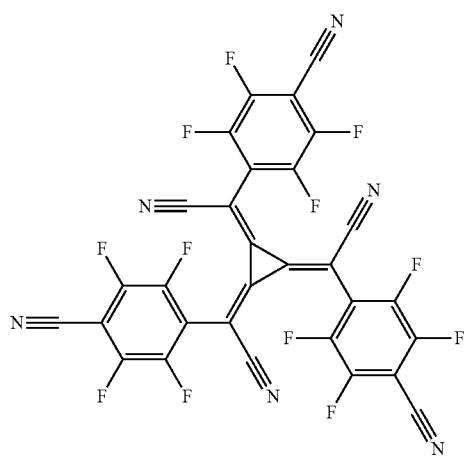
HA
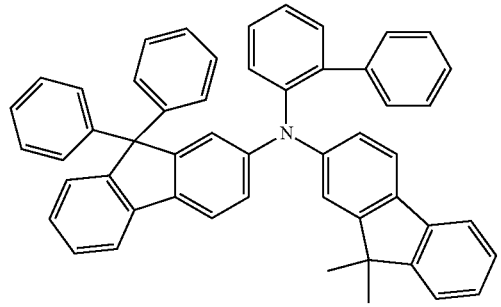
HT
[Formula 148]
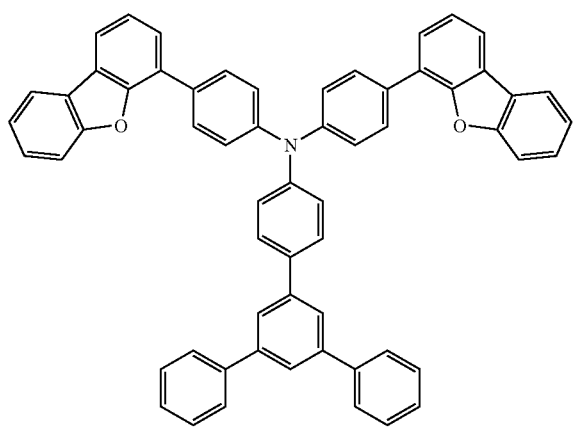
EBL
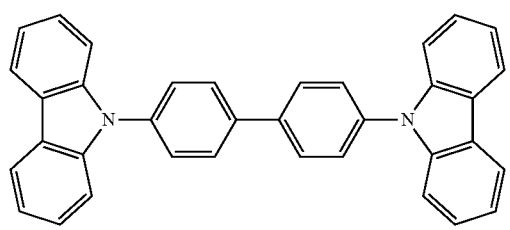
CBP
[Formula 149]
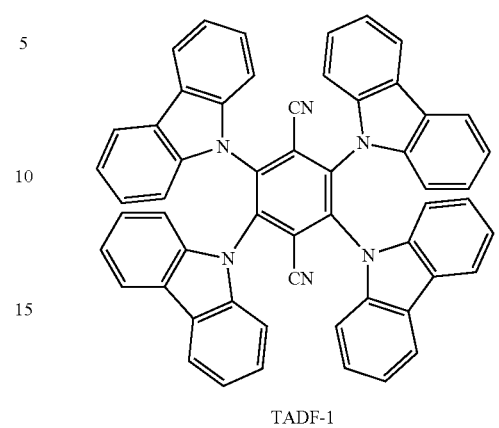
TADF-1
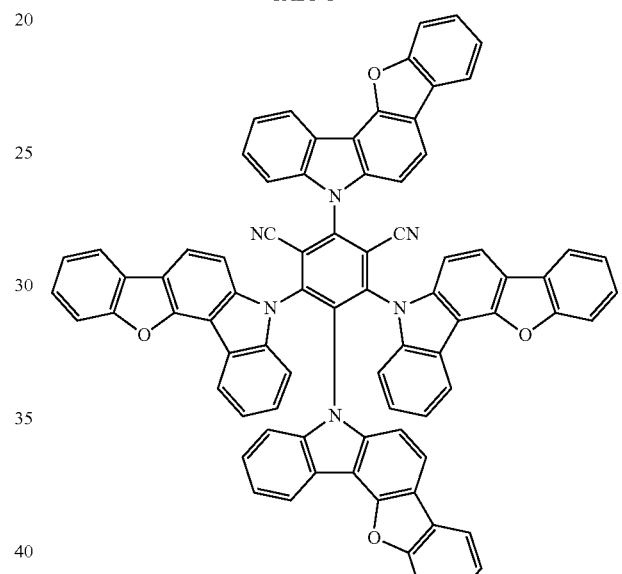
TADF-2
[Formula 150]
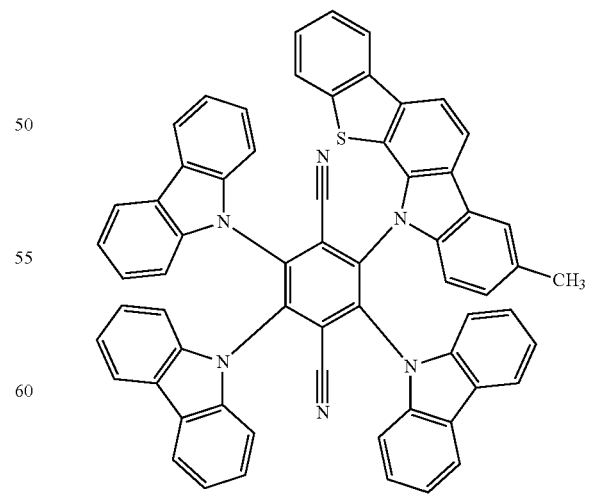
TADF-3

[Formula 151]

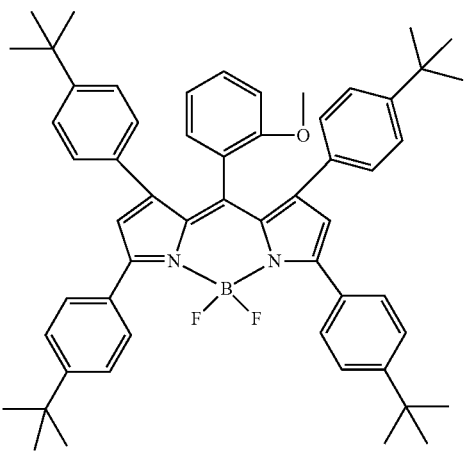

RD

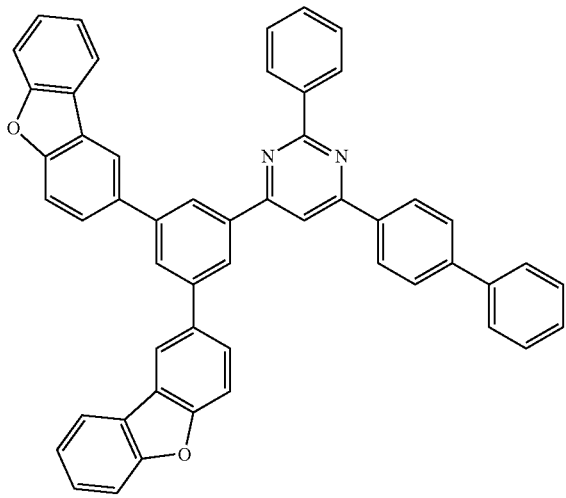

HBL

[Formula 152]

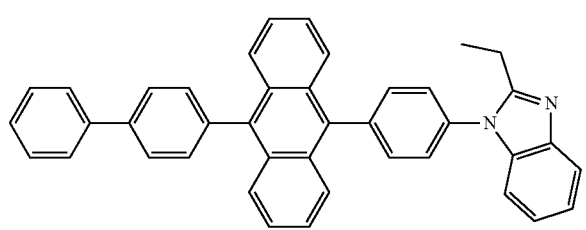

ET

Manufacturing 1 of Organic EL Device

Example 1

A glass substrate (size: 25 mm×75 mm×1.1 mm thick, manufactured by Geomatec Co., Ltd) having an ITO transparent electrode (anode) was ultrasonic-cleaned in isopropyl alcohol for five minutes, and then UV/ozone-cleaned for one minute A film of ITO was 130 nm thick.

After the glass substrate having the transparent electrode line was cleaned, the glass substrate was mounted on a substrate holder of a vacuum evaporation apparatus. Firstly, a compound HT and a compound HA ware co-deposited on a surface of the glass substrate where the transparent electrode line was provided in a manner to cover the transparent electrode, thereby forming a 10-nm-thick hole injecting layer. The concentrations of the compound HT and the compound HA in the hole injecting layer were 97 mass % and 3 mass %, respectively.

Next the compound HT was vapor-deposited on the hole injecting layer to form a 200-nm-thick hole transporting layer.

Next, a compound EBL was vapor-deposited on the hobs transporting layer to form a 10-nm-thick electron blocking layer.

Next a compound RD (the fluorescent compound M1), a compound TADF-1 (the delayed fluorescent compound M2) and the compound 1 (the compound M3) were co-deposited on the electron blocking layer to form a 25-nm-thick emitting layer. The concentrations of the compound RD, the compound TADF-1, and the compound 1 in the knitting layer were 1 mas %, 25 mass %, and 74 mass %, respectively.

Next, a compound HBL was vapor-deposited on the emitting layer to form a 10-nm-thick hole blocking layer.

Next, a compound ET was vapor-deposited on the hole blocking layer to form a 30-nm-thick electron transporting layer.

Lithium fluoride (LiF) was vapor-deposited on the electron transporting layer to form a 1-nm-thick electron injectable electrode (cathode).

Subsequently, metal aluminum (Al) was vapor-deposited on the electron injectable electrode to form an 80-nm-thick metal Al cathode.

A device arrangement of the organic EL device of Example 1 is roughly shown as follows.

ITO(130)/HT:HA(10,97%:3%)/HT(200)/EBL(10)/compound 1: TADF-1:RD(25,74%:25%:1%)/HBL(10)/ET(30)/LiF(1)/Al(80)

Numerals in parentheses represent a film thickness (unit: nm).

The numerals (97%:3%) represented by percentage in the same parentheses each indicate a ratio (mass %) between the compound HT and the compound HA in the hole injecting layer, and the numerals (74%:25%:1%) represented by percentage in the same parentheses each indicate a ratio (mass %) between the compound M3, the compound M2, and the compound M1 in the emitting layer. Similar notations apply to the description below.

Comparatives 1 to 2

The organic EL devices in Comparatives 1 to 2 were manufactured in the same manner as in Example 1 except that compounds shown in a column of the compound M3 in Table 1 were used in place of the compound 1 in Example 1.

Evaluation 1

The organic EL devices manufactured in Example 1 and Comparatives 1 to 2 were evaluated as follows. The measurement results are shown in Table 1.

It should be noted that Ref-1 and Ref-2 used in the emitting layer of Comparatives 1 to 2 are shown in the column of the compound M3 for convenience of explanation.

Drive Voltage

A voltage (unit: V) was measured when current was applied between the anode and the cathode such that a current density was 10 mA/cm$^2$.

External Quantum Efficiency EQE

Voltage was applied on the organic EL devices such that a current density was 10 mA/cm$^2$, where spectral radiance spectrum was measured by a spectroradiometer (CS-2000 manufactured by Konica Minolta, Inc.). The external quantum efficiency EQE (unit: %) was calculated based on the obtained spectral-radiance spectra, assuming that the spectra was provided under a Lambertian radiation.

Lifetime LT95

Voltage was applied on the organic EL devices such that a current density was 50 mA/cm$^2$, a time (unit: hr) elapsed before a luminance intensity was reduced to 95% of the initial luminance intensity was measured using a spectroradiometer CS-200 (manufactured by Konica Minolta, Inc.).

Main Peak Wavelength λp

Voltage was applied on the organic EL devices such that a current density of each of the organic EL devices was 10 mA/cm$^2$, where spectral radiance spectrum was measured by a spectroradiometer CS-2000 (manufactured by Konica Minolta, Inc.). The main peak wavelength $\lambda_p$ (unit: nm) was calculated based on the obtained spectral-radiance spectra.

the compound HA in the hole injecting layer were 97 mass % and 3 mass %, respectively.

Next, the compound HT was vapor-deposited on the hole injecting layer to form a 200-nm-thick hole transporting layer.

Next, a compound CBP was vapor-deposited on the hole transporting layer to form a 10-nm-thick electron blocking layer.

Next, the compound RD (the fluorescent compound M1), the compound TADF-1 (the delayed fluorescent compound M2) and the compound 1 (the compound M3) were co-deposited on the electron blocking layer to form a 25-nm-thick emitting layer. The concentrations of the compound RD, the compound TADF-1, and the compound 1 in the emitting layer were 1 mass %, 25 mass %, and 74 mass %, respectively.

Next, the compound HBL was vapor-deposited on the emitting layer to form a 10-nm-thick hole blocking layer.

Next, the compound ET was vapor-deposited on the hole blocking layer to form a 30-nm-thick electron transporting layer.

Lithium fluoride (LiF) was vapor-deposited on the electron transporting layer to form a 1-nm-thick electron injectable electrode (cathode).

TABLE 1

| | Emitting layer | | | | Evaluation | | |
|---|---|---|---|---|---|---|---|
| | Compound M3 | Compound M2 | Compound M1 | Electron blocking layer Compound | λp [nm] | Drive voltage [V] | EQE [%] | LT95 [h] |
| Example 1 | Compound 1 | TADF-1 | RD | EBL | 621 | 4.33 | 16.6 | 82 |
| Comparative 1 | Ref-1 | TADF-1 | RD | EBL | 621 | 4.41 | 15.6 | 52 |
| Comparative 2 | Ref-2 | TADF-1 | RD | EBL | 621 | 5.18 | 14.5 | 48 |

Explanation of Table 1

λp represents a main peak wavelength [nm] of the organic EL devices. The same applies to Tables 2 and 3.

As shown in Table 1, the organic EL device in Example 1 exhibited a larger value of LT95 than the organic EL device in Comparative 1 for which the compound Ref-1 was used in place of the compound 1 (the compound M3), and the organic EL device in Comparative 2 for which the compound Ref-2 was used in place of the compound 1 (the compound M3). Accordingly, the organic EL device in Example 1 emitted light with a long lifetime.

Further, the organic EL device in Example 1 exhibited a lower drive voltage and a higher external quantum efficiency EQE than the organic EL devices in Comparatives 1 and 2.

Manufacturing 2 of Organic EL Device

Example 2

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for one minute. A film of ITO was 130 nm thick.

After the glass substrate having the transparent electrode line was cleaned, the glass substrate was mounted on a substrate holder of a vacuum evaporation apparatus. Firstly, the compound HT and the compound HA were co-deposited on a surface of the glass substrate where the transparent electrode line was provided in a manner to cover the transparent electrode, thereby forming a 10-nm-thick hole injecting layer. The concentrations of the compound HT and Subsequently, metal aluminum (Al) was vapor-deposited on the electron injectable electrode to form an 80-nm-thick metal Al cathode.

A device arrangement of the organic EL device of Example 2 is roughly shown as follows.

ITO(130)/HT:HA(10,97%:3%)/HT(200)/CBP(10)/compound 1: TADF-1:RD (25,74%:25%: 1%)/HBL(10)/ET(30)/LiF(1)/Al(80)

Numerals in parentheses represent a film thickness (unit: nm).

Examples 3 to 4

The organic EL devices in Examples 3 to 4 were manufactured in the same manner as in Example 2 except that compounds shown in a column of the compound M3 in Table 2 were used in place of the compound 1 in Example 2.

Comparatives 3 to 4

The organic EL devices in Comparatives 3 to 4 were manufactured in the same manner as in Example 2 except that the compounds shown in the column of the compound M3 in Table 2 were used in place of the compound 1 in Example 2.

Evaluation 2

The organic EL devices manufactured in Examples 2 to 4 and Comparatives 3 to 4 were measured for the main peak wavelength λp and the lifetime LT95 in the same manner as in Example 1. The results are shown in Table 2.

It should be noted that Ref-1 and Ref-2 used in the emitting layer of Comparatives 3 to 4 are shown in the column of the compound M3 for convenience of explanation.

TABLE 2

| | Emitting layer | | | Evaluation | |
|---|---|---|---|---|---|
| | Compound M3 | Compound M2 | Compound M1 | Electron blocking layer Compound | λp [nm] | LT95 [h] |
| Example 2 | Compound 1 | TADF-1 | RD | CBP | 621 | 121 |
| Example 3 | Compound 2 | TADF-1 | RD | CBP | 621 | 145 |
| Example 4 | Compound 3 | TADF-1 | RD | CBP | 621 | 148 |
| Comparative 3 | Ref-1 | TADF-1 | RD | CBP | 621 | 80 |
| Comparative 4 | Ref-2 | TADF-1 | RD | CBP | 621 | 78 |

As shown in Table 2, the organic EL devices in Examples 2 to 4 exhibited a larger value of LT95 than the organic EL device in Comparative 3 for which the compound Ref-1 was used in place of the compounds 1 to 3 (the compound M3), and the organic EL device in Comparative 4 for which the compound Ref-2 was used in place of the compounds 1 to 3 (the compound M3). Accordingly, the organic EL devices in Examples 2 to 4 emitted light with a long lifetime.

Manufacturing 3 of Organic EL Device

Example 5

A glass substrate (size: 25 mm×75 mm×1.1 mm thick, manufactured by Geomatec Co., Ltd.) having an ITO transparent electrode (anode) was ultrasonic-cleaned in isopropyl alcohol for five minutes, and then UV/ozone-cleaned for one minute. A film of ITO was 130 nm thick.

After the glass substrate having the transparent electrode line was cleaned, the glass substrate was mounted on a substrate holder of a vacuum evaporation apparatus. Firstly, the compound HT and the compound HA were co-deposited on a surface of the glass substrate where the transparent electrode line was provided in a manner to cover the transparent electrode, thereby forming a 10-nm-thick hole injecting layer. The concentrations of the compound HT and the compound HA in the hole injecting layer were 97 mass % and 3 mass %, respectively.

Next, the compound HT was vapor-deposited on the hole injecting layer to form a 200-nm-thick hole transporting layer.

Next, the compound EBL was vapor-deposited on the hole transporting layer to form a 10-nm-thick electron blocking layer.

Next, the compound RD (the fluorescent compound M1), a compound TADF-2 (the delayed fluorescent compound M2) and the compound 1 (the compound M3) were co-deposited on the electron blocking layer to form a 25-nm-thick emitting layer. The concentrations of the compound RD, the compound TADF-2, and the compound 1 in the emitting layer were 1 mass %, 25 mass %, and 74 mass %, respectively.

Next, the compound HBL was vapor-deposited on the emitting layer to form a 10-nm-thick hole blocking layer.

Next, the compound ET was vapor-deposited on the hole blocking layer to form a 30-nm-thick electron transporting layer.

Lithium fluoride (LiF) was vapor-deposited on the electron transporting layer to form a 1-nm-thick electron injectable electrode (cathode).

Subsequently, metal aluminum (Al) was vapor-deposited on the electron injectable electrode to form an 80-nm-thick metal Al cathode.

A device arrangement of the organic EL device of Example 5 is roughly shown as follows.

ITO(130)/HT:HA(10,97%:3%)/HT(200)/EBL(10)/compound 1: TADF-2: RD (25,74%:25%: 1%)/HBL(10)/ET(30)/LiF(1)/Al(80)

Numerals in parentheses represent a film thickness (unit: nm).

Evaluation 3

The organic EL device manufactured in Example 5 was measured for the main peak wavelength λp, the drive voltage, the external quantum efficiency EQE and the lifetime LT95 in the same manner as in Example 1. The results are shown in Table 3.

TABLE 3

| | Emitting layer | | | Evaluation | | | |
|---|---|---|---|---|---|---|---|
| | Compound M3 | Compound M2 | Compound M1 | Electron blocking layer Compound | λp [nm] | Drive voltage [V] | EQE [%] | LT95 [h] |
| Example 5 | Compound 1 | TADF-2 | RD | EBL | 619 | 4.13 | 15.7 | 75 |

As shown in Table 3, the organic EL device in Example 5 exhibited a large value of LT95. Accordingly, the organic EL device in Example 5 emitted light with a long lifetime.

Manufacturing 4 of Organic EL Device

Example 6

The organic EL device in Example 6 was manufactured in the same manner as in Example 1 except that compounds shown in a column of the compound M2 in Table 4 were used in place of the compound M2 in Example 1.

A device arrangement of the organic EL device of Example 6 is roughly shown as follows.

ITO(130)/HT:HA(10,97%:3%)/HT(200)/EBL(10)/compound 1: TADF-3:RD(25,74%:25%:1%)/HBL(10)/ET(30)/LiF(1)/Al(80)

Examples 7 to 16

The organic EL devices in Examples 7 to 16 were manufactured in the same manner as in Example 6 except that the compounds shown in the column of the compound M3 in Table 4 were used in place of the compound 1 in Example 6.

Comparatives 5 to 6

The organic EL devices in Comparatives 5 to 6 were manufactured in the same manner as in Example 6 except that the compounds shown in the column of the compound M3 in Table 4 were used in place of the compound 1 in Example 6.

Evaluation 4

The organic EL devices manufactured in Examples 6 to 16 and Comparatives 5 to 6 were measured for the main peak wavelength λp, the drive voltage, the external quantum efficiency EQE and the lifetime LT95 in the same manner as in Example 1. The results are shown in Table 4.

It should be noted that Ref-1 and Ref-2 used in the emitting layer of Comparatives 5 to 6 are shown in the column of the compound M3 for convenience of explanation.

0.05 or less at the excitation wavelength to eliminate the contribution of self-absorption. In order to prevent quenching due to oxygen, the sample solution was frozen and degassed and then sealed in a cell with a lid under an argon atmosphere to obtain an oxygen-free sample solution saturated with argon.

The fluorescence spectrum of the above sample solution was measured with a spectrofluorometer FP-8600 (manufactured by JASCO Corporation), and the fluorescence spectrum of a 9,10-diphenylanthracene ethanol solution was measured under the same conditions. Using the fluorescence area intensities of both spectra, the total fluorescence quantum yield was calculated by an equation (1) in Morris et al. J. Phys. Chem. 80 (1976) 969.

Prompt Emission was observed immediately when the excited state was achieved by exciting the compound TADF-1 with a pulse beam (i.e., a beam emitted from a pulse laser) having a wavelength to be absorbed by the compound TADF-1, and Delay Emission was observed not immediately when the excited state was achieved but after the excited state was achieved. The delayed fluorescence in Examples means that an amount of Delay Emission is 5% or more with respect to an amount of Prompt Emission. Specifically, provided that the amount of Prompt emission is denoted by $X_P$ and the amount of Delay emission is denoted by $X_D$, the delayed fluorescence means that a value of $X_D/X_P$ is 0.05 or more.

An amount of Prompt emission, an amount of Delay emission and a ratio between the amounts thereof can be

TABLE 4

| | Emitting layer | | | | Evaluation | | |
|---|---|---|---|---|---|---|---|
| | Compound M3 | Compound M2 | Compound M1 | Electron blocking layer Compound | λp [nm] | Drive voltage [V] | EQE [%] | LT95 [h] |
| Example 6 | Compound 1 | TADF-3 | RD | EBL | 621 | 4.35 | 16.8 | 185 |
| Example 7 | Compound 4 | TADF-3 | RD | EBL | 621 | 4.30 | 16.0 | 154 |
| Example 8 | Compound 5 | TADF-3 | RD | EBL | 621 | 4.41 | 16.6 | 179 |
| Example 9 | Compound 6 | TADF-3 | RD | EBL | 621 | 4.43 | 16.5 | 185 |
| Example 10 | Compound 7 | TADF-3 | RD | EBL | 621 | 4.39 | 16.0 | 188 |
| Example 11 | Compound 9 | TADF-3 | RD | EBL | 621 | 4.41 | 16.6 | 178 |
| Example 12 | Compound 12 | TADF-3 | RD | EBL | 621 | 4.12 | 16.2 | 195 |
| Example 13 | Compound 13 | TADF-3 | RD | EBL | 621 | 4.02 | 16.0 | 195 |
| Example 14 | Compound 14 | TADF-3 | RD | EBL | 621 | 4.40 | 16.2 | 180 |
| Example 15 | Compound 15 | TADF-3 | RD | EBL | 621 | 4.33 | 16.2 | 161 |
| Example 16 | Compound 16 | TADF-3 | RD | EBL | 621 | 4.36 | 16.1 | 170 |
| Comparative 5 | Ref-1 | TADF-3 | RD | EBL | 621 | 4.44 | 16.0 | 130 |
| Comparative 6 | Ref-2 | TADF-3 | RD | EBL | 621 | 4.82 | 14.7 | 118 |

As shown in Table 4, the organic EL devices in Examples 6 to 16 exhibited a greatly improved LT95 as compared with the organic EL devices in Comparatives 5 to 6. Further, the organic EL devices in Examples 6 to 16 exhibited a greatly reduced drive voltage and a greatly improved external quantum efficiency EQE as compared with the organic EL device in Comparative 6.

Evaluation of Compounds

Values of physical properties of the compounds used in the emitting layer of respective Examples and the compounds synthesized in the later-described Synthesis Examples were measured by the following method.
Thermally Activated Delayed Fluorescence
Delayed Fluorescence of Compound TADF-1

Delayed fluorescence properties were checked by measuring transient photoluminescence (PL) using a device shown in FIG. 2. The compound TADF-1 was dissolved in toluene to prepare a dilute solution with an absorbance of obtained according to the method as described in "Nature 492, 234-238, 2012" (Reference Document 1). The amount of Prompt emission and the amount of Delay emission may be calculated using a device different from one described in Reference Document 1 or one shown in FIG. 2.

It was confirmed that the amount of Delay Emission was 5% or more with respect to the amount of Prompt Emission in the compound TADF-1. Specifically, it was found that the value of $X_D/X_P$ was 0.05 or more in the compound TADF-1.

Delayed Fluorescence of Compounds TADF-2 and TADF-3

The compound TADF-2 was checked in terms of delayed fluorescence in the same manner as above except that the compound TADF-2 was replaced by the compound TADF-1. It was found that the value of $X_D/X_P$ was 0.05 or more in the compound TADF-2.

The compound TADF-3 was checked in terms of delayed fluorescence in the same manner as above except that the compound TADF-3 was replaced by the compound TADF-1. It was found that the value of $X_D/X_P$ was 0.05 or more in the compound TADF-3.

Singlet Energy $S_1$

Singlet energy $S_1$ of each of the compounds 1 to 16, TADF-1, TADF-2, TADF-3, RD and Ref-2 was measured according to the above-described solution method. The measurement results are shown in Tables 5 to 7.

Energy Gap at 77 [K]

An energy gap $T_{77K}$ at 77 [K] of each of the compounds TADF-1, TADF-2 and TADF-3 was measured by the above method to calculate $\Delta ST$. The results are shown in Table 6.

Main Peak Wavelength λ of Compound

A main peak wavelength λ of each of the compounds TADF-1, TADF-2, TADF-3 and RD was measured by the following method. The measurement results are shown in Tables 6 to 7.

A 5-μmol/L toluene solution of each of the compounds (measurement target) was prepared and put in a quartz cell. An emission spectrum (ordinate axis: luminous intensity, abscissa axis: wavelength) of each of the samples was measured at a normal temperature (300K). In Examples, the emission spectrum was measured using a spectrophotometer manufactured by Hitachi, Ltd. (device name: F-7000). It should be noted that the machine for measuring the emission spectrum is not limited to the machine used herein. A peak wavelength of the emission spectrum exhibiting the maximum luminous intensity was defined as a main peak wavelength λ.

TABLE 5

| | | $S_1$[eV] |
|---|---|---|
| Compound M3 | Compound 1 | 3.50 |
| | Compound 2 | 3.57 |
| | Compound 3 | 3.36 |
| | Compound 4 | 3.03 |
| | Compound 5 | 3.46 |
| | Compound 6 | 3.49 |
| | Compound 7 | 3.44 |
| | Compound 9 | 3.45 |
| | Compound 12 | 3.41 |
| | Compound 13 | 3.38 |
| | Compound 14 | 3.40 |
| | Compound 15 | 3.42 |
| | Compound 16 | 3.41 |
| Comparative compound | Ref-1 | 3.52 |
| | Ref-2 | 3.55 |

TABLE 6

| | | $S_1$ [eV] | AST [eV] | λ [nm] |
|---|---|---|---|---|
| Compound M2 | TADF-1 | 2.37 | <0.01 | 531 |
| | TADF-2 | 2.44 | <0.01 | 536 |
| | TADF-3 | 2.32 | <0.01 | 545 |

Explanation of Table 6
"<0.01" represents $\Delta ST$ of less than 0.01 eV.

TABLE 7

| | | $S_1$ [eV] | λ [nm] |
|---|---|---|---|
| Compound M1 | RD | 2.02 | 609 |

Synthesis of Compounds

Synthesis Example 1: Synthesis of Compound 1

[Formula 153]

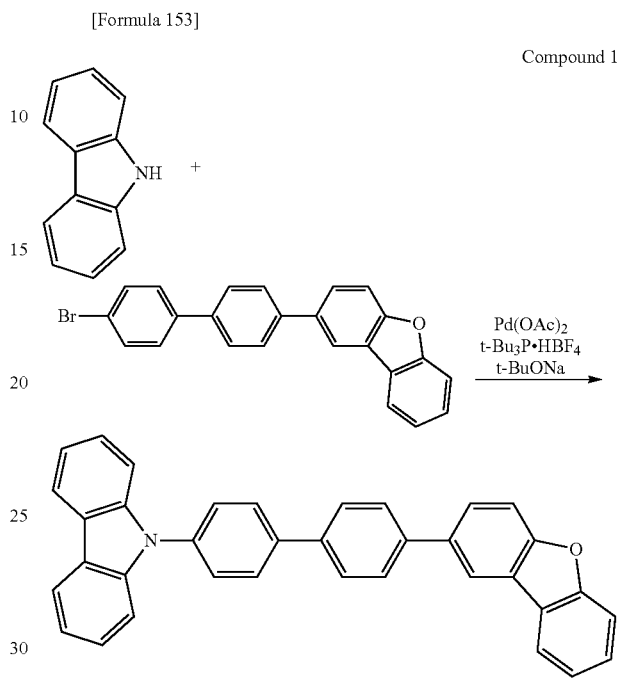

Compound 1

Under nitrogen atmosphere, xylene (50 mL) was added into a mixture of carbazole (1.84 g, 11.0 mmol), 2-(4'-bromo-[1,1'-biphenyl]-4-yl)dibenzo[b,d]furan (4.39 g, 11.0 mmol), palladium acetate (49.4 mg, 0.22 mmol), tri-tert-butylphosphonium tetrafluoroborate (t-Bu$_3$P—HBF$_4$) (122.7 mg, 0.44 mmol) and sodium tert-butoxide (t-BuONa) (2.11 g, 22.0 mmol), and stirred at 130 degrees C. for eight hours. After the reaction, a solid was filtered and recrystallized with toluene to obtain the compound 1 (3.31 g, a yield of 62%). The obtained compound was identified as the compound 1 by analysis according to LC-MS (Liquid chromatography mass spectrometry).

Synthesis Example 2: Synthesis of Compound 2

[Formula 154]

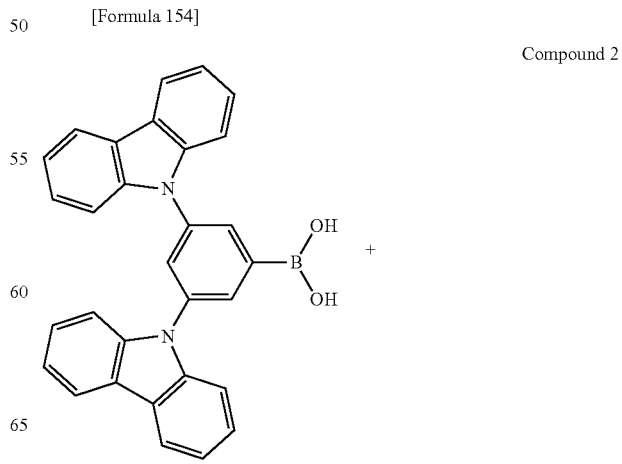

Compound 2

-continued

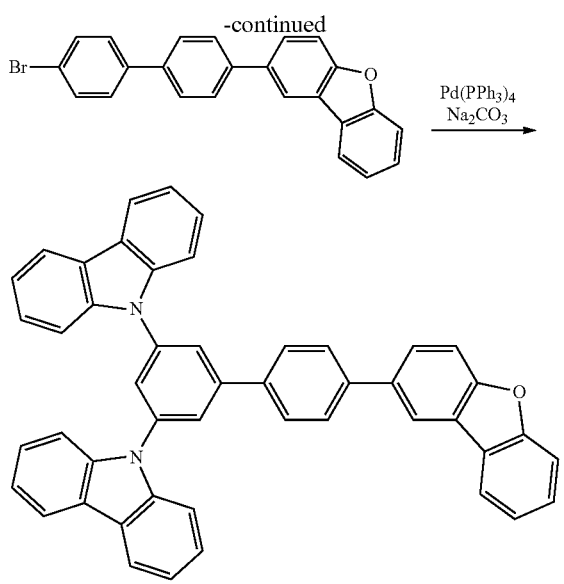

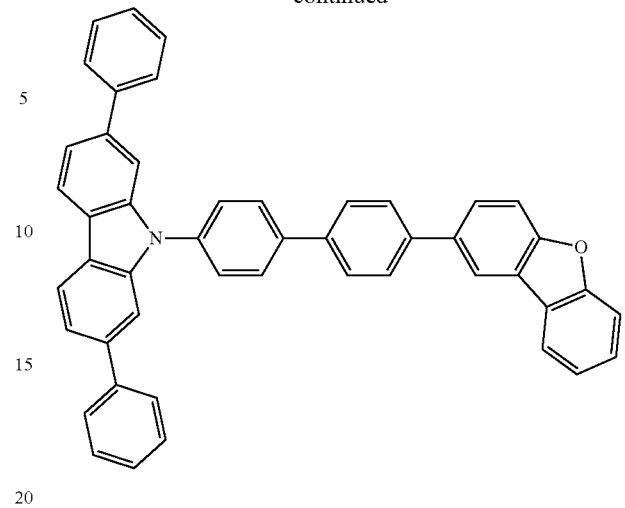

Under nitrogen atmosphere, 1,2-dimethoxyethane (70 mL) and water (35 mL) were added into a mixture of (3,5-di(9H-carbazole-9-yl)phenyl) boronic acid (4.98 g, 11.0 mmol), 2-(4'-bromo-[1,1'-biphenyl]-4-yl)dibenzo[b,d]furan (4.39 g, 11.0 mmol), tetrakistriphenylphosphine palladium (635.6 mg, 0.55 mmol) and sodium carbonate (2.33 g, 22.0 mmol) and stirred at 85 degrees C. for eight hours. After the reaction, a solid was filtrated and recrystallized with toluene to obtain the compound 2 (5.01 g, a yield of 70%). The obtained compound was identified as the compound 2 by analysis according to LC-MS.

Synthesis Example 3: Synthesis of Compound 3

[Formula 155]

Compound 3

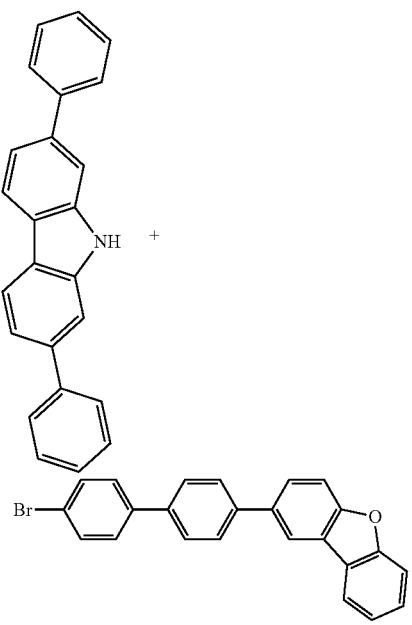

The compound 3 was obtained in the same manner as in Synthesis Example 1 except for using 2,7-diphenyl-9H-carbazole in place of carbazole in Synthesis of Compound 1 of Synthesis Example 1. A yield was 59%. The obtained compound was identified as the compound 3 by analysis according to LC-MS.

Synthesis Example 4: Synthesis of Compound 4

[Formula 156]

Compound 4

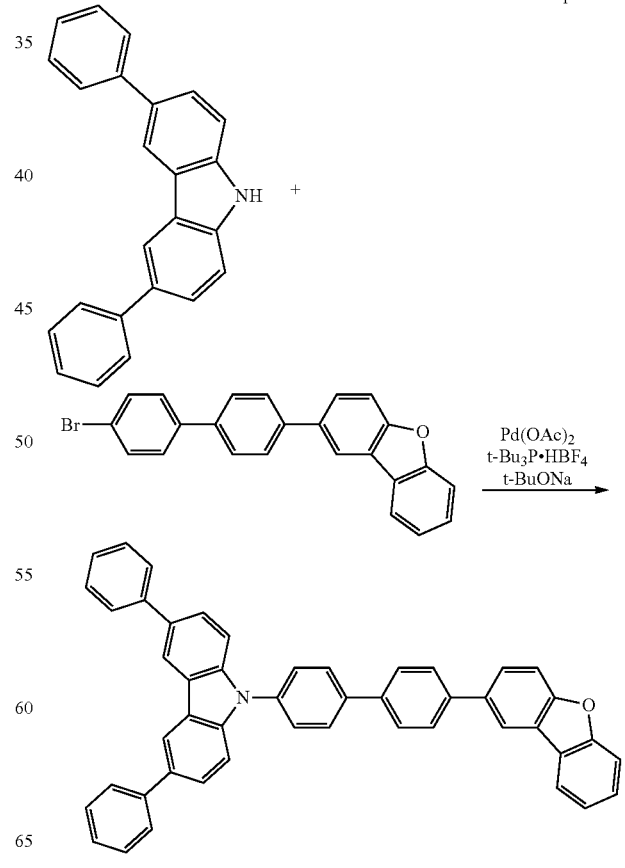

The compound 4 was obtained in the same manner as in Synthesis Example 4 except for using 3,6-diphenyl-9H-carbazole in place of carbazole in Synthesis of Compound 1 of Synthesis Example 1. A yield was 65%. The obtained compound was identified as the compound 4 by analysis according to LC-MS.

Synthesis Example 5: Synthesis of Compound 5

[Formula 157]

Compound 5

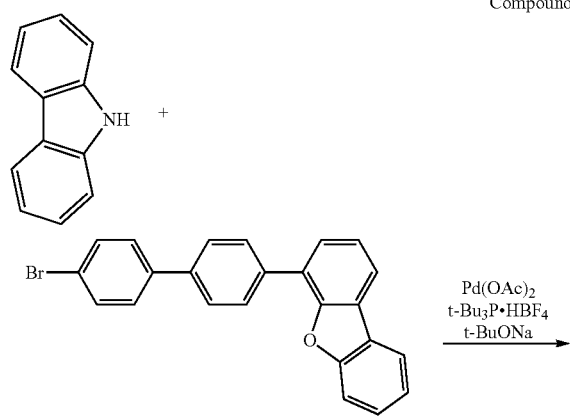

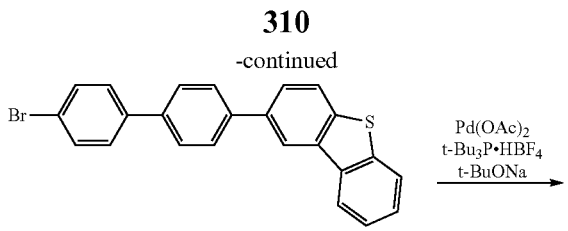

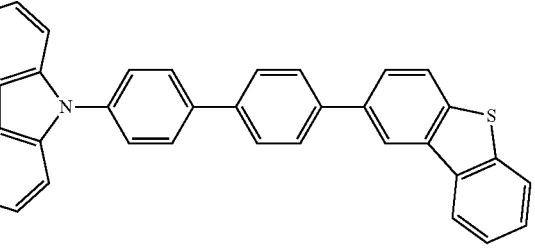

The compound 5 was obtained in the same manner as in Synthesis Example 1 except for using 4-(4'-bromo-[1,1'-biphenyl]-4-yl)dibenzo[b,d]furan in place of 2-(4'-bromo-[1,1'-biphenyl]-4-yl)dibenzo[b,d]furan in Synthesis of Compound 1 of Synthesis Example 1. A yield was 52%. The obtained compound was identified as the compound 5 by analysis according to LC-MS.

Synthesis Example 6: Synthesis of Compound 6

[Formula 158]

Compound 6

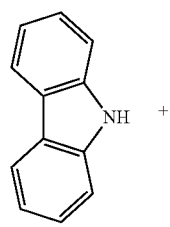

The compound 6 was obtained in the same manner as in Synthesis Example 1 except for using 2-(4'-bromo-[1,1'-biphenyl]-4-yl)dibenzo[b,d]thiophene in place of 2-(4'-bromo-[1,1'-biphenyl]-4-yl)dibenzo[b,d]furan in Synthesis of Compound 1 of Synthesis Example 1. A yield was 65%. The obtained compound was identified as the compound 6 by analysis according to LC-MS.

Synthesis Example 7: Synthesis of Compound 7

[Formula 159]

Compound 7

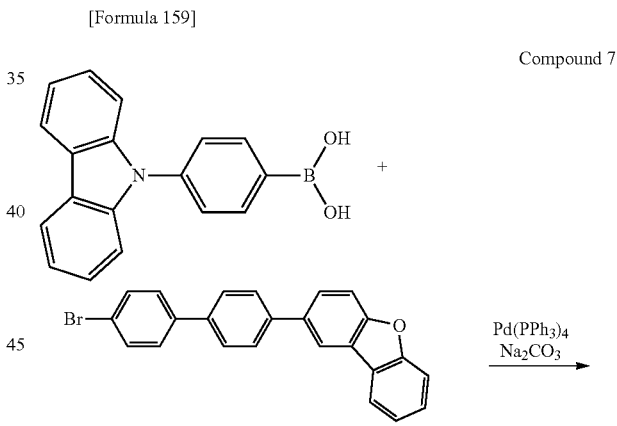

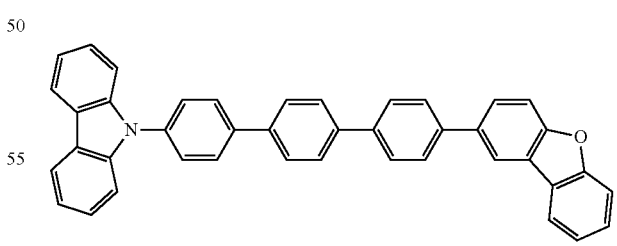

The compound 7 was obtained in the same manner as in Synthesis Example 2 except for using (4-(9H-carbazole-9-yl)phenyl) boronic acid in place of (3,5-di(9H-carbazole-9-yl)phenyl) boronic acid in Synthesis of Compound 2 of Synthesis Example 2. A yield was 43%. The obtained compound was identified as the compound 7 by analysis according to LC-MS.

Synthesis Example 8: Synthesis of Compound 8

[Formula 160]

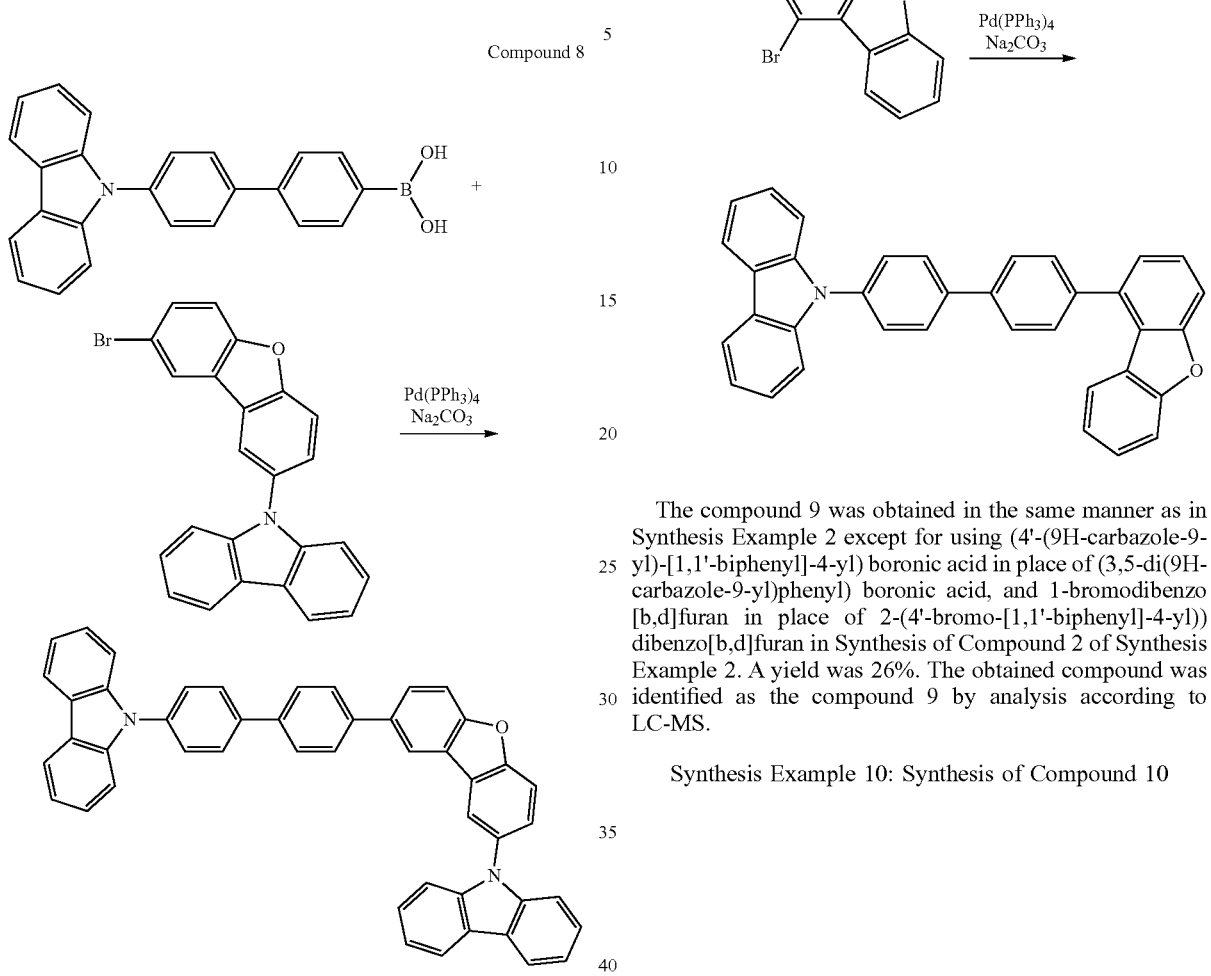

The compound 8 was obtained in the same manner as in Synthesis Example 2 except for using (4'-(9H-carbazole-9-yl)-[1,1'-biphenyl]-4-yl) boronic acid in place of (3,5-di(9H-carbazole-9-yl)phenyl) boronic acid, and 9-(8-bromodibenzo[b,d]furan-2-yl)-9H-carbazole in place of 2-(4'-bromo-[1,1'-biphenyl]-4-yl))dibenzo[b,d]furan in Synthesis of Compound 2 of Synthesis Example 2. A yield was 57%. The obtained compound was identified as the compound 8 by analysis according to LC-MS.

Synthesis Example 9: Synthesis of Compound 9

[Formula 161]

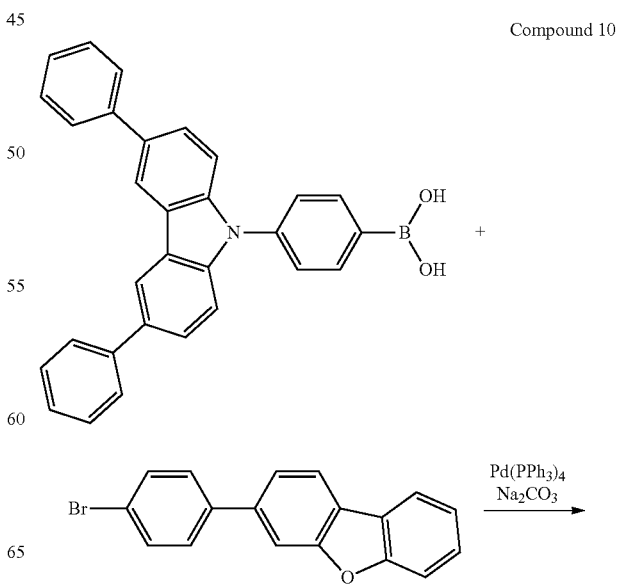

The compound 9 was obtained in the same manner as in Synthesis Example 2 except for using (4'-(9H-carbazole-9-yl)-[1,1'-biphenyl]-4-yl) boronic acid in place of (3,5-di(9H-carbazole-9-yl)phenyl) boronic acid, and 1-bromodibenzo[b,d]furan in place of 2-(4'-bromo-[1,1'-biphenyl]-4-yl)) dibenzo[b,d]furan in Synthesis of Compound 2 of Synthesis Example 2. A yield was 26%. The obtained compound was identified as the compound 9 by analysis according to LC-MS.

Synthesis Example 10: Synthesis of Compound 10

[Formula 162]

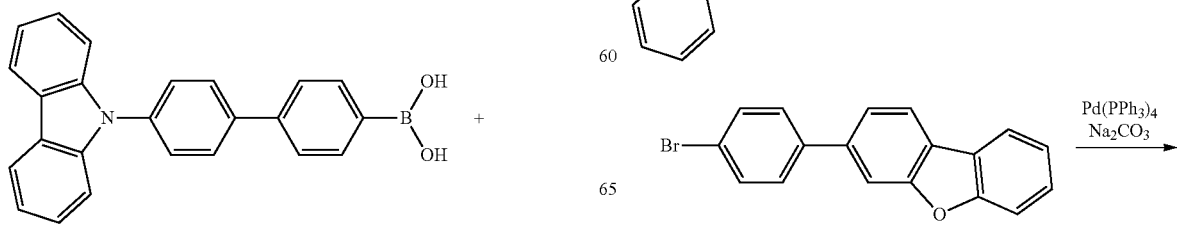

-continued

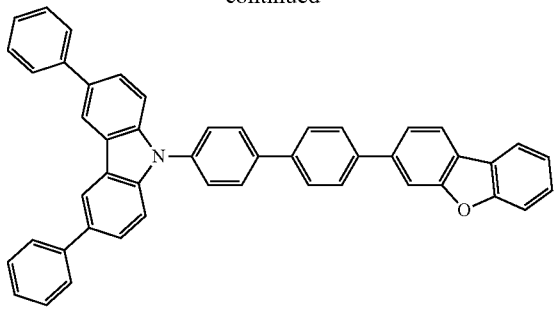

The compound 10 was obtained in the same manner as in Synthesis Example 2 except for using (4-(3,6-diphenyl-9H-carbazole-9H-9-yl)phenyl) boronic acid in place of (3,5-di(9H-carbazole-9-yl)phenyl) boronic acid, and 3-(4-bromophenyl)dibenzo[b,d]furan in place of 2-(4'-bromo-[1,1'-biphenyl]-4-yl))dibenzo[b,d]furan in Synthesis of Compound 2 of Synthesis Example 2. A yield was 46%. The obtained compound was identified as the compound 10 by analysis according to LC-MS.

Synthesis Example 11: Synthesis of Compound 11

[Formula 163]

Compound 11

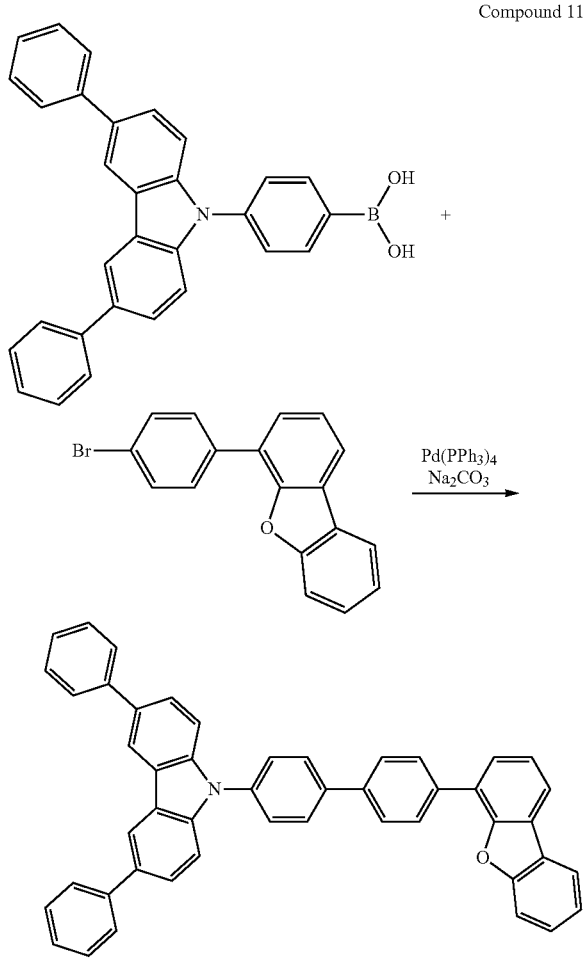

The compound 11 was obtained in the same manner as in Synthesis Example 2 except for using (4-(3,6-diphenyl-9H-carbazole-9-yl)phenyl) boronic acid in place of (3,5-di(9H-carbazole-9-yl)phenyl) boronic acid, and 4-(4-bromophenyl)dibenzo[b,d]furan in place of 2-(4'-bromo-[1,1'-biphenyl]-4-yl))dibenzo[b,d]furan in Synthesis of Compound 2 of Synthesis Example 2. A yield was 55%. The obtained compound was identified as the compound 11 by analysis according to LC-MS.

Synthesis Example 12: Synthesis of Compound 12

[Formula 164]

Compound 12

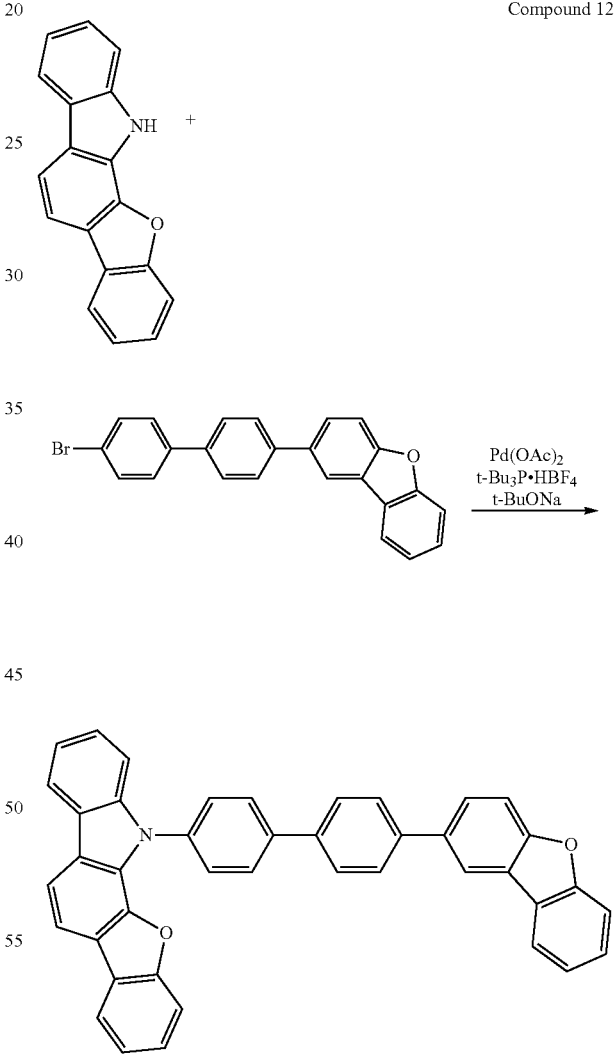

The compound 12 was obtained in the same manner as in Synthesis Example 1 except for using 12H-benzofuro[2,3-a]carbazole in place of carbazole in Synthesis of Compound 1 of Synthesis Example 1. A yield was 61%. The obtained compound was identified as the compound 12 by analysis according to LC-MS.

Synthesis Example 13: Synthesis of Compound 13

[Formula 165]

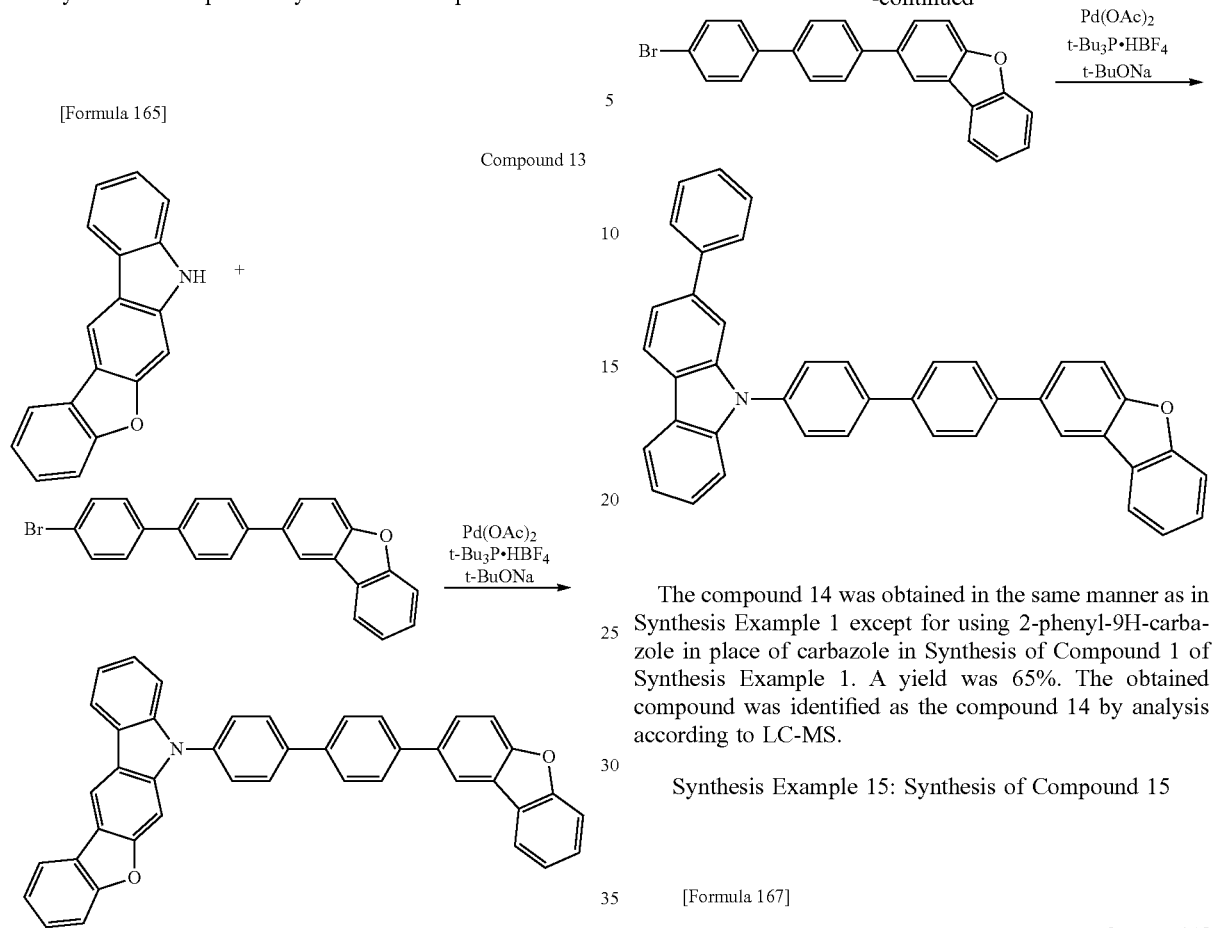

The compound 13 was obtained in the same manner as in Synthesis Example 1 except for using 7H-benzofuro[2,3-b]carbazole in place of carbazole in Synthesis of Compound 1 of Synthesis Example 1. A yield was 59%. The obtained compound was identified as the compound 13 by analysis according to LC-MS.

Synthesis Example 14: Synthesis of Compound 14

[Formula 166]

Compound 14

The compound 14 was obtained in the same manner as in Synthesis Example 1 except for using 2-phenyl-9H-carbazole in place of carbazole in Synthesis of Compound 1 of Synthesis Example 1. A yield was 65%. The obtained compound was identified as the compound 14 by analysis according to LC-MS.

Synthesis Example 15: Synthesis of Compound 15

[Formula 167]

Compound 15

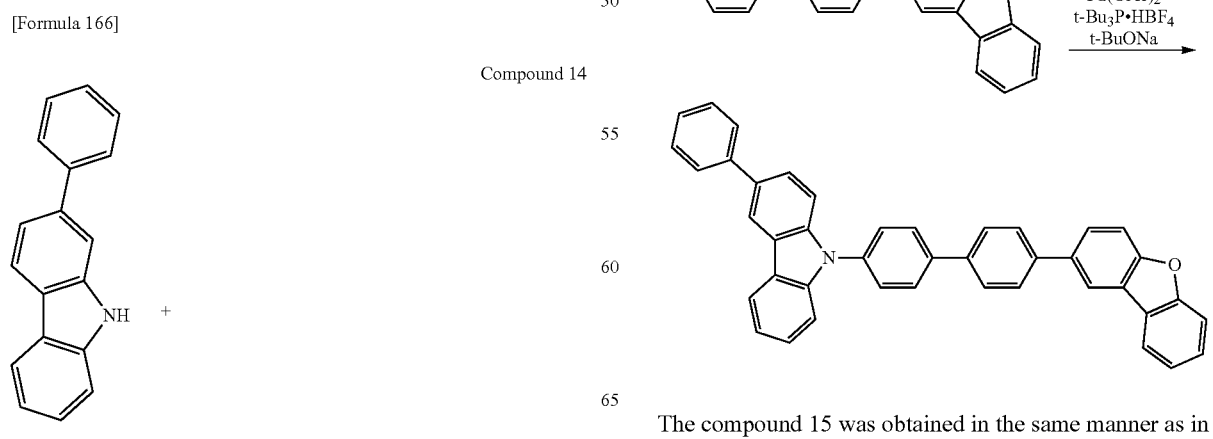

The compound 15 was obtained in the same manner as in Synthesis Example 1 except for using 3-phenyl-9H-carbazole in place of carbazole in Synthesis of Compound 1 of Synthesis Example 1. A yield was 61%. The obtained compound was identified as the compound 15 by analysis according to LC-MS.

Synthesis Example 16: Synthesis of Compound 16

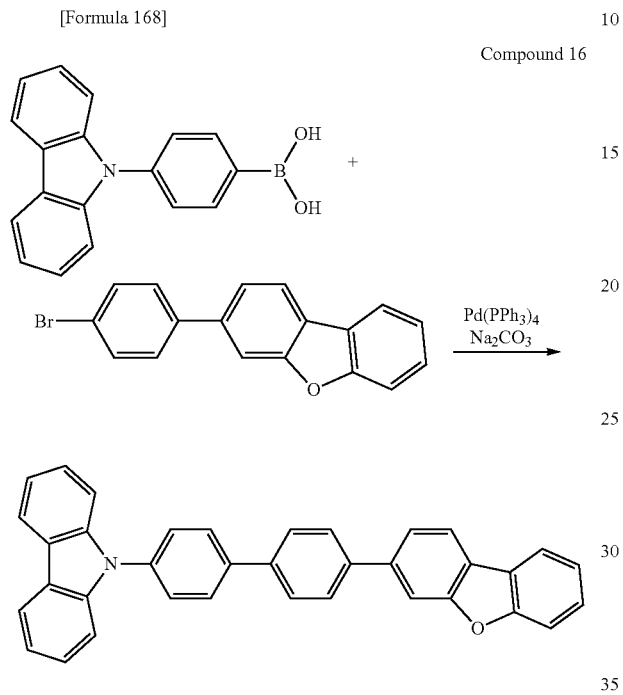

Compound 16

The compound 16 was obtained in the same manner as in Synthesis Example 2 except for using (4-(9H-carbazole-9-yl)phenyl) boronic acid in place of (3,5-di(9H-carbazole-9-yl)phenyl) boronic acid, and 3-(4-bromophenyl)dibenzo[b,d]furan in place of 2-(4'-bromo-[1,1'-biphenyl]-4-yl)) dibenzo[b,d]furan in Synthesis of Compound 2 of Synthesis Example 2. A yield was 50%. The obtained compound was identified as the compound 16 by analysis according to LC-MS.

The invention claimed is:

1. An organic electroluminescence device comprising:
an anode;
a cathode; and
an emitting layer provided between the anode and the cathode,
wherein the emitting layer comprises a delayed fluorescent compound M2 and a compound M3 represented by a formula (100) below,
with the proviso that the compound M3 does not include compound 5

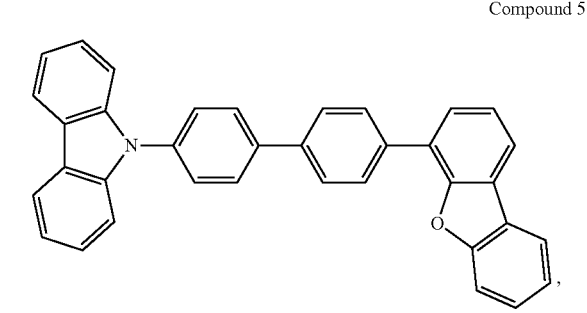 [SMILES: c1ccc2c(c1)oc1c(-c3ccc(-c4ccc(-n5c6ccccc6c6ccccc65)cc4)cc3)cccc12]

Compound 5 and
a singlet energy S (M2) of the compound M2 and a singlet energy S (M3) of the compound M3 satisfy a relationship of a numerical formula (Numerical Formula 1), (Numerical Formula 1)

$S_1(M3) > S_1(M2)$

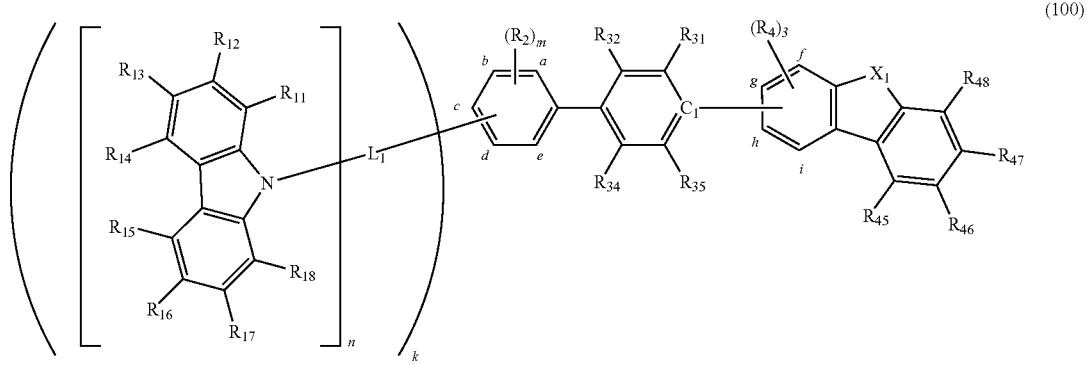

(100)

where: in the formula (100), X, is an oxygen atom or a sulfur atom, $C_1$ is a carbon atom, n is 1, 2 or 3, k is 1, 2 or 3, m is 2, 3, or 4, k+m=5, $R_{11}$ to $R_{18}$ are each independently a hydrogen atom or a substituent, or at least one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ are mutually bonded to form a ring, when at least one of n or k is 2 or more, a plurality of $R_{11}$ are mutually the same or different, a plurality of $R_{12}$ are mutually the same or different, a plurality of $R_{13}$ are mutually the same or different, a plurality of $R_{14}$ are mutually the same or different, a plurality of $R_{15}$ are mutually the same or different, a plurality of $R_{16}$ are mutually the same or different, a plurality of $R_{37}$ are mutually the same or different, and a plurality of Rig are mutually the same or different, $L_1$ is a single bond or a linking group, when $L_1$ is a single bond, n is 1, when k is 2 or more, a plurality of $L_1$ are mutually the same or different, $L_1$ as a linking group is a group derived from a substituted or unsubstituted aryl group having 6 to 30 ring carbon atoms, a group derived from a substituted or unsubstituted heterocyclic group having 5 to 30 ring atoms, or a group in which two groups selected from the group consisting of a group derived from a substituted or unsubstituted aryl group having 6 to 30 ring carbon atoms and a group derived from a substituted or unsubstituted heterocyclic group having 5 to 30 ring atoms are bonded, when k is 1 and m is 4, four $R_2$ are respectively bonded to carbon atoms at any ones of positions of a, b, c, d and e shown in the formula (100), and one $L_1$ is bonded to a carbon atom at the position of a, b, c, d or e which is not bonded to $R_2$, when k is 2 and m is 3, three $R_2$ are respectively bonded to carbon atoms at any ones of the positions of a, b, c, d and e shown in the formula (100), and two $L_1$ are respectively bonded to carbon atoms at any ones of the positions of a, b, c, d and e which are not bonded to $R_2$, when k is 3 and m is 2, two $R_2$ are respectively bonded to carbon atoms at any ones of the positions of a, b, c, d and e shown in the formula (100), and three L; are respectively bonded to carbon atoms at any ones of the positions of a, b, c, d and e which are not bonded to $R_2$, $R_2$, $R_{31}$, $R_{32}$, $R_{34}$ and $R_{35}$ are each independently a hydrogen atom or a substituent, and a plurality of $R_2$ are mutually the same or different when m is 2 or more, $R_4$ and $R_{45}$ to $R_{48}$ are each independently a hydrogen atom or a substituent, or at least one pair of a pair of $R_{45}$ and $R_{46}$, a pair of $R_{46}$ and $R_{47}$, or a pair of $R_{47}$ and $R_{48}$ is mutually bonded to form a ring, or at least one pair of pairs including at least two of a plurality of $R_4$ is mutually bonded to form a ring, three $R_4$ are mutually the same or different, three $R_4$ are respectively bonded to carbon atoms at any ones of positions of f, g, h and i shown in the formula (100), and $C_1$ is bonded to a carbon atom at the position of f, g, h or i which is not bonded to $R_1$, $R_{11}$ to $R_{18}$, $R_4$ and $R_{45}$ to $R_{48}$ as the substituent are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms, and wherein when $R_{13}$ and $R_{16}$ as the substituent are each independently a substituted or unsubstituted heterocyclic group having 5 to 30 ring atoms, $R_{13}$ and $R_{16}$ as the substituent are each independently a substituted or unsubstituted pyridyl group, a substituted or unsubstituted pyrimidinyl group, a substituted or unsubstituted pyrazinyl group, a substituted or unsubstituted pyridazinyl group, a substituted or unsubstituted triazinyl group, a substituted of unsubstituted quinolyl group, a substituted or unsubstituted isoquinolinyl group, a substituted or unsubstituted naphthyridinyl group, a substituted or unsubstituted phthalazinyl group, a substituted or unsubstituted quinoxalinyl group, a substituted or unsubstituted quinazolinyl group, a substituted or unsubstituted phenanthridinyl group, a substituted or unsubstituted acridinyl group, a substituted or unsubstituted phenanthrolinyl group, a substituted or unsubstituted pyrrolyl group, a substituted or unsubstituted imidazolyl group, a substituted or unsubstituted pyrazolyl group, a substituted or unsubstituted triazolyl group, a substituted or unsubstituted tetrazolyl group, a substituted or unsubstituted indolyl group, a substituted or unsubstituted benzimidazolyl group, a substituted or unsubstituted indazolyl group, a substituted or unsubstituted imidazopyridinyl group, a substituted or unsubstituted benzotriazolyl group, a substituted or unsubstituted furyl group, a substituted or unsubstituted thienyl group, a substituted or unsubstituted oxazolyl group, a substituted or unsubstituted thiazolyl group, a substituted or unsubstituted isoxazolyl group, a substituted or unsubstituted isothiazolyl group, a substituted or unsubstituted oxadiazolyl group, a substituted or unsubstituted thiadiazolyl group, a substituted or unsubstituted benzofuranyl group, a substituted or unsubstituted benzothienyl group, a substituted or unsubstituted benzoxazolyl group, a substituted or unsubstituted benzothiazolyl group, a substituted or unsubstituted benzisoxazolyl group, a substituted or unsubstituted benzisothiazolyl group, a substituted or unsubstituted benzoxadiazolyl group, a substituted or unsubstituted benzothiadiazolyl group, a substituted or unsubstituted dibenzofuranyl group, a substituted or unsubstituted dibenzothienyl group, a substituted or unsubstituted piperidinyl group, a substituted or unsubstituted pyrrolidinyl group, a substituted or unsubstituted piperazinyl group, a substituted or unsubstituted morpholyl group, a substituted or unsubstituted phenazinyl group, a substituted or unsubstituted phenothiazinyl group, or a substituted or unsubstituted phenoxazinyl group, and $R_2$, $R_{31}$, $R_{32}$, $R_{34}$ and $R_{35}$ as the substituent are each independently a halogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms.

2. The organic electroluminescence device according to claim 1, wherein the emitting layer further comprises a fluorescent compound M1, and the singlet energy S (M2) of the compound M2 and a singlet energy S (M1) of the compound M1 satisfy a relationship of a numerical formula (Numerical Formula 2), $$S_H(M2) > S_1(M1) \qquad \text{(Numerical Formula 2).}$$

3. The organic electroluminescence device according to claim 1, wherein at least one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ is bonded to each other to form a ring, and a pair of $R_{45}$ and $R_{46}$, a pair of $R_{46}$ and $R_{47}$, a pair of $R_{47}$ and $R_{48}$, and a pair of two or more of a plurality of $R_4$ are not mutually bonded.

4. The organic electroluminescence device according to claim 1, wherein a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, a pair of $R_{17}$ and $R_{18}$, a pair of $R_{45}$ and $R_{46}$, a pair of $R_{46}$ and $R_{47}$, a pair of $R_{47}$ and $R_{48}$ and a pair of two or more of a plurality of $R_4$ are not mutually bonded.

5. The organic electroluminescence device according to claim 1, wherein $R_2$, $R_{31}$, $R_{32}$, $R_{34}$, and $R_{35}$ are hydrogen atoms, and $L_1$ is a single bond, a group derived from an unsubstituted aryl group having 6 to 30 ring carbon atoms, or a group derived from an unsubstituted heterocyclic group having 5 to 30 ring atoms.

6. The organic electroluminescence device according to claim 1, wherein n is 1 or 2, and k is 1 or 2.

7. The organic electroluminescence device according to claim 1, wherein n is 1, and k is 1 or 2.

8. The organic electroluminescence device according to claim 1, wherein n is 2, and k is 1 or 2.

9. The organic electroluminescence device according to claim 1, wherein $R_{11}$ to $R_{18}$, $R_4$ and $R_{45}$ to $R_{48}$ are each independently a hydrogen atom, a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms.

10. The organic electroluminescence device according to claim 1, wherein $R_{11}$ to $R_{18}$, $R_4$ and $R_{45}$ to $R_{48}$ are each independently a hydrogen atom, a substituted or unsubstituted aryl group having 6 to 30 ring carbon atoms, or a substituted or unsubstituted heterocyclic group having 5 to 30 ring atoms.

11. The organic electroluminescence device according to claim 1, wherein $R_{11}$ to $R_{18}$, $R_4$ and $R_{45}$ to $R_{48}$ are each independently a hydrogen atom, or a substituted or unsubstituted aryl group having 6 to 30 ring carbon atoms.

12. The organic electroluminescence device according to claim 1, wherein $R_{11}$ to $R_{18}$, $R_4$ and $R_{45}$ to $R_{48}$ are each independently a hydrogen atom, or a substituted or unsubstituted phenyl group.

13. The organic electroluminescence device according to claim 1, wherein $R_{11}$ to $R_{18}$ are each independently a hydrogen atom, or a substituted or unsubstituted phenyl group, and $R_4$ and $R_{45}$ to $R_{48}$ are each independently a hydrogen atom.

14. The organic electroluminescence device according to claim 1, wherein $L_1$ is a single bond, or a group derived from an unsubstituted aryl group having 6 to 30 ring carbon atoms.

15. The organic electroluminescence device according to claim 1, wherein $L_1$ is a single bond, or a group derived from an unsubstituted benzene ring.

16. The organic electroluminescence device according to claim 1, wherein $L_1$ is a single bond.

17. The organic electroluminescence device according to claim 1, wherein the compound M3 represented by the formula (100) is a compound represented by a formula (100A) or a formula (100B) below,

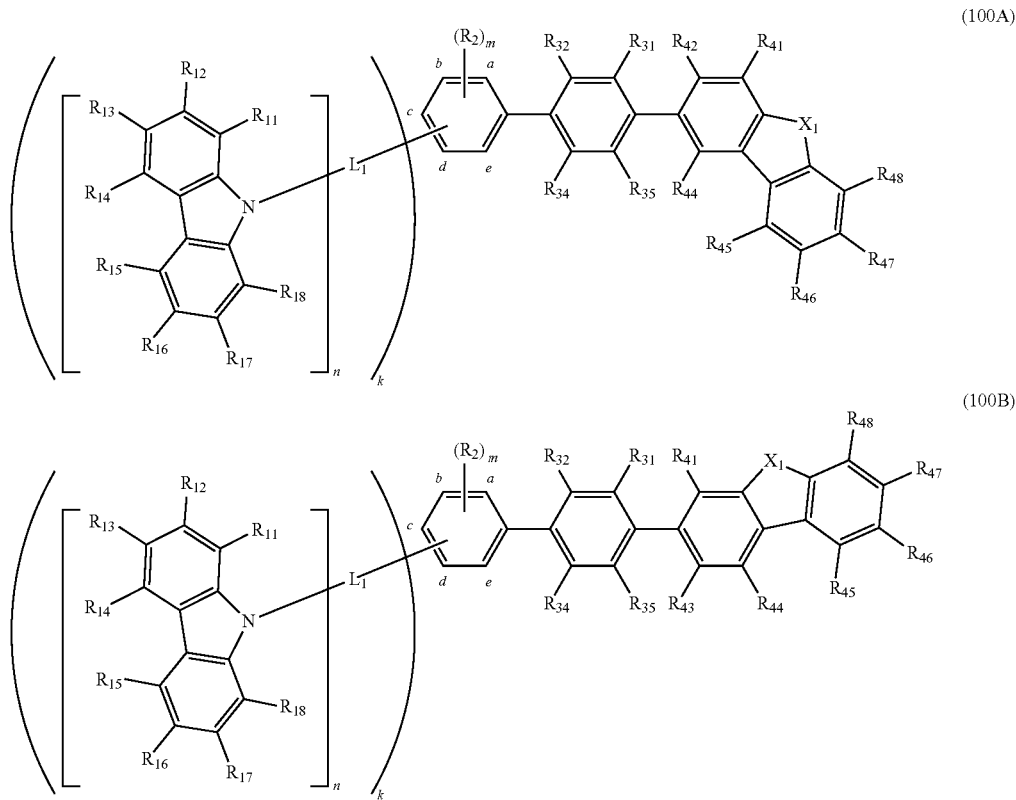

where: in the formulae (100A) and (100B), $X_1$, $R_{11}$ to $R_{18}$, n, k, m, $L_1$, $R_2$, $R_{31}$, $R_{32}$, $R_{34}$, $R_{35}$, and $R_{45}$ to $R_{48}$ respectively represent the same as $X_1$, $R_{11}$ to $R_{18}$, n, k, m, $L_1$, $R_2$, $R_{31}$, $R_{32}$, $R_{34}$, $R_{35}$, and $R_{45}$ to $R_{48}$ in the formula (100), and $R_{41}$ to $R_{44}$ each independently represent the same as $R_4$ in the formula (100).

18. The organic electroluminescence device according to claim 17, wherein the compound M3 represented by the formula (100) is the compound represented by the formula (100A).

19. The organic electroluminescence device according to claim 1, wherein the compound M3 represented by the formula (100) is a compound represented by a formula (100E), where: in the formula (100E), X; and $C_1$ respectively represent the same as $X_1$ and $C_1$ in the formula (100), n is 1 or 2, k is 1 or 2, $R_{11}$ to $R_{18}$, $R_4$ and $R_{45}$ to $R_{48}$ are each independently a hydrogen atom, or a substituted or unsubstituted aryl group having 6 to 30 ring carbon atoms, when at least one of n or k is 2, a plurality of $R_{11}$ are mutually the same or different, a plurality of $R_{12}$ are mutually the same or different, a plurality of $R_{13}$ are mutually the same or different, a plurality of $R_{14}$ are mutually the same or different, a plurality of $R_{15}$ are mutually the same or different, a plurality of Rig are mutually the same or different, a plurality of $R_{17}$ are mutually the same or different, and a plurality of Rig are mutually the same or different,

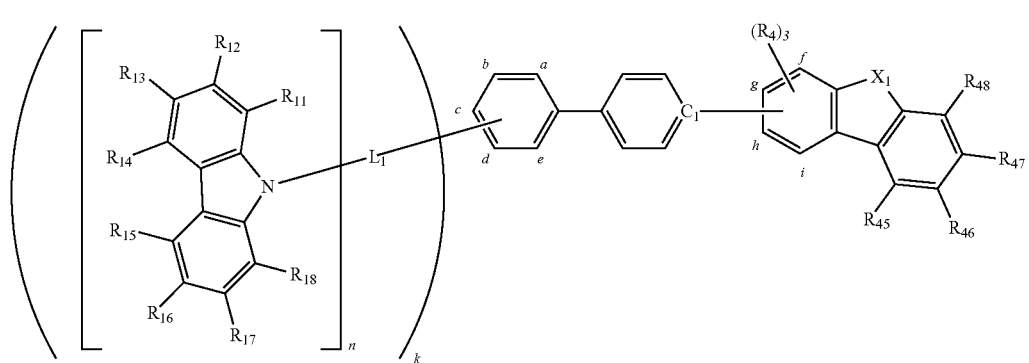

a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, and a pair of $R_{17}$ and $R_{18}$, a pair of $R_{45}$ and $R_{46}$, a pair of $R_{46}$ and $R_{47}$, a pair of $R_{47}$ and $R_{48}$ and a pair of two or more of a plurality of $R_4$ are not mutually bonded, $L_1$ is a single bond or a group derived from an unsubstituted aryl group having 6 to 30 ring carbon atoms, when $L_1$ is a single bond, n is 1, and when k is 2, a plurality of $L_i$ are mutually the same or different, when k is 1, one $L_1$ is bonded to a carbon atom at the position of a, b, c, d or e, and when k is 2, two $L_1$ are respectively bonded to carbon atoms at any ones of the positions of a, b, c, d and e.

20. The organic electroluminescence device according to claim 1, wherein the compound M3 represented by the formula (100) is a compound represented by a formula (100F),

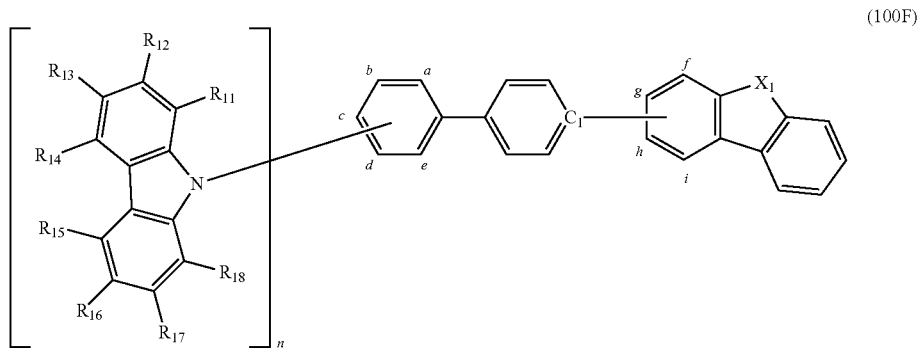

(100F)

where: in the formula (100F), $X_1$ and $C_1$ respectively represent the same as $X_1$ and $C_1$ in the formula (100), n is 1 or 2, when n is 1, a nitrogen atom at a position 9 of one carbazole ring shown in the formula (100F) is bonded to a carbon atom at the position of a, b, c, d or e shown in the formula (100F), and when n is 2, nitrogen atoms at positions 9 of two carbazole rings are respectively bonded to carbon atoms at any ones of the positions of a, b, c, d and e, $R_{11}$ to $R_{18}$ are each independently a hydrogen atom, or a substituted or unsubstituted phenyl group, when n is 2, a plurality of $R_{11}$ are mutually the same or different, a plurality of $R_{12}$ are mutually the same or different, a plurality of $R_{13}$ are mutually the same or different, a plurality of $R_{14}$ are mutually the same or different, a plurality of $R_{15}$ are mutually the same or different, a plurality of $R_{16}$ are mutually the same or different, a plurality of $R_{17}$ are mutually the same or different, and a plurality of $R_{18}$ are mutually the same or different, and a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, and a pair of $R_{17}$ and $R_{18}$ are not mutually bonded.

21. The organic electroluminescence device according to claim 1, wherein the compound M3 represented by the formula (100) is a compound represented by any one of formulae (401) to (406) below,

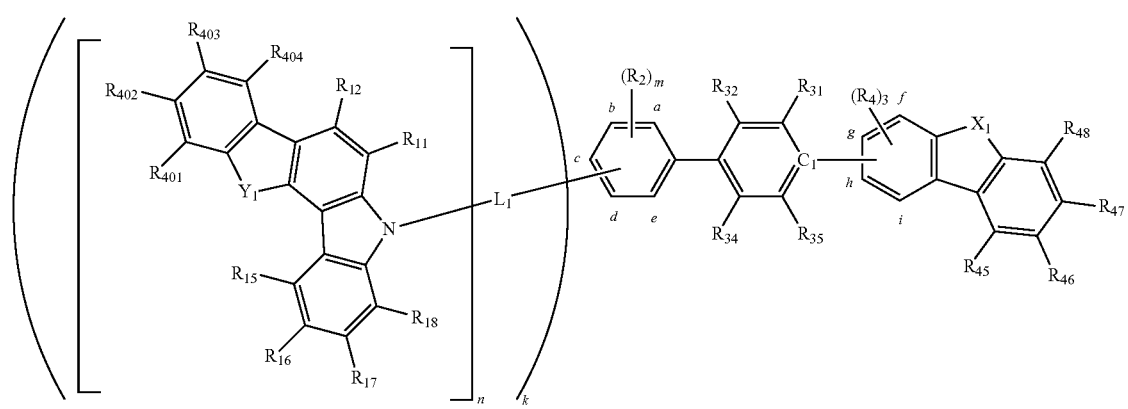

(401)

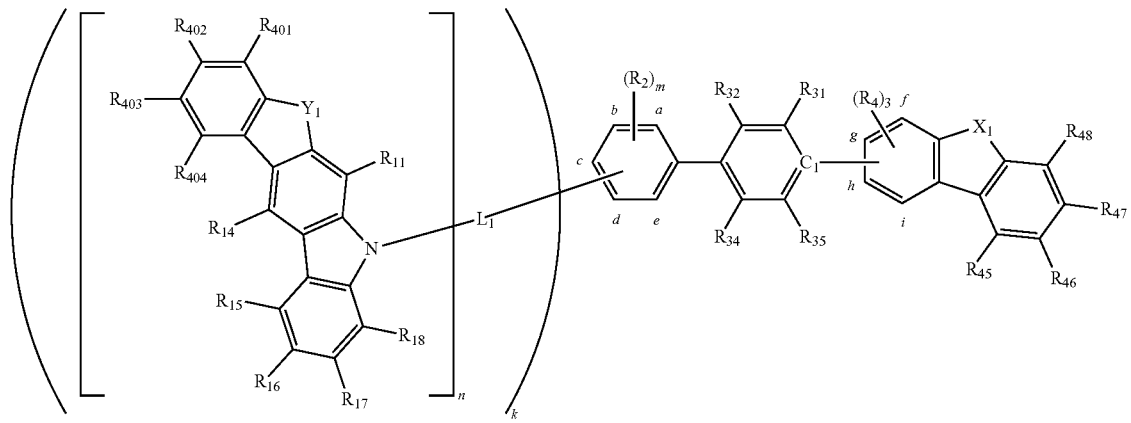
(402)
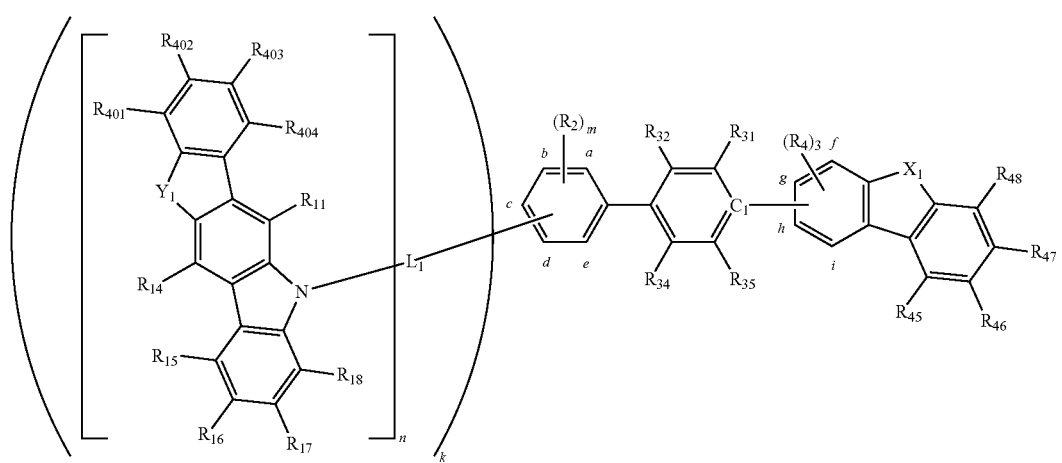
(403)
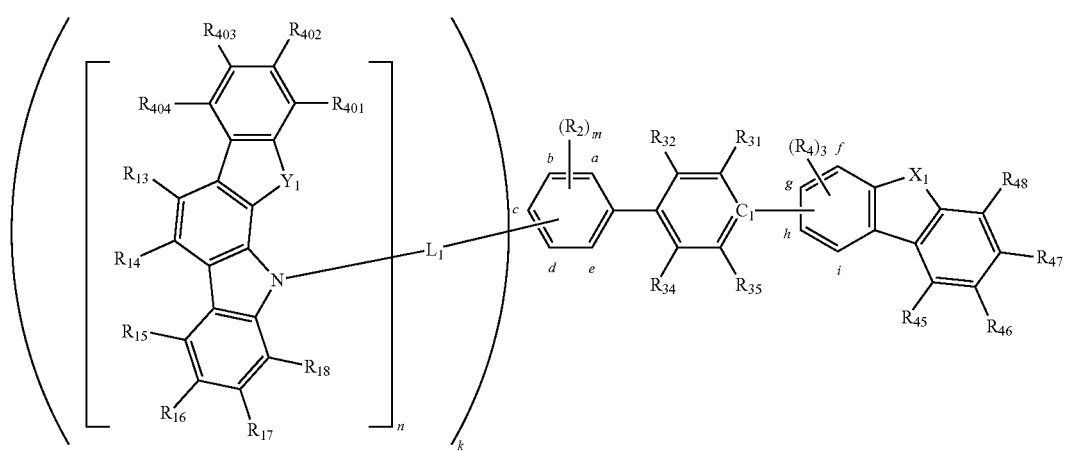
(404)

(405)

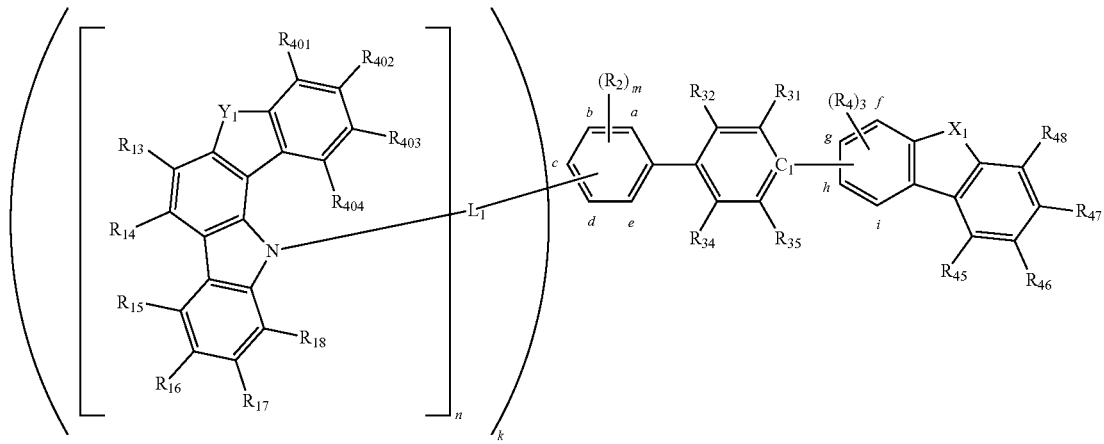

(406)

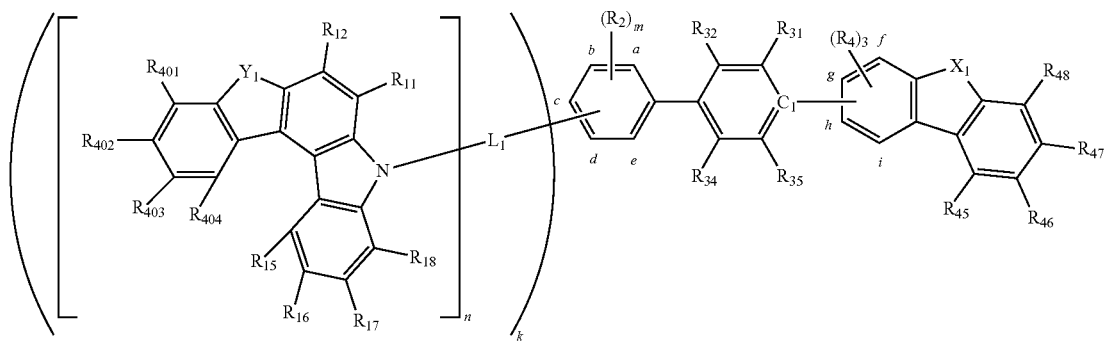

where: in the formulae (401) to (406), $X_1$, $R_4$, $R_{45}$ to $R_{48}$, $C_1$, $R_{31}$ to $R_{32}$, $R_{34}$ to $R_{35}$, $R_2$, $L_1$, $R_{11}$ to $R_{18}$, m, n, and k respectively represent the same as $X_1$, $R_4$, $R_{45}$ to $R_{48}$, $C_1$, $R_{31}$ to $R_{32}$, $R_{34}$ to $R_{35}$, $R_2$, $L_1$, $R_{11}$ to $R_{18}$, m, n, and k in the formula (100), $Y_1$ is an oxygen atom or a sulfur atom, $R_{401}$ to $R_{404}$ each independently represent the same as $R_{11}$ to $R_{18}$ in the formula (100), and at least one pair of a pair of $R_{401}$ and $R_{402}$, a pair of $R_{402}$ and $R_{403}$, or a pair of $R_{403}$ and $R_{404}$ is bonded to each other to form a ring or not bonded.

22. The organic electroluminescence device according to claim 21, wherein n is 1 or 2, and k is 1 or 2.

23. The organic electroluminescence device according to claim 21, wherein the compound M3 represented by the formula (100) is a compound represented by any one of formulae (401A) to (406A) below, (401A)

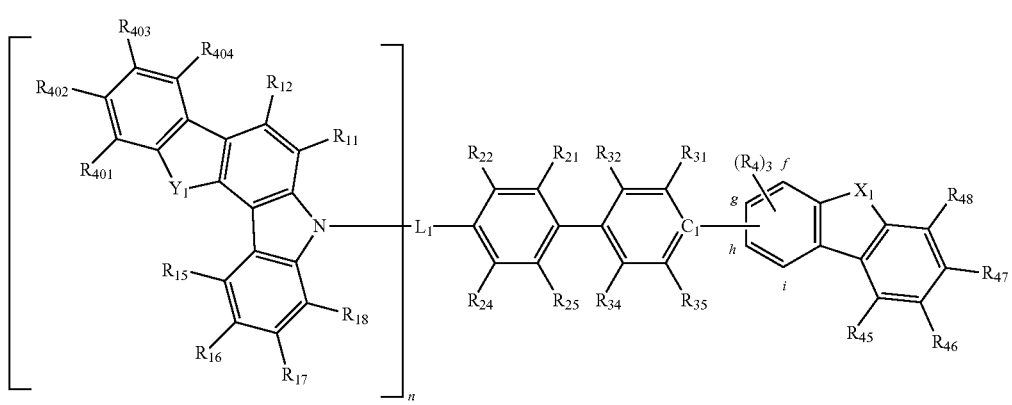

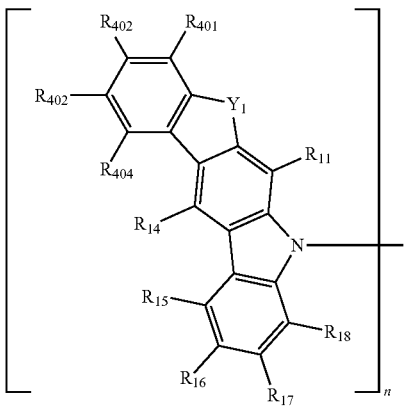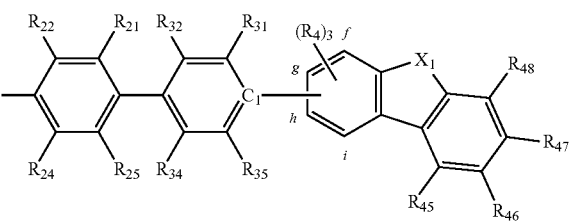
(402A)
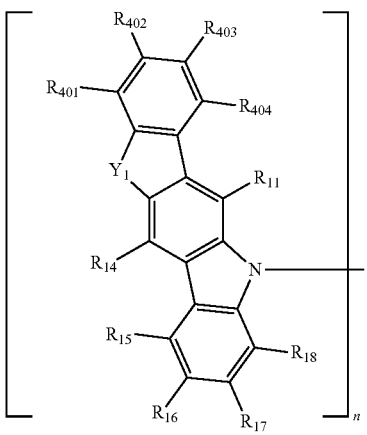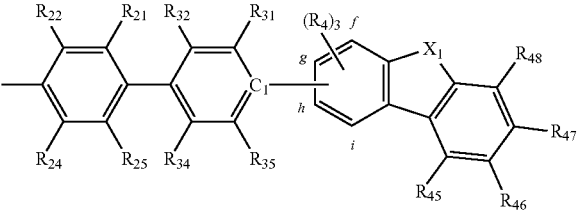
(403A)
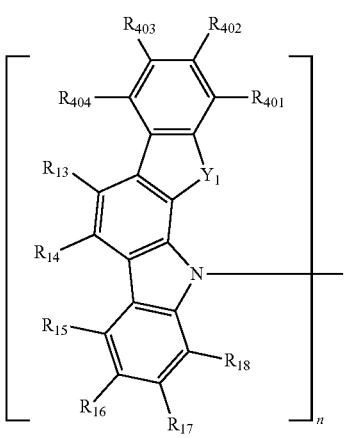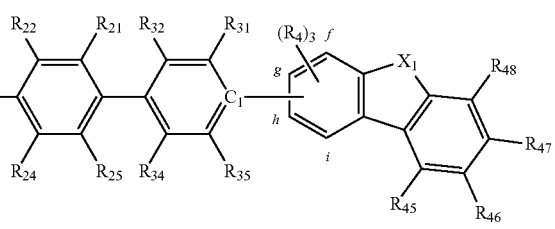
(404A)

(405A)

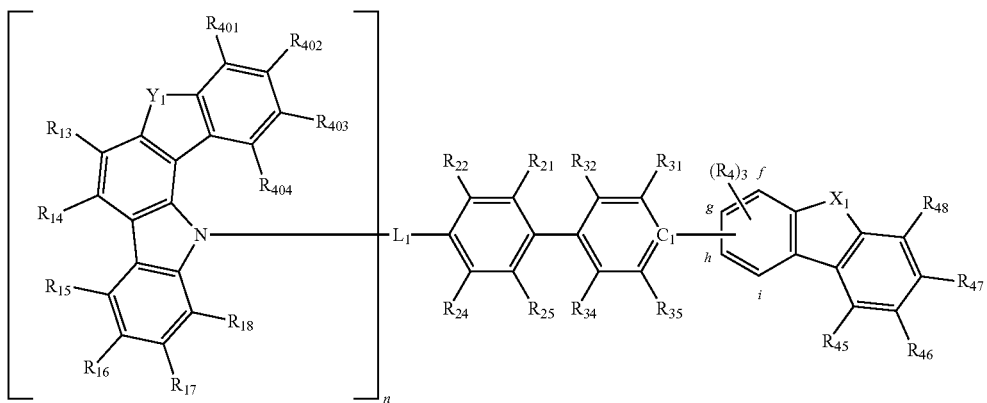

(406A)

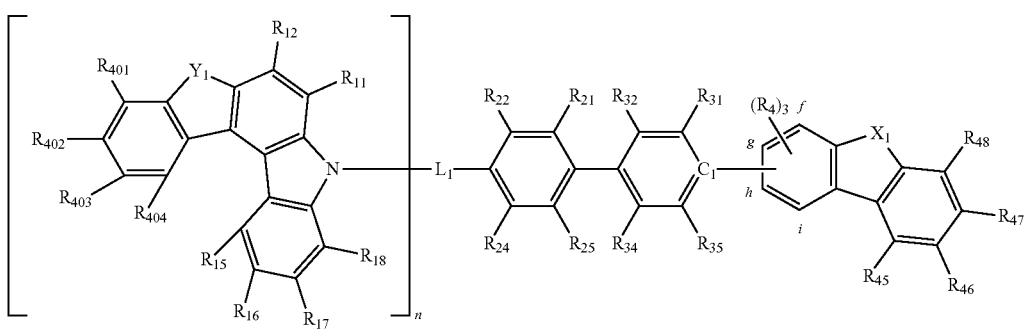

where: in the formulae (401A) to (406A), $X_1$, $R_4$, $R_{45}$ to $R_{48}$, $C_1$, $R_{31}$ to $R_{32}$, $R_{34}$ to $R_{35}$, $L_1$, $R_{11}$ to $R_{18}$, and n respectively represent the same as $X_1$, $R_4$, $R_{45}$ to $R_{48}$, $C_1$, $R_{31}$ to $R_{32}$, $R_{34}$ to $R_{35}$, $L_1$, $R_{11}$ to $R_{18}$, and n in the formula (100), $R_{21}$ to $R_{22}$ and $R_{24}$ to $R_{25}$ each independently represent the same as $R_2$ in the formula (100), $Y_1$ is an oxygen atom or a sulfur atom, $R_{401}$ to $R_{404}$ each independently represent the same as $R_{11}$ to $R_{18}$ in the formula (100), and at least one pair of a pair of $R_{401}$ and $R_{402}$, a pair of $R_{402}$ and $R_{403}$, or a pair of $R_{403}$ and $R_{404}$ is bonded to each other to form a ring or not bonded.

24. The organic electroluminescence device according to claim 23, wherein the compound M3 represented by the formula (100) is a compound represented by any one of formulae (401B) to (406B) below, (401B)

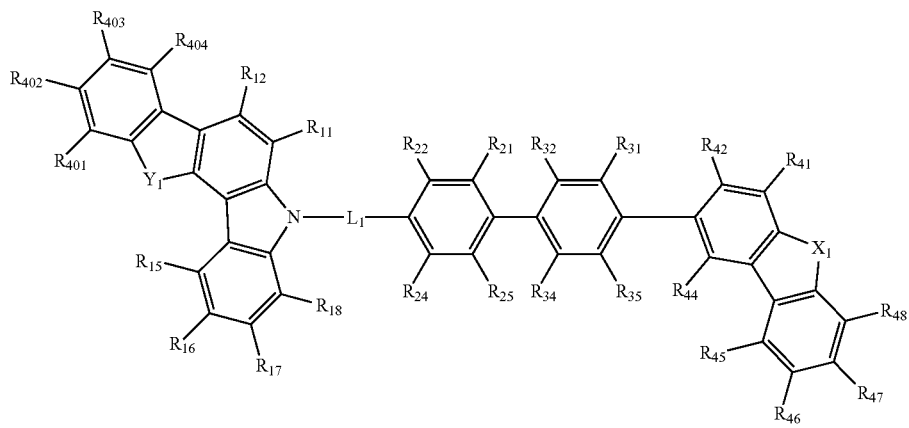

-continued
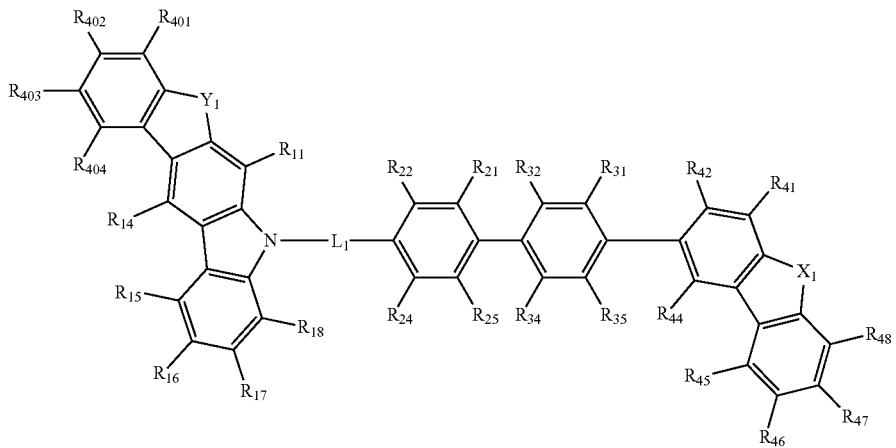
(402B)
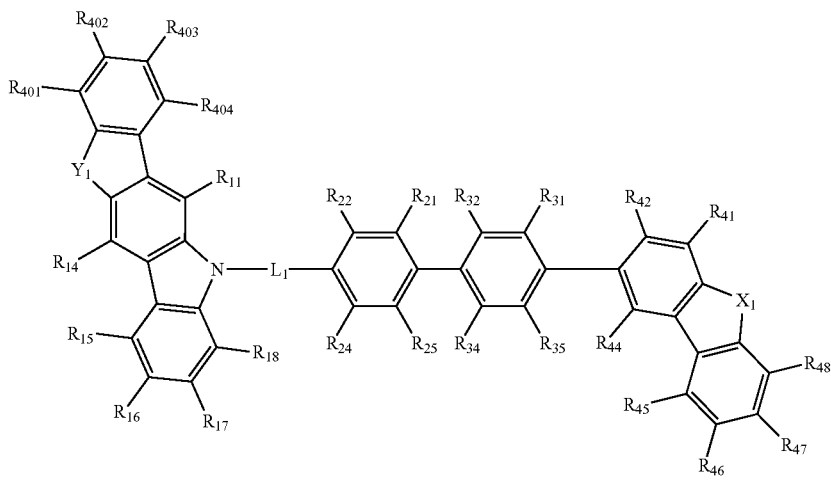
(403B)
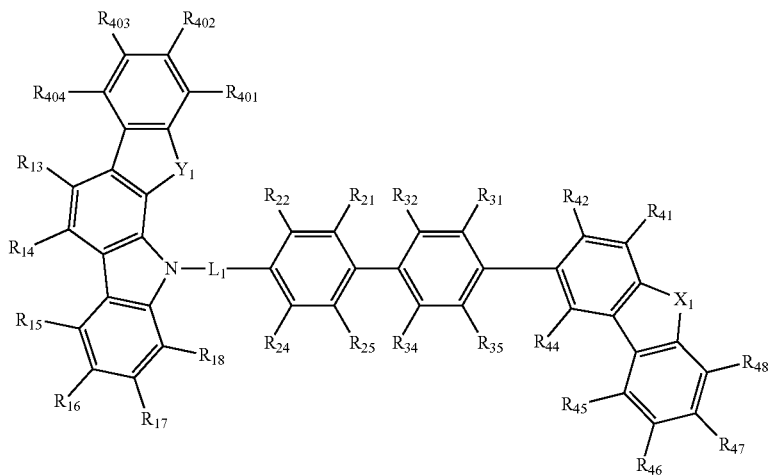
(404B)

-continued (405B)

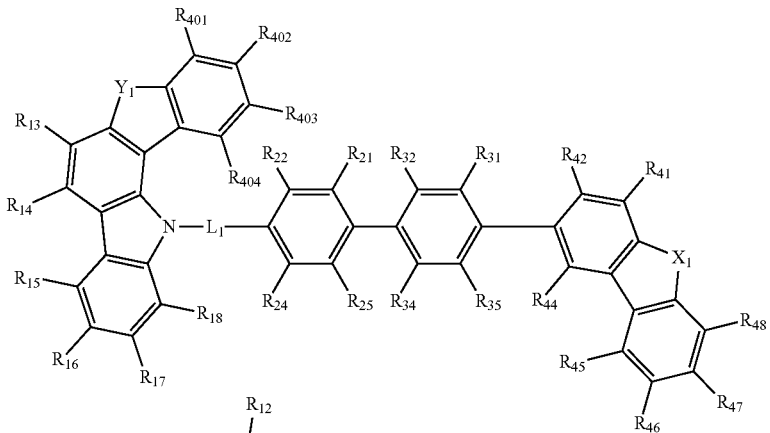

(406B)

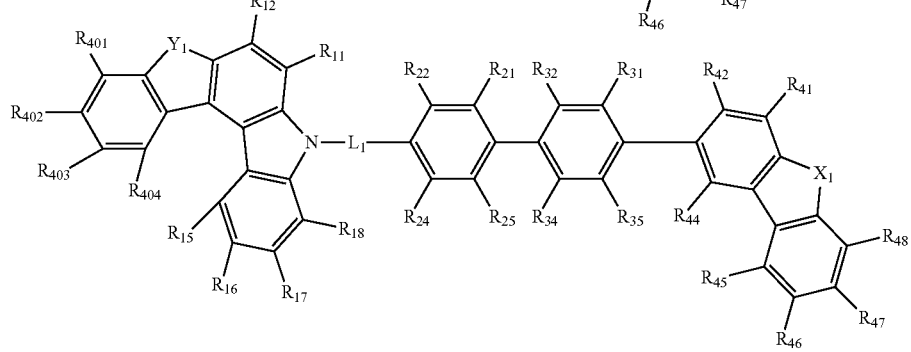

where: in the formulae (401B) to (406B), $X_1$, $R_{45}$ to $R_{48}$, $R_{31}$ to $R_{32}$, $R_{34}$ to $R_{35}$, $L_1$, and $R_{11}$ to $R_{18}$ respectively represent the same as $X_1$, $R_{45}$ to $R_{48}$, $R_{31}$ to $R_{32}$, $R_{34}$ to $R_{35}$, $L_1$, and $R_{11}$ to $R_{18}$ in the formula (100), $R_{41}$, $R_{42}$ and $R_{44}$ each independently represent the same as $R_4$ in the formula (100), $R_{21}$ to $R_{22}$ and $R_{24}$ to $R_{25}$ each independently represent the same as $R_2$ in the formula (100), $Y_1$ is an oxygen atom or a sulfur atom, $R_{401}$ to $R_{404}$ each independently represent the same as $R_{11}$ to $R_{18}$ in the formula (100), and at least one pair of a pair of $R_{401}$ and $R_{402}$, a pair of $R_{402}$ and $R_{403}$, or a pair of $R_{403}$ and $R_{404}$ is bonded to each other to form a ring or not bonded.

25. The organic electroluminescence device according to claim 21, wherein
a pair of $R_{45}$ and $R_{46}$, a pair of $R_{46}$ and $R_{47}$, a pair of $R_{47}$ and $R_{48}$, a pair of $R_{41}$ and $R_{42}$, and a pair of two or more of a plurality of $R_4$ are not mutually bonded.

26. The organic electroluminescence device according to claim 21, wherein
$R_2$, $R_{21}$ to $R_{22}$, $R_{24}$ to $R_{25}$, $R_{31}$ to $R_{32}$ and $R_{34}$ to $R_{35}$ are hydrogen atoms, and
$L_1$ is a single bond, a group derived from an unsubstituted aryl group having 6 to 30 ring carbon atoms, or a group derived from an unsubstituted heterocyclic group having 5 to 30 ring atoms.

27. The organic electroluminescence device according to claim 1, wherein
$X_1$ is an oxygen atom.

28. An electronic device comprising the organic electroluminescence device according to claim 1.

29. The organic electroluminescence device according to claim 1, wherein $R_{32}$ and $R_{34}$ are hydrogen atoms.

30. A compound represented by a formula (201), (202), or (203) below, (201)

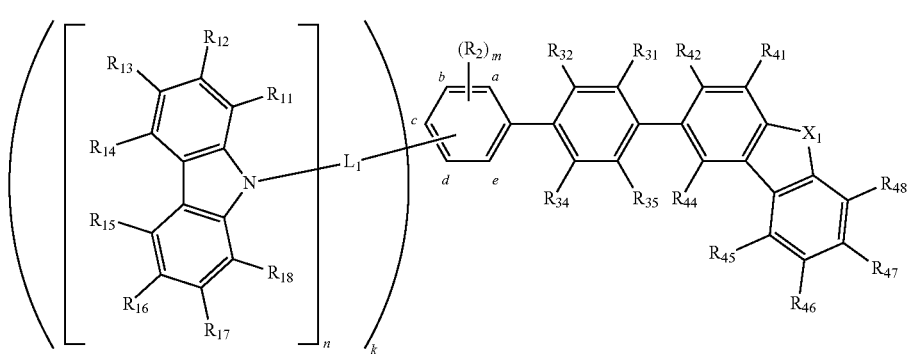

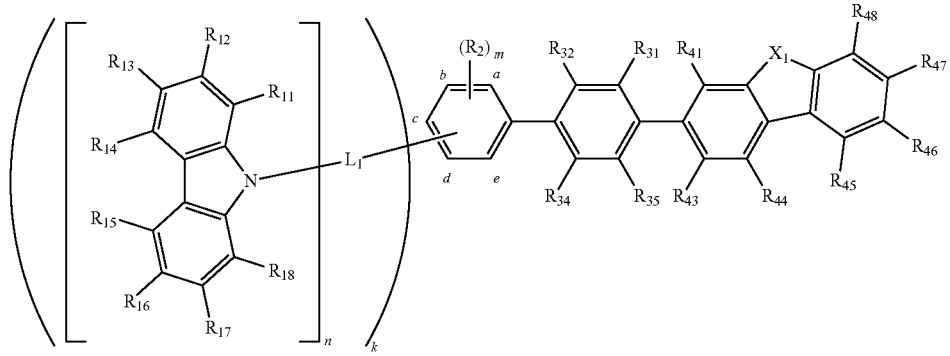

(202)

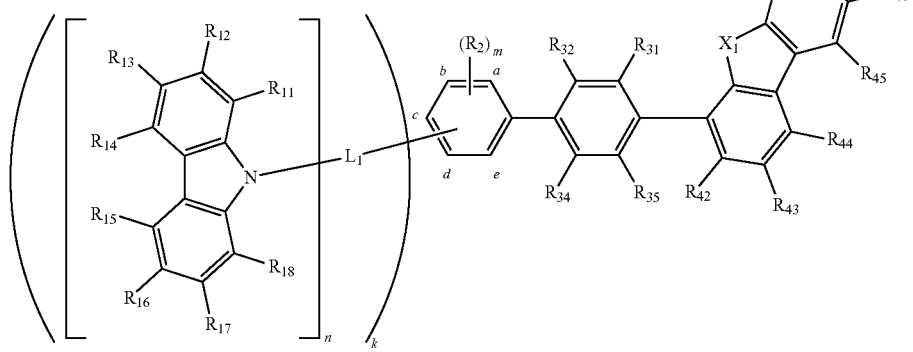

(203)

with the proviso that the compound represented by the formula (202) does not include a compound 29-1 or a compound 29-2, Compound 29-1

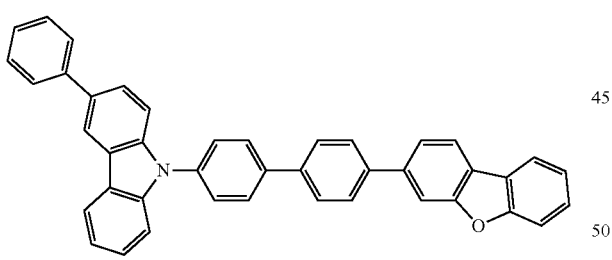

Compound 29-2

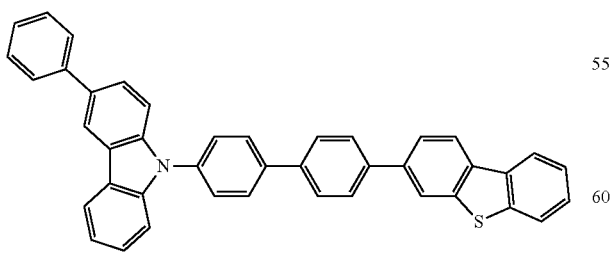

wherein:

in the formulae (201) to (203), $X_1$ is an oxygen atom or a sulfur atom, n is 1, 2 or 3,
k is 1, 2 or 3,
m is 2, 3, or 4,
k+m=5,
$R_{11}$ to $R_{18}$ are each independently a hydrogen atom or a substituent, or
a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, and a pair of $R_{17}$ and $R_{18}$ are not mutually bonded,
when at least one of n or k is 2 or more, a plurality of $R_{11}$ are mutually the same or different, a plurality of $R_{12}$ are mutually the same or different, a plurality of $R_{12}$ are mutually the same or different, a plurality of $R_{14}$ are mutually the same or different, a plurality of $R_{15}$ are mutually the same or different, a plurality of Rag are mutually the same or different, a plurality of $R_{17}$ are mutually the same or different, and a plurality of $R_{18}$ are mutually the same or different,
$L_1$ is a single bond or a linking group,
when $L_1$ is a single bond, n is 1,
when k is 2 or more, a plurality of $L_1$ are mutually the same or different,
$L_1$ as a linking group is a group derived from a substituted or unsubstituted aryl group having 6 to 30 ring carbon atoms, a group derived from a substituted or unsubstituted heterocyclic group having 5 to 30 ring atoms, or a group in which two groups selected from the group consisting of a group derived from a substituted or unsubstituted aryl group having 6 to 30 ring carbon atoms and a group derived from a substituted or unsubstituted heterocyclic group having 5 to 30 ring atoms are bonded, when k is 1 and m is 4, four $R_2$ are respectively bonded to carbon atoms at any ones of positions of a, b, c, d and e shown in the formula (201), (202) or (203), and one $L_1$ is bonded to a carbon atom at the position of a, b, c, d or e which is not bonded to $R_2$, when k is 2 and m is 3, three $R_2$ are respectively bonded to carbon atoms at any ones of the positions of a, b, c, d and e shown in the formula (201), (202) or (203), and two $L_1$ are respectively bonded to carbon atoms at any ones of the positions of a, b, c, d and e which are not bonded to $R_2$, when k is 3 and m is 2, two $R_2$ are respectively bonded to carbon atoms at any ones of the positions of a, b, c, d and e shown in the formula (201), (202) or (203), and three $L_1$ are respectively bonded to carbon atoms at any ones of the positions of a, b, c, d and e which are not bonded to $R_2$, $R_2$, $R_{31}$, $R_{32}$, $R_{34}$ and $R_{35}$ are each independently a hydrogen atom or a substituent, a plurality of $R_2$ are mutually the same or different when m is 2 or more, $R_{41}$ to $R_{48}$ are each independently a hydrogen atom or a substituent, or at least one pair of a pair of $R_{41}$ and $R_{42}$, a pair of $R_{42}$ and $R_{43}$, a pair of $R_{43}$ and $R_{44}$, a pair of $R_{45}$ and $R_{46}$, a pair of $R_{46}$ and $R_{47}$, or a pair of $R_{47}$ and $R_{48}$ are mutually bonded to form a ring, $R_{11}$ to $R_{18}$, and $R_{41}$ to $R_{48}$ as the substituent are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms, $R_2$, $R_{31}$, $R_{32}$, $R_{34}$ and $R_{35}$ as the substituent are each independently a halogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms, and at least one of $R_{11}$ to $R_{18}$ is an unsubstituted aryl group having 6 to 30 ring carbon atoms.

31. The compound according to claim 30, wherein a pair of $R_{41}$ and $R_{42}$, a pair of $R_{42}$ and $R_{43}$, a pair of $R_{43}$ and $R_{44}$, a pair of $R_{45}$ and $R_{46}$, a pair of $R_{46}$ and $R_{47}$, and a pair of $R_{47}$ and $R_{48}$ are not mutually bonded.

32. The compound according to claim 30, wherein $R_2$, $R_{31}$, $R_{32}$, $R_{34}$, and $R_{35}$ are hydrogen atoms, and $L_1$ is a single bond, a group derived from an unsubstituted aryl group having 6 to 30 ring carbon atoms, or a group derived from an unsubstituted heterocyclic group having 5 to 30 ring atoms.

33. The compound according to claim 30, wherein n is 1 or 2, and k is 1 or 2.

34. The compound according to claim 30, wherein $R_{11}$ to $R_{18}$, and $R_{41}$ to $R_{48}$ are each independently a hydrogen atom, a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms.

35. The compound according to claim 30, wherein $L_1$ is a single bond or a group derived from an unsubstituted aryl group having 6 to 30 ring carbon atoms.

36. The compound according to claim 30, wherein $R_2$, $R_{31}$, $R_{32}$, $R_{34}$, and $R_{35}$ are hydrogen atoms, n is 1 or 2, k is 1 or 2, $R_{11}$ to $R_{18}$, and $R_{41}$ to $R_{48}$ are each independently a hydrogen atom, or a substituted or unsubstituted aryl group having 6 to 30 ring carbon atoms, a pair of $R_{41}$ and $R_{42}$, a pair of $R_{42}$ and $R_{43}$, a pair of $R_{43}$ and $R_{44}$, a pair of $R_{45}$ and $R_{46}$, a pair of $R_{46}$ and $R_{47}$, and a pair of $R_{47}$ and $R_{48}$ are not mutually bonded, and $L_1$ is a single bond or a group derived from an unsubstituted aryl group having 6 to 30 ring carbon atoms.

37. The compound according to claim 30, wherein $R_2$, $R_{31}$, $R_{32}$; $R_{34}$, and $R_{35}$ are hydrogen atoms, n is 1 or 2, k is 1 or 2, $R_{11}$ to $R_{18}$ are each independently a hydrogen atom, or a substituted or unsubstituted phenyl group, $R_{11}$ to $R_{48}$ are hydrogen atoms, and $L_1$ is a single bond.

38. An organic-electroluminescence-device material comprising the compound according to claim 30.

39. A compound represented by a formula (300) below,

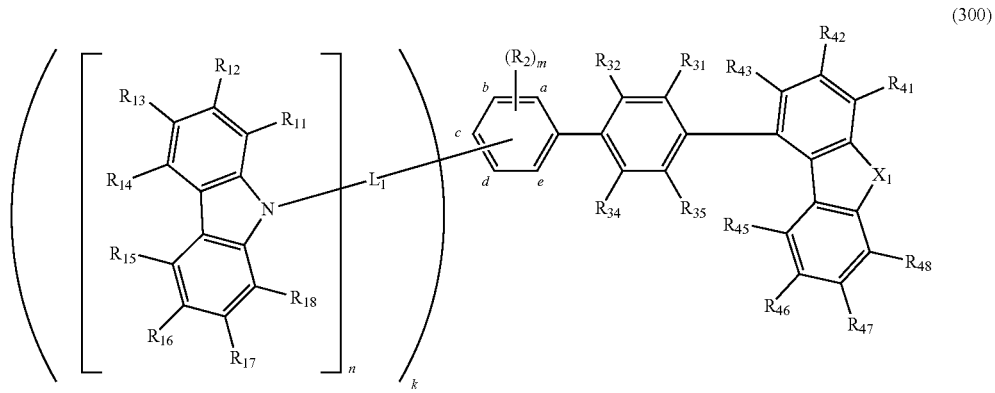

where: in the formula (300), X; is an oxygen atom or a sulfur atom, n is 1, 2 or 3, k is 1, 2 or 3, m is 2, 3, or 4, k+m=5, $R_{11}$ to $R_{18}$ are each independently a hydrogen atom or a substituent, or at least one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ are mutually bonded to form a ring, when at least one of n or k is 2 or more, a plurality of $R_{11}$ are mutually the same or different, a plurality of $R_{12}$ are mutually the same or different, a plurality of Rag are mutually the same or different, a plurality of $R_{14}$ are mutually the same or different, a plurality of $R_{15}$ are mutually the same or different, a plurality of Rag are mutually the same or different, a plurality of $R_{12}$ are mutually the same or different, and a plurality of $R_{18}$ are mutually the same or different, $L_1$ is a single bond or a linking group, when $L_1$ is a single bond, n is 1, when k is 2 or more, a plurality of L; are mutually the same or different, $L_1$ as a linking group is a group derived from a substituted or unsubstituted aryl group having 6 to 30 ring carbon atoms, a group derived from a substituted or unsubstituted heterocyclic group having 5 to 30 ring atoms, or a group in which two groups selected from the group consisting of a group derived from a substituted or unsubstituted aryl group having 6 to 30 ring carbon atoms and a group derived from a substituted or unsubstituted heterocyclic group having 5 to 30 ring atoms are bonded, when k is 1 and m is 4, four $R_2$ are respectively bonded to carbon atoms at any ones of positions of a, b, c, d and e shown in the formula (300), and one La is bonded to a carbon atom at the position of b, c or d which is not bonded to $R_2$, when k is 2 and m is 3, three $R_2$ are respectively bonded to carbon atoms at any ones of the positions of a, b, c, d and e shown in the formula (300), and two $L_1$ are respectively bonded to carbon atoms at any ones of the positions of b, c and d which are not bonded to $R_2$, when k is 3 and m is 2, two $R_2$ are respectively bonded to carbon atoms at any ones of the positions of a, b, c, d and e shown in the formula (300), and three L; are respectively bonded to carbon atoms at any ones of the positions of b, c and d which are not bonded to $R_2$, $R_2$, $R_{31}$, $R_{32}$, $R_{34}$ and $R_{35}$ are each independently a hydrogen atom or a substituent, a plurality of $R_2$ are mutually the same or different when m is 2 or more, $R_{41}$, $R_{42}$, $R_{43}$ and $R_{45}$ to $R_{48}$ are each independently a hydrogen atom or a substituent, or at least one pair of a pair of $R_{41}$ and $R_{42}$, a pair of $R_{42}$ and $R_{43}$, a pair of $R_{45}$ and $R_{46}$, a pair of $R_{46}$ and $R_{47}$, or a pair of $R_{47}$ and Rag are mutually bonded to form a ring, and $R_{11}$ to $R_{18}$, $R_{41}$ to $R_{43}$, and $R_{45}$ to $R_{48}$ as the substituent are each independently a halogen atom, a cyano group, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms, and wherein when $R_{13}$ and $R_{16}$ as the substituent are each independently a substituted or unsubstituted heterocyclic group having 5 to 30 ring atoms, $R_{13}$ and $R_{16}$ as the substituent are each independently a substituted or unsubstituted pyridyl group, a substituted or unsubstituted pyrimidinyl group, a substituted or unsubstituted pyrazinyl group, a substituted or unsubstituted pyridazinyl group, a substituted or unsubstituted triazinyl group, a substituted or unsubstituted quinolyl group, a substituted or unsubstituted isoquinolinyl group, a substituted or unsubstituted naphthyridinyl group, a substituted or unsubstituted phthalazinyl group, a substituted or unsubstituted quinoxalinyl group, a substituted or unsubstituted quinazolinyl group, a substituted or unsubstituted phenanthridinyl group, a substituted or unsubstituted acridinyl group, a substituted or unsubstituted phenanthrolinyl group, a substituted or unsubstituted pyrrolyl group, a substituted or unsubstituted imidazolyl group, a substituted or unsubstituted pyrazolyl group, a substituted or unsubstituted triazolyl group, a substituted or unsubstituted tetrazolyl group, a substituted or unsubstituted indolyl group, a substituted or unsubstituted benzimidazolyl group, a substituted or unsubstituted indazolyl group, a substituted or unsubstituted imidazopyridinyl group, a substituted or unsubstituted benzotriazolyl group, a substituted or unsubstituted carbazolyl group, a substituted or unsubstituted furyl group, a substituted or unsubstituted thienyl group, a substituted or unsubstituted oxazolyl group, a substituted or unsubstituted thiazolyl group, a substituted or unsubstituted isoxazolyl group, a substituted or unsubstituted isothiazolyl group, a substituted or unsubstituted oxadiazolyl group, a substituted or unsubstituted thiadiazolyl group, a substituted or unsubstituted benzofuranyl group, a substituted or unsubstituted benzothienyl group, a substituted or unsubstituted benzoxazolyl group, a substituted or unsubstituted benzothiazolyl group, a substituted or unsubstituted benzisoxazolyl group, a substituted or unsubstituted benzisothiazolyl group, a substituted or unsubstituted benzoxadiazolyl group, a substituted or unsubstituted benzothiadiazolyl group, a substituted or unsubstituted dibenzothienyl group, a substituted or unsubstituted piperidinyl group, a substituted or unsubstituted pyrrolidinyl group, a substituted or unsubstituted piperazinyl group, a substituted or unsubstituted morpholyl group, a substituted or unsubstituted phenazinyl group, a substituted or unsubstituted phenothiazinyl group, or a substituted or unsubstituted phenoxazinyl group, and $R_2$, $R_{31}$, $R_{32}$, $R_{34}$ and $R_{35}$ as the substituent are each independently a halogen atom, a substituted or unsubstituted aryl group having 6 to 30 ring carbon atoms, a substituted or unsubstituted heterocyclic group having 5 to 30 ring atoms, a substituted or unsubstituted alkyl group having 1 to 30 carbon atoms, a substituted or unsubstituted alkyl halide group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted alkylsilyl group having 3 to 30 carbon atoms, a substituted or unsubstituted arylsilyl group having 6 to 60 ring carbon atoms, a substituted or unsubstituted arylphosphoryl group having 6 to 60 ring carbon atoms, a hydroxy group, a substituted or unsubstituted alkoxy group having 1 to 30 carbon atoms, a substituted or unsubstituted aryloxy group having 6 to 30 ring carbon atoms, an amino group, a substituted or unsubstituted alkylamino group having 2 to 30 carbon atoms, a substituted or unsubstituted arylamino group having 6 to 60 ring carbon atoms, a thiol group, a substituted or unsubstituted alkylthio group having 1 to 30 carbon atoms, or a substituted or unsubstituted arylthio group having 6 to 30 ring carbon atoms.

40. The compound according to claim 39, wherein
at least one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ is bonded to each other to form a ring, and
a pair of $R_{41}$ and $R_{42}$, a pair of $R_{42}$ and $R_{43}$, a pair of $R_{43}$ and $R_{44}$, a pair of $R_{45}$ and $R_{46}$, a pair of $R_{46}$ and $R_{47}$, and a pair of $R_{47}$ and $R_{48}$ are not mutually bonded.

41. The compound according to claim 39, wherein
$R_2$, $R_{31}$, $R_{32}$, $R_{34}$, and $R_{35}$ are hydrogen atoms,
n is 1 or 2,
k is 1 or 2,
$R_{11}$ to $R_{18}$, $R_{41}$ to $R_{43}$ and $R_{45}$ to $R_{48}$ are each independently a hydrogen atom, or a substituted or unsubstituted aryl group having 6 to 30 ring carbon atoms,
a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, a pair of $R_{17}$ and $R_{18}$, a pair of $R_{41}$ and $R_{42}$, a pair of $R_{42}$ and $R_{43}$, a pair of $R_{45}$ and $R_{46}$, a pair of $R_{46}$ and $R_{47}$, and a pair of $R_{47}$ and $R_{48}$ are not mutually bonded, and
$L_1$ is a single bond or a group derived from an unsubstituted aryl group having 6 to 30 ring carbon atoms.

42. The compound according to claim 39, wherein
$R_2$, $R_{31}$, $R_{32}$, $R_{34}$, and $R_{35}$ are hydrogen atoms,
n is 1 or 2,
k is 1 or 2,
$R_{11}$ to $R_{18}$ are each independently a hydrogen atom, or a substituted or unsubstituted phenyl group,
a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, and a pair of $R_{17}$ and $R_{18}$ are not mutually bonded,
$R_{41}$ to $R_{43}$ and $R_{45}$ to $R_{48}$ are hydrogen atoms, and
$L_1$ is a single bond.

43. The compound according to claim 39, wherein
at least one pair of a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, or a pair of $R_{17}$ and $R_{18}$ is bonded to each other to form a ring, and
a pair of $R_{41}$ and $R_{42}$, a pair of $R_{42}$ and $R_{43}$, a pair of $R_{43}$ and $R_{44}$, a pair of $R_{45}$ and $R_{46}$, a pair of $R_{46}$ and $R_{47}$, and a pair of $R_{47}$ and $R_{48}$ are not mutually bonded.

44. The compound according to claim 39, wherein
a pair of $R_{11}$ and $R_{12}$, a pair of $R_{12}$ and $R_{13}$, a pair of $R_{13}$ and $R_{14}$, a pair of $R_{15}$ and $R_{16}$, a pair of $R_{16}$ and $R_{17}$, and a pair of $R_{17}$ and $R_{18}$, a pair of $R_{41}$ and $R_{42}$, a pair of $R_{42}$ and $R_{43}$, a pair of $R_{43}$ and $R_{44}$, a pair of $R_{45}$ and $R_{46}$, a pair of $R_{46}$ and $R_{47}$, and a pair of $R_{47}$ and $R_{48}$ are not mutually bonded.

45. The compound according to claim 39, wherein
$R_2$, $R_{31}$, $R_{32}$, $R_{34}$, and $R_{35}$ are hydrogen atoms, and
$L_1$ is a single bond, a group derived from an unsubstituted aryl group having 6 to 30 ring carbon atoms, or a group derived from an unsubstituted heterocyclic group having 5 to 30 ring atoms.

46. The compound according to claim 39, wherein
n is 1 or 2, and k is 1 or 2.

47. The compound according to claim 39, wherein
$R_{11}$ to $R_{18}$, and $R_{41}$ to $R_{48}$ are each independently a hydrogen atom, a substituted or unsubstituted aryl group having 6 to 30 ring carbon atoms, a substituted or unsubstituted heterocyclic group having 5 to 30 ring atoms, or a substituted or unsubstituted alkyl group having 1 to 30 carbon atoms.

48. The compound according to claim 39, wherein
L₁ is a single bond or a group derived from an unsubstituted aryl group having 6 to 30 ring carbon atoms.

49. An organic-electroluminescence-device material comprising the compound according to claim 39.

50. A compound represented by one of formulae (502 to (514) below, (502)
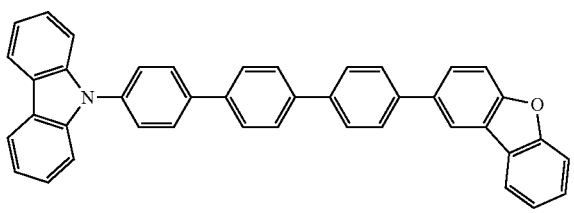

(503)
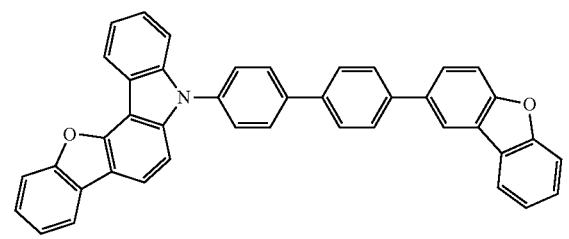

(504)
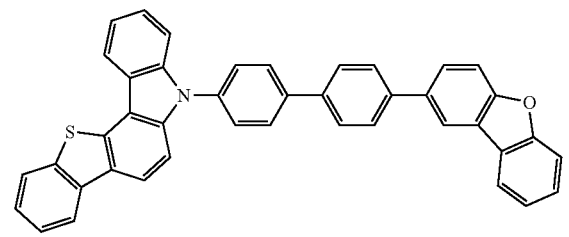

(505)
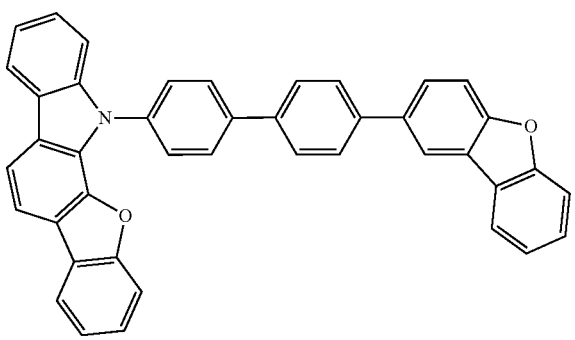

-continued (506)
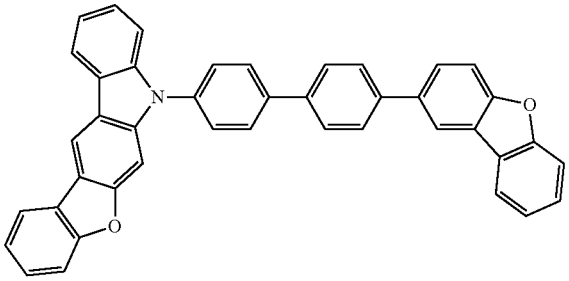

(507)
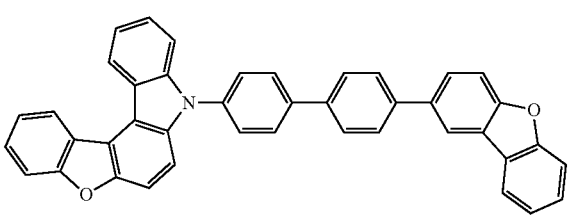

(508)
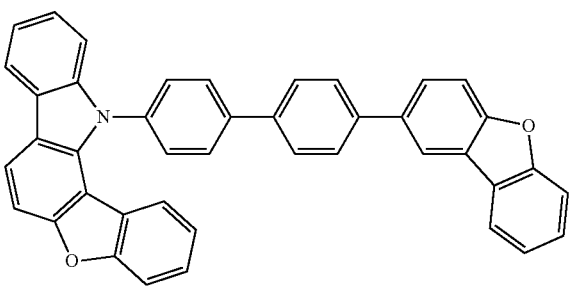

(509)
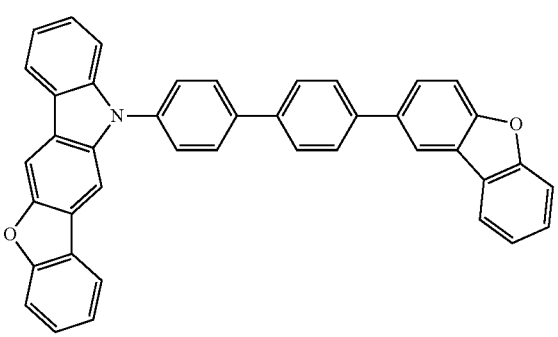

(510)
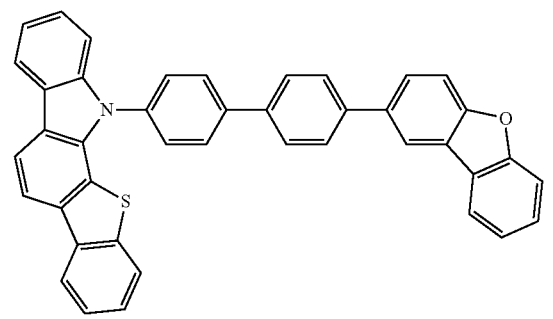

(511)
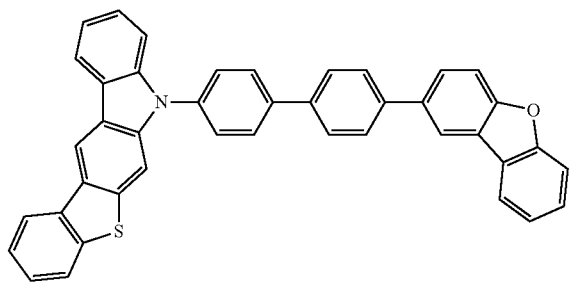
(512)
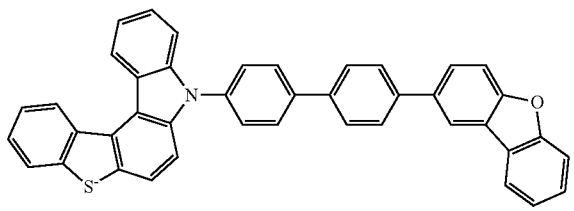
(513)
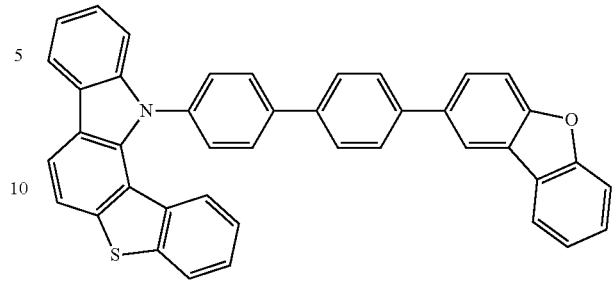
(514)
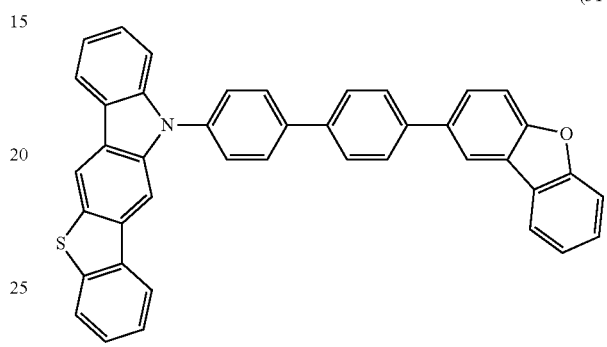
51. An organic-electroluminescence-device material comprising the compound according to claim 50.
* * * * *